United States Patent
Gable et al.

(10) Patent No.: US 8,197,770 B2
(45) Date of Patent: *Jun. 12, 2012

(54) FLUID HANDLING CASSETTE HAVING A SPECTROSCOPIC SAMPLE CELL

(75) Inventors: Jennifer H. Gable, Newark, CA (US);
James R. Braig, Piedmont, CA (US);
Kenneth I. Li, Piedmont, CA (US);
Mark Wechsler, San Mateo, CA (US);
Peng Zheng, Alameda, CA (US);
Richard Keenan, Livermore, CA (US)

(73) Assignee: Optiscan Biomedical Corporation, Hayward, CA (US)

( * ) Notice: Subject to any disclaimer, the term of this patent is extended or adjusted under 35 U.S.C. 154(b) by 25 days.

This patent is subject to a terminal disclaimer.

(21) Appl. No.: 12/359,874

(22) Filed: Jan. 26, 2009

(65) Prior Publication Data
US 2009/0326343 A1 Dec. 31, 2009

Related U.S. Application Data

(63) Continuation of application No. 11/316,672, filed on Dec. 21, 2005, now Pat. No. 7,481,787.

(60) Provisional application No. 60/652,660, filed on Feb. 14, 2005, provisional application No. 60/724,199, filed on Oct. 6, 2005, provisional application No. 60/658,001, filed on Mar. 2, 2005, provisional application No. 60/673,551, filed on Apr. 21, 2005.

(51) Int. Cl.
*B01L 3/00* (2006.01)
(52) U.S. Cl. ............................................ 422/500
(58) Field of Classification Search ............... 422/99, 422/500
See application file for complete search history.

(56) References Cited

U.S. PATENT DOCUMENTS

| | | |
|---|---|---|
| 2,797,149 A | 6/1957 | Skeggs |
| 3,634,039 A | 1/1972 | Broady |
| 3,751,173 A | 8/1973 | Sanz et al. |
| 3,787,124 A | 1/1974 | Lowy et al. |
| 3,910,256 A | 10/1975 | Clark et al. |
| 3,972,614 A | 8/1976 | Johansen et al. |

(Continued)

FOREIGN PATENT DOCUMENTS

EP 0212314 3/1987

(Continued)

OTHER PUBLICATIONS

U.S. Appl. No. 10/825,072, filed Apr. 15, 2003, titled "Sample Element For Use In Material Analysis.", Braig et al.

(Continued)

*Primary Examiner* — Bobby Ramdhanie
(74) *Attorney, Agent, or Firm* — Knobbe Martens Olson & Bear LLP

(57) ABSTRACT

A fluid handling module is configured for removable engagement with a reusable main fluid handling instrument. The module includes a module housing and a first fluid passageway extending from the module housing. The first fluid passageway has a patient end remote from the housing. The first fluid passageway is configured to provide fluid communication with a bodily fluid in a patient. A fluid component separator is in fluid communication with the first fluid passageway. The fluid component separator is configured to separate at least one component from a portion of the bodily fluid drawn from the patient. A spectroscopic sample cell is configured to hold at least a portion of the first component.

22 Claims, 63 Drawing Sheets

U.S. PATENT DOCUMENTS

| | | | |
|---|---|---|---|
| 4,028,056 A | 6/1977 | Snyder et al. |
| 4,088,448 A | 5/1978 | Lilja et al. |
| 4,092,233 A | 5/1978 | Clemens et al. |
| 4,127,111 A | 11/1978 | Drolet |
| 4,151,845 A | 5/1979 | Clemens |
| 4,240,438 A | 12/1980 | Updike |
| 4,303,376 A | 12/1981 | Siekmann |
| 4,305,659 A | 12/1981 | Bilstand et al. |
| 4,328,185 A | 5/1982 | Reasons et al. |
| 4,342,516 A | 8/1982 | Chamran et al. |
| 4,350,441 A | 9/1982 | Wicnienski |
| 4,405,235 A | 9/1983 | Rossiter |
| 4,421,503 A | 12/1983 | Latham et al. |
| 4,427,889 A | 1/1984 | Muller |
| 4,440,301 A | 4/1984 | Intengan |
| 4,447,150 A | 5/1984 | Heinemann |
| 4,464,051 A | 8/1984 | Talmadge et al. |
| 4,477,190 A | 10/1984 | Liston et al. |
| 4,519,792 A | 5/1985 | Dawe |
| 4,526,569 A | 7/1985 | Bernardi |
| 4,535,786 A | 8/1985 | Kater |
| 4,537,561 A | 8/1985 | Xanthopoulos |
| 4,563,090 A | 1/1986 | Witte |
| 4,573,968 A | 3/1986 | Parker |
| 4,613,322 A | 9/1986 | Edelson |
| 4,654,197 A | 3/1987 | Lilja et al. |
| 4,655,225 A | 4/1987 | Dahne et al. |
| 4,657,490 A | 4/1987 | Abbott |
| 4,657,529 A | 4/1987 | Prince et al. |
| 4,696,798 A | 9/1987 | Timgren |
| 4,704,029 A | 11/1987 | Van Heuvelen |
| 4,739,380 A | 4/1988 | Lauks et al. |
| 4,753,776 A | 6/1988 | Hillman |
| 4,756,884 A | 7/1988 | Hillman |
| 4,758,228 A | 7/1988 | Williams |
| 4,761,381 A | 8/1988 | Blatt et al. |
| 4,784,157 A | 11/1988 | Halls et al. |
| 4,786,394 A | 11/1988 | Enzer et al. |
| 4,790,640 A | 12/1988 | Nason |
| 4,796,644 A | 1/1989 | Polaschegg |
| 4,798,589 A | 1/1989 | Tseo |
| 4,810,090 A | 3/1989 | Boucher et al. |
| 4,818,190 A | 4/1989 | Pelmulder et al. |
| 4,818,493 A | 4/1989 | Coville et al. |
| 4,840,542 A | 6/1989 | Abbott |
| 4,850,980 A | 7/1989 | Lentz et al. |
| 4,854,836 A | 8/1989 | Borsanyi |
| 4,863,425 A | 9/1989 | Slate et al. |
| 4,873,993 A | 10/1989 | Meserol et al. |
| 4,882,492 A | 11/1989 | Schlager |
| 4,900,302 A | 2/1990 | Newton |
| 4,919,596 A | 4/1990 | Slate et al. |
| 4,940,527 A | 7/1990 | Kazlauskas et al. |
| 4,948,961 A | 8/1990 | Hillman et al. |
| 4,963,498 A | 10/1990 | Hillman et al. |
| 4,974,592 A | 12/1990 | Branco |
| 4,976,270 A | 12/1990 | Parl et al. |
| 5,004,923 A | 4/1991 | Hillman et al. |
| 5,009,230 A | 4/1991 | Hutchinson |
| 5,036,198 A | 7/1991 | Spaeth |
| 5,045,473 A | 9/1991 | Cassaday et al. |
| 5,048,537 A | 9/1991 | Messinger |
| 5,066,859 A | 11/1991 | Karkar et al. |
| 5,134,079 A | 7/1992 | Cusack et al. |
| 5,140,161 A | 8/1992 | Hillman et al. |
| 5,147,606 A | 9/1992 | Charlton et al. |
| 5,148,811 A | 9/1992 | Messinger |
| 5,149,501 A | 9/1992 | Babson |
| 5,164,598 A | 11/1992 | Hillman et al. |
| 5,165,406 A | 11/1992 | Wong |
| 5,173,193 A | 12/1992 | Schembri |
| 5,178,603 A | 1/1993 | Prince et al. |
| 5,186,844 A | 2/1993 | Burd |
| 5,204,525 A | 4/1993 | Hillman et al. |
| 5,209,231 A | 5/1993 | Cote et al. |
| 5,223,219 A | 6/1993 | Subramanian et al. |
| 5,249,584 A | 10/1993 | Karkar et al. |
| 5,271,815 A | 12/1993 | Wong |
| 5,273,517 A | 12/1993 | Barone |
| 5,279,150 A | 1/1994 | Katzer et al. |
| 5,286,454 A | 2/1994 | Nilsson et al. |
| 5,296,706 A | 3/1994 | Braig et al. |
| 5,300,779 A | 4/1994 | Hillman et al. |
| 5,304,348 A | 4/1994 | Burd |
| 5,371,020 A | 12/1994 | Frischauf |
| 5,377,674 A | 1/1995 | Kuestner |
| 5,380,665 A | 1/1995 | Cusack et al. |
| 5,430,542 A | 7/1995 | Shepherd |
| 5,434,412 A | 7/1995 | Sodickson et al. |
| 5,437,635 A | 8/1995 | Fields et al. |
| 5,470,757 A | 11/1995 | Gagnon |
| 5,505,828 A | 4/1996 | Wong et al. |
| 5,515,847 A | 5/1996 | Braig et al. |
| 5,582,184 A | 12/1996 | Erickson |
| 5,596,992 A | 1/1997 | Haaland et al. |
| 5,605,837 A | 2/1997 | Karimi et al. |
| 5,606,164 A | 2/1997 | Price et al. |
| 5,609,572 A | 3/1997 | Lang |
| 5,627,041 A | 5/1997 | Shartle |
| 5,636,633 A | 6/1997 | Messerschmidt et al. |
| 5,655,530 A | 8/1997 | Messerschmidt |
| 5,674,457 A | 10/1997 | Williamsson |
| 5,681,529 A | 10/1997 | Taguchi et al. |
| 5,693,233 A | 12/1997 | Schembri |
| 5,697,366 A | 12/1997 | Kimball et al. |
| 5,697,899 A | 12/1997 | Hillman et al. |
| 5,700,695 A | 12/1997 | Yassinzadeh et al. |
| 5,746,217 A | 5/1998 | Erickson et al. |
| 5,758,643 A | 6/1998 | Wong et al. |
| 5,773,301 A | 6/1998 | Ziegler |
| 5,798,031 A | 8/1998 | Charlton et al. |
| 5,801,057 A | 9/1998 | Smart et al. |
| 5,804,048 A | 9/1998 | Wong |
| 5,815,258 A | 9/1998 | Nakanishi |
| 5,817,007 A | 10/1998 | Fodgaard et al. |
| 5,827,746 A | 10/1998 | Duic |
| 5,844,686 A | 12/1998 | Treptow et al. |
| 5,857,462 A | 1/1999 | Thomas et al. |
| 5,900,632 A | 5/1999 | Sterling et al. |
| 5,902,253 A | 5/1999 | Pfeiffer et al. |
| 5,916,201 A | 6/1999 | Wilson |
| 5,935,062 A | 8/1999 | Messerschmidt et al. |
| 5,944,660 A | 8/1999 | Kimball et al. |
| 5,947,911 A | 9/1999 | Wong |
| 5,963,335 A | 10/1999 | Boutelle |
| 5,971,941 A | 10/1999 | Simons et al. |
| 5,976,085 A | 11/1999 | Kimball et al. |
| 5,977,545 A | 11/1999 | Haar et al. |
| 6,017,318 A | 1/2000 | Gauthier et al. |
| 6,025,597 A | 2/2000 | Sterling et al. |
| 6,030,581 A | 2/2000 | Virtanen |
| 6,036,924 A | 3/2000 | Simons et al. |
| 6,040,578 A | 3/2000 | Malin et al. |
| 6,048,352 A | 4/2000 | Douglas et al. |
| 6,049,727 A | 4/2000 | Crothall |
| 6,049,728 A | 4/2000 | Chou |
| 6,049,762 A | 4/2000 | Ganz et al. |
| 6,072,180 A | 6/2000 | Kramer et al. |
| 6,077,055 A | 6/2000 | Vilks |
| 6,084,660 A | 7/2000 | Shartle |
| 6,084,661 A | 7/2000 | Mendelson et al. |
| 6,087,182 A | 7/2000 | Jeng et al. |
| 6,101,406 A | 8/2000 | Hacker et al. |
| 6,119,026 A | 9/2000 | McNulty et al. |
| 6,120,676 A | 9/2000 | Heller et al. |
| 6,122,042 A | 9/2000 | Wunderman et al. |
| 6,122,052 A | 9/2000 | Barnes et al. |
| 6,128,519 A | 10/2000 | Say |
| 6,143,164 A | 11/2000 | Heller et al. |
| 6,152,876 A | 11/2000 | Robinson et al. |
| 6,157,041 A | 12/2000 | Thomas et al. |
| 6,161,028 A | 12/2000 | Braig et al. |
| 6,188,476 B1 | 2/2001 | Hafeman et al. |
| 6,197,494 B1 | 3/2001 | Oberhardt |
| 6,198,949 B1 | 3/2001 | Braig et al. |
| 6,200,287 B1 | 3/2001 | Keller et al. |
| 6,226,082 B1 | 5/2001 | Roe |

| | | |
|---|---|---|
| 6,230,034 B1 | 5/2001 | Messerschmidt et al. |
| 6,236,047 B1 | 5/2001 | Malin et al. |
| 6,236,870 B1 | 5/2001 | Madarasz et al. |
| 6,240,306 B1 | 5/2001 | Rohrscheib et al. |
| 6,261,065 B1 | 7/2001 | Nayak et al. |
| 6,261,519 B1 | 7/2001 | Harding et al. |
| 6,262,798 B1 | 7/2001 | Shepherd et al. |
| 6,269,704 B1 | 8/2001 | Ziv et al. |
| 6,278,889 B1 | 8/2001 | Robinson |
| 6,285,448 B1 | 9/2001 | Kuenstner et al. |
| 6,312,888 B1 | 11/2001 | Wong et al. |
| 6,372,182 B1 | 4/2002 | Mauro et al. |
| 6,484,044 B1 | 11/2002 | Lilienfeld-Toal |
| 6,491,656 B1 | 12/2002 | Morris |
| 6,512,577 B1 | 1/2003 | Ozanich |
| 6,531,095 B2 | 3/2003 | Hammer |
| 6,556,850 B1 | 4/2003 | Braig et al. |
| 6,580,934 B1 | 6/2003 | Braig et al. |
| 6,591,124 B2 | 7/2003 | Sherman et al. |
| 6,595,942 B2 | 7/2003 | Kleinekofort |
| 6,622,032 B1 | 9/2003 | Robinson et al. |
| 6,622,033 B2 | 9/2003 | Messerschmidt et al. |
| 6,636,759 B2 | 10/2003 | Robinson |
| 6,649,416 B1 | 11/2003 | Kauer et al. |
| 6,694,157 B1 | 2/2004 | Stone et al. |
| 6,718,189 B2 | 4/2004 | Rohrscheib et al. |
| 6,836,332 B2 | 12/2004 | Mosley et al. |
| 6,862,534 B2 | 3/2005 | Sterling et al. |
| 6,890,291 B2 | 5/2005 | Robinson et al. |
| 6,926,834 B2 | 8/2005 | Coville et al. |
| 6,958,809 B2 | 10/2005 | Sterling et al. |
| RE38,869 E | 11/2005 | Polaschegg et al. |
| 6,983,177 B2 | 1/2006 | Rule et al. |
| 6,989,891 B2 | 1/2006 | Braig et al. |
| 7,009,180 B2 | 3/2006 | Sterling et al. |
| 7,011,742 B2 | 3/2006 | Rosiello |
| 7,050,157 B2 | 5/2006 | Braig et al. |
| 7,061,593 B2 | 6/2006 | Braig et al. |
| 7,481,787 B2 | 1/2009 | Gable et al. |
| 7,738,085 B2 | 6/2010 | Braig et al. |
| 2002/0045525 A1* | 4/2002 | Marziali ..................... 494/31 |
| 2003/0086073 A1 | 5/2003 | Braig et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0130616 A1 | 7/2003 | Steil et al. |
| 2003/0199803 A1 | 10/2003 | Robinson et al. |
| 2003/0229302 A1 | 12/2003 | Robinson et al. |
| 2004/0027659 A1 | 2/2004 | Messerschmidt |
| 2004/0132167 A1 | 7/2004 | Rule et al. |
| 2004/0132168 A1 | 7/2004 | Rule et al. |
| 2004/0147034 A1 | 7/2004 | Gore et al. |
| 2004/0241736 A1 | 12/2004 | Hendee et al. |
| 2004/0249308 A1 | 12/2004 | Forssell |
| 2005/0037384 A1 | 2/2005 | Braig et al. |
| 2005/0038357 A1 | 2/2005 | Hartstein et al. |
| 2005/0094127 A1 | 5/2005 | O'Mahony et al. |
| 2005/0105095 A1 | 5/2005 | Pesach et al. |
| 2005/0106749 A1 | 5/2005 | Braig et al. |
| 2005/0203360 A1 | 9/2005 | Brauker et al. |
| 2006/0004267 A1 | 1/2006 | Rule et al. |
| 2006/0009727 A1 | 1/2006 | O'Mahony et al. |
| 2006/0079809 A1 | 4/2006 | Goldberger et al. |
| 2006/0189925 A1 | 8/2006 | Gable et al. |
| 2006/0189925 A1 | 8/2006 | Hall et al. |
| 2006/0194325 A1 | 8/2006 | Gable et al. |
| 2006/0195045 A1 | 8/2006 | Gable et al. |
| 2006/0195058 A1 | 8/2006 | Gable et al. |
| 2006/0200070 A1 | 9/2006 | Callicoat et al. |
| 2006/0216209 A1 | 9/2006 | Braig et al. |
| 2006/0229531 A1 | 10/2006 | Goldberger et al. |
| 2006/0235348 A1 | 10/2006 | Callicoat et al. |
| 2007/0060872 A1 | 3/2007 | Hall et al. |
| 2007/0142720 A1 | 6/2007 | Ridder et al. |
| 2007/0225675 A1 | 9/2007 | Robinson et al. |
| 2007/0240497 A1 | 10/2007 | Robinson et al. |
| 2007/0244381 A1 | 10/2007 | Robinson et al. |
| 2007/0244382 A1 | 10/2007 | Robinson et al. |

FOREIGN PATENT DOCUMENTS

| | | |
|---|---|---|
| EP | 0483117 | 4/1992 |
| EP | 0485368 | 5/1992 |
| EP | 0488994 | 6/1992 |
| EP | 0 549 341 | 6/1993 |
| EP | 549341 A1 * | 6/1993 |
| EP | 0 992 256 A2 | 4/2000 |
| EP | 1 491 144 | 12/2004 |
| JP | 08-114539 | 5/1996 |
| JP | 2000-107279 | 4/2000 |
| JP | 2002-527212 | 8/2002 |
| JP | 2004-286475 | 10/2004 |
| WO | WO 99/17114 | 4/1999 |
| WO | WO 99/40411 | 8/1999 |
| WO | WO 99/52633 | 10/1999 |
| WO | 0023140 | 4/2000 |
| WO | WO 00/22413 | 4/2000 |
| WO | WO 01/53806 | 7/2001 |
| WO | WO 01/60248 | 8/2001 |
| WO | WO 02/43866 | 6/2002 |
| WO | WO 03/016882 | 2/2003 |
| WO | WO 03/039362 | 5/2003 |
| WO | WO 2004/016171 | 2/2004 |
| WO | WO 2004/092715 | 10/2004 |
| WO | WO 2005/110601 | 11/2005 |
| WO | WO 2006039310 A2 * | 4/2006 |

OTHER PUBLICATIONS

U.S. Appl. No. 11/477,151, filed Jun. 28, 2006, titled "Method of Determining an Analyte Concentration in a Sample From an Absorption Spectrum."
U.S. Appl. No. 60/614,122, filed Sep. 29, 2004, Goldberger.
European Search Report dated Mar. 16, 2011 and issued to related European patent application EP 10 18 3603.
International Search Report for Application No. PCT/US03/25352, mailed Dec. 18, 2003.
International Search Report for Application No. PCT/US02/35707, mailed Apr. 3, 2003.
Ward et al., "Post-Prandial Blood Glucose Determination by Quantitative Mid-Infrared Spectroscopy," *Applied Spectroscopy*, vol. 46, No. 6, pp. 959-965 (1992).
Heise et al., "Multicomponent Assay for Blood Substrates in Human Plasma by Mid-Infrared Spectroscopy and its Evaluation for Clinical Analysis," *Applied Spectroscopy*, vol. 48, No. 1, pp. 85-95 (1994).
Petibois et al., "Glucose and Lactate Concentration Determination on Single Microsamples by Fourier-Transform Infrared Spectroscopy," *Journal of Laboratory and Clinical Medicine*, vol. 135, No. 2, pp. 210-215 (Feb. 2000).
Berger et al., "An Enhanced Algorithm for Linear Multivariate Calibration"; Analytical Chemistry, vol. 70, No. 3, pp. 623-627, Feb. 1, 1998.
Haaland D., et al. "Reagentless Near-Infrared Determination of Glucose in Whole Blood Using Multivariate Calibration," Applied Spectroscopy, 1992, vol. 46, No. 10, pp. 1575-1578, ISSN: 0003-7028.
Widness, et al., *Clinical Performance of an In-Line Point-of-Care Monitor in Neonates*, Pediatrics, vol. 106 No. 3, pp. 497-504 (Sep. 2000).
Ray, et al., *Pilot study of the accuracy of bedside glucometry in the intensive care unit*, Critical Care Medicine, vol. 29 No. 11, pp. 2205-2207 (Nov. 2001).
Maser, et al., *Use of arterial blood with bedside glucose reflectance meters in an intensive care unit: Are they accurate?*, Critical Care Medicine, vol. 22 No. 4, pp. 595-599 (Apr. 1994).
Glucon.com, *Glucon Critical Care Blood Glucose Monitor*, product description, 2pgs.
Fogt, et al., *Development and Evaluation of Glucose Analyzer for a Glucose-Controlled Insulin Infusion System (Biostator®)*, Clinical Chemistry, vol. 24 No. 8, pp. 1366-1372 (1978).
Vonach et al., "Application of Mid-Infrared Transmission Spectrometry to the Direct Determination of Glucose in Whole Blood," Applied Spectroscopy, vol. 52, No. 6, 1998, pp. 820-822.
Finkielman, et al., *Agreement Between Bedside Blood and Plasma Glucose Measurement in the ICU Setting*, Chest Journal, vol. 127 No. 5, pp. 1749-1751 (May 2005).

Billman, et al., *Clinical Performance of an In-Line, ex Vivo Point-of-Care Monitor: A Multicenter Study*, Clinical Chemistry, vol. 48 No. 11, pp. 2030-2043 (2002).

McNichols, et al., *Optical glucose sensing in biological fluids: an overview*, Journal of Biomedical Optics, vol. 5 No. 1, pp. 5-16 (Jan. 2000).

Gable et al., co-pending U.S. Appl. No. 11/316,676, filed Dec. 21, 2005.

International Search Report in International Application No. PCT/US2006/005112 mailed Nov. 28, 2006.

English Translation of the Office Action in Japanese Patent Application No. 2007-555333 dated Mar. 27, 2012.

Office Action in Australian Patent Application No. 2006216939 dated Mar. 15, 2012.

* cited by examiner

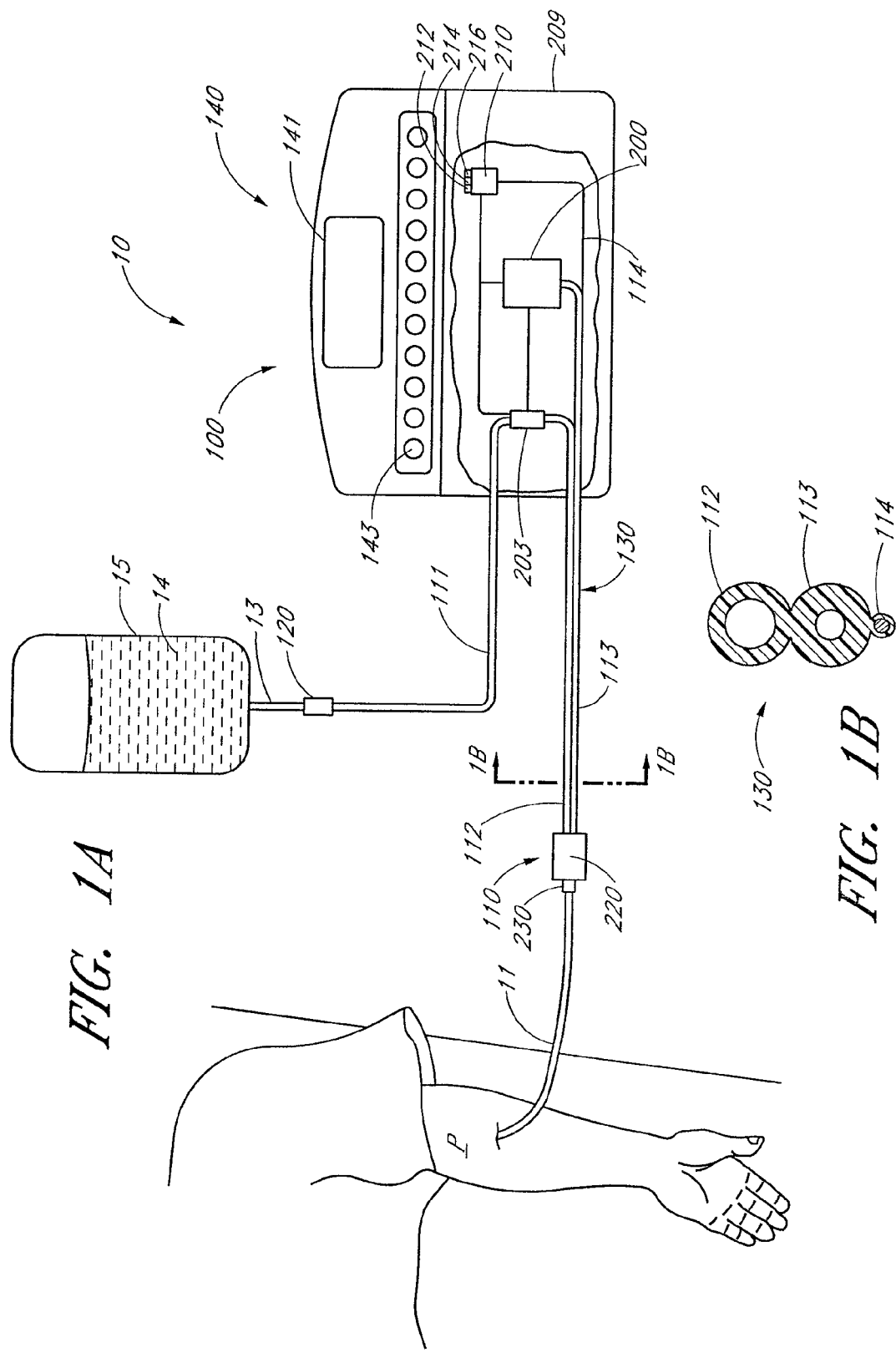

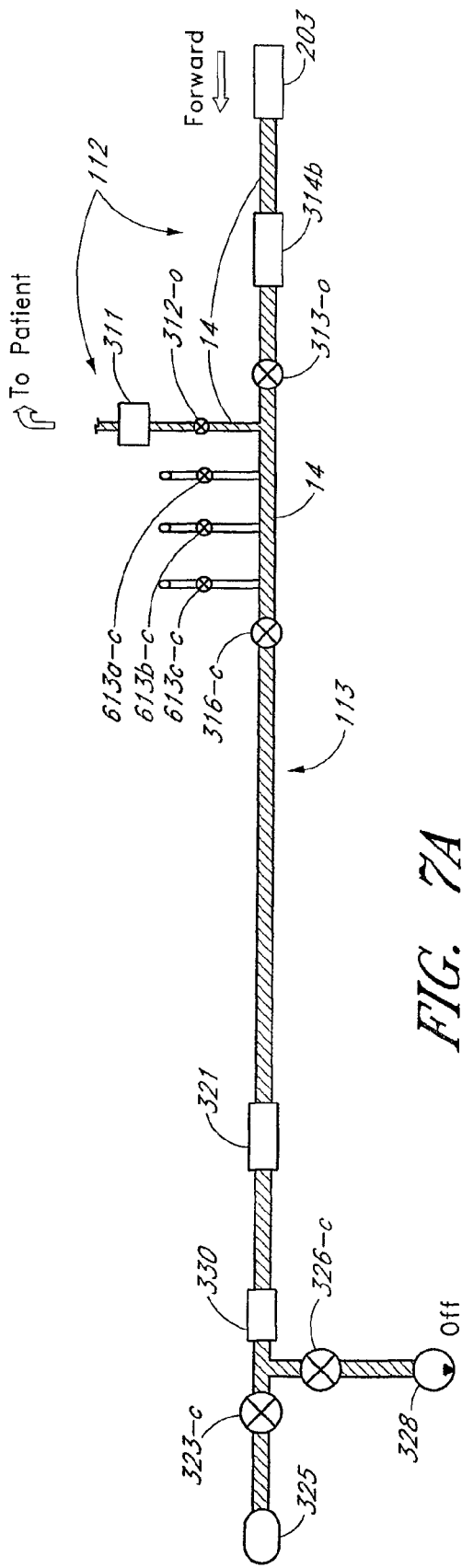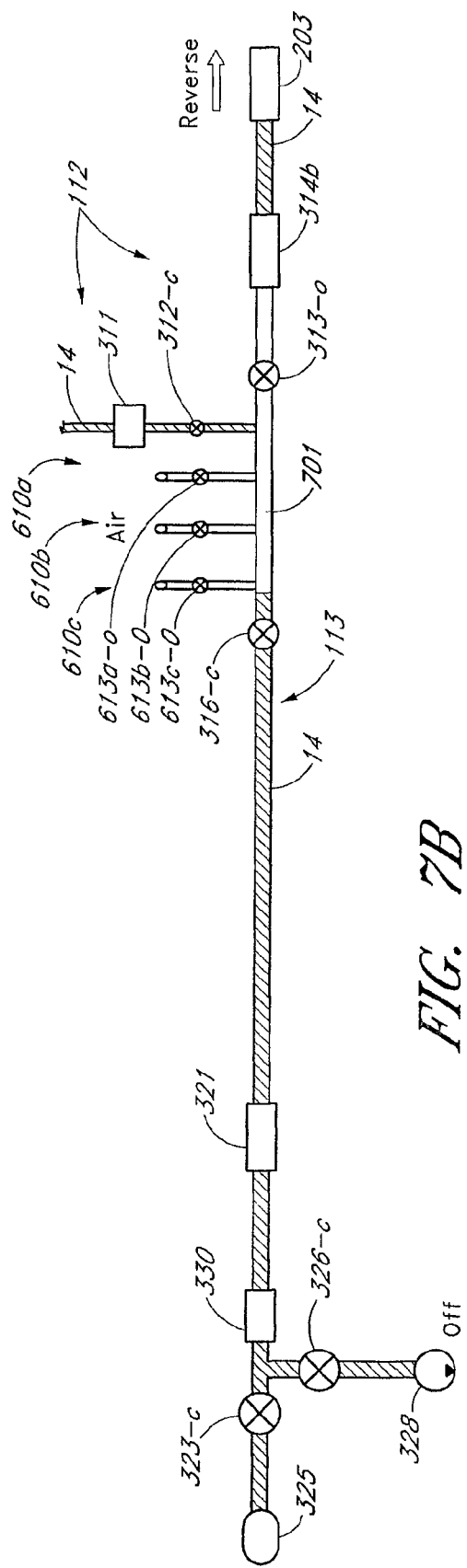
FIG. 7A
FIG. 7B

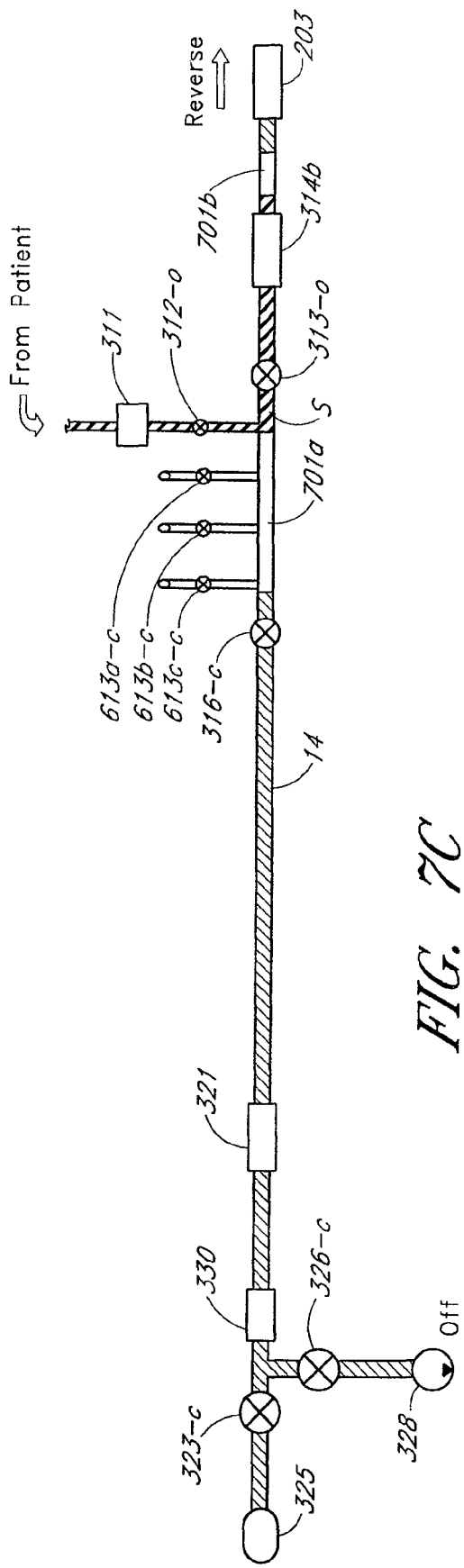
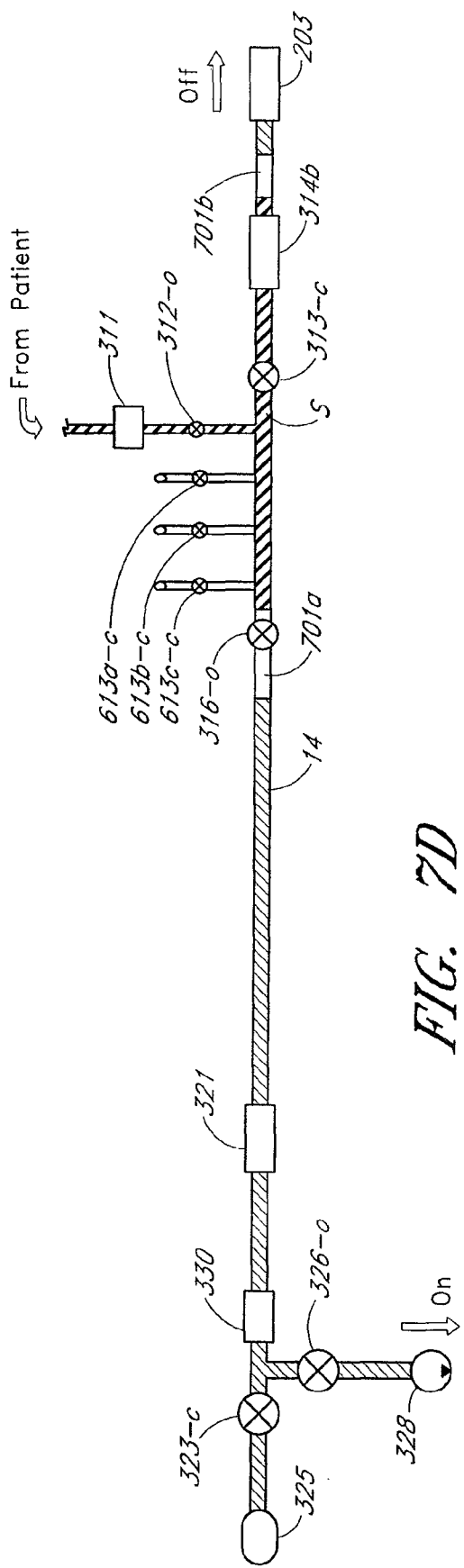
FIG. 7C
FIG. 7D

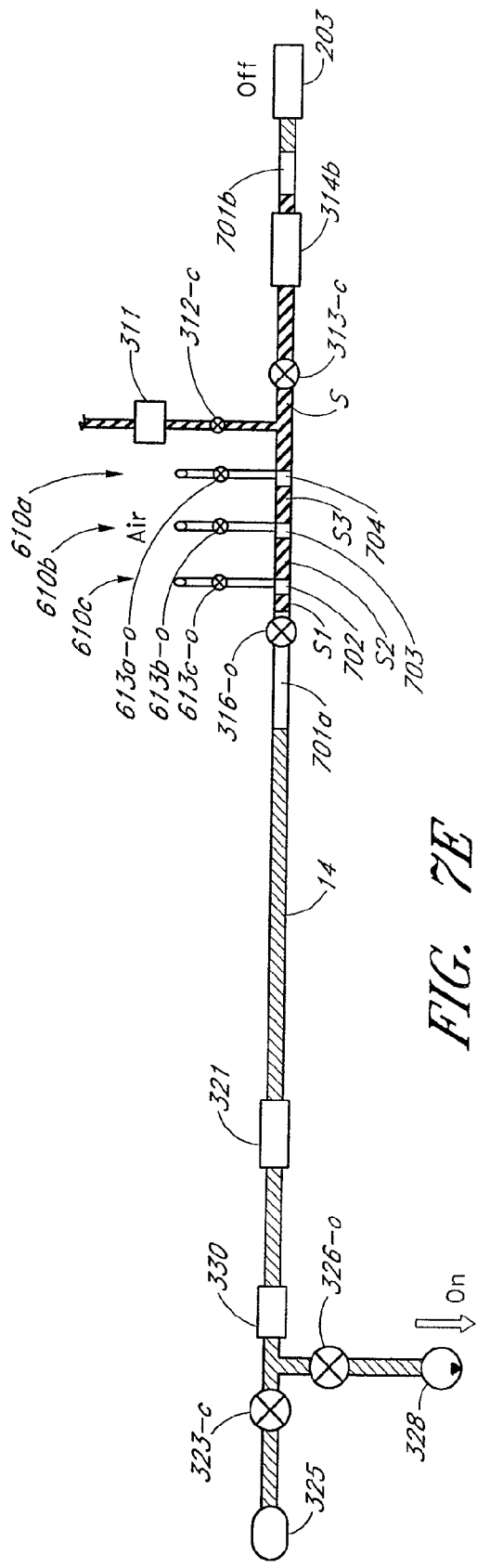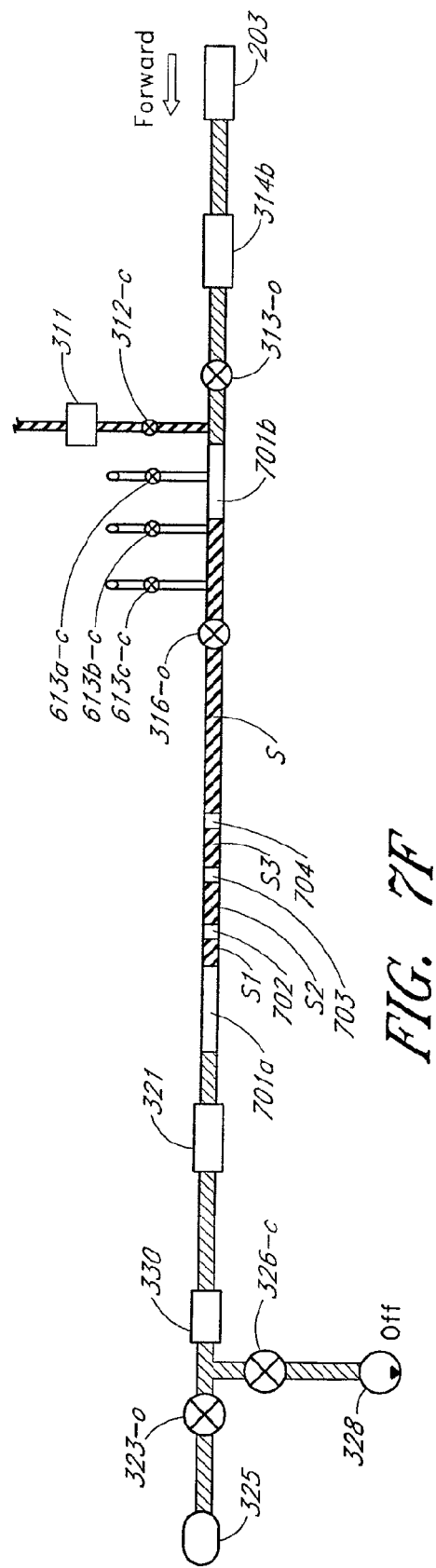

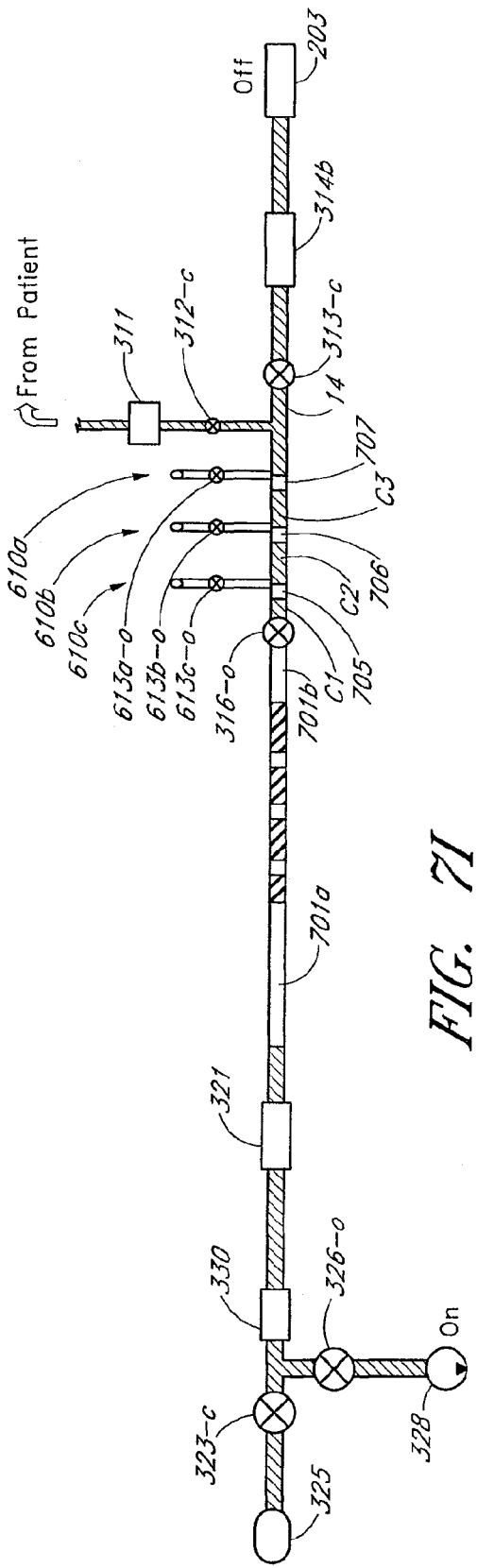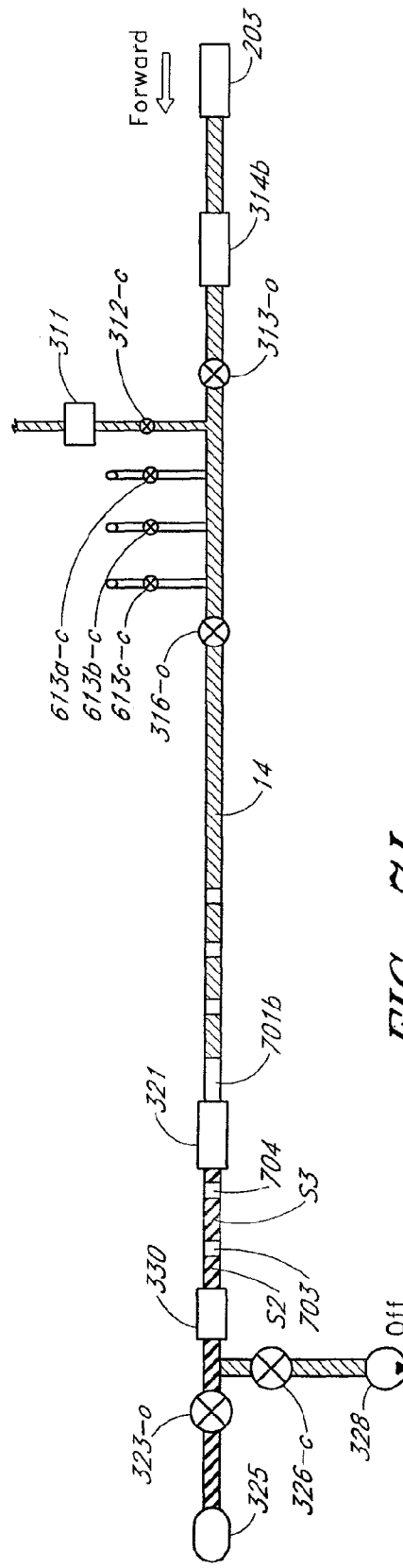

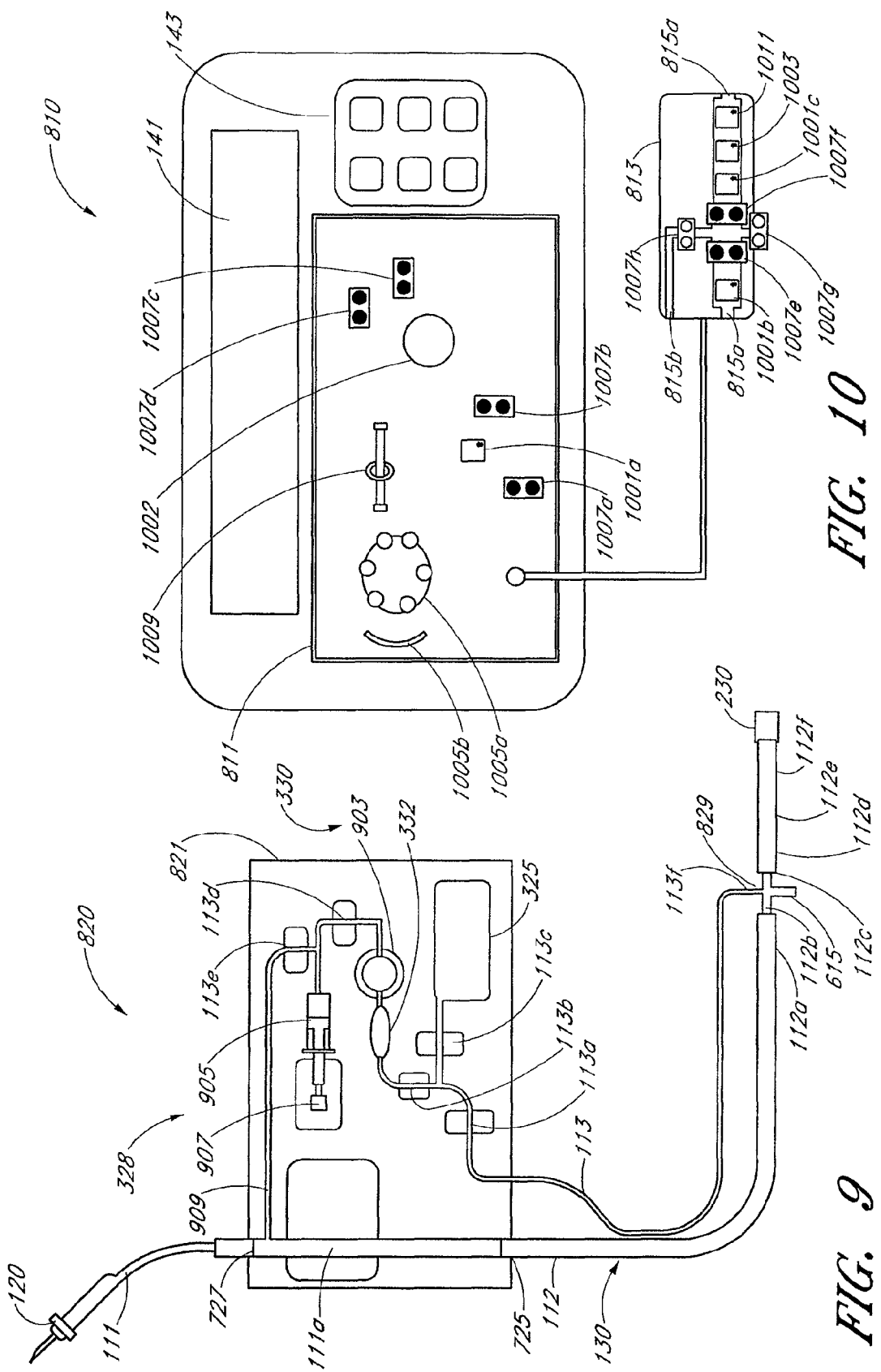

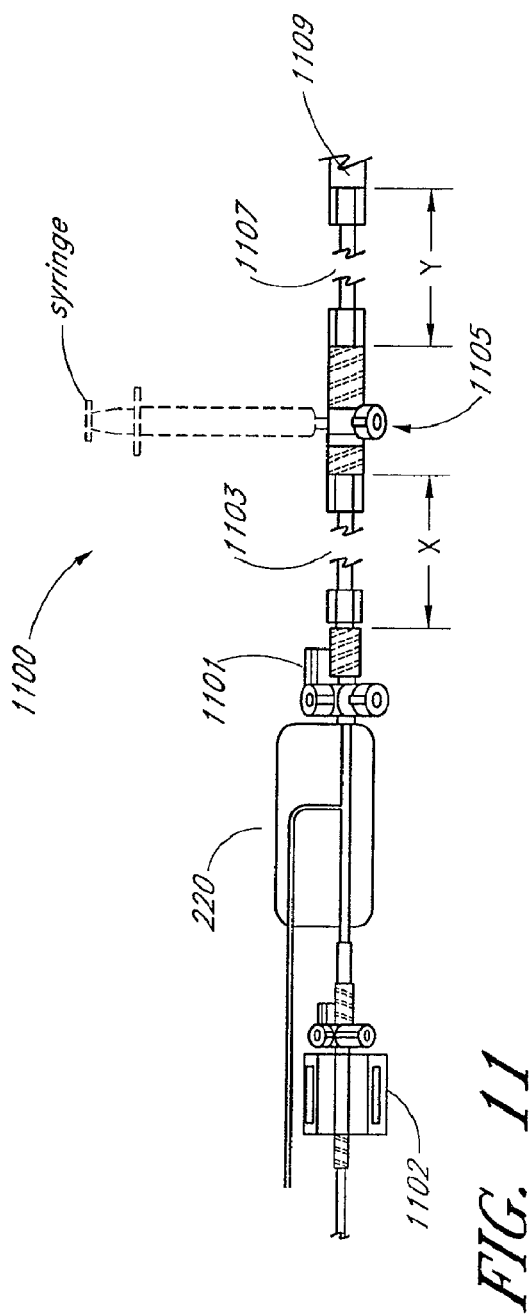
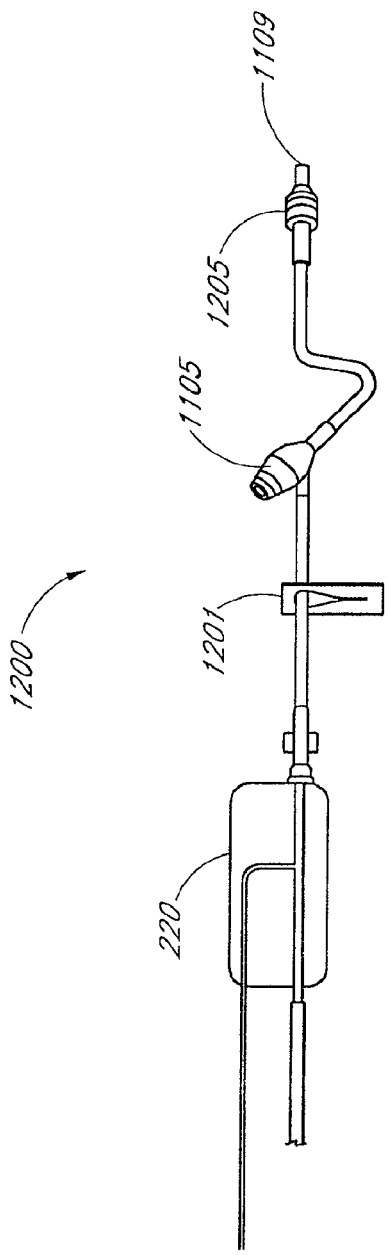
FIG. 11
FIG. 12

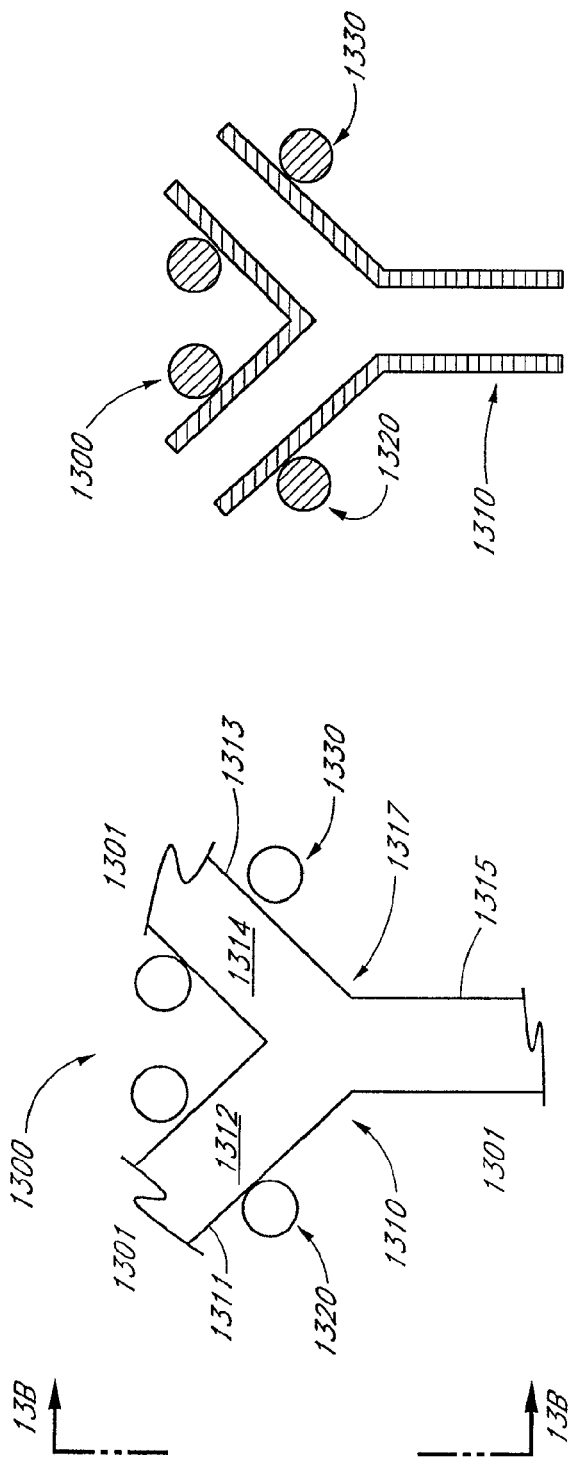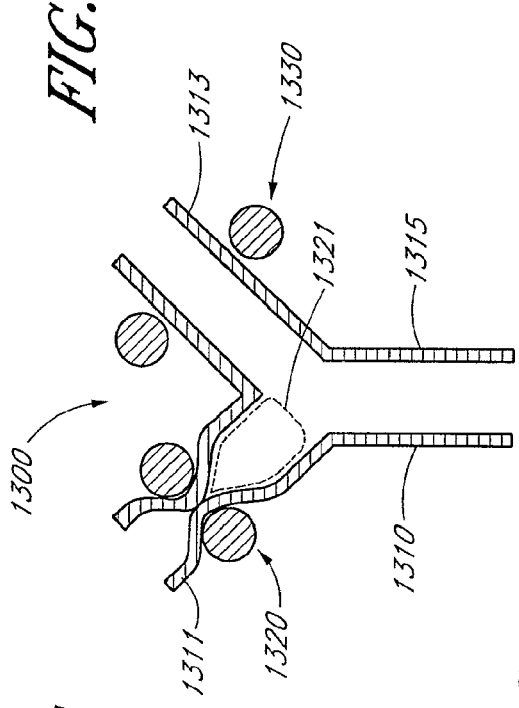

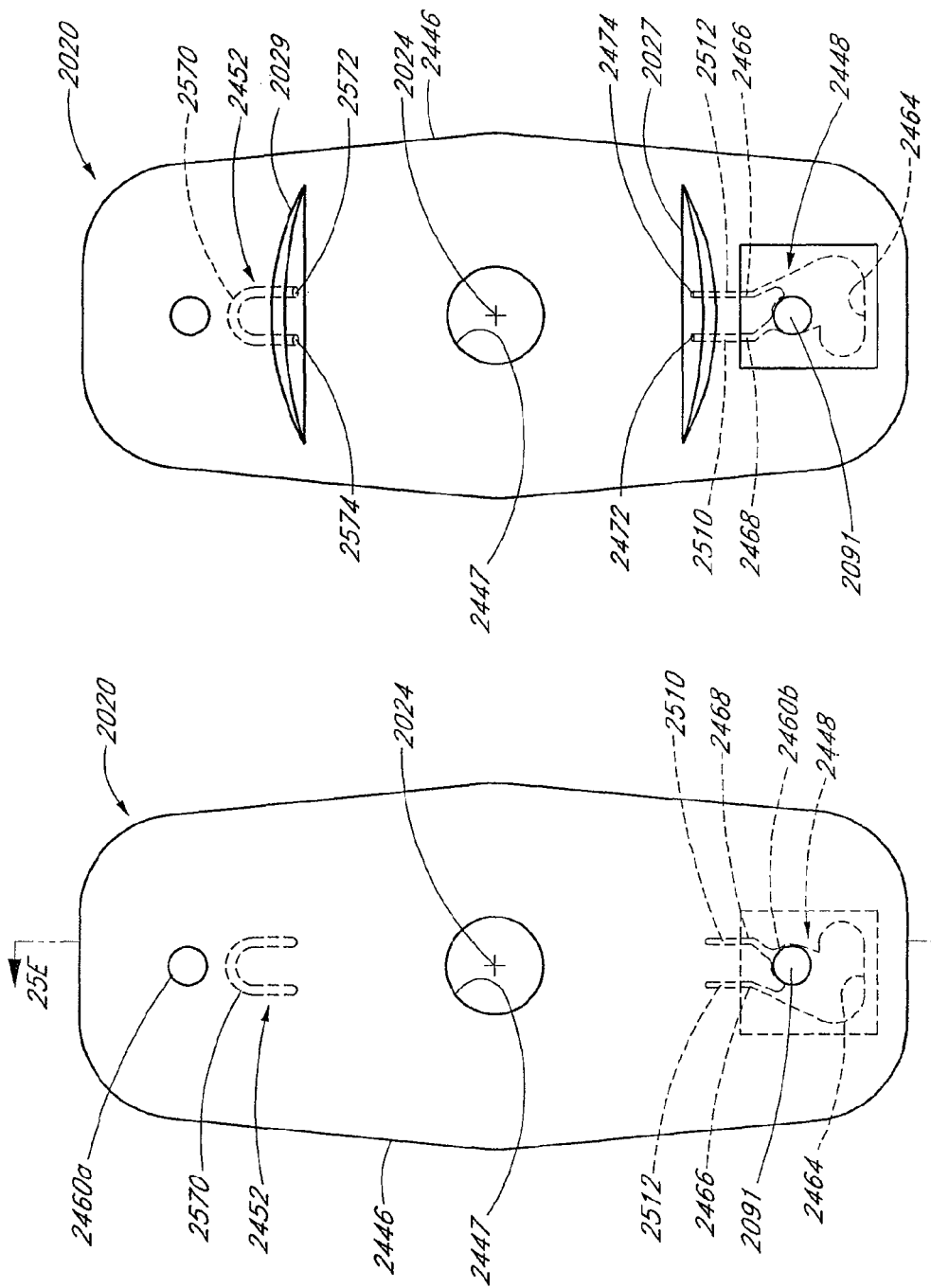

FLUID HANDLING CASSETTE HAVING A SPECTROSCOPIC SAMPLE CELL

RELATED APPLICATIONS

This application is a continuation of prior U.S. application Ser. No. 11/316,672, filed Dec. 21, 2005, titled FLUID HANDLING CASSETTE HAVING A SPECTROSCOPIC SAMPLE CELL, (issued Jan. 27, 2009 as U.S. Pat. No. 7,481,787), which claims the benefit under 35 U.S.C. §119(e) of U.S. Provisional Application No. 60/652,660, filed Feb. 14, 2005, titled ANALYTE DETECTION SYSTEM; U.S. Provisional Application No. 60/724,199, filed Oct. 6, 2005, titled INTENSIVE CARE UNIT BLOOD ANALYSIS SYSTEM AND METHOD; U.S. Provisional Application No. 60/658,001, filed Mar. 2, 2005, titled SEPARATING BLOOD SAMPLE FOR ANALYTE DETECTION SYSTEM; and of U.S. Provisional Application No. 60/673,551, filed Apr. 21, 2005, titled APPARATUS AND METHODS FOR SEPARATING SAMPLE FOR ANALYTE DETECTION SYSTEM. The entire contents of each of the above-listed applications are hereby incorporated by reference herein and made part of this specification.

BACKGROUND

1. Field

Certain embodiments disclosed herein relate to methods and apparatus for determining the concentration of an analyte in a sample, such as an analyte in a sample of bodily fluid, as well as methods and apparatus which can be used to support the making of such determinations.

2. Description of the Related Art

It is a common practice to measure the levels of certain analytes, such as glucose, in a bodily fluid, such as blood. Often this is done in a hospital or clinical setting when there is a risk that the levels of certain analytes may move outside a desired range, which in turn can jeopardize the health of a patient. Certain currently known systems for analyte monitoring in a hospital or clinical setting suffer from various drawbacks.

SUMMARY

In some embodiments, a fluid handling module is configured for removable engagement with a reusable main fluid handling instrument. The module comprises a module housing and a first fluid passageway extending from the module housing. The first fluid passageway has a patient end remote from the housing. The first fluid passageway is configured to provide fluid communication with a bodily fluid in a patient. A fluid component separator is in fluid communication with the first fluid passageway. The fluid component separator is configured to separate at least one component from a portion of the bodily fluid drawn from the patient. A spectroscopic sample cell is configured to hold at least a portion of the first component.

In some embodiments, a system for measuring an analyte in a bodily fluid comprises a main analysis and control instrument comprising an analyte detection system. A fluid handling module is removably engageable with the main instrument. The fluid handling module further comprises a centrifuge having a centrifuge rotor which is rotatable about a centrifuge axis, and a sample cell located on the rotor. The sample cell is rotatable with the rotor about the centrifuge axis. The rotor and the sample cell are rotatable to a measurement position in which the sample cell operatively engages the analyte detection system.

In some embodiments, a method for extracting and analyzing a bodily fluid of a patient is provided. The method comprises attaching a fluid handling module to a reusable fluid handling instrument, wherein the fluid handling module comprises a fluid component separator, a spectroscopic sample cell, and a first fluid passageway. The reusable fluid handling instrument comprises an analyte detection system. A volume of a bodily fluid is drawn from the patient into the first fluid passageway. The fluid component separator separates a first component from the volume of bodily fluid drawn from the patient. At least a portion of the first component of the bodily fluid is held in the spectroscopic sample cell. The analyte detection system analyzes the first component to determine a concentration of an analyte.

Certain objects and advantages of the invention(s) are described herein. Of course, it is to be understood that not necessarily all such objects or advantages may be achieved in accordance with any particular embodiment. Thus, for example, those skilled in the art will recognize that the invention(s) may be embodied or carried out in a manner that achieves or optimizes one advantage or group of advantages as taught herein without necessarily achieving other objects or advantages as may be taught or suggested herein.

Certain embodiments are summarized above. However, despite the foregoing discussion of certain embodiments, only the appended claims (and not the present summary) are intended to define the invention(s). The summarized embodiments, and other embodiments, will become readily apparent to those skilled in the art from the following detailed description of the preferred embodiments having reference to the attached figures, the invention(s) not being limited to any particular embodiment(s) disclosed.

BRIEF DESCRIPTION OF THE DRAWINGS

FIG. 1A is a schematic of a fluid handling system, wherein a fluid handling and analysis apparatus of the fluid handling system is shown in a cutaway view;

FIG. 1B is a cross-sectional view of a bundle of the fluid handling system of FIG. 1A taken along the line 1B-1B;

FIGS. 7A-7J are schematics illustrating methods of using the infusion and blood analysis system of the present invention, where FIG. 7A shows one embodiment of a method of infusing a patient, and FIGS. 7B-7J illustrate steps in a method of sampling from a patient, where FIG. 7B shows fluid being cleared from a portion of the first and second passageways; FIG. 7C shows a sample being drawn into the first passageway; FIG. 7D shows a sample being drawn into second passageway;

FIG. 7E shows air being injected into the sample; FIG. 7F shows bubbles being cleared from the second passageway; FIGS. 7H and 7I show the sample being pushed part way into the second passageway followed by fluid and more bubbles; and FIG. 7J shows the sample being pushed to analyzer;

FIG. 9 is a schematic front view of one embodiment of a sampling apparatus cassette of the present invention;

FIG. 10 is a schematic front view of one embodiment of a sampling apparatus instrument of the present invention;

FIG. 11 is an illustration of one embodiment of an arterial patient connection of the present invention;

FIG. 12 is an illustration of one embodiment of a venous patient connection of the present invention;

FIGS. 13A, 13B, and 13C are various views of one embodiment of a pinch valve of the present invention, where FIG. 13A is a front view, FIG. 13B is a sectional view, and FIG. 13C is a sectional view showing one valve in a closed position;

FIG. 14A is a front view and FIG. 14B is a sectional view showing one valve in a closed position;

FIG. 25A is a front elevational view of a rotor having a sample element for holding sample fluid;

FIG. 25B is a rear elevational view of the rotor of FIG. 25A;

Reference symbols are used in the Figures to indicate certain components, aspects or features shown therein, with reference symbols common to more than one Figure indicating like components, aspects or features shown therein.

DETAILED DESCRIPTION OF THE PREFERRED EMBODIMENTS

Although certain preferred embodiments and examples are disclosed below, it will be understood by those skilled in the art that the inventive subject matter extends beyond the specifically disclosed embodiments to other alternative embodiments and/or uses of the invention, and to obvious modifications and equivalents thereof. Thus it is intended that the scope of the inventions herein disclosed should not be limited by the particular disclosed embodiments described below. Thus, for example, in any method or process disclosed herein, the acts or operations making up the method/process may be performed in any suitable sequence, and are not necessarily limited to any particular disclosed sequence. For purposes of contrasting various embodiments with the prior art, certain aspects and advantages of these embodiments are described where appropriate herein. Of course, it is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein. While the systems and methods discussed herein can be used for invasive techniques, the systems and methods can also be used for non-invasive techniques or other suitable techniques, and can be used in hospitals, healthcare facilities, ICUs, or residences.

Overview of Embodiments of Fluid Handling Systems

Figure 1:
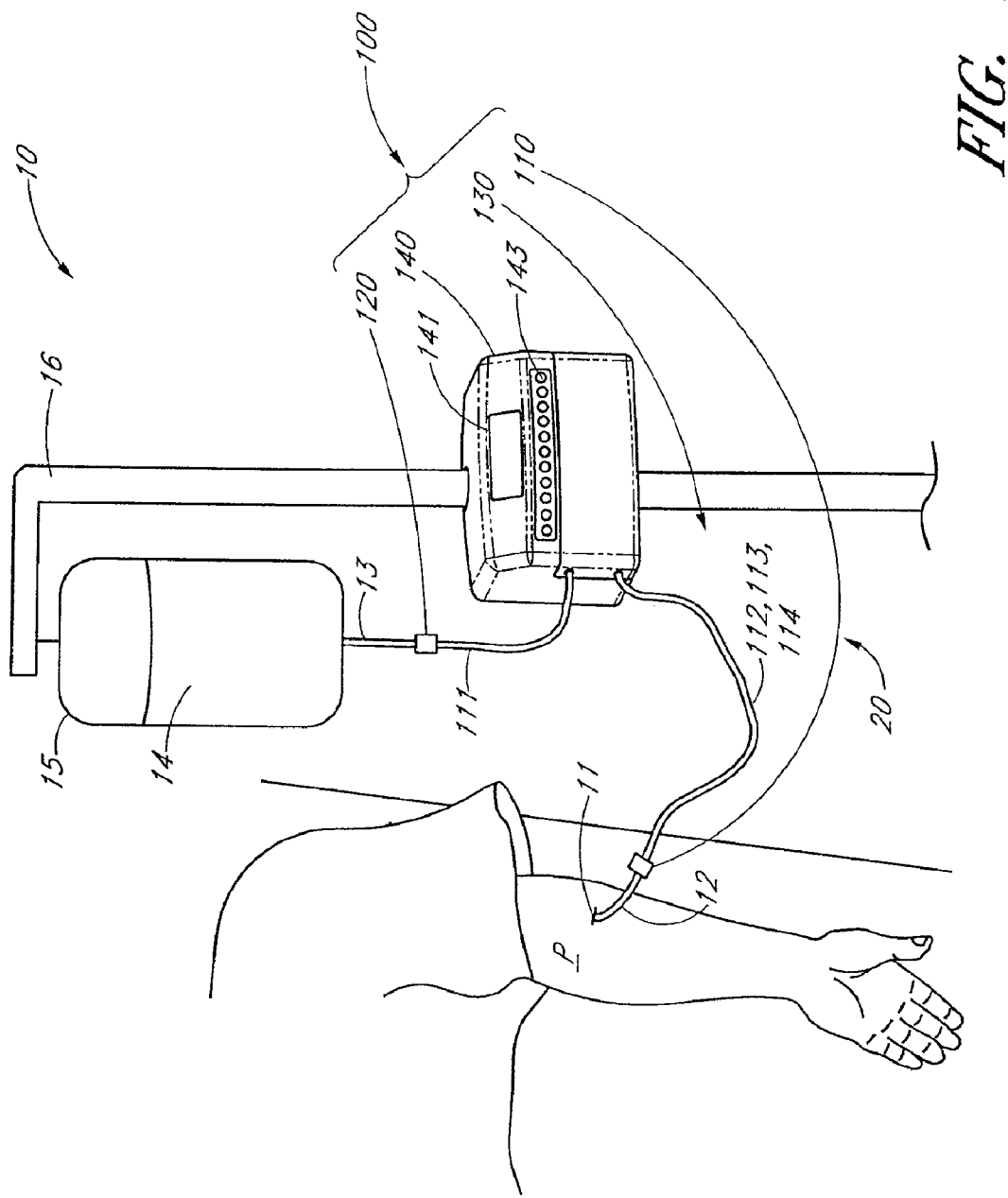
FIG. 1 is a schematic of a fluid handling system in accordance with one embodiment.

Disclosed herein are fluid handling systems and various methods of analyzing sample fluids. FIG. 1 illustrates an embodiment of a fluid handling system 10 which can determine the concentration of one or more substances in a sample fluid, such as a whole blood sample from a patient P. The fluid handling system 10 can also deliver an infusion fluid 14 to the patient P.

The fluid handling system 10 is located bedside and generally comprises a container 15 holding the infusion fluid 14 and a sampling system 100 which is in communication with both the container 15 and the patient P. A tube 13 extends from the container 15 to the sampling system 100. A tube 12 extends from the sampling system 100 to the patient P. In some embodiments, one or more components of the fluid handling system 10 can be located at another facility, room, or other suitable remote location. One or more components of the fluid handling system 10 can communicate with one or more other components of the fluid handling system 10 (or with other devices) by any suitable communication means, such as communication interfaces including, but not limited to, optical interfaces, electrical interfaces, and wireless interfaces. These interfaces can be part of a local network, internet, wireless network, or other suitable networks.

The Infusion fluid 14 can comprise water, saline, dextrose, lactated Ringer's solution, drugs, insulin, mixtures thereof, or other suitable substances. The illustrated sampling system 100 allows the infusion fluid to pass to the patient P and/or uses the infusion fluid in the analysis. In some embodiments, the fluid handling system 10 may not employ infusion fluid. The fluid handling system 10 may thus draw samples without delivering any fluid to the patient P.

The sampling system 100 can be removably or permanently coupled to the tube 13 and tube 12 via connectors 110, 120. The patient connector 110 can selectively control the flow of fluid through a bundle 130, which includes a patient connection passageway 112 and a sampling passageway 113, as shown in FIG. 1B. The sampling system 100 can also draw one or more samples from the patient P by any suitable means. The sampling system 100 can perform one or more analyses on the sample, and then returns the sample to the patient or a waste container. In some embodiments, the sampling system 100 is a modular unit that can be removed and replaced as desired. The sampling system 100 can include, but is not limited to, fluid handling and analysis apparatuses, connectors, passageways, catheters, tubing, fluid control elements, valves, pumps, fluid sensors, pressure sensors, temperature sensors, hematocrit sensors, hemoglobin sensors, colorimetric sensors, and gas (or "bubble") sensors, fluid conditioning elements, gas injectors, gas filters, blood plasma separators, and/or communication devices (e.g., wireless devices) to permit the transfer of information within the sampling system or between sampling system 100 and a network. The illustrated sampling system 100 has a patient connector 110 and a fluid handling and analysis apparatus 140, which analyzes a sample drawn from the patient P. The fluid handling and analysis apparatus 140 and patient connector 110 cooperate to control the flow of infusion fluid into, and/or samples withdrawn from, the patient P. Samples can also be withdrawn and transferred in other suitable manners.

FIG. 1A is a close up view of the fluid handling and analysis apparatus 140 which is partially cutaway to reveal some of its internal components. The fluid handling and analysis apparatus 140 preferably includes a pump 203 that controls the flow of fluid from the container 15 to the patient P and/or the flow of fluid drawn from the patient P. The pump 203 can selectively control fluid flow rates, direction(s) of fluid flow(s), and other fluid flow parameters as desired. As used herein, the term "pump" is a broad term and means, without limitation, a pressurization/pressure device, vacuum device, or any other suitable means for causing fluid flow. The pump 203 can include, but is not limited to, a reversible peristaltic pump, two unidirectional pumps that work in concert with valves to provide flow in two directions, a unidirectional pump, a displacement pump, a syringe, a diaphragm pump, roller pump, or other suitable pressurization device.

The illustrated fluid handling and analysis apparatus 140 has a display 141 and input devices 143. The illustrated fluid handling and analysis apparatus 140 can also have a sampling unit 200 configured to analyze the drawn fluid sample. The sampling unit 200 can thus receive a sample, prepare the sample, and/or subject the sample (prepared or unprepared) to one or more tests. The sampling unit 200 can then analyze results from the tests. The sampling unit 200 can include, but is not limited to, separators, filters, centrifuges, sample elements, and/or detection systems, as described in detail below. The sampling unit 200 (see FIG. 3) can include an analyte detection system for detecting the concentration of one or more analytes in the body fluid sample. In some embodiments, the sampling unit 200 can prepare a sample for analysis. If the fluid handling and analysis apparatus 140 performs an analysis on plasma contained in whole blood taken from the patient P, filters, separators, centrifuges, or other types of sample preparation devices can be used to separate plasma from other components of the blood. After the separation process, the sampling unit 200 can analyze the plasma to determine, for example, the patient P's glucose level. The sampling unit 200 can employ spectroscopic methods, colorimetric methods, electrochemical methods, or other suitable methods for analyzing samples.

With continued reference to FIGS. 1 and 1A, the fluid 14 in the container 15 can flow through the tube 13 and into a fluid source passageway 111. The fluid can further flow through the passageway 111 to the pump 203, which can pressurize the fluid. The fluid 14 can then flow from the pump 203 through the patient connection passageway 112 and catheter 11 into the patient P. To analyze the patient's P body fluid (e.g., whole blood, blood plasma, interstitial fluid, bile, sweat, excretions, etc.), the fluid handling and analysis apparatus 140 can draw a sample from the patient P through the catheter 11 to a patient connector 110. The patient connector 110 directs the fluid sample into the sampling passageway 113 which leads to the sampling unit 200. The sampling unit 200 can perform one or more analyses on the sample. The fluid handling and analysis apparatus 140 can then output the results obtained by the sampling unit 200 on the display 141.

In some embodiments, the fluid handling system 10 can draw and analyze body fluid sample(s) from the patient P to provide real-time or near-real-time measurement of glucose levels. Body fluid samples can be drawn from the patient P continuously, at regular intervals (e.g., every 5, 10, 15, 20, 30 or 60 minutes), at irregular intervals, or at any time or sequence for desired measurements. These measurements can be displayed bedside with the display 141 for convenient monitoring of the patient P.

The illustrated fluid handling system 10 is mounted to a stand 16 and can be used in hospitals, ICUs, residences, healthcare facilities, and the like. In some embodiments, the fluid handling system 10 can be transportable or portable for an ambulatory patient. The ambulatory fluid handling system 10 can be coupled (e.g., strapped, adhered, etc.) to a patient, and may be smaller than the bedside fluid handling system 10 illustrated in FIG. 1. In some embodiments, the fluid handling system 10 is an implantable system sized for subcutaneous implantation and can be used for continuous monitoring. In some embodiments, the fluid handling system 10 is miniaturized so that the entire fluid handling system can be implanted. In other embodiments, only a portion of the fluid handling system 10 is sized for implantation.

In some embodiments, the fluid handling system 10 is a disposable fluid handling system and/or has one or more disposable components. As used herein, the term "disposable" when applied to a system or component (or combination of components), such as a cassette or sample element, is a broad term and means, without limitation, that the component in question is used a finite number of times and then discarded. Some disposable components are used only once and then discarded. Other disposable components are used more than once and then discarded. For example, the fluid handling and analysis apparatus 140 can have a main instrument and a disposable cassette that can be installed onto the main instrument, as discussed below. The disposable cassette can be used for predetermined length of time, to prepare a predetermined amount of sample fluid for analysis, etc. In some embodiments, the cassette can be used to prepare a plurality of samples for subsequent analyses by the main instrument. The reusable main instrument can be used with any number of cassettes as desired. Additionally or alternatively, the cassette can be a portable, handheld cassette for convenient transport. In these embodiments, the cassette can be manually mounted to or removed from the main instrument. In some embodiments, the cassette may be a non disposable cassette which can be permanently coupled to the main instrument, as discussed below.

Disclosed herein are a number of embodiments of fluid handling systems, sampling systems, fluid handling and analysis apparatuses, analyte detection systems, and methods of using the same. Section I below discloses various embodiments of the fluid handling system that may be used to transport fluid from a patient for analysis. Section II below discloses several embodiments of fluid handling methods that may be used with the apparatus discussed in Section I. Section III below discloses several embodiments of a sampling system that may be used with the apparatus of Section I or the methods of Section II. Section IV below discloses various embodiments of a sample analysis system that may be used to detect the concentration of one or more analytes in a material sample. Section V below discloses methods for determining analyte concentrations from sample spectra.

Section I—Fluid Handling System

FIG. 1 is a schematic of the fluid handling system 10 which includes the container 15 supported by the stand 16 and having an interior that is fillable with the fluid 14, the catheter 11, and the sampling system 100. Fluid handling system 10 includes one or more passageways 20 that form conduits between the container, the sampling system, and the catheter. Generally, sampling system 100 is adapted to accept a fluid supply, such as fluid 14, and to be connected to a patient, including, but not limited to catheter 11 which is used to catheterize a patient P. Fluid 14 includes, but is not limited to, fluids for infusing a patient such as saline, lactated Ringer's solution, or water. Sampling system 100, when so connected, is then capable of providing fluid to the patient. In addition, sampling system 100 is also capable of drawing samples, such as blood, from the patient through catheter 11 and passageways 20, and analyzing at least a portion of the drawn sample. Sampling system 100 measures characteristics of the drawn sample including, but not limited to, one or more of the blood plasma glucose, blood urea nitrogen (BUN), hematocrit, hemoglobin, or lactate levels. Optionally, sampling system 100 includes other devices or sensors to measure other patient or apparatus related information including, but not limited to, patient blood pressure, pressure changes within the sampling system, or sample draw rate.

More specifically, FIG. 1 shows sampling system 100 as including the patient connector 110, the fluid handling and analysis apparatus 140, and the connector 120. Sampling system 100 may include combinations of passageways, fluid control and measurement devices, and analysis devices to direct, sample, and analyze fluid. Passageways 20 of sampling system 100 include the fluid source passageway 111 from connector 120 to fluid handling and analysis apparatus 140, the patient connection passageway 112 from the fluid handling and analysis apparatus to patient connector 110, and the sampling passageway 113 from the patient connector to the fluid handling and analysis apparatus. The reference of passageways 20 as including one or more passageway, for example passageways 111, 112, and 113 are provided to facilitate discussion of the system. It is understood that passageways may include one or more separate components and may include other intervening components including, but not limited to, pumps, valves, manifolds, and analytic equipment.

As used herein, the term "passageway" is a broad term and is used in its ordinary sense and includes, without limitation except as explicitly stated, as any opening through a material through which a fluid, such as a liquid or a gas, may pass so as to act as a conduit. Passageways include, but are not limited to, flexible, inflexible or partially flexible tubes, laminated structures having openings, bores through materials, or any other structure that can act as a conduit and any combination or connections thereof. The internal surfaces of passageways that provide fluid to a patient or that are used to transport blood are preferably biocompatible materials, including but not limited to silicone, polyetheretherketone (PEEK), or polyethylene (PE). One type of preferred passageway is a flexible tube having a fluid contacting surface formed from a biocompatible material. A passageway, as used herein, also includes separable portions that, when connected, form a passageway.

The inner passageway surfaces may include coatings of various sorts to enhance certain properties of the conduit, such as coatings that affect the ability of blood to clot or to reduce friction resulting from fluid flow. Coatings include, but are not limited to, molecular or ionic treatments.

As used herein, the term "connected" is a broad term and is used in its ordinary sense and includes, without limitation except as explicitly stated, with respect to two or more things (e.g., elements, devices, patients, etc.): a condition of physical contact or attachment, whether direct, indirect (via, e.g., intervening member(s)), continuous, selective, or intermittent; and/or a condition of being in fluid, electrical, or optical-signal communication, whether direct, indirect, continuous, selective (e.g., where there exist one or more intervening valves, fluid handling components, switches, loads, or the like), or intermittent. A condition of fluid communication is considered to exist whether or not there exists a continuous or contiguous liquid or fluid column extending between or among the two or more things in question. Various types of connectors can connect components of the fluid handling system described herein. As used herein, the term "connector" is a broad term and is used in its ordinary sense and includes, without limitation except as explicitly stated, as a device that connects passageways or electrical wires to provide communication (whether direct, indirect, continuous, selective, or intermittent) on either side of the connector. Connectors contemplated herein include a device for connecting any opening through which a fluid may pass. These connectors may have intervening valves, switches, fluid handling devices, and the like for affecting fluid flow. In some embodiments, a connector may also house devices for the measurement, control, and preparation of fluid, as described in several of the embodiments.

Fluid handling and analysis apparatus 140 may control the flow of fluids through passageways 20 and the analysis of samples drawn from a patient P, as described subsequently. Fluid handling and analysis apparatus 140 includes the display 141 and input devices, such as buttons 143. Display 141 provides information on the operation or results of an analysis performed by fluid handling and analysis apparatus 140. In one embodiment, display 141 indicates the function of buttons 143, which are used to input information into fluid handling and analysis apparatus 140. Information that may be input into or obtained by fluid handling and analysis apparatus 140 includes, but is not limited to, a required infusion or dosage rate, sampling rate, or patient specific information which may include, but is not limited to, a patient identification number or medical information. In an other alternative embodiment, fluid handling and analysis apparatus 140 obtains information on patient P over a communications network, for example an hospital communication network having patient specific information which may include, but is not limited to, medical conditions, medications being administered, laboratory blood reports, gender, and weight. As one example of the use of fluid handling system 10, which is not meant to limit the scope of the present invention, FIG. 1 shows catheter 11 connected to patient P.

As discussed subsequently, fluid handling system 10 may catheterize a patient's vein or artery. Sampling system 100 is releasably connectable to container 15 and catheter 11. Thus, for example, FIG. 1 shows container 15 as including the tube 13 to provide for the passage of fluid to, or from, the container, and catheter 11 as including the tube 12 external to the patient. Connector 120 is adapted to join tube 13 and passageway 111. Patient connector 110 is adapted to join tube 12 and to provide for a connection between passageways 112 and 113.

Patient connector 110 may also include one or more devices that control, direct, process, or otherwise affect the flow through passageways 112 and 113. In some embodiments, one or more lines 114 are provided to exchange signals between patient connector 110 and fluid handling and analysis apparatus 140. The lines 114 can be electrical lines, optical communicators, wireless communication channels, or other means for communication. As shown in FIG. 1, sampling system 100 may also include passageways 112 and 113, and lines 114. The passageways and electrical lines between apparatus 140 and patient connector 110 are referred to, without limitation, as the bundle 130.

In various embodiments, fluid handling and analysis apparatus 140 and/or patient connector 110, includes other elements (not shown in FIG. 1) that include, but are not limited to: fluid control elements, including but not limited to valves and pumps; fluid sensors, including but not limited to pressure sensors, temperature sensors, hematocrit sensors, hemoglobin sensors, colorimetric sensors, and gas (or "bubble") sensors; fluid conditioning elements, including but not limited to gas injectors, gas filters, and blood plasma separators; and wireless communication devices to permit the transfer of information within the sampling system or between sampling system 100 and a wireless network.

In one embodiment, patient connector 110 includes devices to determine when blood has displaced fluid 14 at the connector end, and thus provides an indication of when a sample is available for being drawn through passageway 113 for sampling. The presence of such a device at patient connector 110 allows for the operation of fluid handling system 10 for analyzing samples without regard to the actual length of tube 12. Accordingly, bundle 130 may include elements to provide fluids, including air, or information communication between patient connector 110 and fluid handling and analysis apparatus 140 including, but not limited to, one or more other passageways and/or wires.

In one embodiment of sampling system 100, the passageways and lines of bundle 130 are sufficiently long to permit locating patient connector 110 near patient P, for example with tube 12 having a length of less than 0.1 to 0.5 meters, or preferably approximately 0.15 meters and with fluid handling and analysis apparatus 140 located at a convenient distance, for example on a nearby stand 16. Thus, for example, bundle 130 is from 0.3 to 3 meters, or more preferably from 1.5 to 2.0 meters in length. It is preferred, though not required, that patient connector 110 and connector 120 include removable connectors adapted for fitting to tubes 12 and 13, respectively. Thus, in one embodiment, container 15/tube 13 and catheter 11/tube 12 are both standard medical components, and sampling system 100 allows for the easy connection and disconnection of one or both of the container and catheter from fluid handling system 10.

In another embodiment of sampling system 100, tubes 12 and 13 and a substantial portion of passageways 111 and 112 have approximately the same internal cross-sectional area. It is preferred, though not required, that the internal cross-sectional area of passageway 113 is less than that of passageways 111 and 112 (see FIG. 1B). As described subsequently, the difference in areas permits fluid handling system 10 to transfer a small sample volume of blood from patient connector 110 into fluid handling and analysis apparatus 140.

Thus, for example, in one embodiment passageways 111 and 112 are formed from a tube having an inner diameter from 0.3 millimeter to 1.50 millimeter, or more preferably having a diameter from 0.60 millimeter to 1.2 millimeter. Passageway 113 is formed from a tube having an inner diameter from 0.3 millimeter to 1.5 millimeter, or more preferably having an inner diameter of from 0.6 millimeter to 1.2 millimeter.

While FIG. 1 shows sampling system 100 connecting a patient to a fluid source, the scope of the present disclosure is not meant to be limited to this embodiment. Alternative embodiments include, but are not limited to, a greater or fewer number of connectors or passageways, or the connectors may be located at different locations within fluid handling system 10, and alternate fluid paths. Thus, for example, passageways 111 and 112 may be formed from one tube, or may be formed from two or more coupled tubes including, for example, branches to other tubes within sampling system 100, and/or there may be additional branches for infusing or obtaining samples from a patient. In addition, patient connector 110 and connector 120 and sampling system 100 alternatively include additional pumps and/or valves to control the flow of fluid as described below.

Figure 2:
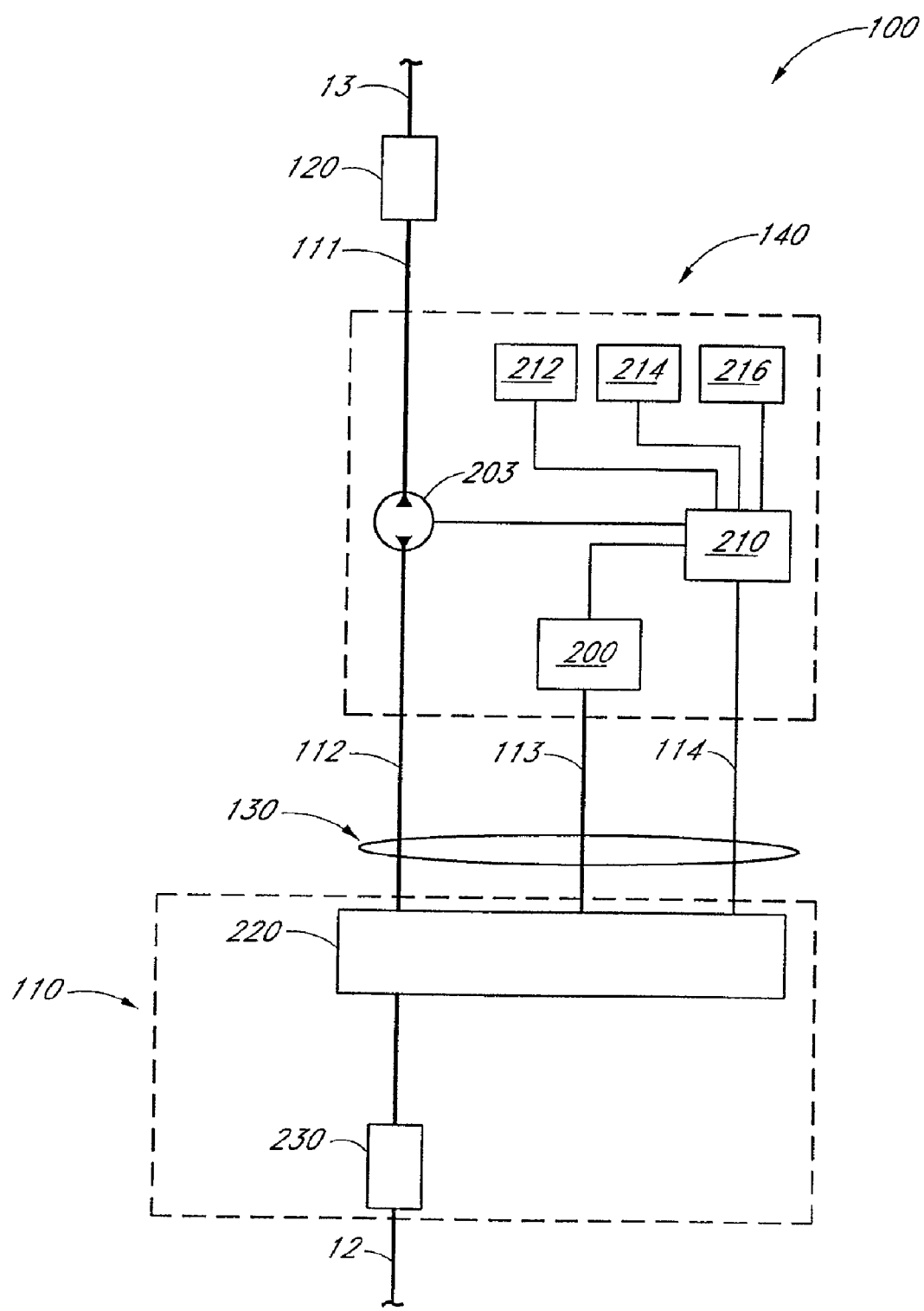
FIG. 2 is a schematic of an embodiment of a sampling apparatus of the present invention.

FIGS. 1A and 2 illustrate a sampling system 100 configured to analyze blood from patient P which may be generally similar to the embodiment of the sampling system illustrated in FIG. 1, except as further detailed below. Where possible, similar elements are identified with identical reference numerals in the depiction of the embodiments of FIGS. 1 to 2. FIGS. 1A and 2 show patient connector 110 as including a sampling assembly 220 and a connector 230, portions of passageways 111 and 113, and lines 114, and fluid handling and analysis apparatus 140 as including the pump 203, the sampling unit 200, and a controller 210. The pump 203, sampling unit 200, and controller 210 are contained within a housing 209 of the fluid handling and analysis apparatus 140. The passageway 111 extends from the connector 120 through the housing 209 to the pump 203. The bundle 130 extends from the pump 203, sampling unit 200, and controller 210 to the patient connector 110.

In FIGS. 1A and 2, the passageway 111 provides fluid communication between connector 120 and pump 203 and passageway 113 provides fluid communication between pump 203 and connector 110. Controller 210 is in communication with pump 203, sampling unit 200, and sampling assembly 220 through lines 114. Controller 210 has access to memory 212, and optionally has access to a media reader 214, including but not limited to a DVD or CD-ROM reader, and communications link 216, which can comprise a wired or wireless communications network, including but not limited to a dedicated line, an intranet, or an Internet connection.

As described subsequently in several embodiments, sampling unit 200 may include one or more passageways, pumps and/or valves, and sampling assembly 220 may include passageways, sensors, valves, and/or sample detection devices. Controller 210 collects information from sensors and devices within sampling assembly 220, from sensors and analytical equipment within sampling unit 200, and provides coordinated signals to control pump 203 and pumps and valves, if present, in sampling assembly 220.

Fluid handling and analysis apparatus 140 includes the ability to pump in a forward direction (towards the patient) and in a reverse direction (away from the patient). Thus, for example, pump 203 may direct fluid 14 into patient P or draw a sample, such as a blood sample from patient P, from catheter 11 to sampling assembly 220, where it is further directed through passageway 113 to sampling unit 200 for analysis. Preferably, pump 203 provides a forward flow rate at least sufficient to keep the patient vascular line open. In one embodiment, the forward flow rate is from 1 to 5 ml/hr. In some embodiments, the flow rate of fluid is about 0.05 ml/hr, 0.1 ml/hr, 0.2 ml/hr, 0.4 ml/hr, 0.6 ml/hr, 0.8 ml/hr, 1.0 ml/hr, and ranges encompassing such flow rates. In some embodiments, for example, the flow rate of fluid is less than about 1.0 ml/hr. In certain embodiments, the flow rate of fluid may be about 0.1 ml/hr or less. When operated in a reverse direction, fluid handling and analysis apparatus 140 includes the ability to draw a sample from the patient to sampling assembly 220 and through passageway 113. In one embodiment, pump 203 provides a reverse flow to draw blood to sampling assembly 220, preferably by a sufficient distance past the sampling assembly to ensure that the sampling assembly contains an undiluted blood sample. In one embodiment, passageway 113 has an inside diameter of from 25 to 200 microns, or more preferably from 50 to 100 microns. Sampling unit 200 extracts a small sample, for example from 10 to 100 microliters of blood, or more preferably approximately 40 microliters volume of blood, from sampling assembly 220.

In one embodiment, pump 203 is a directionally controllable pump that acts on a flexible portion of passageway 111. Examples of a single, directionally controllable pump include, but are not limited to a reversible peristaltic pump or two unidirectional pumps that work in concert with valves to provide flow in two directions. In an alternative embodiment, pump 203 includes a combination of pumps, including but not limited to displacement pumps, such as a syringe, and/or valve to provide bi-directional flow control through passageway 111.

Controller 210 includes one or more processors for controlling the operation of fluid handling system 10 and for analyzing sample measurements from fluid handling and analysis apparatus 140. Controller 210 also accepts input from buttons 143 and provides information on display 141. Optionally, controller 210 is in bi-directional communication with a wired or wireless communication system, for example a hospital network for patient information. The one or more processors comprising controller 210 may include one or more processors that are located either within fluid handling and analysis apparatus 140 or that are networked to the unit.

The control of fluid handling system 10 by controller 210 may include, but is not limited to, controlling fluid flow to infuse a patient and to sample, prepare, and analyze samples. The analysis of measurements obtained by fluid handling and analysis apparatus 140 of may include, but is not limited to, analyzing samples based on inputted patient specific information, from information obtained from a database regarding patient specific information, or from information provided over a network to controller 210 used in the analysis of measurements by apparatus 140.

Fluid handling system 10 provides for the infusion and sampling of a patient blood as follows. With fluid handling system 10 connected to bag 15 having fluid 14 and to a patient P, controller 210 infuses a patient by operating pump 203 to direct the fluid into the patient. Thus, for example, in one embodiment, the controller directs that samples be obtained from a patient by operating pump 203 to draw a sample. In one embodiment, pump 203 draws a predetermined sample volume, sufficient to provide a sample to sampling assembly 220. In another embodiment, pump 203 draws a sample until a device within sampling assembly 220 indicates that the sample has reached the patient connector 110. As an example which is not meant to limit the scope of the present invention, one such indication is provided by a sensor that detects changes in the color of the sample. Another example is the use of a device that indicates changes in the material within passageway 111 including, but not limited to, a decrease in the amount of fluid 14, a change with time in the amount of fluid, a measure of the amount of hemoglobin, or an indication of a change from fluid to blood in the passageway.

When the sample reaches sampling assembly 220, controller 210 provides an operating signal to valves and/or pumps in sampling system 100 (not shown) to draw the sample from sampling assembly 220 into sampling unit 200. After a sample is drawn towards sampling unit 200, controller 210 then provides signals to pump 203 to resume infusing the patient. In one embodiment, controller 210 provides signals to pump 203 to resume infusing the patient while the sample is being drawn from sampling assembly 220. In an alternative embodiment, controller 210 provides signals to pump 203 to stop infusing the patient while the sample is being drawn from sampling assembly 220. In another alternative embodiment, controller 210 provides signals to pump 203 to slow the drawing of blood from the patient while the sample is being drawn from sampling assembly 220.

In another alternative embodiment, controller 210 monitors indications of obstructions in passageways or catheterized blood vessels during reverse pumping and moderates the pumping rate and/or direction of pump 203 accordingly. Thus, for example, obstructed flow from an obstructed or kinked passageway or of a collapsing or collapsed catheterized blood vessel that is being pumped will result in a lower pressure than an unobstructed flow. In one embodiment, obstructions are monitored using a pressure sensor in sampling assembly 220 or along passageways 20. If the pressure begins to decrease during pumping, or reaches a value that is lower than a predetermined value then controller 210 directs pump 203 to decrease the reverse pumping rate, stop pumping, or pump in the forward direction in an effort to reestablish unobstructed pumping.

Figure 3:
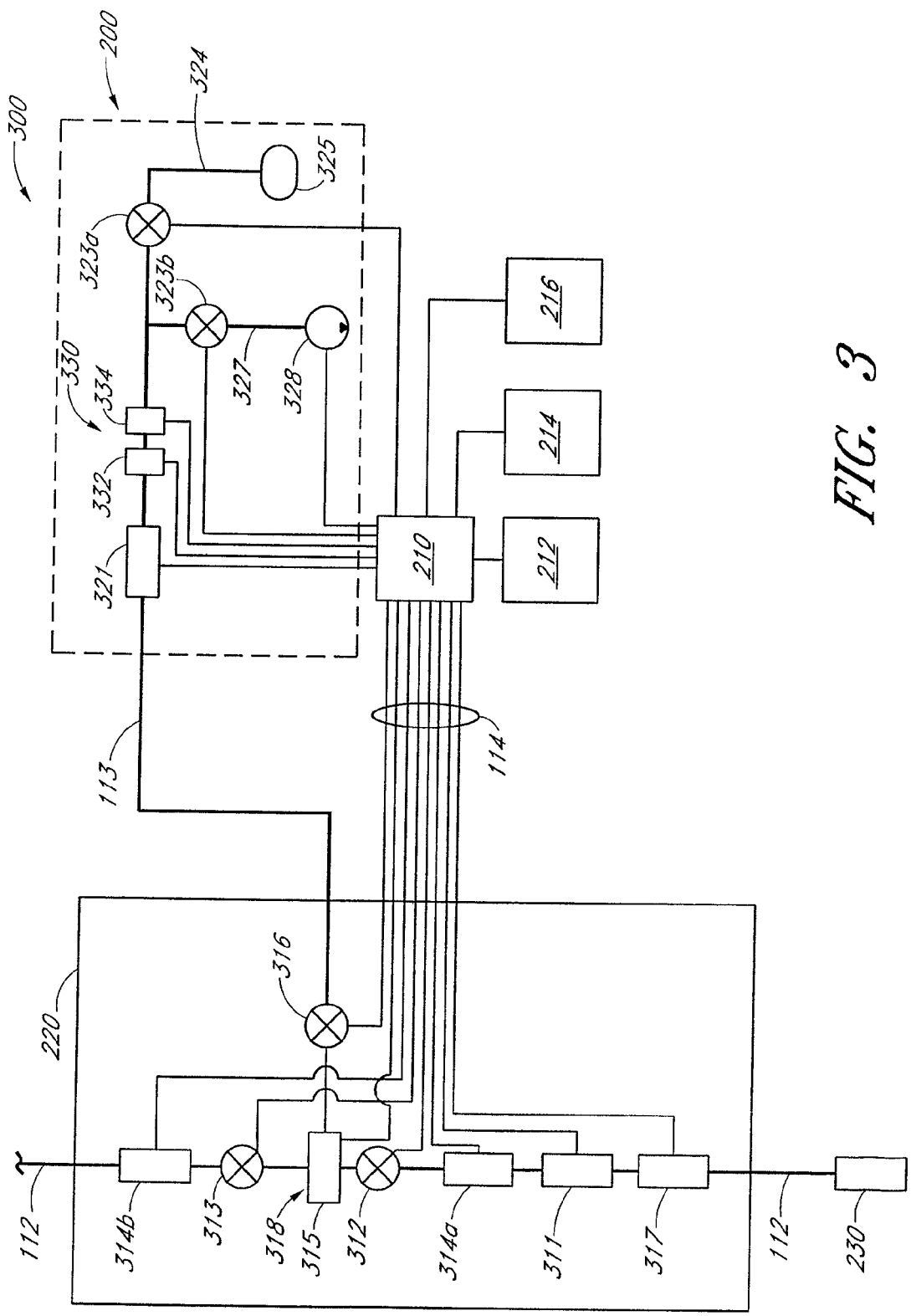
FIG. 3 is a schematic showing details of an embodiment of a sampling apparatus of the present invention.

FIG. 3 is a schematic showing details of a sampling system 300 which may be generally similar to the embodiments of sampling system 100 as illustrated in FIGS. 1 and 2, except as further detailed below. Sampling system 300 includes sampling assembly 220 having, along passageway 112: connector 230 for connecting to tube 12, a pressure sensor 317, a colorimetric sensor 311, a first bubble sensor 314a, a first valve 312, a second valve 313, and a second bubble sensor 314b. Passageway 113 forms a "T" with passageway 111 at a junction 318 that is positioned between the first valve 312 and second valve 313, and includes a gas injector manifold 315 and a third valve 316. The lines 114 comprise control and/or signal lines extending from colorimetric sensor 311, first, second, and third valves (312, 313, 316), first and second bubble sensors (314a, 314b), gas injector manifold 315, and pressure sensor 317. Sampling system 300 also includes sampling unit 200 which has a bubble sensor 321, a sample analysis device 330, a first valve 323a, a waste receptacle 325, a second valve 323b, and a pump 328. Passageway 113 forms a "T" to form a waste line 324 and a pump line 327.

It is preferred, though not necessary, that the sensors of sampling system 100 are adapted to accept a passageway through which a sample may flow and that sense through the walls of the passageway. As described subsequently, this arrangement allows for the sensors to be reusable and for the passageways to be disposable. It is also preferred, though not necessary, that the passageway is smooth and without abrupt dimensional changes which may damage blood or prevent smooth flow of blood. In addition, is also preferred that the passageways that deliver blood from the patient to the analyzer not contain gaps or size changes that permit fluid to stagnate and not be transported through the passageway.

In one embodiment, the respective passageways on which valves 312, 313, 316, and 323 are situated along passageways that are flexible tubes, and valves 312, 313, 316, and 323 are "pinch valves," in which one or more movable surfaces compress the tube to restrict or stop flow therethrough. In one embodiment, the pinch valves include one or more moving surfaces that are actuated to move together and "pinch" a flexible passageway to stop flow therethrough. Examples of a pinch valve include, for example, Model PV256 Low Power Pinch Valve (Instech Laboratories, Inc., Plymouth Meeting, Pa.). Alternatively, one or more of valves 312, 313, 316, and 323 may be other valves for controlling the flow through their respective passageways.

Colorimetric sensor 311 accepts or forms a portion of passageway 111 and provides an indication of the presence or absence of blood within the passageway. In one embodiment, colorimetric sensor 311 permits controller 210 to differentiate between fluid 14 and blood. Preferably, colorimetric sensor 311 is adapted to receive a tube or other passageway for detecting blood. This permits, for example, a disposable tube to be placed into or through a reusable colorimetric sensor. In an alternative embodiment, colorimetric sensor 311 is located adjacent to bubble sensor 314b. Examples of a colorimetric sensor include, for example, an Optical Blood Leak/Blood vs. Saline Detector available from Introtek International (Edgewood, N.J.).

As described subsequently, sampling system 300 injects a gas—referred to herein and without limitation as a "bubble"—into passageway 113. Sampling system 300 includes gas injector manifold 315 at or near junction 318 to inject one or more bubbles, each separated by liquid, into passageway 113. The use of bubbles is useful in preventing longitudinal mixing of liquids as they flow through passageways both in the delivery of a sample for analysis with dilution and for cleaning passageways between samples. Thus, for example the fluid in passageway 113 includes, in one embodiment of the invention, two volumes of liquids, such as sample S or fluid 14 separated by a bubble, or multiple volumes of liquid each separated by a bubble therebetween.

Bubble sensors 314a, 314b and 321 each accept or form a portion of passageway 112 or 113 and provide an indication of the presence of air, or the change between the flow of a fluid and the flow of air, through the passageway. Examples of bubble sensors include, but are not limited to ultrasonic or optical sensors, that can detect the difference between small bubbles or foam from liquid in the passageway. Once such bubble detector is an MEC Series Air Bubble/Liquid Detection Sensor (Introtek International, Edgewood, N.Y.). Preferably, bubble sensor 314a, 314b, and 321 are each adapted to receive a tube or other passageway for detecting bubbles. This permits, for example, a disposable tube to be placed through a reusable bubble sensor.

Pressure sensor 317 accepts or forms a portion of passageway 111 and provides an indication or measurement of a fluid within the passageway. When all valves between pressure sensor 317 and catheter 11 are open, pressure sensor 317 provides an indication or measurement of the pressure within the patient's catheterized blood vessel. In one embodiment, the output of pressure sensor 317 is provided to controller 210 to regulate the operation of pump 203. Thus, for example, a pressure measured by pressure sensor 317 above a predetermined value is taken as indicative of a properly working system, and a pressure below the predetermined value is taken as indicative of excessive pumping due to, for example, a blocked passageway or blood vessel. Thus, for example, with pump 203 operating to draw blood from patient P, if the pressure as measured by pressure sensor 317 is within a range of normal blood pressures, it may be assumed that blood is being drawn from the patient and pumping continues. However, if the pressure as measured by pressure sensor 317 falls below some level, then controller 210 instructs pump 203 to slow or to be operated in a forward direction to reopen the blood vessel. One such pressure sensor is a Deltran IV part number DPT-412 (Utah Medical Products, Midvale, Utah).

Sample analysis device 330 receives a sample and performs an analysis. In several embodiments, device 330 is configured to prepare of the sample for analysis. Thus, for example, device 330 may include a sample preparation unit 332 and an analyte detection system 334, where the sample preparation unit is located between the patient and the analyte detection system. In general, sample preparation occurs between sampling and analysis. Thus, for example, sample preparation unit 332 may take place removed from analyte detection, for example within sampling assembly 220, or may take place adjacent or within analyte detection system 334.

As used herein, the term "analyte" is a broad term and is used in its ordinary sense and includes, without limitation, any chemical species the presence or concentration of which is sought in the material sample by an analyte detection system. For example, the analyte(s) include, but are not limited to, glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, electrolytes, sodium, potassium, chloride, bicarbonate, and hormones. As used herein, the term "material sample" (or, alternatively, "sample") is a broad term and is used in its ordinary sense and includes, without limitation, any collection of material which is suitable for analysis. For example, a material sample may comprise whole blood, blood components (e.g., plasma or serum), interstitial fluid, intercellular fluid, saliva, urine, sweat and/or other organic or inorganic materials, or derivatives of any of these materials. In one embodiment, whole blood or blood components may be drawn from a patient's capillaries.

In one embodiment, sample preparation unit 332 separates blood plasma from a whole blood sample or removes contaminants from a blood sample and thus comprises one or more devices including, but not limited to, a filter, membrane, centrifuge, or some combination thereof. In alternative embodiments, analyte detection system 334 is adapted to analyze the sample directly and sample preparation unit 332 is not required.

Figure 4:
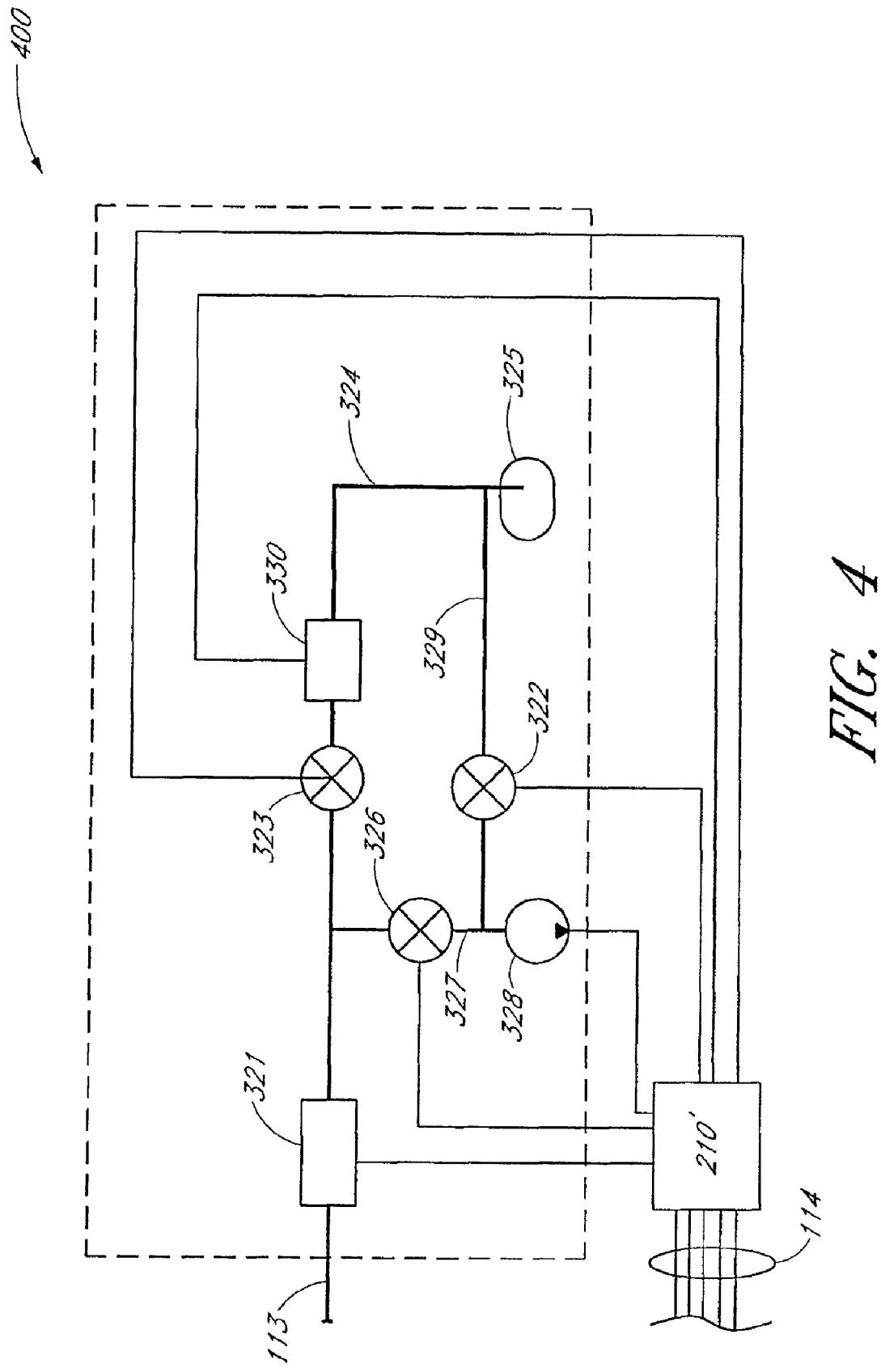
FIG. 4 is a schematic of an embodiment of a sampling unit of the present invention.

Generally, sampling assembly 220 and sampling unit 200 direct the fluid drawn from sampling assembly 220 into passageway 113 into sample analysis device 330. FIG. 4 is a schematic of an embodiment of a sampling unit 400 that permits some of the sample to bypass sample analysis device 330. Sampling unit 400 may be generally similar to sampling unit 200, except as further detailed below. Sampling unit 400 includes bubble sensor 321, valve 323, sample analysis device 330, waste line 324, waste receptacle 325, valve 326, pump line 327, pump 328, a valve 322, and a waste line 329. Waste line 329 includes valve 322 and forms a "T" at pump line 337 and waste line 329. Valves 316, 322, 323, and 326 permit a flow through passageway 113 to be routed through sample analysis device 330, to be routed to waste receptacle 325, or to be routed through waste line 324 to waste receptacle 325.

Figure 5:
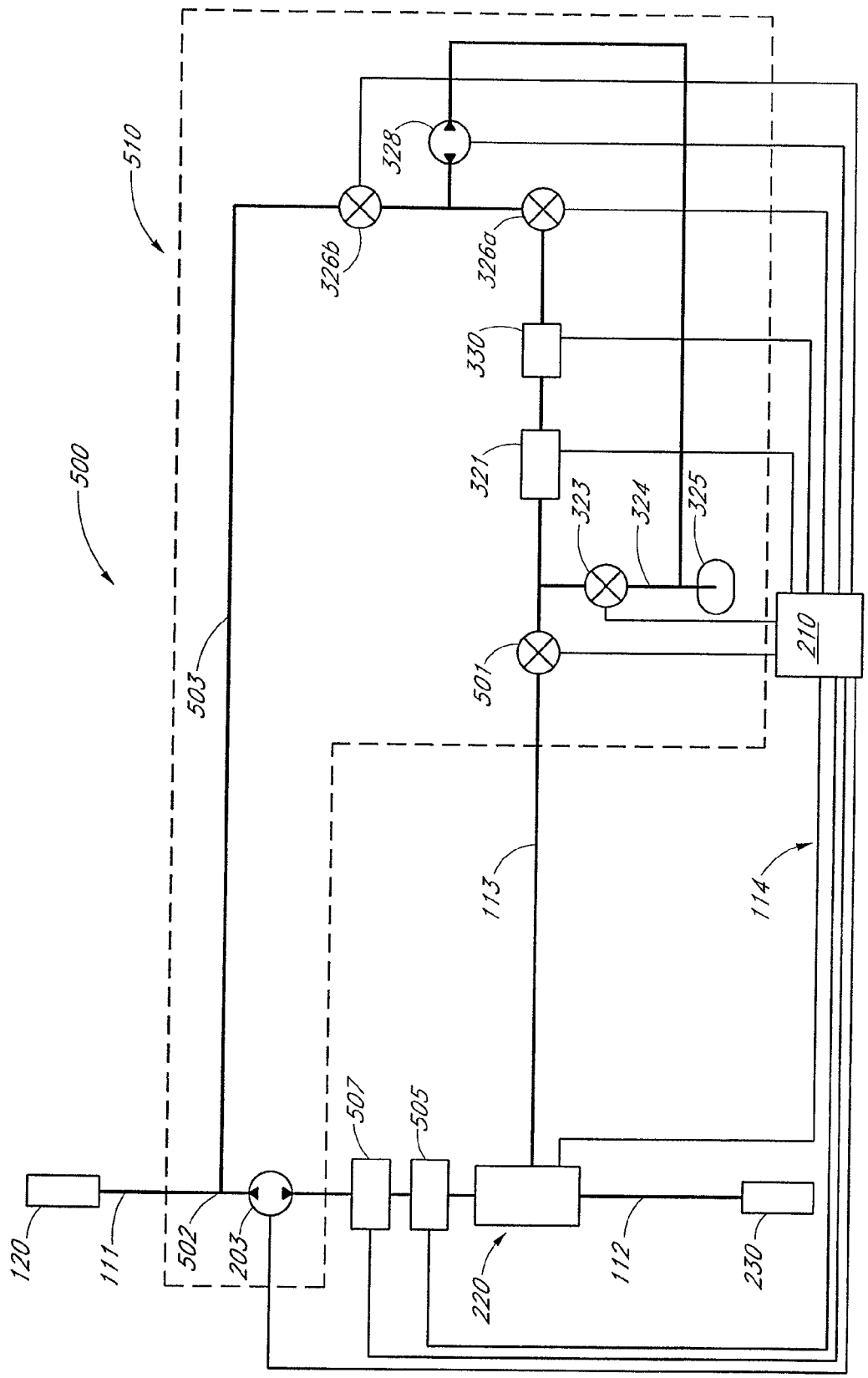
FIG. 5 is a schematic of an embodiment of a sampling apparatus of the present invention.

FIG. 5 is a schematic of one embodiment of a sampling system 500 which may be generally similar to the embodiments of sampling system 100 or 300 as illustrated in FIGS. 1 through 4, except as further detailed below. Sampling system 500 includes an embodiment of a sampling unit 510 and differs from sampling system 300 in part, in that liquid drawn from passageway 111 may be returned to passageway 111 at a junction 502 between pump 203 and connector 120.

With reference to FIG. 5, sampling unit 510 includes a return line 503 that intersects passageway 111 on the opposite side of pump 203 from passageway 113, a bubble sensor 505 and a pressure sensor 507, both of which are controlled by controller 210. Bubble sensor 505 is generally similar to bubble sensors 314a, 314b and 321 and pressure sensor 507 is generally similar to pressure sensor 317. Pressure sensor 507 is useful in determining the correct operation of sampling system 500 by monitoring pressure in passageway 111. Thus, for example, the pressure in passageway 111 is related to the pressure at catheter 11 when pressure sensor 507 is in fluid communication with catheter 11 (that is, when any intervening valve(s) are open). The output of pressure sensor 507 is used in a manner similar to that of pressure sensor 317 described previously in controlling pumps of sampling system 500.

Sampling unit 510 includes valves 501, 326a, and 326b under the control of controller 210. Valve 501 provides additional liquid flow control between sampling unit 200 and sampling unit 510. Pump 328 is preferably a bi-directional pump that can draw fluid from and into passageway 113. Fluid may either be drawn from and returned to passageway 501, or may be routed to waste receptacle 325. Valves 326a and 326b are situated on either side of pump 328. Fluid can be drawn through passageway 113 and into return line 503 by the coordinated control of pump 328 and valves 326a and 326b. Directing flow from return line 503 can be used to prime sampling system 500 with fluid. Thus, for example, liquid may be pulled into sampling unit 510 by operating pump 328 to pull liquid from passageway 113 while valve 326a is open and valve 326b is closed. Liquid may then be pumped back into passageway 113 by operating pump 328 to push liquid into passageway 113 while valve 326a is closed and valve 326b is open.

Figure 6A:
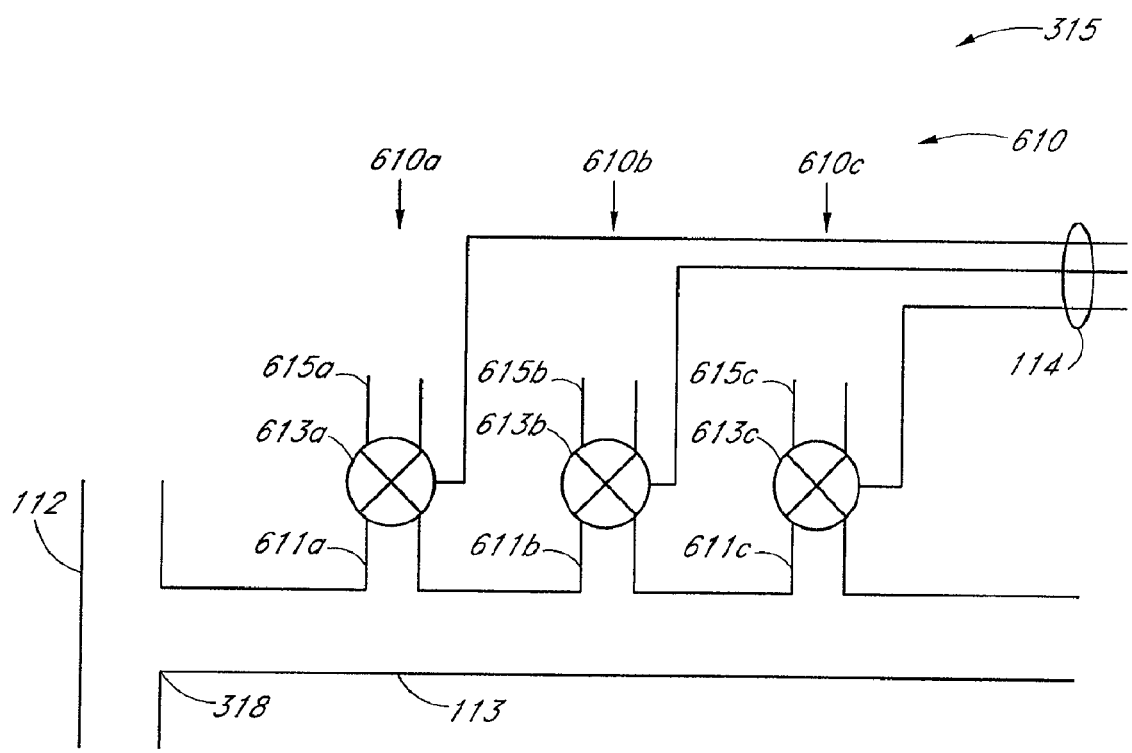
FIG. 6A is a schematic of an embodiment of gas injector manifold of the present invention.

FIG. 6A is a schematic of an embodiment of gas injector manifold 315 which may be generally similar or included within the embodiments illustrated in FIGS. 1 through 5, except as further detailed below. Gas injector manifold 315 is a device that injects one or more bubbles in a liquid within passageway 113 by opening valves to the atmosphere and lowering the liquid pressure within the manifold to draw in air. As described subsequently, gas injector manifold 315 facilitates the injection of air or other gas bubbles into a liquid within passageway 113. Gas injector manifold 315 has three gas injectors 610 including a first injector 610a, a second injector 610b, and a third injector 610c. Each injector 610 includes a corresponding passageway 611 that begins at one of several laterally spaced locations along passageway 113 and extends through a corresponding valve 613 and terminates at a corresponding end 615 that is open to the atmosphere. In an alternative embodiment, a filter is placed in end 615 to filter out dust or particles in the atmosphere. As described subsequently, each injector 610 is capable of injecting a bubble into a liquid within passageway 113 by opening the corresponding valve 613, closing a valve on one end of passageway 113 and operating a pump on the opposite side of the passageway to lower the pressure and pull atmospheric air into the fluid. In one embodiment of gas injector manifold 315, passageways 113 and 611 are formed within a single piece of material (e.g., as bores formed in or through a plastic or metal housing (not shown)). In an alternative embodiment, gas injector manifold 315 includes fewer than three injectors, for example one or two injectors, or includes more than three injectors. In another alternative embodiment, gas injector manifold 315 includes a controllable high pressure source of gas for injection into a liquid in passageway 113. It is preferred that valves 613 are located close to passageway 113 to minimize trapping of fluid in passageways 611.

Importantly, gas injected into passageways 20 should be prevented from reaching catheter 11. As a safety precaution, one embodiment prevents gas from flowing towards catheter 11 by the use of bubble sensor 314a as shown, for example, in FIG. 3. If bubble sensor 314a detects gas within passageway 111, then one of several alternative embodiments prevents unwanted gas flow. In one embodiment, flow in the vicinity of sampling assembly 220 is directed into line 113 or through line 113 into waste receptacle 325. With further reference to FIG. 3, upon the detection of gas by bubble sensor 314a, valves 316 and 323a are opened, valve 313 and the valves 613a, 613b and 613c of gas injector manifold 315 are closed, and pump 328 is turned on to direct flow away from the portion of passageway 111 between sampling assembly 220 and patient P into passageway 113. Bubble sensor 321 is monitored to provide an indication of when passageway 113 clears out. Valve 313 is then opened, valve 312 is closed, and the remaining portion of passageway 111 is then cleared. Alternatively, all flow is immediately halted in the direction of catheter 11, for example by closing all valves and stopping all pumps. In an alternative embodiment of sampling assembly 220, a gas-permeable membrane is located within passageway 113 or within gas injector manifold 315 to remove unwanted gas from fluid handling system 10, e.g., by venting such gas through the membrane to the atmosphere or a waste receptacle.

Figure 6B:
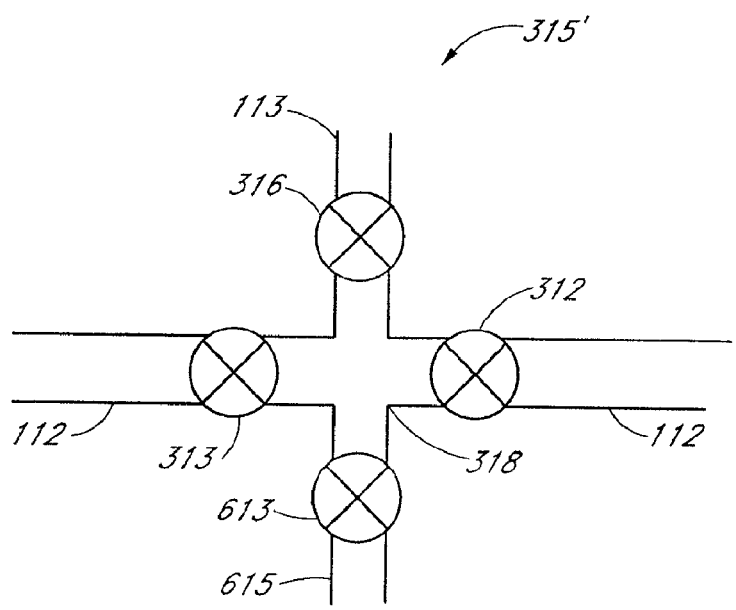
FIG. 6B is a schematic of an embodiment of gas injector manifold of the present invention.

FIG. 6B is a schematic of an embodiment of gas injector manifold 315' which may be generally similar to, or included within, the embodiments illustrated in FIGS. 1 through 6A, except as further detailed below. In gas injector manifold 315', air line 615 and passageway 113 intersect at junction 318. Bubbles are injected by opening valve 316 and 613 while drawing fluid into passageway 113. Gas injector manifold 315' is thus more compact that gas injector manifold 315, resulting in a more controllable and reliable gas generator.

Section II—Fluid Handling Methods

One embodiment of a method of using fluid handling system 10, including sampling assembly 220 and sampling unit 200 of FIGS. 2, 3 and 6A, is illustrated in Table 1 and in the schematic fluidic diagrams of FIGS. 7A-7J. In general, the pumps and valves are controlled to infuse a patient, to extract a sample from the patient up passageway 111 to passageway 113, and to direct the sample along passageway 113 to device 330. In addition, the pumps and valves are controlled to inject bubbles into the fluid to isolate the fluid from the diluting effect of previous fluid and to clean the lines between sampling. The valves in FIGS. 7A-7J are labeled with suffices to indicate whether the valve is open or closed. Thus a valve "x," for example, is shown as valve "x-o" if the valve is open and "x-c" if the valve is closed.

TABLE 1

Methods of operating system 10 as illustrated in FIGS. 7A-7J

| Mode | Step | Pump 203 | Pump 328 | Valve 312 | Valve 313 | Valve 613a | Valve 613b | Valve 613c | Valve 316 | Valve 323a | Valve 323b |
|---|---|---|---|---|---|---|---|---|---|---|---|
| Infuse patient | (FIG. 7A) Infuse patient | F | Off | O | O | C | C | C | C | C | C |
| Sample patient | (FIG. 7B) Clear fluid from passageways | R | Off | C | O | O | one or more are open O | O | C | C | C |
| | (FIG. 7C) Draw sample until after colorimetric sensor 311 senses blood | R | Off | O | O | C | C | C | C | C | C |
| | (FIG. 7D) Inject sample into bubble manifold | Off | On | O | C | C | C | C | O | C | O |
| | Alternative to FIG. 7D | R | On | O | O | C | C | C | O | C | O |
| | (FIG. 7E) Inject bubbles | Off | On | C | C | O | sequentially O | O | O | C | O |
| | (FIG. 7F) Clear bubbles from | F | Off | C | O | C | C | C | O | O | C |

TABLE 1-continued

Methods of operating system 10 as illustrated in FIGS. 7A-7J

| Mode | Step | Pump 203 | Pump 328 | Valve 312 | Valve 313 | Valve 613a | Valve 613b | Valve 613c | Valve 316 | Valve 323a | Valve 323b |
|---|---|---|---|---|---|---|---|---|---|---|---|
| | patient line (FIG. 7G) | F | Off | O | O | C | C | C | C | C | C |
| | Clear blood from patient line (FIG. 7H) | F | Off | C | O | C | C | C | O | O | C |
| | Move bubbles out of bubbler (FIG. 7I) Add cleaning bubbles | Off | On | C | C | O | sequentially O | O | O | C | O |
| | (FIG. 7J) Push sample to analyzer until bubble sensor 321 detects bubble | F | Off | C | O | C | C | C | O | O | C |

F = Forward (fluid into patient),
R = Reverse (fluid from patient),
O = Open,
C = Closed FIG. 7A illustrates one embodiment of a method of infusing a patient. In the step of FIG. 7A, pump 203 is operated forward (pumping towards the patient) pump 328 is off, or stopped, valves 313 and 312 are open, and valves 613a, 613b, 613c, 316, 323a, and 323b are closed. With these operating conditions, fluid 14 is provided to patient P. In a preferred embodiment, all of the other passageways at the time of the step of FIG. 7A substantially contain fluid 14.

Figure 7G:
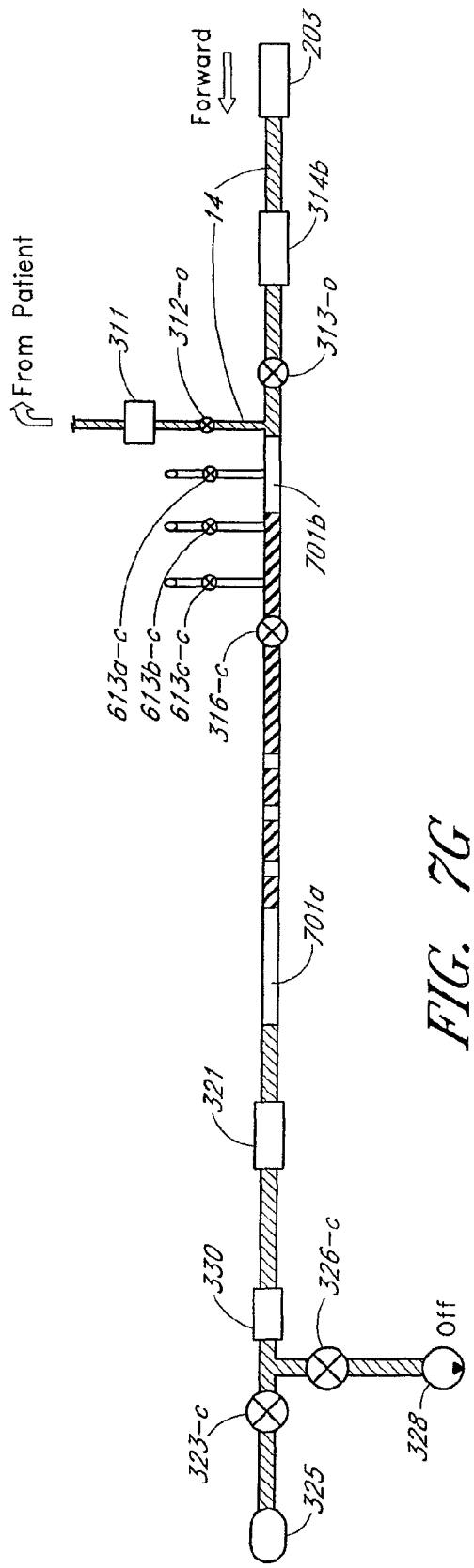

The next nine figures (FIGS. 7B-7J) illustrate steps in a method of sampling from a patient. The following steps are not meant to be inclusive of all of the steps of sampling from a patient, and it is understood that alternative embodiments may include more steps, fewer steps, or a different ordering of steps. FIG. 7B illustrates a first sampling step, where liquid is cleared from a portion of patient connection passageway and sampling passageways 112 and 113. In the step of FIG. 7B, pump 203 is operated in reverse (pumping away from the patient), pump 328 is off, valve 313 is open, one or more of valves 613a, 613b, and 613c are open, and valves 312, 316, 323a, and 326b are closed. With these operating conditions, air 701 is drawn into sampling passageway 113 and back into patient connection passageway 112 until bubble sensor 314b detects the presence of the air.

FIG. 7C illustrates a second sampling step, where a sample is drawn from patient P into patient connection passageway 112. In the step of FIG. 7C, pump 203 is operated in reverse, pump 328 is off, valves 312 and 313 are open, and valves 316, 613a, 613b, 613c, 323a, and 323b are closed. Under these operating conditions, a sample S is drawn into passageway 112, dividing air 701 into air 701a within sampling passageway 113 and air 701b within the patient connection passageway 112. Preferably this step proceeds until sample S extends just past the junction of passageways 112 and 113. In one embodiment, the step of FIG. 7C proceeds until variations in the output of colorimetric sensor 311 indicate the presence of a blood (for example by leveling off to a constant value), and then proceeds for an additional set amount of time to ensure the presence of a sufficient volume of sample S.

FIG. 7D illustrates a third sampling step, where a sample is drawn into sampling passageway 113. In the step of FIG. 7D, pump 203 is off, or stopped, pump 328 is on, valves 312, 316, and 326b are open, and valves 313, 613a, 613b, 613c and 323a are closed. Under these operating conditions, blood is drawn into passageway 113. Preferably, pump 328 is operated to pull a sufficient amount of sample S into passageway 113.

In one embodiment, pump 328 draws a sample S having a volume from 30 to 50 microliters. In an alternative embodiment, the sample is drawn into both passageways 112 and 113. Pump 203 is operated in reverse, pump 328 is on, valves 312, 313, 316, and 323b are open, and valves 613a, 613b, 613c and 323a are closed to ensure fresh blood in sample S.

FIG. 7E illustrates a fourth sampling step, where air is injected into the sample. Bubbles which span the cross-sectional area of sampling passageway 113 are useful in preventing contamination of the sample as it is pumped along passageway 113. In the step of FIG. 7E, pump 203 is off, or stopped, pump 328 is on, valves 316, and 323b are open, valves 312, 313 and 323a are closed, and valves 613a, 613b, 613c are each opened and closed sequentially to draw in three separated bubbles. With these operating conditions, the pressure in passageway 113 falls below atmospheric pressure and air is drawn into passageway 113. Alternatively, valves 613a, 613b, 613c may be opened simultaneously for a short period of time, generating three spaced bubbles. As shown in FIG. 7E, injectors 610a, 610b, and 610c inject bubbles 704, 703, and 702, respectively, dividing sample S into a forward sample S1, a middle sample S2, and a rear sample S3.

FIG. 7F illustrates a fifth sampling step, where bubbles are cleared from patient connection passageway 112. In the step of FIG. 7F, pump 203 is operated in a forward direction, pump 328 is off, valves 313, 316, and 323a are open, and valves 312, 613a, 613b, 613c, and 323b are closed. With these operating conditions, the previously injected air 701b is drawn out of first passageway 111 and into second passageway 113. This step proceeds until air 701b is in passageway 113.

FIG. 7G illustrates a sixth sampling step, where blood in passageway 112 is returned to the patient. In the step of FIG. 7G, pump 203 is operated in a forward direction, pump 328 is off, valves 312 and 313 are open, and valves 316, 323a, 613a, 613b, 613c and 323b are closed. With these operating conditions, the previously injected air remains in passageway 113 and passageway 111 is filled with fluid 14.

Figure 7H:
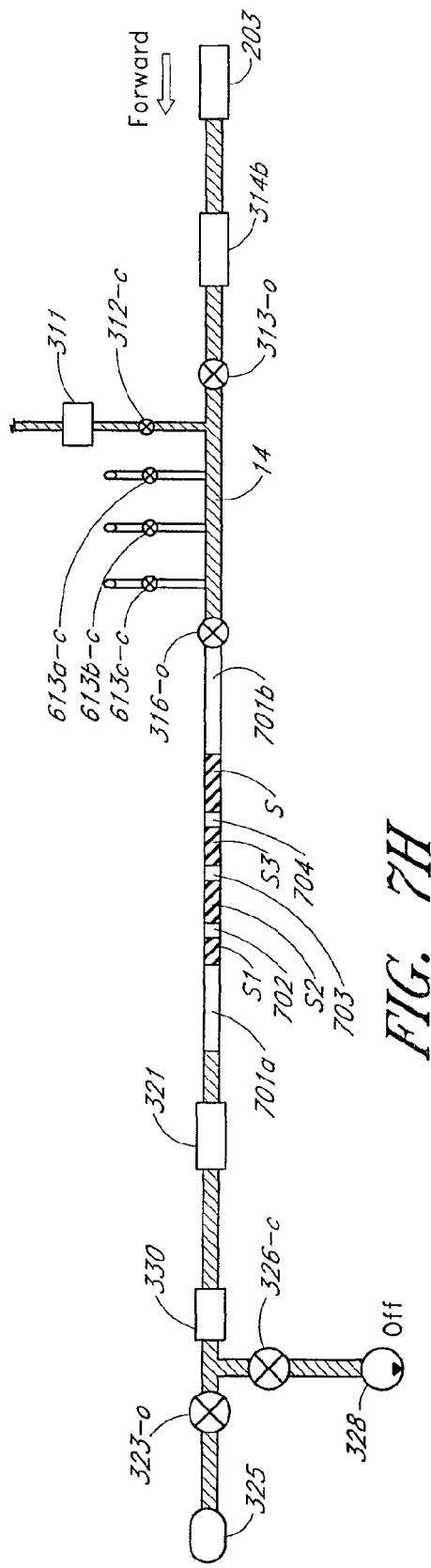

FIGS. 7H and 7I illustrates a seventh and eighth sampling steps, where the sample is pushed part way into passageway 113 followed by fluid 14 and more bubbles. In the step of FIG. 7H, pump 203 is operated in a forward direction, pump 328 is off, valves 313, 316, and 323a are open, and valves 312, 613a, 613b, 613c, and 323b are closed. With these operating conditions, sample S is moved partway into passageway 113 with bubbles injected, either sequentially or simultaneously, into fluid 14 from injectors 610a, 610b, and 610c. In the step of FIG. 7I, the pumps and valves are operated as in the step of FIG. 7E, and fluid 14 is divided into a forward solution C1, a middle solution C2, and a rear solution C3 separated by bubbles 705, 706, and 707.

The last step shown in FIG. 7 is FIG. 7J, where middle sample S2 is pushed to sample analysis device 330. In the step of FIG. 7J, pump 203 is operated in a forward direction, pump 328 is off, valves 313, 316, and 323a are open, and valves 312, 613a, 613b, 613c, and 323b are closed. In this configuration, the sample is pushed into passageway 113. When bubble sensor 321 detects bubble 702, pump 203 continues pumping until sample S2 is taken into device sample analysis 330. Additional pumping using the settings of the step of FIG. 7J permits the sample S2 to be analyzed and for additional bubbles and solutions to be pushed into waste receptacle 325, cleansing passageway 113 prior to accepting a next sample.

Section III—Sampling System

Figure 8:
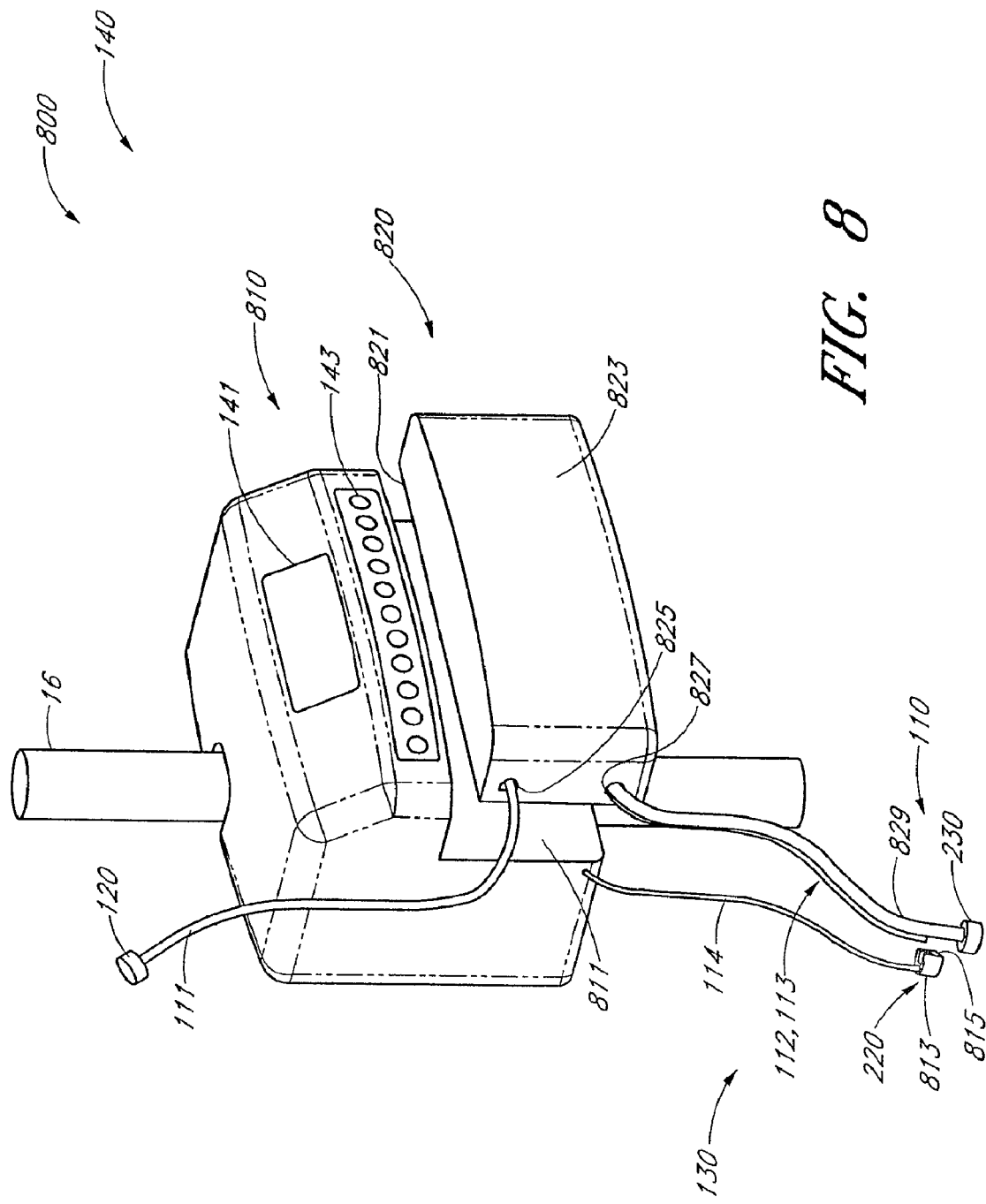
FIG. 8 is a perspective front view of an embodiment of a sampling apparatus of the present invention.

FIG. 8 is a perspective front view of a third embodiment of a sampling system 800 of the present invention which may be generally similar to sampling system 100, 300 or 500 and the embodiments illustrated in FIGS. 1 through 7, except as further detailed below. The fluid handling and analysis apparatus 140 of sampling system 800 includes the combination of an instrument 810 and a sampling system cassette 820. FIG. 8 illustrates instrument 810 and cassette 820 partially removed from each other. Instrument 810 includes controller 210 (not shown), display 141 and input devices 143, a cassette interface 811, and lines 114. Cassette 820 includes passageway 111 which extends from connector 120 to connector 230, and further includes passageway 113, a junction 829 of passageways 111 and 113, an instrument interface 821, a front surface 823, an inlet 825 for passageway 111, and an inlet 827 for passageways 111 and 113. In addition, sampling assembly 220 is formed from a sampling assembly instrument portion 813 having an opening 815 for accepting junction 829. The interfaces 811 and 821 engage the components of instrument 810 and cassette 820 to facilitate pumping fluid and analyzing samples from a patient, and sampling assembly instrument portion 813 accepts junction 829 in opening 815 to provide for sampling from passageway 111.

FIGS. 9 and 10 are front views of a sampling system cassette 820 and instrument 810, respectively, of a sampling system 800. Cassette 820 and instrument 810, when assembled, form various components of FIGS. 9 and 10 that cooperate to form an apparatus consisting of sampling unit 510 of FIG. 5, sampling assembly 220 of FIG. 3, and gas injection manifold 315' of FIG. 6B.

More specifically, as shown in FIG. 9, cassette 820 includes passageways 20 including: passageway 111 having portions 111a, 112a, 112b, 112c, 112d, 112e, and 112f; passageway 113 having portions 113a, 113b, 113c, 113d, 113e, and 113f; passageway 615; waste receptacle 325; disposable components of sample analysis device 330 including, for example, a sample preparation unit 332 adapted to allow only blood plasma to pass therethrough and a sample chamber 903 for placement within analyte detection system 334 for measuring properties of the blood plasma; and a displacement pump 905 having a piston control 907.

As shown in FIG. 10, instrument 810 includes bubble sensor units 1001a, 1001b, and 1001c, colorimetric sensor, which is a hemoglobin sensor unit 1003, a peristaltic pump roller 1005a and a roller support 1005b, pincher pairs 1007a, 1007b, 1007c, 1007d, 1007e, 1007f, 1007g, and 1007h, an actuator 1009, and a pressure sensor unit 1011. In addition, instrument 810 includes portions of sample analysis device 330 which are adapted to measure a sample contained within sample chamber 903 when located near or within a probe region 1002 of an optical analyte detection system 334.

Passageway portions of cassette 820 contact various components of instrument 810 to form sampling system 800. With reference to FIG. 5 for example, pump 203 is formed from portion 111a placed between peristaltic pump roller 1005a and roller support 1005b to move fluid through passageway 111 when the roller is actuated; valves 501, 323, 326a, and 326b are formed with pincher pairs 1007a, 1007b, 1007c, and 1007d surrounding portions 113a, 113c, 113d, and 113e, respectively, to permit or block fluid flow therethrough. Pump 328 is formed from actuator 1009 positioned to move piston control 907. It is preferred that the interconnections between the components of cassette 820 and instrument 810 described in this paragraph are made with one motion. Thus for example the placement of interfaces 811 and 821 places the passageways against and/or between the sensors, actuators, and other components.

In addition to placement of interface 811 against interface 821, the assembly of apparatus 800 includes assembling sampling assembly 220. More specifically, an opening 815a and 815b are adapted to receive passageways 111 and 113, respectively, with junction 829 within sampling assembly instrument portion 813. Thus, for example, with reference to FIG. 3, valves 313 and 312 are formed when portions 112b and 112c are placed within pinchers of pinch valves 1007e and 1007f, respectively, bubble sensors 314b and 314a are formed when bubble sensor units 1001b, and 1001c are in sufficient contact with portions 112a and 112d, respectively, to determine the presence of bubbles therein; hemoglobin detector is formed when hemoglobin sensor 1003 is in sufficient contact with portion 112e, and pressure sensor 317 is formed when portion 112f is in sufficient contact with pressure sensor unit 1011 to measure the pressure of a fluid therein. With reference to FIG. 6B, valves 316 and 613 are formed when portions 113f and 615 are placed within pinchers of pinch valves 1007h and 1007g, respectively.

In operation, the assembled main instrument 810 and cassette 820 of FIGS. 9-10 can function as follows. The system can be considered to begin in an idle state or infusion mode in which the roller pump 1005 operates in a forward direction (with the impeller 1005a turning counterclockwise as shown in FIG. 10) to pump infusion fluid from the container 15 through the passageway 111 and the passageway 112, toward and into the patient P. In this infusion mode the pump 1005 delivers infusion fluid to the patient at a suitable infusion rate as discussed elsewhere herein.

When it is time to conduct a measurement, air is first drawn into the system to clear liquid from a portion of the passageways 112, 113, in a manner similar to that shown in FIG. 7B. Here, the single air injector of FIG. 9 (extending from the junction 829 to end 615, opposite the passageway 813) functions in place of the manifold shown in FIGS. 7A-7J. Next, to draw a sample, the pump 1005 operates in a sample draw mode, by operating in a reverse direction and pulling a sample of bodily fluid (e.g. blood) from the patient into the passageway 112 through the connector 230. The sample is drawn up to the hemoglobin sensor 1003, and is preferably drawn until the output of the sensor 1003 reaches a desired plateau level indicating the presence of an undiluted blood sample in the passageway 112 adjacent the sensor 1003.

From this point the pumps 905, 1005, valves 1007e, 1007f, 1007g, 1007h, bubble sensors 1001b, 1001c and/or hemoglobin sensor 1003 can be operated to move a series of air bubbles and sample-fluid columns into the passageway 113, in a manner similar to that shown in FIGS. 7D-7F. The pump 905, in place of the pump 328, is operable by moving the piston control 907 of the pump 905 in the appropriate direction (to the left or right as shown in FIGS. 9-10) with the actuator 1009.

Once a portion of the bodily fluid sample and any desired bubbles have moved into the passageway 113, the valve 1007h can be closed, and the remainder of the initial drawn sample or volume of bodily fluid in the passageway 112 can be returned to the patient, by operating the pump 1005 in the forward or infusion direction until the passageway 112 is again filled with infusion fluid.

With appropriate operation of the valves 1007a-1007h, and the pump(s) 905 and/or 1005, at least a portion of the bodily fluid sample in the passageway 113 (which is 10-100 microliters in volume, or 20, 30, 40, 50 or 60 microliters, in various embodiments) is moved through the sample preparation unit 332 (in the depicted embodiment a filter or membrane; alternatively a centrifuge as discussed in greater detail below). Thus, only one or more components of the bodily fluid (e.g., only the plasma of a blood sample) passes through the unit 332 or filter/membrane and enters the sample chamber or cell 903. Alternatively, where the unit 332 is omitted, the "whole" fluid moves into the sample chamber 903 for analysis.

Once the component(s) or whole fluid is in the sample chamber 903, the analysis is conducted to determine a level or concentration of one or more analytes, such as glucose, lactate, carbon dioxide, blood urea nitrogen, hemoglobin, and/or any other suitable analytes as discussed elsewhere herein. Where the analyte detection system 1700 is spectroscopic (e.g. the system 1700 of FIG. 17 or 44-46), a spectroscopic analysis of the component(s) or whole fluid is conducted.

After the analysis, the body fluid sample within the passageway 113 is moved into the waste receptacle 325. Preferably, the pump 905 is operated via the actuator 1009 to push the body fluid, behind a column of saline or infusion fluid obtained via the passageway 909, back through the sample chamber 903 and sample preparation unit 332, and into the receptacle 325. Thus, the chamber 903 and unit 332 are back-flushed and filled with saline or infusion fluid while the bodily fluid is delivered to the waste receptacle. Following this flush a second analysis can be made on the saline or infusion fluid now in the chamber 903, to provide a "zero" or background reading. At this point, the fluid handling network of FIG. 9, other than the waste receptacle 325, is empty of bodily fluid, and the system is ready to draw another bodily fluid sample for analysis.

In some embodiments of the apparatus 140, a pair of pinch valve pinchers acts to switch flow between one of two branches of a passageway. FIGS. 13A and 13B are front view and sectional view, respectively, of a first embodiment pinch valve 1300 in an open configuration that can direct flow either one or both of two branches, or legs, of a passageway. Pinch valve 1300 includes two separately controllable pinch valves acting on a "Y" shaped passageway 1310 to allow switch of fluid between various legs. In particular, the internal surface of passageway 1310 forms a first leg 1311 having a flexible pinch region 1312, a second leg 1313 having a flexible pinch region 1314, and a third leg 1315 that joins the first and second legs at an intersection 1317. A first pair of pinch valve pinchers 1320 is positioned about pinch region 1312 and a second pair of pinch valve pinchers 1330 is positioned about pinch region 1314. Each pair of pinch valve pinchers 1320 and 1330 is positioned on opposite sides of their corresponding pinch regions 1312, 1314 and perpendicular to passageway 1310, and are individually controllable by controller 210 to open and close, that is allow or prohibit fluid communication across the pinch regions. Thus, for example, when pinch valve pinchers 1320 (or 1330) are brought sufficiently close, each part of pinch region 1312 (or 1314) touches another part of the pinch region and fluid may not flow across the pinch region.

As an example of the use of pinch valve 1300, FIG. 13B shows the first and second pair of pinch valve pinchers 1320, 1330 in an open configuration. FIG. 13C is a sectional view showing the pair of pinch valve pinchers 1320 brought together, thus closing off a portion of first leg 1311 from the second and third legs 1313, 1315. In part as a result of the distance between pinchers 1320 and intersection 1317 there is a volume 1321 associated with first leg 1311 that is not isolated ("dead space"). It is preferred that dead space is minimized so that fluids of different types can be switched between the various legs of the pinch valve. In one embodiment, the dead space is reduced by placing the placing the pinch valves close to the intersection of the legs. In another embodiment, the dead space is reduced by having passageway walls of varying thickness. Thus, for example, excess material between the pinch valves and the intersection will more effectively isolate a valved leg by displacing a portion of volume 1321.

As an example of the use of pinch valve 1300 in sampling system 300, pinchers 1320 and 1330 are positioned to act as valve 323 and 326, respectively.

Figure 14B:
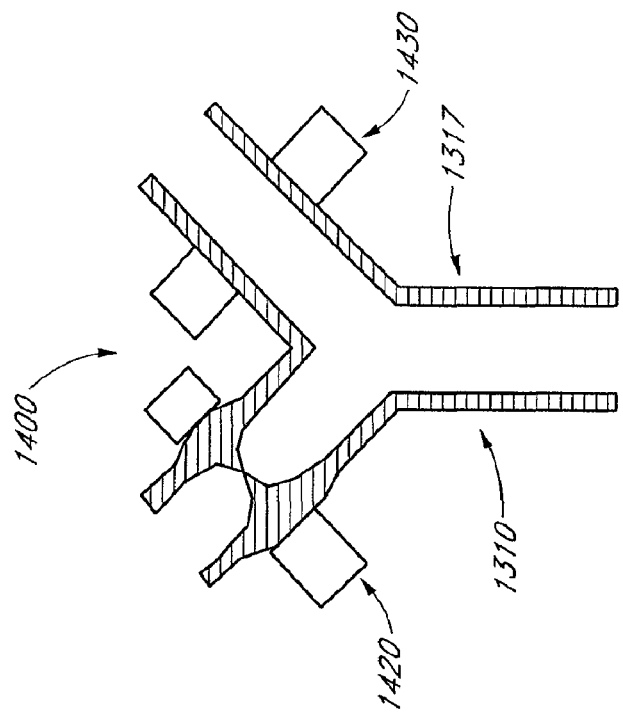
FIGS. 14A and 14B are various views of one embodiment of a pinch valve of the present invention, where
Figure 14A:
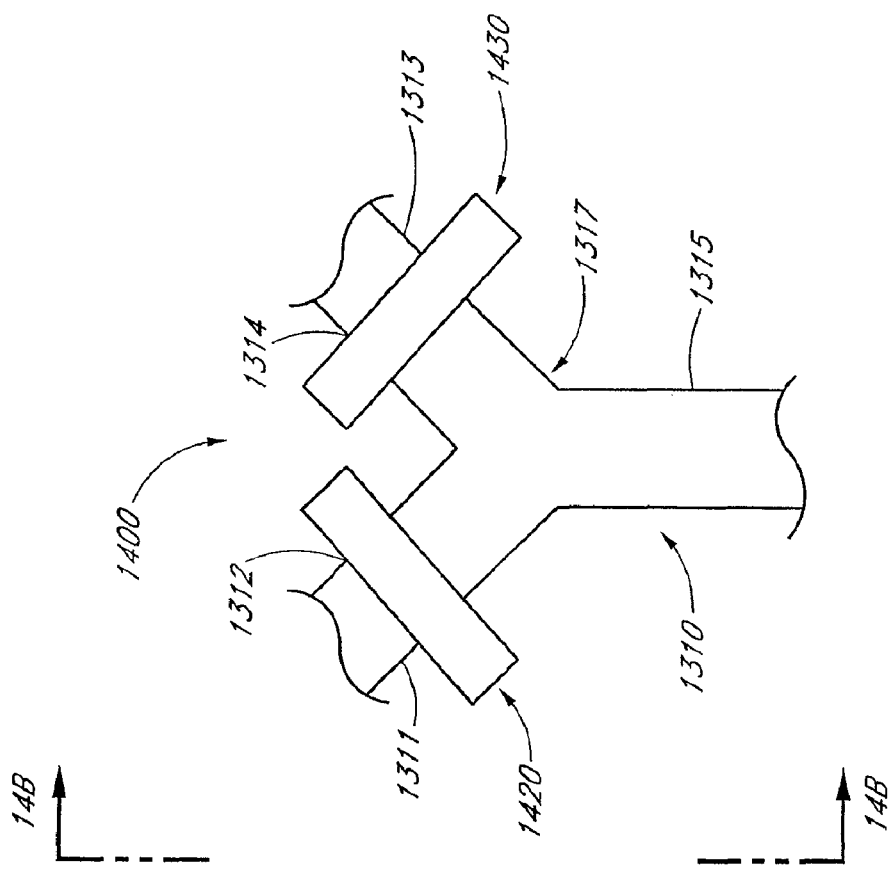

FIGS. 14A and 14B are various views of a second embodiment pinch valve 1400, where FIG. 14A is a front view and FIG. 14B is a sectional view showing one valve in a closed position. Pinch valve 1400 differs from pinch valve 1300 in that the pairs of pinch valve pinchers 1320 and 1330 are replaced by pinchers 1420 and 1430, respectively, that are aligned with passageway 1310.

Alternative embodiment of pinch valves includes 2, 3, 4, or more passageway segments that meet at a common junction, with pinchers located at one or more passageways near the junction.

FIGS. 11 and 12 illustrate various embodiment of connector 230 which may also form or be attached to disposable portions of cassette 820 as one embodiment of an arterial patient connector 1100 and one embodiment a venous patient connector 1200. Connectors 1100 and 1200 may be generally similar to the embodiment illustrated in FIGS. 1-10, except as further detailed below.

As shown in FIG. 11, arterial patient connector 1100 includes a stopcock 1101, a first tube portion 1103 having a length X, a blood sampling port 1105 to acquire blood samples for laboratory analysis, and fluid handling and analysis apparatus 140, a second tube 1107 having a length Y, and a tube connector 1109. Arterial patient connector 1100 also includes a pressure sensor unit 1102 that is generally similar to pressure sensor unit 1011, on the opposite side of sampling assembly 220. Length X is preferably from to 6 inches (0.15 meters) to 50 inches (1.27 meters) or approximately 48 inches (1.2 meters) in length. Length Y is preferably from 1 inch (25 millimeters) to 20 inches (0.5 meters), or approximately 12 inches (0.3 meters) in length. As shown in FIG. 12, venous patient connector 1200 includes a clamp 1201, injection port 1105, and tube connector 1109.

Section IV—Sample Analysis System

In several embodiments, analysis is performed on blood plasma. For such embodiments, the blood plasma must be separated from the whole blood obtained from the patient. In general, blood plasma may be obtained from whole blood at any point in fluid handling system 10 between when the blood is drawn, for example at patient connector 110 or along passageway 113, and when it is analyzed. For systems where measurements are preformed on whole blood, it may not be necessary to separate the blood at the point of or before the measurements is performed.

For illustrative purposes, this section describes several embodiments of separators and analyte detection systems which may form part of system 10. The separators discussed in the present specification can, in certain embodiments, comprise fluid component separators. As used herein, the term "fluid component separator" is a broad term and is used in its ordinary sense and includes, without limitation, any device that is operable to separate one or more components of a fluid to generate two or more unlike substances. For example, a fluid component separator can be operable to separate a sample of whole blood into plasma and non-plasma components, and/or to separate a solid-liquid mix (e.g. a solids-contaminated liquid) into solid and liquid components. A fluid component separator need not achieve complete separation between or among the generated unlike substances. Examples of fluid component separators include filters, membranes, centrifuges, electrolytic devices, or components of any of the foregoing. Fluid component separators can be "active" in that they are operable to separate a fluid more quickly than is possible through the action of gravity on a static, "standing" fluid. Section IV.A below discloses a filter which can be used as a blood separator in certain embodiments of the apparatus disclosed herein. Section IV.B below discloses an analyte detection system which can be used in certain embodiments of the apparatus disclosed herein. Section IV.C below discloses a sample element which can be used in certain embodiments of the apparatus disclosed herein. Section IV.D below discloses a centrifuge and sample chamber which can be used in certain embodiments of the apparatus disclosed herein.

Section IV.A—Blood Filter

Figure 15:
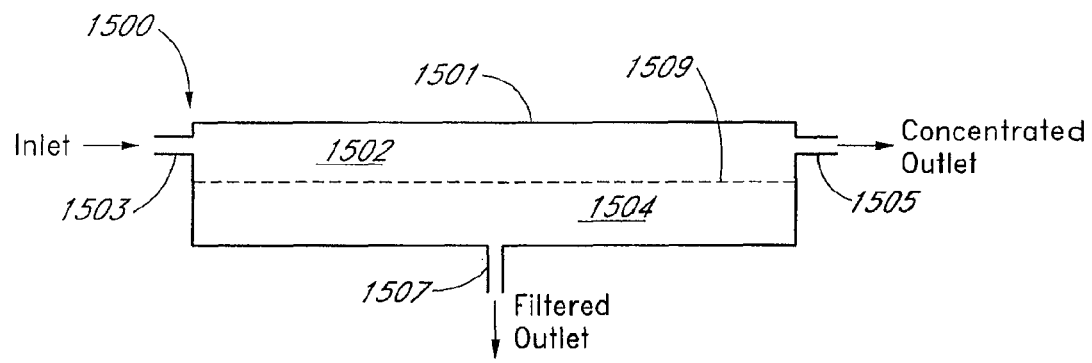
FIG. 15 is a side view of one embodiment of a separator.
Figure 16:
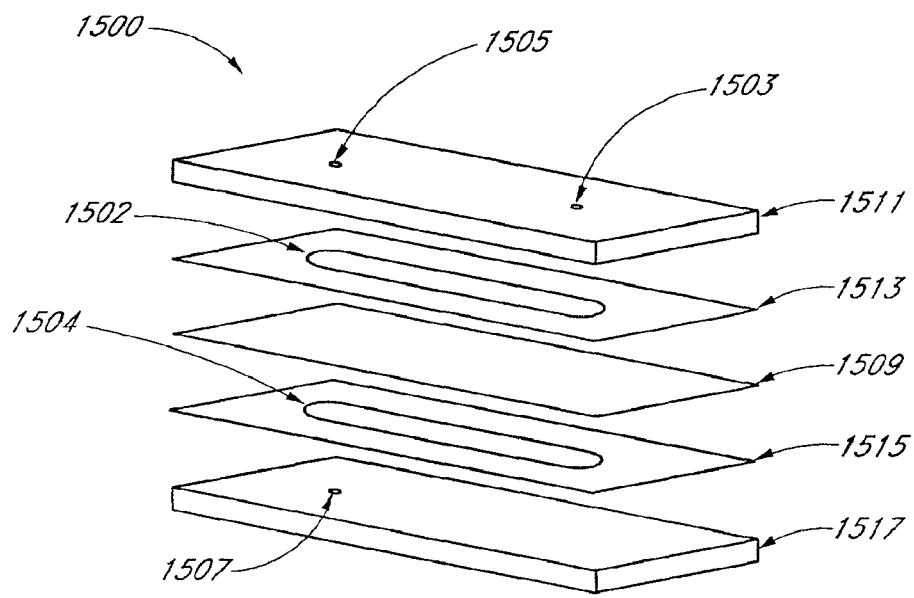
FIG. 16 is an exploded perspective view of the separator of FIG. 15.

Without limitation as to the scope of the present invention, one embodiment of sample preparation unit 332 is shown as a blood filter 1500, as illustrated in FIGS. 15 and 16, where FIG. 15 is a side view of one embodiment of a filter, and FIG. 16 is an exploded perspective view of the filter.

As shown in the embodiment of FIG. 15, filter 1500 that includes a housing 1501 with an inlet 1503, a first outlet 1505 and a second outlet 1507. Housing 1501 contains a membrane 1509 that divides the internal volume of housing 1501 into a first volume 1502 that include inlet 1503 and first outlet 1505 and a second volume 1504. FIG. 16 shows one embodiment of filter 1500 as including a first plate 1511 having inlet 1503 and outlet 1505, a first spacer 1513 having an opening forming first volume 1502, a second spacer 1515 having an opening forming second volume 1504, and a second plate 1517 having outlet 1507.

Filter 1500 provides for a continuous filtering of blood plasma from whole blood. Thus, for example, when a flow of whole blood is provided at inlet 1503 and a slight vacuum is applied to the second volume 1504 side of membrane 1509, the membrane filters blood cells and blood plasma passes through second outlet 1507. Preferably, there is transverse blood flow across the surface of membrane 1509 to prevent blood cells from clogging filter 1500. Accordingly, in one embodiment of the inlet 1503 and first outlet 1505 may be configured to provide the transverse flow across membrane 1509.

In one embodiment, membrane 1509 is a thin and strong polymer film. For example, the membrane filter may be a 10 micron thick polyester or polycarbonate film. Preferably, the membrane filter has a smooth glass-like surface, and the holes are uniform, precisely sized, and clearly defined. The material of the film may be chemically inert and have low protein binding characteristics.

One way to manufacture membrane 1509 is with a Track Etching process. Preferably, the "raw" film is exposed to charged particles in a nuclear reactor, which leaves "tracks" in the film. The tracks may then be etched through the film, which results in holes that are precisely sized and uniformly cylindrical. For example, GE Osmonics, Inc. (4636 Somerton Rd. Trevose, Pa. 19053-6783) utilizes a similar process to manufacture a material that adequately serves as the membrane filter. The surface the membrane filter depicted above is a GE Osmonics Polycarbonate TE film.

As one example of the use of filter 1500, the plasma from 3 cc of blood may be extracted using a polycarbonate track etch film ("PCTE") as the membrane filter. The PCTE may have a pore size of 2 μm and an effective area of 170 millimeter$^2$. Preferably, the tubing connected to the supply, exhaust and plasma ports has an internal diameter of 1 millimeter. In one embodiment of a method employed with this configuration, 100 μl of plasma can be initially extracted from the blood. After saline is used to rinse the supply side of the cell, another 100 μl of clear plasma can be extracted. The rate of plasma extraction in this method and configuration can be about 15-25 μl/min.

Using a continuous flow mechanism to extract plasma may provide several benefits. In one preferred embodiment, the continuous flow mechanism is reusable with multiple samples, and there is negligible sample carryover to contaminate subsequent samples. One embodiment may also eliminate most situations in which plugging may occur. Additionally, a preferred configuration provides for a low internal volume.

Additional information on filters, methods of use thereof, and related technologies may be found in U.S. patent application Publication No. 2005/0038357, published on Feb. 17, 2005, titled SAMPLE ELEMENT WITH BARRIER MATERIAL; and U.S. patent application Ser. No. 11/122,794, filed on May 5, 2005, titled SAMPLE ELEMENT WITH SEPARATOR. The entire contents of the above noted publication and patent application are hereby incorporated by reference herein and made a part of this specification.

Section IV.B—Analyte Detection System

Figure 17:
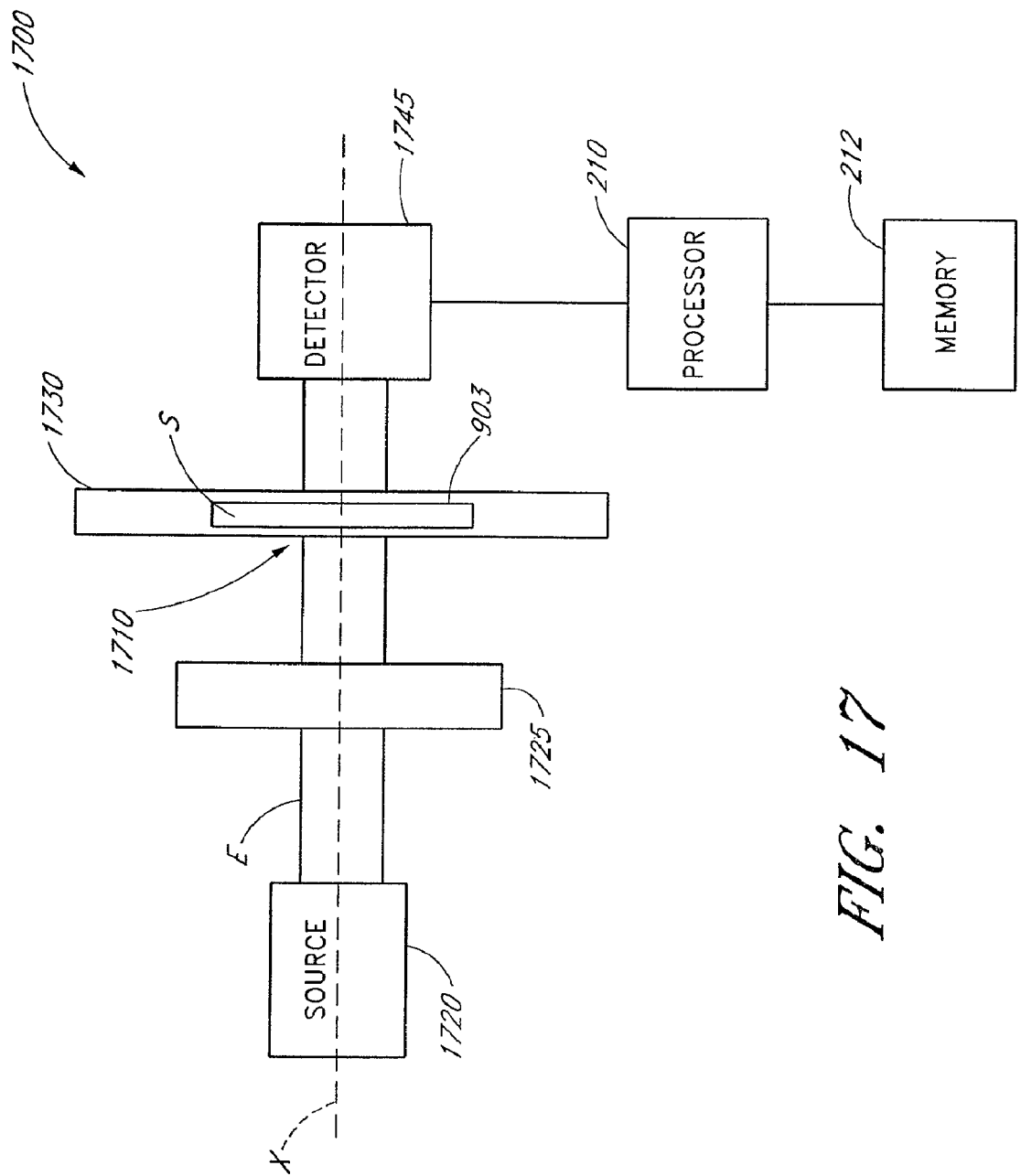
FIG. 17 is one embodiment of a fluid analysis apparatus of the present invention.

One embodiment of analyte detection system 334, which is not meant to limit the scope of the present invention, is shown in FIG. 17 as an optical analyte detection system 1700. Analyte detection system 1700 is adapted to measure spectra of blood plasma. The blood plasma provided to analyte detection system 334 may be provided by sample preparation unit 332, including but not limited to a filter 1500.

Analyte detection system 1700 comprises an energy source 1720 disposed along a major axis X of system 1700. When activated, the energy source 1720 generates an energy beam E which advances from the energy source 1720 along the major axis X. In one embodiment, the energy source 1720 comprises an infrared source and the energy beam E comprises an infrared energy beam.

The energy beam E passes through an optical filter 1725 also situated on the major axis X, before reaching a probe region 1710. Probe region 1710 is portion of apparatus 322 in the path of an energized beam E that is adapted to accept a material sample S. In one embodiment, as shown in FIG. 17, probe region 1710 is adapted to accept a sample element or cuvette 1730, which supports or contains the material sample S. In one embodiment of the present invention, sample element 1730 is a portion of passageway 113, such as a tube or an optical cell. After passing through the sample element 1730 and the sample S, the energy beam E reaches a detector 1745.

As used herein, "sample element" is a broad term and is used in its ordinary sense and includes, without limitation, structures that have a sample chamber and at least one sample chamber wall, but more generally includes any of a number of structures that can hold, support or contain a material sample and that allow electromagnetic radiation to pass through a sample held, supported or contained thereby; e.g., a cuvette, test strip, etc.

In one embodiment of the present invention, sample element 1730 forms a disposable portion of cassette 820, and the remaining portions of system 1700 form portions of instrument 810, and probe region 1710 is probe region 1002.

With further reference to FIG. 17, the detector 1745 responds to radiation incident thereon by generating an electrical signal and passing the signal to processor 210 for analysis. Based on the signal(s) passed to it by the detector 1745, the processor computes the concentration of the analyte(s) of interest in the sample S, and/or the absorbance/transmittance characteristics of the sample S at one or more wavelengths or wavelength bands employed to analyze the sample. The processor 210 computes the concentration(s), absorbance(s), transmittance(s), etc. by executing a data processing algorithm or program instructions residing within memory 212 accessible by the processor 210.

In the embodiment shown in FIG. 17, the filter 1725 may comprise a varying-passband filter, to facilitate changing, over time and/or during a measurement taken with apparatus 322, the wavelength or wavelength band of the energy beam E that may pass the filter 1725 for use in analyzing the sample S. (In various other embodiments, the filter 1725 may be omitted altogether.) Some examples of a varying-passband filter usable with apparatus 322 include, but are not limited to, a filter wheel (discussed in further detail below), an electronically tunable filter, such as those manufactured by Aegis Semiconductor (Woburn, Mass.), a custom filter using an "Active Thin Films platform," a Fabry-Perot interferometer, such as those manufactured by Scientific Solutions, Inc. (North Chelmsford, Mass.), a custom liquid crystal Fabry-Perot (LCFP) Tunable Filter, or a tunable monochrometer, such as a HORIBA (Jobin Yvon, Inc. (Edison, N.J.) H1034 type with 7-10 µm grating, or a custom designed system.

In one embodiment detection system 1700, filter 1725 comprises a varying-passband filter, to facilitate changing, over time and/or during a measurement taken with the detection system 1700, the wavelength or wavelength band of the energy beam E that may pass the filter 25 for use in analyzing the sample S. When the energy beam E is filtered with a varying-passband filter, the absorption/transmittance characteristics of the sample S can be analyzed at a number of wavelengths or wavelength bands in a separate, sequential manner. As an example, assume that it is desired to analyze the sample S at N separate wavelengths (Wavelength 1 through Wavelength N). The varying-passband filter is first operated or tuned to permit the energy beam E to pass at Wavelength 1, while substantially blocking the beam E at most or all other wavelengths to which the detector 1745 is sensitive (including Wavelengths 2-N). The absorption/transmittance properties of the sample S are then measured at Wavelength 1, based on the beam E that passes through the sample S and reaches the detector 1745. The varying-passband filter is then operated or tuned to permit the energy beam E to pass at Wavelength 2, while substantially blocking other wavelengths as discussed above; the sample S is then analyzed at Wavelength 2 as was done at Wavelength 1. This process is repeated until all of the wavelengths of interest have been employed to analyze the sample S. The collected absorption/transmittance data can then be analyzed by the processor 210 to determine the concentration of the analyte(s) of interest in the material sample S. The measured spectra of sample S is referred to herein in general as $C_s(\lambda_i)$, that is, a wavelength dependent spectra in which $C_s$ is, for example, a transmittance, an absorbance, an optical density, or some other measure of the optical properties of sample S having values at or about a number of wavelengths $\lambda_i$, where i ranges over the number of measurements taken. The measurement $C_s(\lambda_i)$ is a linear array of measurements that is alternatively written as $Cs_i$.

The spectral region of system 1700 depends on the analysis technique and the analyte and mixtures of interest. For example, one useful spectral region for the measurement of glucose in blood using absorption spectroscopy is the mid-IR (for example, about 4 microns to about 11 microns). In one embodiment system 1700, energy source 1720 produces a beam E having an output in the range of about 4 microns to about 11 microns. Although water is the main contributor to the total absorption across this spectral region, the peaks and other structures present in the blood spectrum from about 6.8 microns to 10.5 microns are due to the absorption spectra of other blood components. The 4 to 11 micron region has been found advantageous because glucose has a strong absorption peak structure from about 8.5 to 10 microns, whereas most other blood constituents have a low and flat absorption spectrum in the 8.5 to 10 micron range. The main exceptions are water and hemoglobin, both of which are interferents in this region.

The amount of spectral detail provided by system 1700 depends on the analysis technique and the analyte and mixture of interest. For example, the measurement of glucose in blood by mid-IR absorption spectroscopy is accomplished with from 11 to 25 filters within a spectral region. In one embodiment system 1700, energy source 1720 produces a beam E having an output in the range of about 4 microns to about 11 microns, and filter 1725 include a number of narrow band filters within this range, each allowing only energy of a certain wavelength or wavelength band to pass therethrough. Thus, for example, one embodiment filter 1725 includes a filter wheel having 11 filters with a nominal wavelength approximately equal to one of the following: 3 µm, 4.06 µm, 4.6 µm, 4.9 µm, 5.25 µm, 6.12 µm, 6.47 µm, 7.98 µm, 8.35 µm, 9.65 µm, and 12.2 µm.

In one embodiment, individual infrared filters of the filter wheel are multi-cavity, narrow band dielectric stacks on germanium or sapphire substrates, manufactured by either OCLI (JDS Uniphase, San Jose, Calif.) or Spectrogon US, Inc. (Parsippany, N.J.). Thus, for example, each filter may nominally be 1 millimeter thick and 10 millimeter square. The peak transmission of the filter stack is typically between 50% and 70%, and the bandwidths are typically between 150 nm and 350 nm with center wavelengths between 4 and 10 µm. Alternatively, a second blocking IR filter is also provided in front of the individual filters. The temperature sensitivity is preferably <0.01% per degree C. to assist in maintaining nearly constant measurements over environmental conditions.

In one embodiment, the detection system 1700 computes an analyte concentration reading by first measuring the electromagnetic radiation detected by the detector 1745 at each center wavelength, or wavelength band, without the sample element 1730 present on the major axis X (this is known as an "air" reading). Second, the system 1700 measures the electromagnetic radiation detected by the detector 1745 for each center wavelength, or wavelength band, with the material sample S present in the sample element 1730, and the sample element and sample S in position on the major axis X (i.e., a "wet" reading). Finally, the processor 210 computes the concentration(s), absorbance(s) and/or transmittances relating to the sample S based on these compiled readings.

In one embodiment, the plurality of air and wet readings are used to generate a pathlength corrected spectrum as follows. First, the measurements are normalized to give the transmission of the sample at each wavelength. Using both a signal and reference measurement at each wavelength, and letting $S_i$ represent the signal of detector 1745 at wavelength i and $R_i$ represent the signal of the detector at wavelength i, the transmittance, $T_i$ at wavelength i may computed as $T_i=S_i$(wet)/$S_i$(air). Optionally, the spectra may be calculated as the optical density, $OD_i$, as $-Log(T_i)$. Next, the transmission over the wavelength range of approximately 4.5 μm to approximately 5.5 μm is analyzed to determine the pathlength. Specifically, since water is the primary absorbing species of blood over this wavelength region, and since the optical density is the product of the optical pathlength and the known absorption coefficient of water (OD=L σ, where L is the optical pathlength and σ is the absorption coefficient), any one of a number of standard curve fitting procedures may be used to determine the optical pathlength, L from the measured OD. The pathlength may then be used to determine the absorption coefficient of the sample at each wavelength. Alternatively, the optical pathlength may be used in further calculations to convert absorption coefficients to optical density.

Blood samples may be prepared and analyzed by system 1700 in a variety of configurations. In one embodiment, sample S is obtained by drawing blood, either using a syringe or as part of a blood flow system, and transferring the blood into sample chamber 903. In another embodiment, sample S is drawn into a sample container that is a sample chamber 903 adapted for insertion into system 1700.

Figure 44:
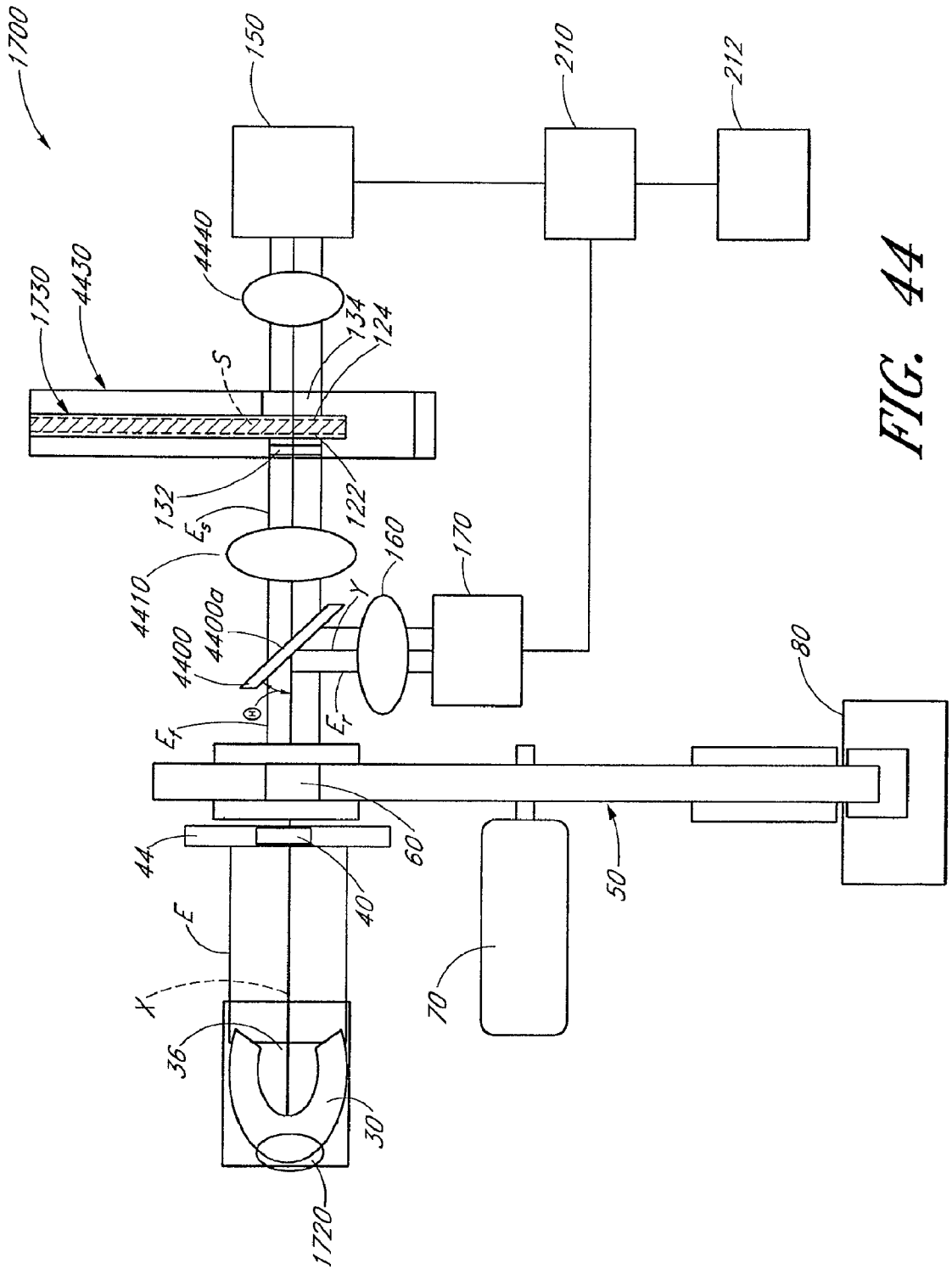
FIG. 44 is a schematic illustration of another embodiment of the analyte detection system.

FIG. 44 depicts another embodiment of the analyte detection system 1700, which may be generally similar to the embodiment illustrated in FIG. 17, except as further detailed below. Where possible, similar elements are identified with identical reference numerals in the depiction of the embodiments of FIGS. 17 and 44.

The detection system 1700 shown in FIG. 44 includes a collimator 30 located between source 1720 and filter 1725 and a beam sampling optics 90 between the filter and sample element 1730. Filter 1725 includes a primary filter 40 and a filter wheel assembly 4420 which can insert one of a plurality of optical filters into energy beam E. System 1700 also includes a sample detector 150 may be generally similar to sample detector 1725, except as further detailed below.

As shown in FIG. 44, energy beam E from source 1720 passes through collimator 30 through which the before reaching a primary optical filter 40 which is disposed downstream of a wide end 36 of the collimator 30. Filter 1725 is aligned with the source 1720 and collimator 30 on the major axis X and is preferably configured to operate as a broadband filter, allowing only a selected band, e.g. between about 2.5 μm and about 12.5 μm, of wavelengths emitted by the source 1720 to pass therethrough, as discussed below. In one embodiment, the energy source 1720 comprises an infrared source and the energy beam E comprises an infrared energy beam. One suitable energy source 1720 is the TOMA TECH™ IR-50 available from HawkEye Technologies of Milford, Conn.

With further reference to FIG. 44, primary filter 40 is mounted in a mask 44 so that only those portions of the energy beam E which are incident on the primary filter 40 can pass the plane of the mask-primary filter assembly. The primary filter 40 is generally centered on and oriented orthogonal to the major axis X and is preferably circular (in a plane orthogonal to the major axis X) with a diameter of about 8 mm. Of course, any other suitable size or shape may be employed. As discussed above, the primary filter 40 preferably operates as a broadband filter. In the illustrated embodiment, the primary filter 40 preferably allows only energy wavelengths between about 4 μm and about 11 μm to pass therethrough. However, other ranges of wavelengths can be selected. The primary filter 40 advantageously reduces the filtering burden of secondary optical filter(s) 60 disposed downstream of the primary filter 40 and improves the rejection of electromagnetic radiation having a wavelength outside of the desired wavelength band. Additionally, the primary filter 40 can help minimize the heating of the secondary filter(s) 60 by the energy beam E passing therethrough. Despite these advantages, the primary filter 40 and/or mask 44 may be omitted in alternative embodiments of the system 1700 shown in FIG. 44.

The primary filter 40 is preferably configured to substantially maintain its operating characteristics (center wavelength, passband width) where some or all of the energy beam E deviates from normal incidence by a cone angle of up to about twelve degrees relative to the major axis X. In further embodiments, this cone angle may be up to about 15 to 35 degrees, or from about 15 degrees or 20 degrees. The primary filter 40 may be said to "substantially maintain" its operating characteristics where any changes therein are insufficient to affect the performance or operation of the detection system 1700 in a manner that would raise significant concerns for the user(s) of the system in the context in which the system 1700 is employed.

In the embodiment illustrated in FIG. 44, filter wheel assembly 4420 includes an optical filter wheel 50 and a stepper motor 70 connected to the filter wheel and configured to generate a force to rotate the filter wheel 50. Additionally, a position sensor 80 is disposed over a portion of the circumference of the filter wheel 50 and may be configured to detect the angular position of the filter wheel 50 and to generate a corresponding filter wheel position signal, thereby indicating which filter is in position on the major axis X. Alternatively, the stepper motor 70 may be configured to track or count its own rotation(s), thereby tracking the angular position of the filter wheel, and pass a corresponding position signal to the processor 210. Two suitable position sensors are models EE-SPX302-W2A and EE-SPX402-W2A available from Omron Corporation of Kyoto, Japan.

Optical filter wheel 50 is employed as a varying-passband filter, to selectively position the secondary filter(s) 60 on the major axis X and/or in the energy beam E. The filter wheel 50 can therefore selectively tune the wavelength(s) of the energy beam E downstream of the wheel 50. These wavelength(s) vary according to the characteristics of the secondary filter(s) 60 mounted in the filter wheel 50. The filter wheel 50 positions the secondary filter(s) 60 in the energy beam E in a "one-at-a-time" fashion to sequentially vary, as discussed above, the wavelengths or wavelength bands employed to analyze the material sample S. An alternative to filter wheel 50 is a linear filter translated by a motor (not shown). The linear filter may be, for example, a linear array of separate filters or a single filter with filter properties that change in a linear dimension.

In alternative arrangements, the single primary filter 40 depicted in FIG. 44 may be replaced or supplemented with additional primary filters mounted on the filter wheel 50 upstream of each of the secondary filters 60. As yet another alternative, the primary filter 40 could be implemented as a primary filter wheel (not shown) to position different primary filters on the major axis X at different times during operation of the detection system 1700, or as a tunable filter.

Figure 45:
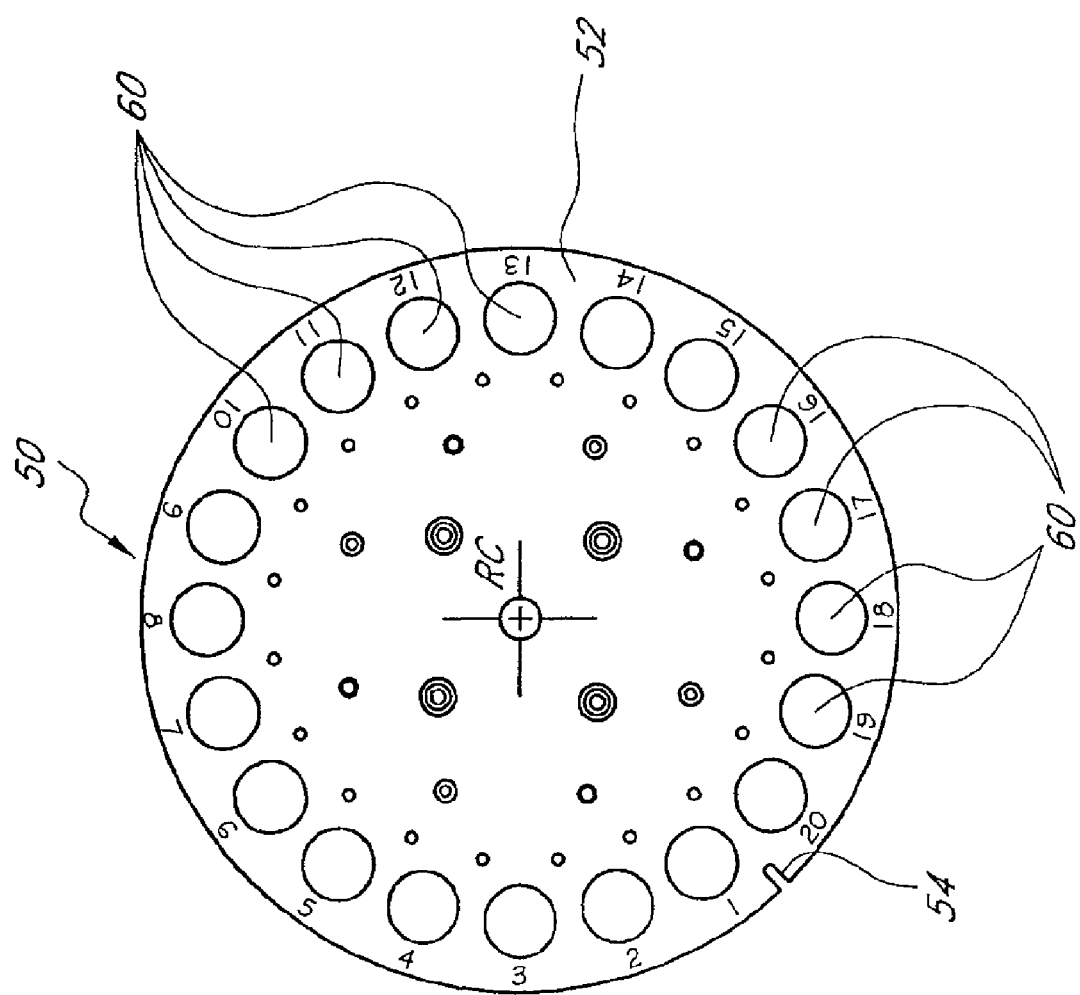
FIG. 45 is a plan view of one embodiment of a filter wheel suitable for use in the analyte detection system depicted in FIG. 44.

The filter wheel 50, in the embodiment depicted in FIG. 45, can comprise a wheel body 52 and a plurality of secondary filters 60 disposed on the body 52, the center of each filter being equidistant from a rotational center RC of the wheel body. The filter wheel 50 is configured to rotate about an axis which is (i) parallel to the major axis X and (ii) spaced from the major axis X by an orthogonal distance approximately equal to the distance between the rotational center RC and any of the center(s) of the secondary filter(s) 60. Under this arrangement, rotation of the wheel body 52 advances each of the filters sequentially through the major axis X, so as to act upon the energy beam E. However, depending on the analyte (s) of interest or desired measurement speed, only a subset of the filters on the wheel 50 may be employed in a given measurement run. A home position notch 54 may be provided to indicate the home position of the wheel 50 to a position sensor 80.

In one embodiment, the wheel body 52 can be formed from molded plastic, with each of the secondary filters 60 having, for example a thickness of 1 mm and a 10 mm×10 mm or a 5 mm×5 mm square configuration. Each of the filters 60, in this embodiment of the wheel body, is axially aligned with a circular aperture of 4 mm diameter, and the aperture centers define a circle of about 1.70 inches diameter, which circle is concentric with the wheel body 52. The body 52 itself is circular, with an outside diameter of 2.00 inches.

Each of the secondary filter(s) 60 is preferably configured to operate as a narrow band filter, allowing only a selected energy wavelength or wavelength band (i.e., a filtered energy beam (Ef) to pass therethrough. As the filter wheel 50 rotates about its rotational center RC, each of the secondary filter(s) 60 is, in turn, disposed along the major axis X for a selected dwell time corresponding to each of the secondary filter(s) 60.

The "dwell time" for a given secondary filter 60 is the time interval, in an individual measurement run of the system 1700, during which both of the following conditions are true: (i) the filter is disposed on the major axis X; and (ii) the source 1720 is energized. The dwell time for a given filter may be greater than or equal to the time during which the filter is disposed on the major axis X during an individual measurement run. In one embodiment of the analyte detection system 1700, the dwell time corresponding to each of the secondary filter(s) 60 is less than about 1 second. However, the secondary filter(s) 60 can have other dwell times, and each of the filter(s) 60 may have a different dwell time during a given measurement run.

From the secondary filter 60, the filtered energy beam (Ef) passes through a beam sampling optics 90, which includes a beam splitter 4400 disposed along the major axis X and having a face 4400a disposed at an included angle θ relative to the major axis X. The splitter 4400 preferably separates the filtered energy beam (Ef) into a sample beam (Es) and a reference beam (Er).

With further reference to FIG. 44, the sample beam (Es) passes next through a first lens 4410 aligned with the splitter 4400 along the major axis X. The first lens 4410 is configured to focus the sample beam (Es) generally along the axis X onto the material sample S. The sample S is preferably disposed in a sample element 1730 between a first window 122 and a second window 124 of the sample element 1730. The sample element 1730 is further preferably removably disposed in a holder 4430, and the holder 4430 has a first opening 132 and a second opening 134 configured for alignment with the first window 122 and second window 124, respectively. Alternatively, the sample element 1730 and sample S may be disposed on the major axis X without use of the holder 4430.

At least a fraction of the sample beam (Es) is transmitted through the sample S and continues onto a second lens 4440 disposed along the major axis X. The second lens 4440 is configured to focus the sample beam (Es) onto a sample detector 150, thus increasing the flux density of the sample beam (Es) incident upon the sample detector 150. The sample detector 150 is configured to generate a signal corresponding to the detected sample beam (Es) and to pass the signal to a processor 210, as discussed in more detail below.

Beam sampling optics 90 further includes a third lens 160 and a reference detector 170. The reference beam (Er) is directed by beam sampling optics 90 from the beam splitter 4400 to a third lens 160 disposed along a minor axis Y generally orthogonal to the major axis X. The third lens 160 is configured to focus the reference beam (Er) onto reference detector 170, thus increasing the flux density of the reference beam (Er) incident upon the reference detector 170. In one embodiment, the lenses 4410, 4440, 160 may be formed from a material which is highly transmissive of infrared radiation, for example germanium or silicon. In addition, any of the lenses 4410, 4440 and 160 may be implemented as a system of lenses, depending on the desired optical performance. The reference detector 170 is also configured to generate a signal corresponding to the detected reference beam (Er) and to pass the signal to the processor 210, as discussed in more detail below. Except as noted below, the sample and reference detectors 150, 170 may be generally similar to the detector 1745 illustrated in FIG. 17. Based on signals received from the sample and reference detectors 150, 170, the processor 210 computes the concentration(s), absorbance(s), transmittance(s), etc. relating to the sample S by executing a data processing algorithm or program instructions residing within the memory 212 accessible by the processor 210.

In further variations of the detection system 1700 depicted in FIG. 44, beam sampling optics 90, including the beam splitter 4400, reference detector 170 and other structures on the minor axis Y may be omitted, especially where the output intensity of the source 1720 is sufficiently stable to obviate any need to reference the source intensity in operation of the detection system 1700. Thus, for example, sufficient signals may be generated by detectors 170 and 150 with one or more of lenses 4410, 4440, 160 omitted. Furthermore, in any of the embodiments of the analyte detection system 1700 disclosed herein, the processor 210 and/or memory 212 may reside partially or wholly in a standard personal computer ("PC") coupled to the detection system 1700.

Figure 46:
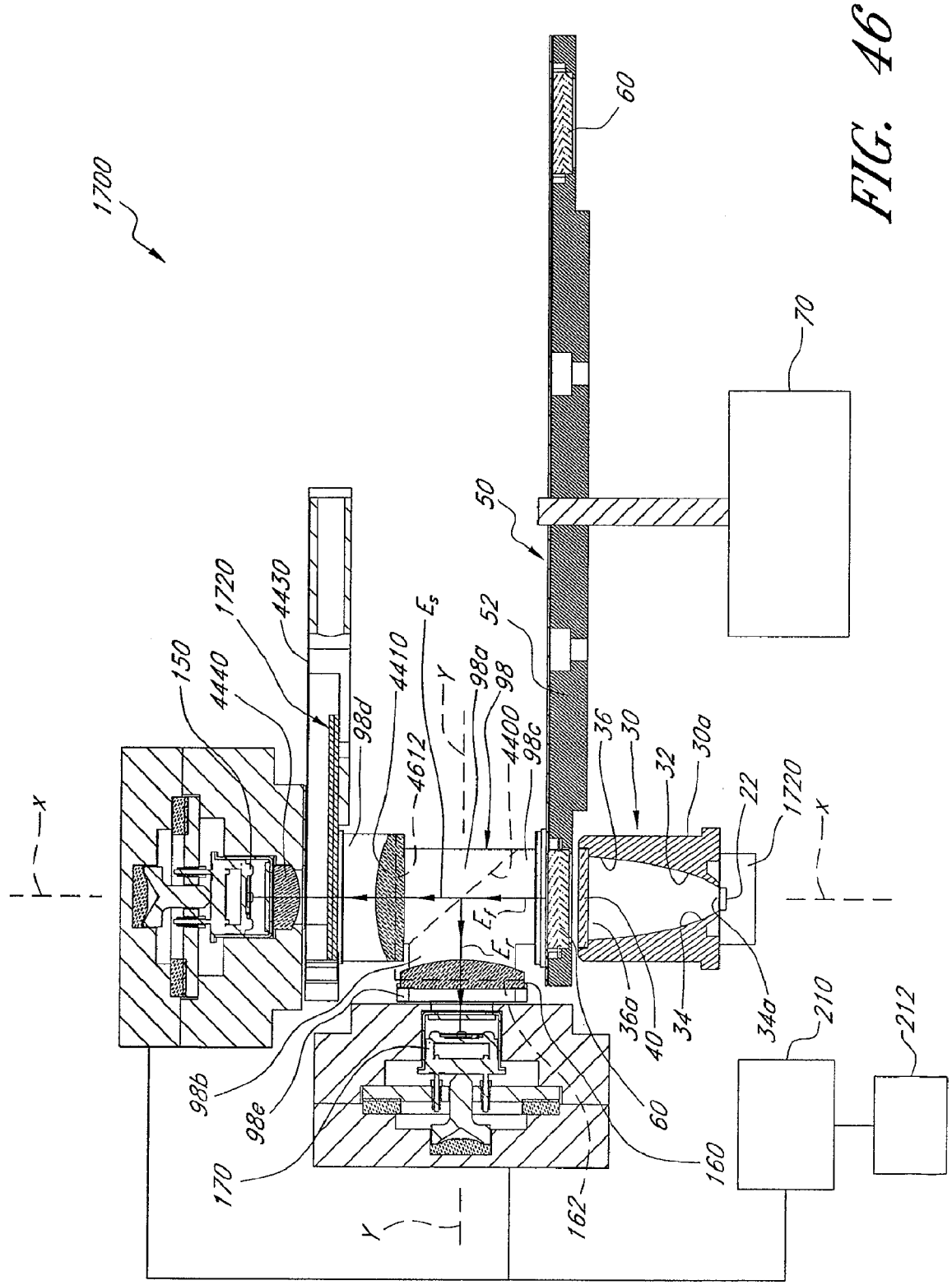
FIG. 46 is a partial sectional view of another embodiment of an analyte detection system.

FIG. 46 depicts a partial cross-sectional view of another embodiment of an analyte detection system 1700, which may be generally similar to any of the embodiments illustrated in FIGS. 17, 44, and 45, except as further detailed below. Where possible, similar elements are identified with identical reference numerals in the depiction of the embodiments of FIGS. 17, 44, and 45.

The energy source 1720 of the embodiment of FIG. 46 preferably comprises an emitter area 22 which is substantially centered on the major axis X. In one embodiment, the emitter area 22 may be square in shape. However the emitter area 22 can have other suitable shapes, such as rectangular, circular, elliptical, etc. One suitable emitter area 22 is a square of about 1.5 mm on a side; of course, any other suitable shape or dimensions may be employed.

The energy source 1720 is preferably configured to selectably operate at a modulation frequency between about 1 Hz and 30 Hz and have a peak operating temperature of between about 1070 degrees Kelvin and 1170 degrees Kelvin. Additionally, the source 1720 preferably operates with a modulation depth greater than about 80% at all modulation frequencies. The energy source 1720 preferably emits electromagnetic radiation in any of a number of spectral ranges, e.g., within infrared wavelengths; in the mid-infrared wavelengths; above about 0.8 µm; between about 5.0 µm and about 20.0 µm; and/or between about 5.25 µm and about 12.0 µm. However, in other embodiments, the detection system 1700 may employ an energy source 1720 which is unmodulated and/or which emits in wavelengths found anywhere from the visible spectrum through the microwave spectrum, for example anywhere from about 0.4 µm to greater than about 100 µm. In still other embodiments, the energy source 1720 can emit electromagnetic radiation in wavelengths between about 3.5 µm and about 14 µm, or between about 0.8 µm and about 2.5 µm, or between about 2.5 µm and 20 µm, or between about 20 µm and about 100 µm, or between about 6.85 µm and about 10.10 µm. In yet other embodiments, the energy source 1720 can emit electromagnetic radiation within the radio frequency (RF) range or the terahertz range. All of the above-recited operating characteristics are merely exemplary, and the source 1720 may have any operating characteristics suitable for use with the analyte detection system 1700.

A power supply (not shown) for the energy source 1720 is preferably configured to selectably operate with a duty cycle of between about 30% and about 70%. Additionally, the power supply is preferably configured to selectably operate at a modulation frequency of about 10 Hz, or between about 1 Hz and about 30 Hz. The operation of the power supply can be in the form of a square wave, a sine wave, or any other waveform defined by a user.

With further reference to FIG. 46, the collimator 30 comprises a tube 30a with one or more highly-reflective inner surfaces 32 which diverge from a relatively narrow upstream end 34 to a relatively wide downstream end 36 as they extend downstream, away from the energy source 1720. The narrow end 34 defines an upstream aperture 34a which is situated adjacent the emitter area 22 and permits radiation generated by the emitter area to propagate downstream into the collimator. The wide end 36 defines a downstream aperture 36a. Like the emitter area 22, each of the inner surface(s) 32, upstream aperture 34a and downstream aperture 36a is preferably substantially centered on the major axis X.

As illustrated in FIG. 46, the inner surface(s) 32 of the collimator may have a generally curved shape, such as a parabolic, hyperbolic, elliptical or spherical shape. One suitable collimator 30 is a compound parabolic concentrator (CPC). In one embodiment, the collimator 30 can be up to about 20 mm in length. In another embodiment, the collimator 30 can be up to about 30 mm in length. However, the collimator 30 can have any length, and the inner surface(s) 32 may have any shape, suitable for use with the analyte detection system 1700.

The inner surfaces 32 of the collimator 30 cause the rays making up the energy beam E to straighten (i.e., propagate at angles increasingly parallel to the major axis X) as the beam E advances downstream, so that the energy beam E becomes increasingly or substantially cylindrical and oriented substantially parallel to the major axis X. Accordingly, the inner surfaces 32 are highly reflective and minimally absorptive in the wavelengths of interest, such as infrared wavelengths.

The tube 30a itself may be fabricated from a rigid material such as aluminum, steel, or any other suitable material, as long as the inner surfaces 32 are coated or otherwise treated to be highly reflective in the wavelengths of interest. For example, a polished gold coating may be employed. Preferably, the inner surface(s) 32 of the collimator 30 define a circular cross-section when viewed orthogonal to the major axis X; however, other cross-sectional shapes, such as a square or other polygonal shapes, parabolic or elliptical shapes may be employed in alternative embodiments.

As noted above, the filter wheel 50 shown in FIG. 46 comprises a plurality of secondary filters 60 which preferably operate as narrow band filters, each filter allowing only energy of a certain wavelength or wavelength band to pass therethrough. In one configuration suitable for detection of glucose in a sample S, the filter wheel 50 comprises twenty or twenty-two secondary filters 60, each of which is configured to allow a filtered energy beam (Ef) to travel therethrough with a nominal wavelength approximately equal to one of the following: 3 µm, 4.06 µm, 4.6 µm, 4.9 µm, 5.25 µm, 6.12 µm, 6.47 µm, 7.98 µm, 8.35 µm, 9.65 µm, and 12.2 µm. (Moreover, this set of wavelengths may be employed with or in any of the embodiments of the analyte detection system 1700 disclosed herein.) Each secondary filter's 60 center wavelength is preferably equal to the desired nominal wavelength plus or minus about 2%. Additionally, the secondary filters 60 are preferably configured to have a bandwidth of about 0.2 µm, or alternatively equal to the nominal wavelength plus or minus about 2%-10%.

In another embodiment, the filter wheel 50 comprises twenty secondary filters 60, each of which is configured to allow a filtered energy beam (Ef) to travel therethrough with a nominal center wavelengths of: 4.275 µm, 4.5 µm, 4.7 µm, 5.0 µm, 5.3 µm, 6.056 µm, 7.15 µm, 7.3 µm, 7.55 µm, 7.67 µm, 8.06 µm, 8.4 µm, 8.56 µm, 8.87 µm, 9.15 µm, 9.27 µm, 9.48 µm, 9.68 µm, 9.82 µm, and 10.06 µm. (This set of wavelengths may also be employed with or in any of the embodiments of the analyte detection system 1700 disclosed herein.) In still another embodiment, the secondary filters 60 may conform to any one or combination of the following specifications: center wavelength tolerance of ±0.01 µm; half-power bandwidth tolerance of ±0.01 µm; peak transmission greater than or equal to 75%; cut-on/cut-off slope less than 2%; center-wavelength temperature coefficient less than 0.01% per degree Celsius; out of band attenuation greater than OD 5 from 3 µm to 12 µm; flatness less than 1.0 waves at 0.6328 µm; surface quality of E-E per Mil-F-48616; and overall thickness of about 1 mm.

In still another embodiment, the secondary filters mentioned above may conform to any one or combination of the following half-power bandwidth ("HPBW") specifications:

| Center Wavelength (µm) | HPBW (µm) |
|---|---|
| 4.275 | 0.05 |
| 4.5 | 0.18 |
| 4.7 | 0.13 |
| 5.0 | 0.1 |
| 5.3 | 0.13 |
| 6.056 | 0.135 |
| 7.15 | 0.19 |
| 7.3 | 0.19 |
| 7.55 | 0.18 |
| 7.67 | 0.197 |
| 8.06 | 0.3 |
| 8.4 | 0.2 |
| 8.56 | 0.18 |
| 8.87 | 0.2 |
| 9.15 | 0.15 |
| 9.27 | 0.14 |
| 9.48 | 0.23 |
| 9.68 | 0.3 |

-continued

| Center Wavelength (μm) | HPBW (μm) |
|---|---|
| 9.82 | 0.34 |
| 10.06 | 0.2 |

In still further embodiments, the secondary filters may have a center wavelength tolerance of ±0.5% and a half-power bandwidth tolerance of ±0.02 μm.

Of course, the number of secondary filters employed, and the center wavelengths and other characteristics thereof, may vary in further embodiments of the system 1700, whether such further embodiments are employed to detect glucose, or other analytes instead of or in addition to glucose. For example, in another embodiment, the filter wheel 50 can have fewer than fifty secondary filters 60. In still another embodiment, the filter wheel 50 can have fewer than twenty secondary filters 60. In yet another embodiment, the filter wheel 50 can have fewer than ten secondary filters 60.

In one embodiment, the secondary filters 60 each measure about 10 mm long by 10 mm wide in a plane orthogonal to the major axis X, with a thickness of about 1 mm. However, the secondary filters 60 can have any other (e.g., smaller) dimensions suitable for operation of the analyte detection system 1700. Additionally, the secondary filters 60 are preferably configured to operate at a temperature of between about 5° C. and about 35° C. and to allow transmission of more than about 75% of the energy beam E therethrough in the wavelength(s) which the filter is configured to pass.

According to the embodiment illustrated in FIG. 46, the primary filter 40 operates as a broadband filter and the secondary filters 60 disposed on the filter wheel 50 operate as narrow band filters. However, one of ordinary skill in the art will realize that other structures can be used to filter energy wavelengths according to the embodiments described herein. For example, the primary filter 40 may be omitted and/or an electronically tunable filter or Fabry-Perot interferometer (not shown) can be used in place of the filter wheel 50 and secondary filters 60. Such a tunable filter or interferometer can be configured to permit, in a sequential, "one-at-a-time" fashion, each of a set of wavelengths or wavelength bands of electromagnetic radiation to pass therethrough for use in analyzing the material sample S.

A reflector tube 98 is preferably positioned to receive the filtered energy beam (Ef) as it advances from the secondary filter(s) 60. The reflector tube 98 is preferably secured with respect to the secondary filter(s) 60 to substantially prevent introduction of stray electromagnetic radiation, such as stray light, into the reflector tube 98 from outside of the detection system 1700. The inner surfaces of the reflector tube 98 are highly reflective in the relevant wavelengths and preferably have a cylindrical shape with a generally circular cross-section orthogonal to the major and/or minor axis X, Y. However, the inner surface of the tube 98 can have a cross-section of any suitable shape, such as oval, square, rectangular, etc. Like the collimator 30, the reflector tube 98 may be formed from a rigid material such as aluminum, steel, etc., as long as the inner surfaces are coated or otherwise treated to be highly reflective in the wavelengths of interest. For example, a polished gold coating may be employed.

According to the embodiment illustrated in FIG. 46, the reflector tube 98 preferably comprises a major section 98a and a minor section 98b. As depicted, the reflector tube 98 can be T-shaped with the major section 98a having a greater length than the minor section 98b. In another example, the major section 98a and the minor section 98b can have the same length. The major section 98a extends between a first end 98c and a second end 98d along the major axis X. The minor section 98b extends between the major section 98a and a third end 98e along the minor axis Y.

The major section 98a conducts the filtered energy beam (Ef) from the first end 98c to the beam splitter 4400, which is housed in the major section 98a at the intersection of the major and minor axes X, Y. The major section 98a also conducts the sample beam (Es) from the beam splitter 4400, through the first lens 4410 and to the second end 98d. From the second end 98d the sample beam (Es) proceeds through the sample element 1730, holder 4430 and second lens 4440, and to the sample detector 150. Similarly, the minor section 98b conducts the reference beam (Er) through beam sampling optics 90 from the beam splitter 4400, through the third lens 160 and to the third end 98e. From the third end 98e the reference beam (Er) proceeds to the reference detector 170.

The sample beam (Es) preferably comprises from about 75% to about 85% of the energy of the filtered energy beam (Ef). More preferably, the sample beam (Es) comprises about 80% of the energy of the filtered energy beam (Es). The reference beam (Er) preferably comprises from about 10% and about 50% of the energy of the filtered energy beam (Es). More preferably, the reference beam (Er) comprises about 20% of the energy of the filtered energy beam (Ef). Of course, the sample and reference beams may take on any suitable proportions of the energy beam E.

The reflector tube 98 also houses the first lens 4410 and the third lens 160. As illustrated in FIG. 46, the reflector tube 98 houses the first lens 4410 between the beam splitter 4400 and the second end 98d. The first lens 4410 is preferably disposed so that a plane 4612 of the lens 4410 is generally orthogonal to the major axis X. Similarly, the tube 98 houses the third lens 160 between the beam splitter 4400 and the third end 98e. The third lens 160 is preferably disposed so that a plane 162 of the third lens 160 is generally orthogonal to the minor axis Y. The first lens 4410 and the third lens 160 each has a focal length configured to substantially focus the sample beam (Es) and reference beam (Er), respectively, as the beams (Es, Er) pass through the lenses 4410, 160. In particular, the first lens 4410 is configured, and disposed relative to the holder 4430, to focus the sample beam (Es) so that substantially the entire sample beam (Es) passes through the material sample S, residing in the sample element 1730. Likewise, the third lens 160 is configured to focus the reference beam (Er) so that substantially the entire reference beam (Er) impinges onto the reference detector 170.

The sample element 1730 is retained within the holder 4430, which is preferably oriented along a plane generally orthogonal to the major axis X. The holder 4430 is configured to be slidably displaced between a loading position and a measurement position within the analyte detection system 1700. In the measurement position, the holder 4430 contacts a stop edge 136 which is located to orient the sample element 1730 and the sample S contained therein on the major axis X.

The structural details of the holder 4430 depicted in FIG. 46 are unimportant, so long as the holder positions the sample element 1730 and sample S on and substantially orthogonal to the major axis X, while permitting the energy beam E to pass through the sample element and sample. As with the embodiment depicted in FIG. 44, the holder 4430 may be omitted and the sample element 1730 positioned alone in the depicted location on the major axis X. However, the holder 4430 is useful where the sample element 1730 (discussed in further detail below) is constructed from a highly brittle or fragile material, such as barium fluoride, or is manufactured to be extremely thin.

As with the embodiment depicted in FIG. 44, the sample and reference detectors 150, 170 shown in FIG. 46 respond to radiation incident thereon by generating signals and passing them to the processor 210. Based these signals received from the sample and reference detectors 150, 170, the processor 210 computes the concentration(s), absorbance(s), transmittance(s), etc. relating to the sample S by executing a data processing algorithm or program instructions residing within the memory 212 accessible by the processor 210. In further variations of the detection system 1700 depicted in FIG. 46, the beam splitter 4400, reference detector 170 and other structures on the minor axis Y may be omitted, especially where the output intensity of the source 1720 is sufficiently stable to obviate any need to reference the source intensity in operation of the detection system 1700.

Figure 47:
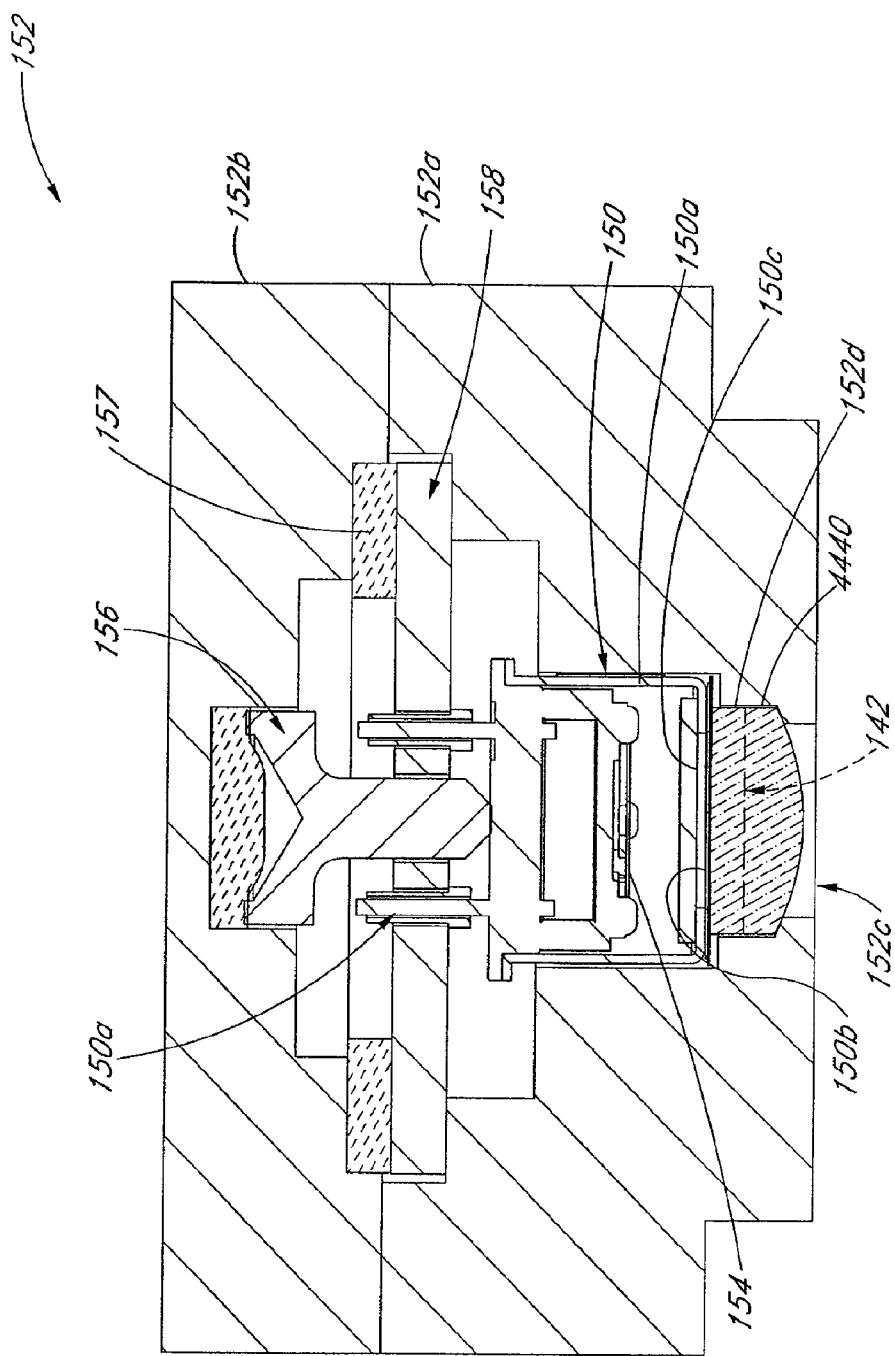
FIG. 47 is a detailed sectional view of a sample detector of the analyte detection system illustrated in FIG. 46.

FIG. 47 depicts a sectional view of the sample detector 150 in accordance with one embodiment. Sample detector 150 is mounted in a detector housing 152 having a receiving portion 152a and a cover 152b. However, any suitable structure may be used as the sample detector 150 and housing 152. The receiving portion 152a preferably defines an aperture 152c and a lens chamber 152d, which are generally aligned with the major axis X when the housing 152 is mounted in the analyte detection system 1700. The aperture 152c is configured to allow at least a fraction of the sample beam (Es) passing through the sample S and the sample element 1730 to advance through the aperture 152c and into the lens chamber 152d.

The receiving portion 152a houses the second lens 4440 in the lens chamber 152d proximal to the aperture 152c. The sample detector 150 is also disposed in the lens chamber 152d downstream of the second lens 4440 such that a detection plane 154 of the detector 150 is substantially orthogonal to the major axis X. The second lens 4440 is positioned such that a plane 142 of the lens 4440 is substantially orthogonal to the major axis X. The second lens 4440 is configured, and is preferably disposed relative to the holder 4430 and the sample detector 150, to focus substantially all of the sample beam (Es) onto the detection plane 154, thereby increasing the flux density of the sample beam (Es) incident upon the detection plane 154.

With further reference to FIG. 47, a support member 156 preferably holds the sample detector 150 in place in the receiving portion 152a. In the illustrated embodiment, the support member 156 is a spring 156 disposed between the sample detector 150 and the cover 152b. The spring 156 is configured to maintain the detection plane 154 of the sample detector 150 substantially orthogonal to the major axis X. A gasket 157 is preferably disposed between the cover 152b and the receiving portion 152a and surrounds the support member 156.

The receiving portion 152a preferably also houses a printed circuit board 158 disposed between the gasket 157 and the sample detector 150. The board 158 connects to the sample detector 150 through at least one connecting member 150a. The sample detector 150 is configured to generate a detection signal corresponding to the sample beam (Es) incident on the detection plane 154. The sample detector 150 communicates the detection signal to the circuit board 158 through the connecting member 150a, and the board 158 transmits the detection signal to the processor 210.

In one embodiment, the sample detector 150 comprises a generally cylindrical housing 150a, e.g. a type TO-39 "metal can" package, which defines a generally circular housing aperture 150b at its "upstream" end. In one embodiment, the housing 150a has a diameter of about 0.323 inches and a depth of about 0.248 inches, and the aperture 150b may have a diameter of about 0.197 inches.

A detector window 150c is disposed adjacent the aperture 150b, with its upstream surface preferably about 0.078 inches (+/−0.004 inches) from the detection plane 154. (The detection plane 154 is located about 0.088 inches (+/−0.004 inches) from the upstream edge of the housing 150a, where the housing has a thickness of about 0.010 inches.) The detector window 150c is preferably transmissive of infrared energy in at least a 3-12 micron passband; accordingly, one suitable material for the window 150c is germanium. The endpoints of the passband may be "spread" further to less than 2.5 microns, and/or greater than 12.5 microns, to avoid unnecessary absorbance in the wavelengths of interest. Preferably, the transmittance of the detector window 150c does not vary by more than 2% across its passband. The window 150c is preferably about 0.020 inches in thickness. The sample detector 150 preferably substantially retains its operating characteristics across a temperature range of −20 to +60 degrees Celsius.

Figure 48:
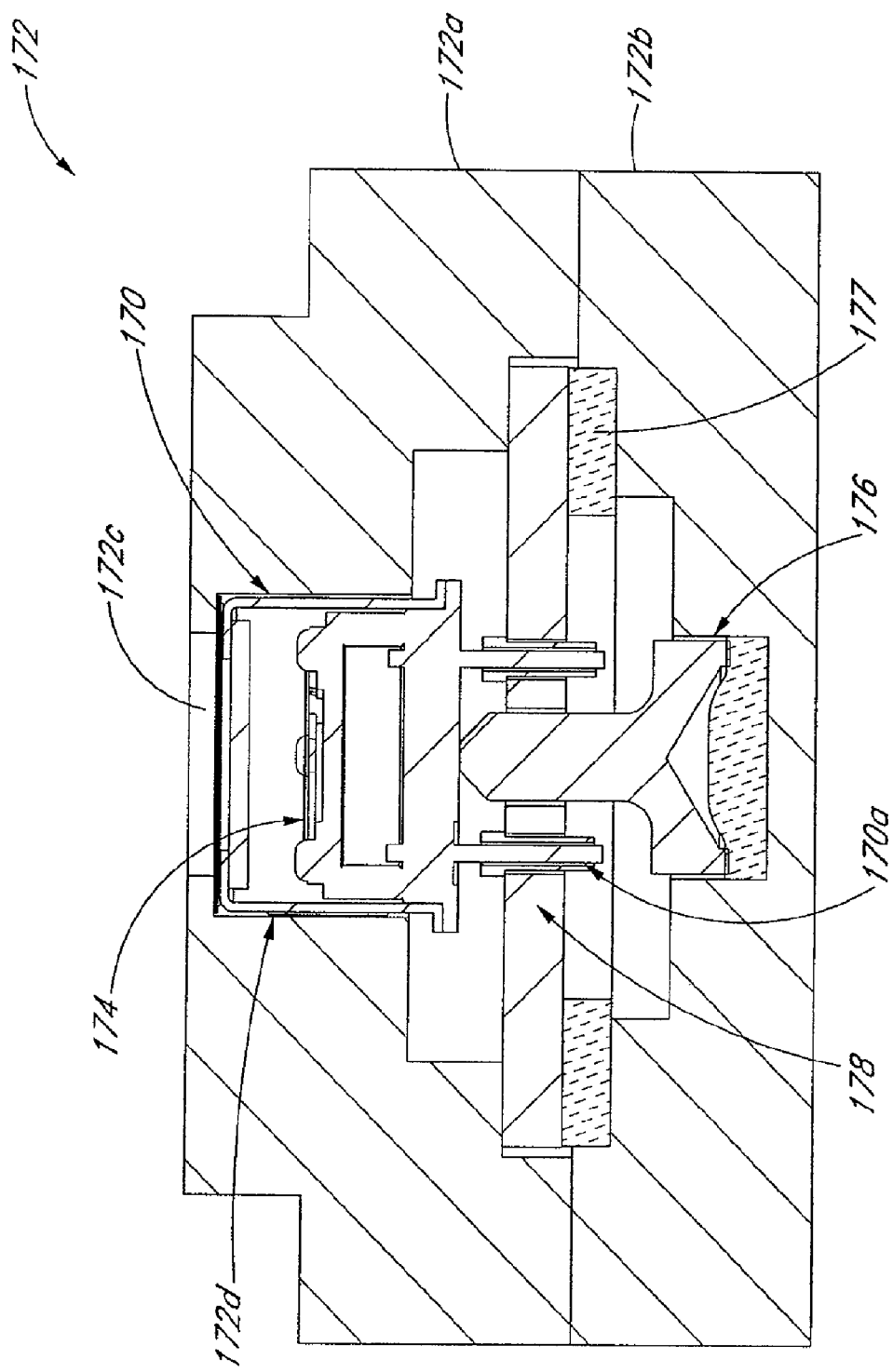
FIG. 48 is a detailed sectional view of a reference detector of the analyte detection system illustrated in FIG. 46.

FIG. 48 depicts a sectional view of the reference detector 170 in accordance with one embodiment. The reference detector 170 is mounted in a detector housing 172 having a receiving portion 172a and a cover 172b. However, any suitable structure may be used as the sample detector 150 and housing 152. The receiving portion 172a preferably defines an aperture 172c and a chamber 172d which are generally aligned with the minor axis Y, when the housing 172 is mounted in the analyte detection system 1700. The aperture 172c is configured to allow the reference beam (Er) to advance through the aperture 172c and into the chamber 172d.

The receiving portion 172a houses the reference detector 170 in the chamber 172d proximal to the aperture 172c. The reference detector 170 is disposed in the chamber 172d such that a detection plane 174 of the reference detector 170 is substantially orthogonal to the minor axis Y. The third lens 160 is configured to substantially focus the reference beam (Er) so that substantially the entire reference beam (Er) impinges onto the detection plane 174, thus increasing the flux density of the reference beam (Er) incident upon the detection plane 174.

With further reference to FIG. 48, a support member 176 preferably holds the reference detector 170 in place in the receiving portion 172a. In the illustrated embodiment, the support member 176 is a spring 176 disposed between the reference detector 170 and the cover 172b. The spring 176 is configured to maintain the detection plane 174 of the reference detector 170 substantially orthogonal to the minor axis Y. A gasket 177 is preferably disposed between the cover 172b and the receiving portion 172a and surrounds the support member 176.

The receiving portion 172a preferably also houses a printed circuit board 178 disposed between the gasket 177 and the reference detector 170. The board 178 connects to the reference detector 170 through at least one connecting member 170a. The reference detector 170 is configured to generate a detection signal corresponding to the reference beam (Er) incident on the detection plane 174. The reference detector 170 communicates the detection signal to the circuit board 178 through the connecting member 170a, and the board 178 transmits the detection signal to the processor 210.

In one embodiment, the construction of the reference detector 170 is generally similar to that described above with regard to the sample detector 150.

In one embodiment, the sample and reference detectors 150, 170 are both configured to detect electromagnetic radiation in a spectral wavelength range of between about 0.8 μm and about 25 μm. However, any suitable subset of the foregoing set of wavelengths can be selected. In another embodiment, the detectors 150, 170 are configured to detect electromagnetic radiation in the wavelength range of between about 4 μm and about 12 μm. The detection planes 154, 174 of the detectors 150, 170 may each define an active area about 2 mm by 2 mm or from about 1 mm by 1 mm to about 5 mm by 5 mm; of course, any other suitable dimensions and proportions may be employed. Additionally, the detectors 150, 170 may be configured to detect electromagnetic radiation directed thereto within a cone angle of about 45 degrees from the major axis X.

In one embodiment, the sample and reference detector subsystems 150, 170 may further comprise a system (not shown) for regulating the temperature of the detectors. Such a temperature-regulation system may comprise a suitable electrical heat source, thermistor, and a proportional-plus-integral-plus-derivative (PID) control. These components may be used to regulate the temperature of the detectors 150, 170 at about 35° C. The detectors 150, 170 can also optionally be operated at other desired temperatures. Additionally, the PID control preferably has a control rate of about 60 Hz and, along with the heat source and thermistor, maintains the temperature of the detectors 150, 170 within about 0.1° C. of the desired temperature.

The detectors 150, 170 can operate in either a voltage mode or a current mode, wherein either mode of operation preferably includes the use of a pre-amp module. Suitable voltage mode detectors for use with the analyte detection system 1700 disclosed herein include: models LIE 302 and 312 by InfraTec of Dresden, Germany; model L2002 by BAE Systems of Rockville, Md.; and model LTS-1 by Dias of Dresden, Germany. Suitable current mode detectors include: InfraTec models LIE 301, 315, 345 and 355; and 2×2 current-mode detectors available from Dias.

In one embodiment, one or both of the detectors 150, 170 may meet the following specifications, when assuming an incident radiation intensity of about $9.26 \times 10^{-4}$ watts (rms) per cm$^2$, at 10 Hz modulation and within a cone angle of about 15 degrees: detector area of 0.040 cm$^2$ (2 mm×2 mm square); detector input of $3.70 \times 10^{-5}$ watts (rms) at 10 Hz; detector sensitivity of 360 volts per watt at 10 Hz; detector output of $1.333 \times 10^{-2}$ volts (rms) at 10 Hz; noise of $8.00 \times 10^{-8}$ volts/sqrtHz at 10 Hz; and signal-to-noise ratios of $1.67 \times 10^5$ rms/sqrtHz and 104.4 dB/sqrtHz; and detectivity of $1.00 \times 10^9$ cm sqrtHz/watt.

In alternative embodiments, the detectors 150, 170 may comprise microphones and/or other sensors suitable for operation of the detection system 1700 in a photoacoustic mode.

The components of any of the embodiments of the analyte detection system 1700 may be partially or completely contained in an enclosure or casing (not shown) to prevent stray electromagnetic radiation, such as stray light, from contaminating the energy beam E. Any suitable casing may be used. Similarly, the components of the detection system 1700 may be mounted on any suitable frame or chassis (not shown) to maintain their operative alignment as depicted in FIGS. 17, 44, and 46. The frame and the casing may be formed together as a single unit, member or collection of members.

In one method of operation, the analyte detection system 1700 shown in FIG. 44 or 46 measures the concentration of one or more analytes in the material sample S, in part, by comparing the electromagnetic radiation detected by the sample and reference detectors 150, 170. During operation of the detection system 1700, each of the secondary filter(s) 60 is sequentially aligned with the major axis X for a dwell time corresponding to the secondary filter 60. (Of course, where an electronically tunable filter or Fabry-Perot interferometer is used in place of the filter wheel 50, the tunable filter or interferometer is sequentially tuned to each of a set of desired wavelengths or wavelength bands in lieu of the sequential alignment of each of the secondary filters with the major axis X.) The energy source 1720 is then operated at (any) modulation frequency, as discussed above, during the dwell time period. The dwell time may be different for each secondary filter 60 (or each wavelength or band to which the tunable filter or interferometer is tuned). In one embodiment of the detection system 1700, the dwell time for each secondary filter 60 is less than about 1 second. Use of a dwell time specific to each secondary filter 60 advantageously allows the detection system 1700 to operate for a longer period of time at wavelengths where errors can have a greater effect on the computation of the analyte concentration in the material sample S. Correspondingly, the detection system 1700 can operate for a shorter period of time at wavelengths where errors have less effect on the computed analyte concentration. The dwell times may otherwise be nonuniform among the filters/wavelengths/bands employed in the detection system.

For each secondary filter 60 selectively aligned with the major axis X, the sample detector 150 detects the portion of the sample beam (Es), at the wavelength or wavelength band corresponding to the secondary filter 60, that is transmitted through the material sample S. The sample detector 150 generates a detection signal corresponding to the detected electromagnetic radiation and passes the signal to the processor 210. Simultaneously, the reference detector 170 detects the reference beam (Er) transmitted at the wavelength or wavelength band corresponding to the secondary filter 60. The reference detector 170 generates a detection signal corresponding to the detected electromagnetic radiation and passes the signal to the processor 210. Based on the signals passed to it by the detectors 150, 170, the processor 210 computes the concentration of the analyte(s) of interest in the sample S, and/or the absorbance/transmittance characteristics of the sample S at one or more wavelengths or wavelength bands employed to analyze the sample. The processor 210 computes the concentration(s), absorbance(s), transmittance(s), etc. by executing a data processing algorithm or program instructions residing within the memory 212 accessible by the processor 210.

The signal generated by the reference detector may be used to monitor fluctuations in the intensity of the energy beam emitted by the source 1720, which fluctuations often arise due to drift effects, aging, wear or other imperfections in the source itself. This enables the processor 210 to identify changes in intensity of the sample beam (Es) that are attributable to changes in the emission intensity of the source 1720, and not to the composition of the sample S. By so doing, a potential source of error in computations of concentration, absorbance, etc. is minimized or eliminated.

In one embodiment, the detection system 1700 computes an analyte concentration reading by first measuring the electromagnetic radiation detected by the detectors 150, 170 at each center wavelength, or wavelength band, without the sample element 1730 present on the major axis X (this is known as an "air" reading). Second, the system 1700 measures the electromagnetic radiation detected by the detectors 150, 170 for each center wavelength, or wavelength band, with the material sample S present in the sample element 1730, and the sample element 1730 and sample S in position on the major axis X (i.e., a "wet" reading). Finally, the processor 180 computes the concentration(s), absorbance(s) and/or transmittances relating to the sample S based on these compiled readings.

In one embodiment, the plurality of air and wet readings are used to generate a pathlength corrected spectrum as follows. First, the measurements are normalized to give the transmission of the sample at each wavelength. Using both a signal and reference measurement at each wavelength, and letting $S_i$ represent the signal of detector 150 at wavelength i and $R_i$ represent the signal of detector 170 at wavelength i, the transmission, $\tau_i$ is computed as $\tau_i = S_i(\text{wet})/R_i(\text{wet})/S_i(\text{air})/R_i(\text{air})$. Optionally, the spectra may be calculated as the optical density, $OD_i$, as $-\text{Log}(T_i)$.

Next, the transmission over the wavelength range of approximately 4.5 μm to approximately 5.5 μm is analyzed to determine the pathlength. Specifically, since water is the primary absorbing species of blood over this wavelength region, and since the optical density is the product of the optical pathlength and the known absorption coefficient of water (OD=L σ, where L is the optical pathlength and σ is the absorption coefficient), any one of a number of standard curve fitting procedures may be used to determine the optical pathlength, L from the measured OD. The pathlength may then be used to determine the absorption coefficient of the sample at each wavelength. Alternatively, the optical pathlength may be used in further calculations to convert absorption coefficients to optical density.

Additional information on analyte detection systems, methods of use thereof, and related technologies may be found in the above-mentioned and incorporated U.S. patent application Publication No. 2005/0038357, published on Feb. 17, 2005, titled SAMPLE ELEMENT WITH BARRIER MATERIAL.

Section IV.C—Sample Element

Figure 18:
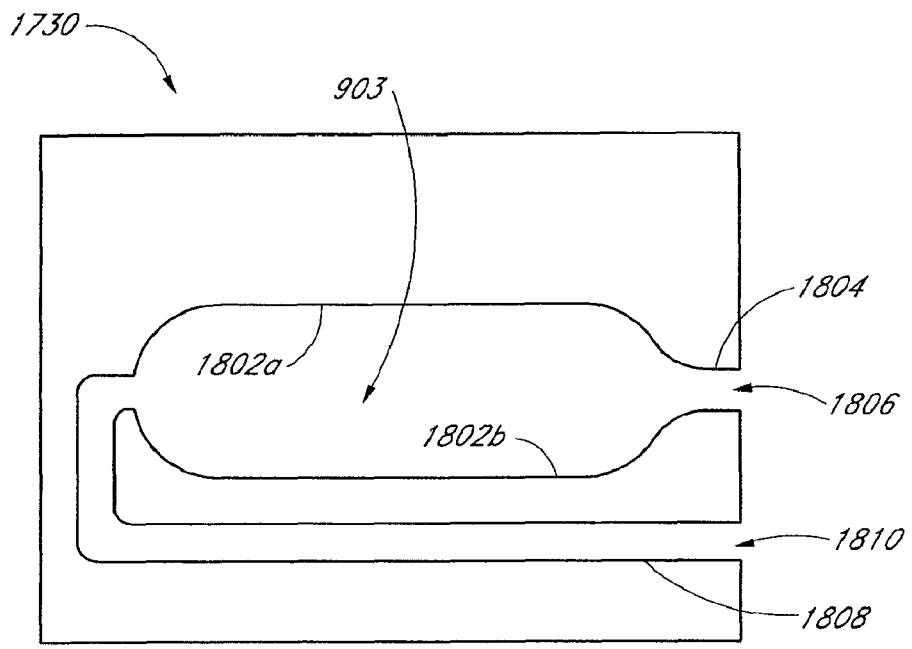
FIG. 18 is a top view of a cuvette for use in the apparatus of FIG. 17.
Figure 19:
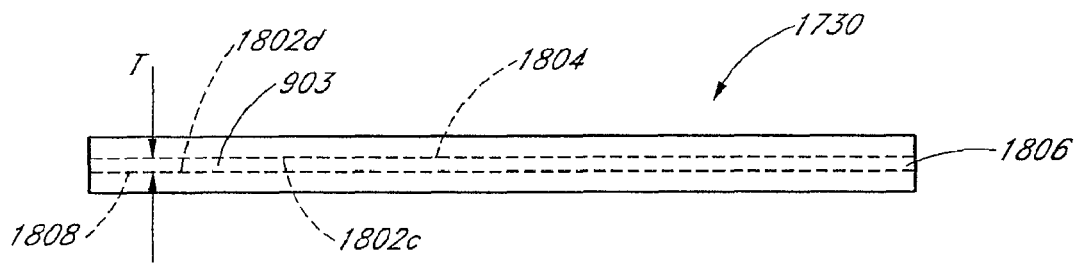
FIG. 19 is a side view of the cuvette of FIG. 18.
Figure 20:
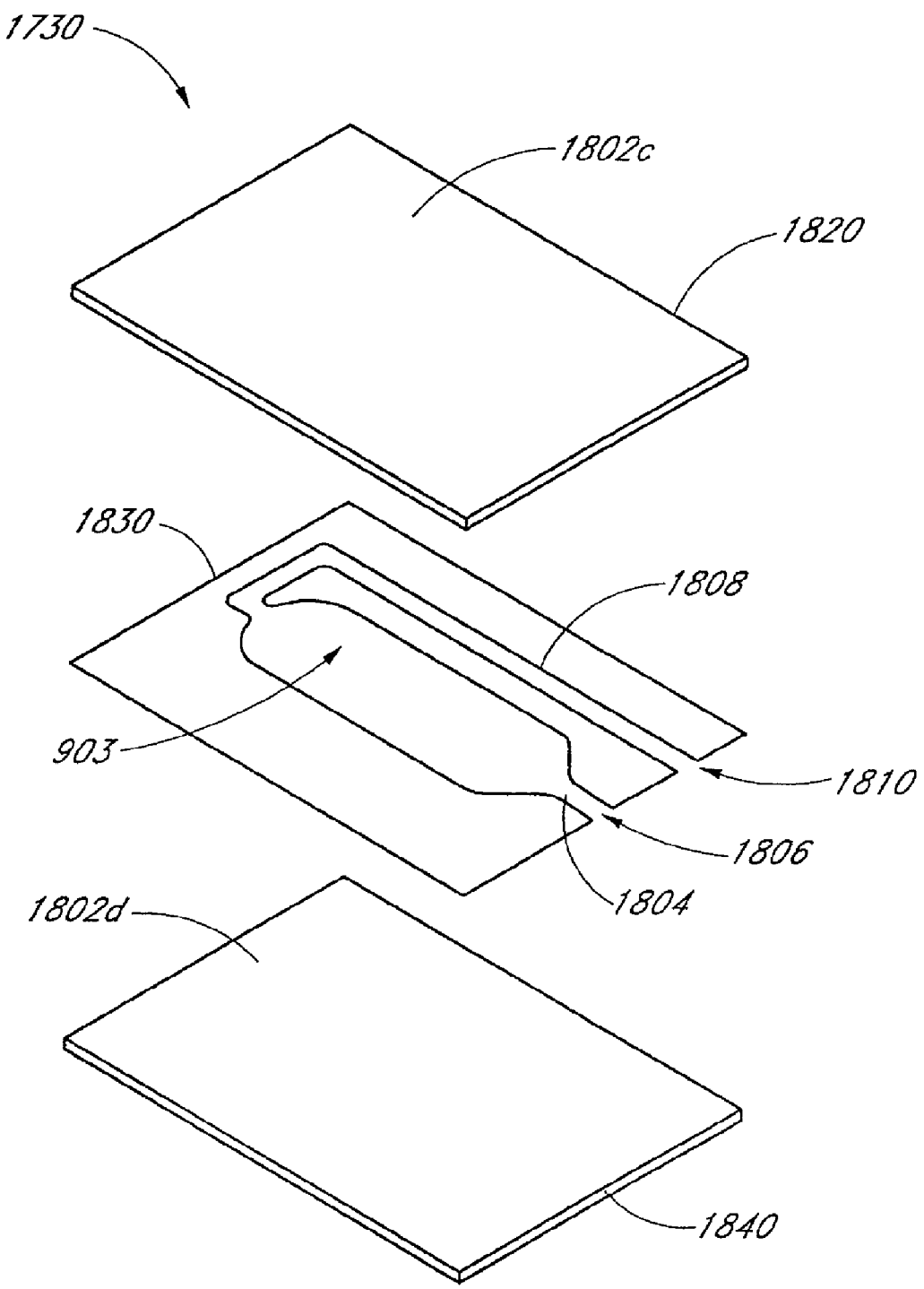
FIG. 20 is an exploded perspective view of the cuvette of FIG. 18.

FIG. 18 is a top view of a sample element 1730, FIG. 19 is a side view of the sample element, and FIG. 20 is an exploded perspective view of the sample element. In one embodiment of the present invention, sample element 1730 includes sample chamber 903 that is in fluid communication with and accepts filtered blood from sample preparation unit 332. The sample element 1730 comprises a sample chamber 903 defined by sample chamber walls 1802. The sample chamber 903 is configured to hold a material sample which may be drawn from a patient, for analysis by the detection system with which the sample element 1730 is employed.

In the embodiment illustrated in FIGS. 18-19, the sample chamber 903 is defined by first and second lateral chamber walls 1802a, 1802b and upper and lower chamber walls 1802c, 1802d; however, any suitable number and configuration of chamber walls may be employed. At least one of the upper and lower chamber walls 1802c, 1802d is formed from a material which is sufficiently transmissive of the wavelength(s) of electromagnetic radiation that are employed by the sample analysis apparatus 322 (or any other system with which the sample element is to be used). A chamber wall which is so transmissive may thus be termed a "window;" in one embodiment, the upper and lower chamber walls 1802c, 1802d comprise first and second windows so as to permit the relevant wavelength(s) of electromagnetic radiation to pass through the sample chamber 903. In another embodiment, only one of the upper and lower chamber walls 1802c, 1802d comprises a window; in such an embodiment, the other of the upper and lower chamber walls may comprise a reflective surface configured to back-reflect any electromagnetic energy emitted into the sample chamber 903 by the analyte detection system with which the sample element 1730 is employed. Accordingly, this embodiment is well suited for use with an analyte detection system in which a source and a detector of electromagnetic energy are located on the same side as the sample element.

In various embodiments, the material that makes up the window(s) of the sample element 1730 is completely transmissive, i.e., it does not absorb any of the electromagnetic radiation from the source 1720 and filters 1725 that is incident upon it. In another embodiment, the material of the window(s) has some absorption in the electromagnetic range of interest, but its absorption is negligible. In yet another embodiment, the absorption of the material of the window(s) is not negligible, but it is stable for a relatively long period of time. In another embodiment, the absorption of the window(s) is stable for only a relatively short period of time, but sample analysis apparatus 322 is configured to observe the absorption of the material and eliminate it from the analyte measurement before the material properties can change measurably. Materials suitable for forming the window(s) of the sample element 1730 include, but are not limited to, calcium fluoride, barium fluoride, germanium, silicon, polypropylene, polyethylene, or any polymer with suitable transmissivity (i.e., transmittance per unit thickness) in the relevant wavelength(s). Where the window(s) are formed from a polymer, the selected polymer can be isotactic, atactic or syndiotactic in structure, so as to enhance the flow of the sample between the window(s). One type of polyethylene suitable for constructing the sample element 1730 is type 220, extruded or blow molded, available from KUBE Ltd. of Staefa, Switzerland.

In one embodiment, the sample element 1730 is configured to allow sufficient transmission of electromagnetic energy having a wavelength of between about 4 μm and about 10.5 μm through the window(s) thereof. However, the sample element 1730 can be configured to allow transmission of wavelengths in any spectral range emitted by the energy source 1720. In another embodiment, the sample element 1730 is configured to receive an optical power of more than about 1.0 MW/cm$^2$ from the sample beam (Es) incident thereon for any electromagnetic radiation wavelength transmitted through the filter 1725. Preferably, the sample chamber 903 of the sample element 1730 is configured to allow a sample beam (Es) advancing toward the material sample S within a cone angle of 45 degrees from the major axis X (see FIG. 17) to pass therethrough.

In the embodiment illustrated in FIGS. 18-19, the sample element further comprises a supply passage 1804 extending from the sample chamber 903 to a supply opening 1806 and a vent passage 1808 extending from the sample chamber 903 to a vent opening 1810. While the vent and supply openings 1806, 1810 are shown at one end of the sample element 1730, in other embodiments the openings may be positioned on other sides of the sample element 1730, so long as it is in fluid communication with the passages 1804 and 1808, respectively.

In operation, the supply opening 1806 of the sample element 1730 is placed in contact with the material sample S, such as a fluid flowing from a patient. The fluid is then transported through the sample supply passage 1804 and into the sample chamber 903 via an external pump or by capillary action.

Where the upper and lower chamber walls 1802c, 1802d comprise windows, the distance T (measured along an axis substantially orthogonal to the sample chamber 903 and/or windows 1802a, 1802b, or, alternatively, measured along an axis of an energy beam (such as but not limited to the energy beam E discussed above) passed through the sample chamber 903) between them comprises an optical pathlength. In various embodiments, the pathlength is between about 1 µm and about 300 µm, between about 1 µm and about 100 µm, between about 25 µm and about 40 µm, between about 10 µm and about 40 µm, between about 25 µm and about 60 µm, or between about 30 µm and about 50 µm. In still other embodiments, the optical pathlength is about 50 µm, or about 25 µm. In some instances, it is desirable to hold the pathlength T to within about plus or minus 1 µm from any pathlength specified by the analyte detection system with which the sample element 1730 is to be employed. Likewise, it may be desirable to orient the walls 1802c, 1802d with respect to each other within plus or minus 1 µm of parallel, and/or to maintain each of the walls 1802c, 1802d to within plus or minus 1 µm of planar (flat), depending on the analyte detection system with which the sample element 1730 is to be used. In alternative embodiments, walls 1802c, 1802d are flat, textured, angled, or some combination thereof.

In one embodiment, the transverse size of the sample chamber 903 (i.e., the size defined by the lateral chamber walls 1802a, 1802b) is about equal to the size of the active surface of the sample detector 1745. Accordingly, in a further embodiment the sample chamber 903 is round with a diameter of about 4 millimeter to about 12 millimeter, and more preferably from about 6 millimeter to about 8 millimeter.

The sample element 1730 shown in FIGS. 18-19 has, in one embodiment, sizes and dimensions specified as follows. The supply passage 1804 preferably has a length of about 15 millimeter, a width of about 1.0 millimeter, and a height equal to the pathlength T. Additionally, the supply opening 1806 is preferably about 1.5 millimeter wide and smoothly transitions to the width of the sample supply passage 1804. The sample element 1730 is about 0.5 inches (12 millimeters) wide and about one inch (25 millimeters) long with an overall thickness of between about 1.0 millimeter and about 4.0 millimeter. The vent passage 1808 preferably has a length of about 1.0 millimeter to 5.0 millimeter and a width of about 1.0 millimeter, with a thickness substantially equal to the pathlength between the walls 1802c, 1802d. The vent aperture 1810 is of substantially the same height and width as the vent passage 1808. Of course, other dimensions may be employed in other embodiments while still achieving the advantages of the sample element 1730.

The sample element 1730 is preferably sized to receive a material sample S having a volume less than or equal to about 15 µL (or less than or equal to about 10 µL, or less than or equal to about 5 µL) and more preferably a material sample S having a volume less than or equal to about 2 µL. Of course, the volume of the sample element 1730, the volume of the sample chamber 903, etc. can vary, depending on many variables, such as the size and sensitivity of the sample detector 1745, the intensity of the radiation emitted by the energy source 1720, the expected flow properties of the sample, and whether flow enhancers are incorporated into the sample element 1730. The transport of fluid to the sample chamber 903 is achieved preferably through capillary action, but may also be achieved through wicking or vacuum action, or a combination of wicking, capillary action, peristaltic, pumping, and/or vacuum action.

FIG. 20 depicts one approach to constructing the sample element 1730. In this approach, the sample element 1730 comprises a first layer 1820, a second layer 1830, and a third layer 1840. The second layer 1830 is preferably positioned between the first layer 1820 and the third layer 1840. The first layer 1820 forms the upper chamber wall 1802c, and the third layer 1840 forms the lower chamber wall 1802d. Where either of the chamber walls 1802c, 1802d comprises a window, the window(s)/wall(s) 1802c/1802d in question may be formed from a different material as is employed to form the balance of the layer(s) 1820/1840 in which the wall(s) are located. Alternatively, the entirety of the layer(s) 1820/1840 may be formed of the material selected to form the window(s)/wall(s) 1802c, 1802d. In this case, the window(s)/wall(s) 1802c, 1802d are integrally formed with the layer(s) 1820, 1840 and simply comprise the regions of the respective layer(s) 1820, 1840 which overlie the sample chamber 903.

With further reference to FIG. 20, second layer 1830 may be formed entirely of an adhesive that joins the first and third layers 1820, 1840. In other embodiments, the second layer 1830 may be formed from similar materials as the first and third layers, or any other suitable material. The second layer 1830 may also be formed as a carrier with an adhesive deposited on both sides thereof. The second layer 1830 includes voids which at least partially form the sample chamber 903, sample supply passage 1804, supply opening 1806, vent passage 1808, and vent opening 1810. The thickness of the second layer 1830 can be the same as any of the pathlengths disclosed above as suitable for the sample element 1730. The first and third layers can be formed from any of the materials disclosed above as suitable for forming the window(s) of the sample element 1730. In one embodiment, layers 1820, 1840 are formed from material having sufficient structural integrity to maintain its shape when filled with a sample S. Layers 1820, 1830 may be, for example, calcium fluoride having a thickness of 0.5 millimeter. In another embodiment, the second layer 1830 comprises the adhesive portion of Adhesive Transfer Tape no. 9471LE available from 3M Corporation. In another embodiment, the second layer 1830 comprises an epoxy, available, for example, from TechFilm (31 Dunham Road, Billerica, Mass. 01821), that is bound to layers 1820, 1840 as a result of the application of pressure and heat to the layers.

The sample chamber 903 preferably comprises a reagentless chamber. In other words, the internal volume of the sample chamber 903 and/or the wall(s) 1802 defining the chamber 903 are preferably inert with respect to the sample to be drawn into the chamber for analysis. As used herein, "inert" is a broad term and is used in its ordinary sense and includes, without limitation, substances which will not react with the sample in a manner which will significantly affect any measurement made of the concentration of analyte(s) in the sample with sample analysis apparatus 322 or any other suitable system, for a sufficient time (e.g., about 1-30 minutes) following entry of the sample into the chamber 903, to permit measurement of the concentration of such analyte(s). Alternatively, the sample chamber 903 may contain one or more reagents to facilitate use of the sample element in sample assay techniques which involve reaction of the sample with a reagent.

In one embodiment of the present invention, sample element 1730 is used for a limited number of measurements and is disposable. Thus, for example, with reference to FIGS. 8-10, sample element 1730 forms a disposable portion of cassette 820 adapted to place sample chamber 903 within probe region 1002.

Additional information on sample elements, methods of use thereof, and related technologies may be found in the above-mentioned and incorporated U.S. patent application Publication No. 2005/0038357, published on Feb. 17, 2005, titled SAMPLE ELEMENT WITH BARRIER MATERIAL; and in the above-mentioned and incorporated U.S. patent application Ser. No. 11/122,794, filed on May 5, 2005, titled SAMPLE ELEMENT WITH SEPARATOR.

Section IV.D—Centrifuge

Figure 21:
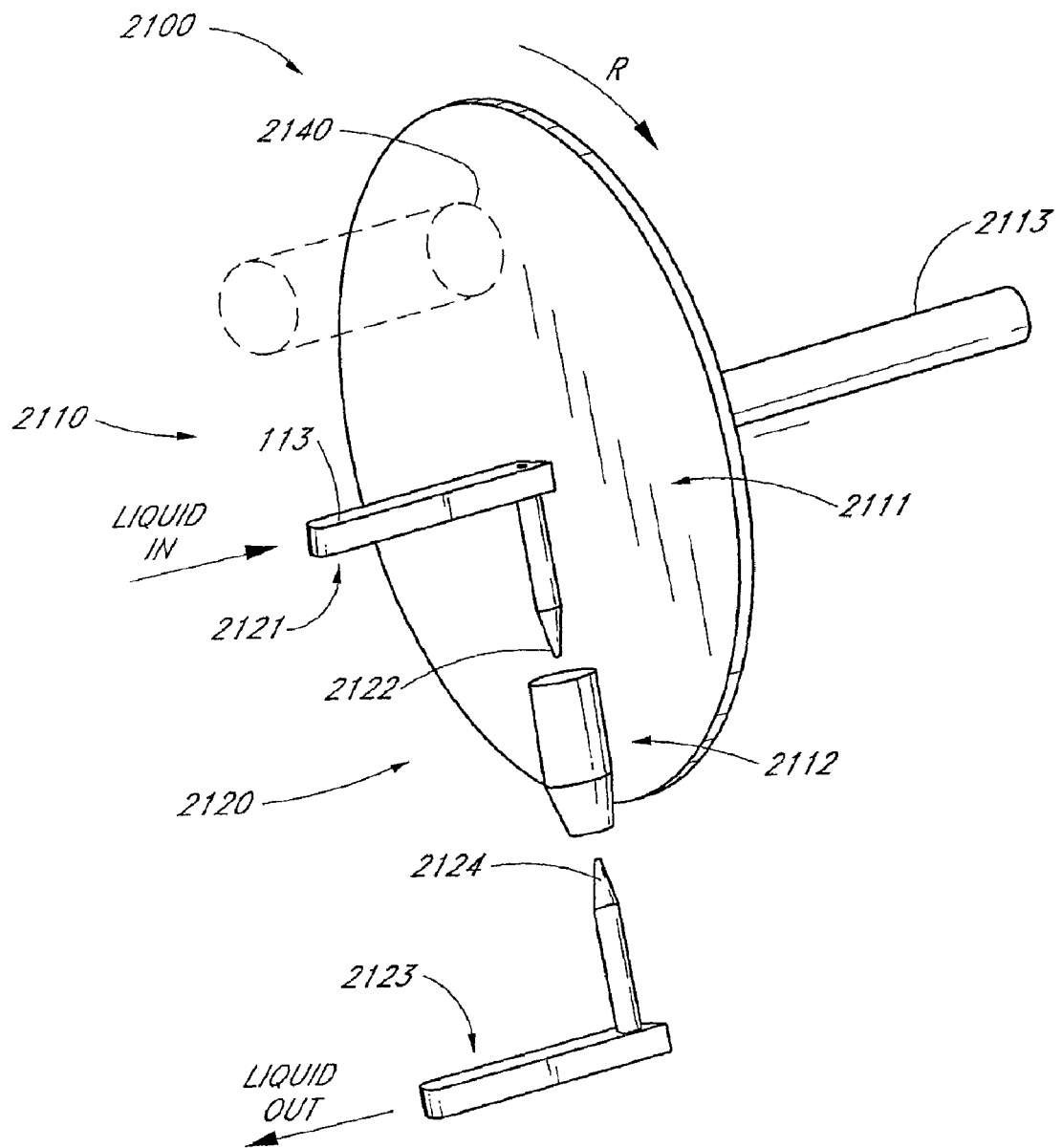
FIG. 21 is a schematic of an embodiment of a sample preparation unit.

FIG. 21 is a schematic of one embodiment of a sample preparation unit 2100 utilizing a centrifuge and which may be generally similar to the sample preparation unit 332, except as further detailed below. In general, the sample preparation unit 332 includes a centrifuge in place of, or in addition to a filter, such as the filter 1500. Sample preparation unit 2100 includes a fluid handling element in the form of a centrifuge 2110 having a sample element 2112 and a fluid interface 2120. Sample element 2112 is illustrated in FIG. 21 as a somewhat cylindrical element. This embodiment is illustrative, and the sample element may be cylindrical, planar, or any other shape or configuration that is compatible with the function of holding a material (preferably a liquid) in the centrifuge 2110. The centrifuge 2110 can be used to rotate the sample element 2112 such that the material held in the sample element 2112 is separated.

In some embodiments, the fluid interface 2120 selectively controls the transfer of a sample from the passageway 113 and into the sample element 2112 to permit centrifuging of the sample. In another embodiment, the fluid interface 2120 also permits a fluid to flow though the sample element 2112 to cleanse or otherwise prepare the sample element for obtaining an analyte measurement. Thus, the fluid interface 2120 can be used to flush and fill the sample element 2112.

As shown in FIG. 21, the centrifuge 2110 comprises a rotor 2111 that includes the sample element 2112 and an axle 2113 attached to a motor, not shown, which is controlled by the controller 210. The sample element 2112 is preferably generally similar to the sample element 1730 except as described subsequently.

As is further shown in FIG. 21, fluid interface 2120 includes a fluid injection probe 2121 having a first needle 2122 and a fluid removal probe 2123. The fluid removal probe 2123 has a second needle 2124. When sample element 2112 is properly oriented relative to fluid interface 2120, a sample, fluid, or other liquid is dispensed into or passes through the sample element 2112. More specifically, fluid injection probe 2121 includes a passageway to receive a sample, such as a bodily fluid from the patient connector 110. The bodily fluid can be passed through the fluid injection probe 2121 and the first needle 2122 into the sample element 2112. To remove material from the sample element 2112, the sample 2112 can be aligned with the second needle 2124, as illustrated. Material can be passed through the second needle 2124 into the fluid removal probe 2123. The material can then pass through a passageway of the removal probe 2123 away from the sample element 2112.

One position that the sample element 2112 may be rotated through or to is a sample measurement location 2140. The location 2140 may coincide with a region of an analysis system, such as an optical analyte detection system. For example, the location 2140 may coincide with a probe region 1002, or with a measurement location of another apparatus.

The rotor 2111 may be driven in a direction indicated by arrow R, resulting in a centrifugal force on sample(s) within sample element 2112. The rotation of a sample(s) located a distance from the center of rotation creates centrifugal force. In some embodiments, the sample element 2112 holds whole blood. The centrifugal force may cause the denser parts of the whole blood sample to move further out from the center of rotation than lighter parts of the blood sample. As such, one or more components of the whole blood can be separated from each other. Other fluids or samples can also be removed by centrifugal forces. In one embodiment, the sample element 2112 is a disposable container that is mounted on to a disposable rotor 2111. Preferably, the container is plastic, reusable and flushable. In other embodiments, the sample element 2112 is a non-disposable container that is permanently attached to the rotor 2111.

The illustrated rotor 2111 is a generally circular plate that is fixedly coupled to the axle 2113. The rotor 2111 can alternatively have other shapes. The rotor 2111 preferably comprises a material that has a low density to keep the rotational inertia low and that is sufficiently strong and stable to maintain shape under operating loads to maintain close optical alignment. For example, the rotor 2111 can be comprised of GE brand ULTEM (trademark) polyetherimide (PEI). This material is available in a plate form that is stable but can be readily machined. Other materials having similar properties can also be used.

The size of the rotor 2111 can be selected to achieve the desired centrifugal force. In some embodiments, the diameter of rotor 2111 is from about 75 millimeters to about 125 millimeters, or more preferably from about 100 millimeters to about 125 millimeters. The thickness of rotor 2111 is preferably just thick enough to support the centrifugal forces and can be, for example, from about 1.0 to 2.0 millimeter thick.

In an alternative embodiment, the fluid interface 2120 selectively removes blood plasma from the sample element 2112 after centrifuging. The blood plasma is then delivered to an analyte detection system for analysis. In one embodiment, the separated fluids are removed from the sample element 2112 through the bottom connector. Preferably, the location and orientation of the bottom connector and the container allow the red blood cells to be removed first. One embodiment may be configured with a red blood cell detector. The red blood cell detector may detect when most of the red blood cells have exited the container by determining the haemostatic level. The plasma remaining in the container may then be diverted into the analysis chamber. After the fluids have been removed from the container, the top connector may inject fluid (e.g., saline) into the container to flush the system and prepare it for the next sample.

FIGS. 22A to 23C illustrate another embodiment of a fluid handling and analysis apparatus 140, which employs a removable, disposable fluid handling cassette 820. The cassette 820 is equipped with a centrifuge rotor assembly 2016 to facilitate preparation and analysis of a sample. Except as further described below, the apparatus 140 of FIGS. 22A-22C can in certain embodiments be similar to any of the other embodiments of the apparatus 140 discussed herein, and the cassette 820 can in certain embodiments be similar to any of the embodiments of the cassettes 820 disclosed herein.

The removable fluid handling cassette 820 can be removably engaged with a main analysis instrument 810. When the fluid handling cassette 820 is coupled to the main instrument 810, a drive system 2030 of the main instrument 810 mates with the rotor assembly 2016 of the cassette 820 (FIG. 22B). Once the cassette 820 is coupled to the main instrument 810, the drive system 2030 engages and can rotate the rotor assembly 2016 to apply a centrifugal force to a body fluid sample carried by the rotor assembly 2016.

In some embodiments, the rotor assembly 2016 includes a rotor 2020 sample element 2448 (FIG. 22C) for holding a sample for centrifuging. When the rotor 2020 is rotated, a centrifugal force is applied to the sample contained within the sample element 2448. The centrifugal force causes separation of one or more components of the sample (e.g., separation of plasma from whole blood). The separated component(s) can then be analyzed by the apparatus 140, as will be discussed in further detail below.

The main instrument 810 includes both the centrifuge drive system 2030 and an analyte detection system 1700, a portion of which protrudes from a housing 2049 of the main instrument 810. The drive system 2030 is configured to releasably couple with the rotor assembly 2016, and can impart rotary motion to the rotor assembly 2016 to rotate the rotor 2020 at a desired speed. After the centrifuging process, the analyte detection system 1700 can analyze one or more components separated from the sample carried by the rotor 2020. The projecting portion of the illustrated detection system 1700 forms a slot 2074 for receiving a portion of the rotor 2020 carrying the sample element 2448 so that the detection system 1700 can analyze the sample or component(s) carried in the sample element 2448.

Figure 22A:
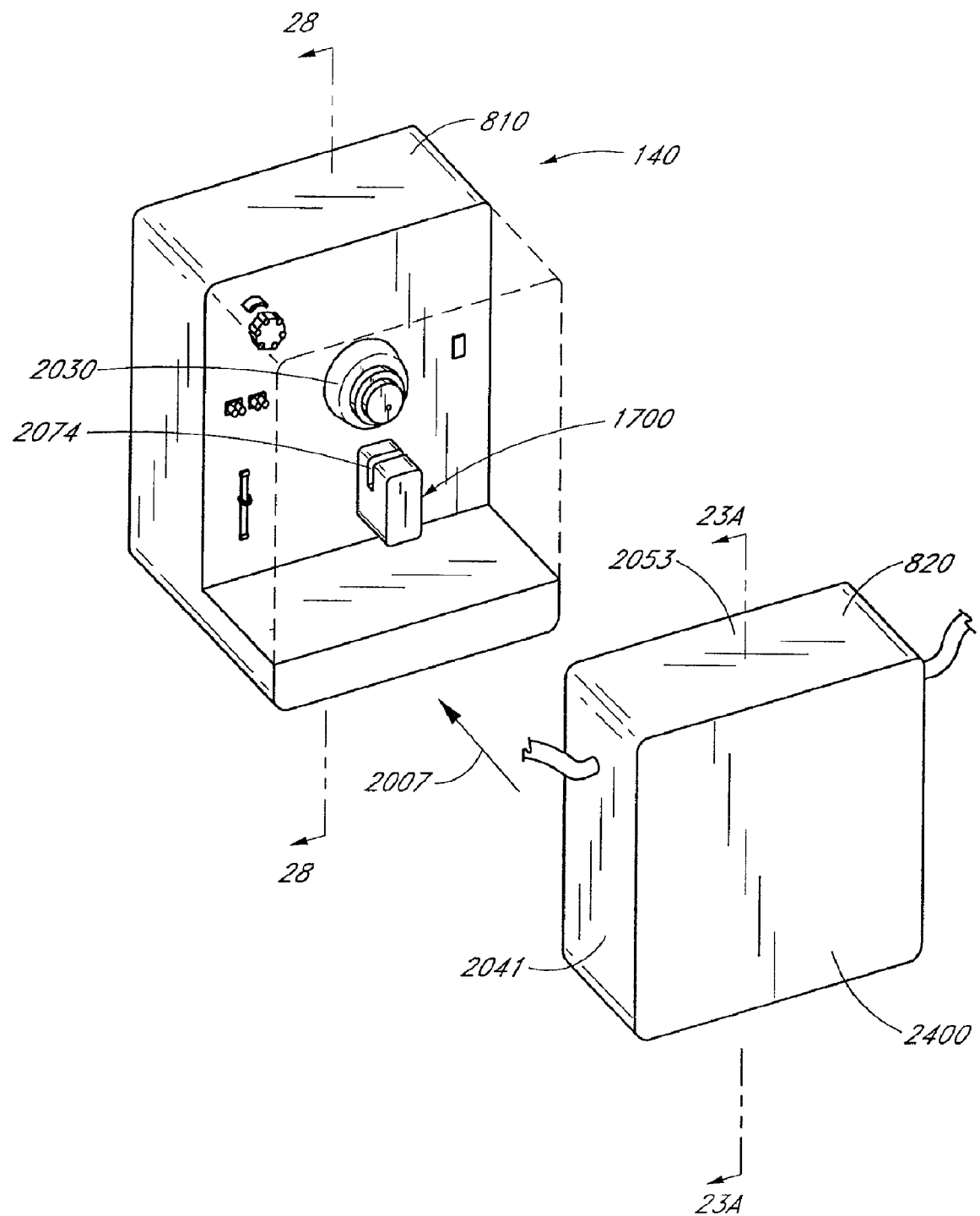
FIG. 22A is a perspective view of another embodiment of a fluid handling and analysis apparatus having a main instrument and removable cassette.
Figure 22B:
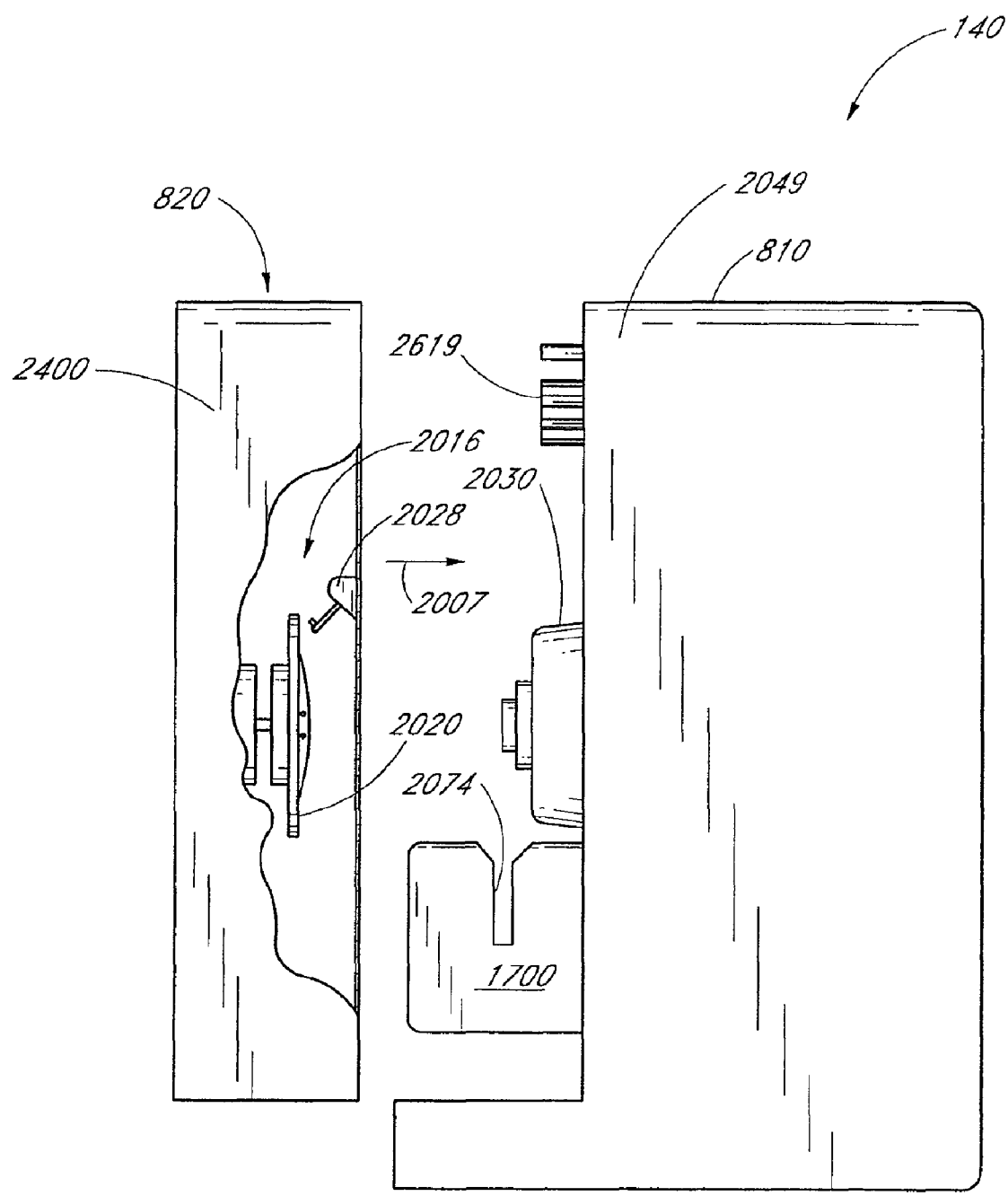
FIG. 22B is a partial cutaway, side elevational view of the fluid handling and analysis apparatus with the cassette spaced from the main instrument.
Figure 22C:
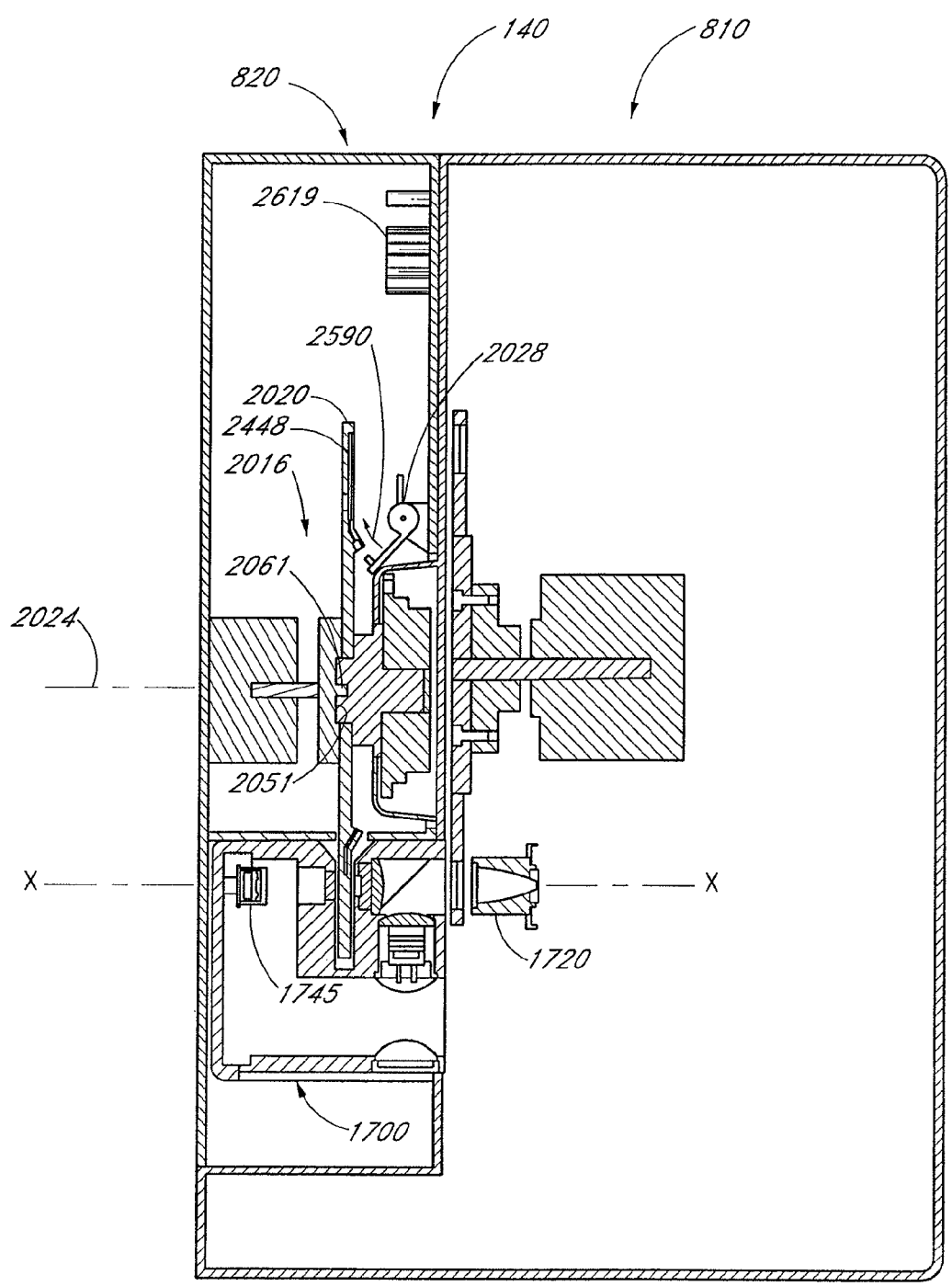
FIG. 22C is a cross-sectional view of the fluid handling and analysis apparatus of FIG. 22A wherein the cassette is installed onto the main instrument.

To assemble the fluid handling and analysis apparatus 140 as shown in FIG. 22C, the cassette 820 is placed on the main instrument 810, as indicated by the arrow 2007 of FIGS. 22A and 22B. The rotor assembly 2016 is accessible to the drive system 2030, so that once the cassette 820 is properly mounted on the main instrument 810, the drive system 2030 is in operative engagement with the rotor assembly 2016. The drive system 2030 is then energized to spin the rotor 2020 at a desired speed. The spinning rotor 2020 can pass repeatedly through the slot 2074 of the detection system 1700.

After the centrifuging process, the rotor 2020 is rotated to an analysis position (see FIGS. 22B and 23C) wherein the sample element 2448 is positioned within the slot 2074. With the rotor 2020 and sample element 2448 in the analysis position, the analyte detection system 1700 can analyze one or more of the components of the sample carried in the sample element 2448. For example, the detection system 1700 can analyze at least one of the components that is separated out during the centrifuging process. After using the cassette 820, the cassette 820 can be removed from the main instrument 810 and discarded. Another cassette 820 can then be mounted to the main instrument 810.

Figure 23A:
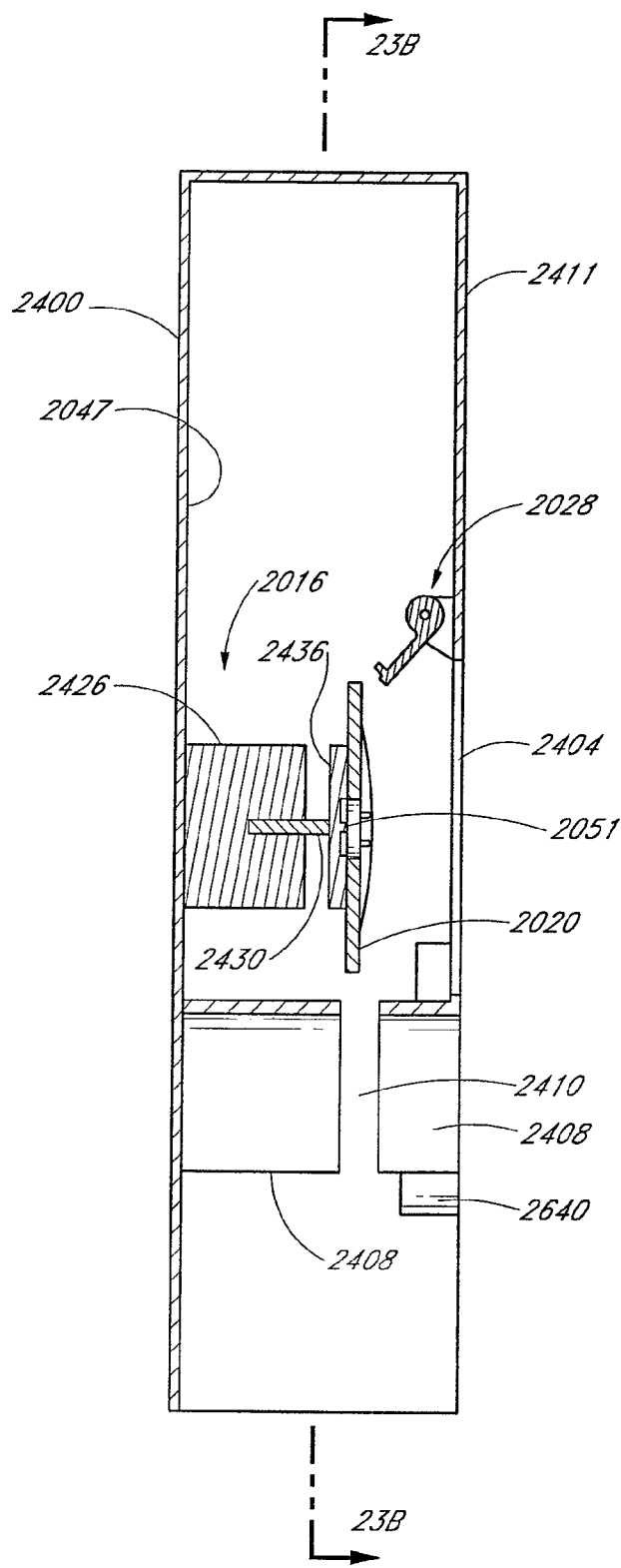
FIG. 23A is a cross-sectional view of the cassette of the fluid handling and analysis apparatus of FIG. 22A taken along the line 23A-23A.

With reference to FIG. 23A, the illustrated cassette 820 includes the housing 2400 that surrounds the rotor assembly 2016, and the rotor 2020 is pivotally connected to the housing 2400 by the rotor assembly 2016. The rotor 2020 includes a rotor interface 2051 for driving engagement with the drive system 2030 upon placement of the cassette 820 on the main instrument 810.

In some embodiments, the cassette 820 is a disposable fluid handling cassette. The reusable main instrument 810 can be used with any number of cassettes 820 as desired. Additionally or alternatively, the cassette 820 can be a portable, handheld cassette for convenient transport. In these embodiments, the cassette 820 can be manually mounted to or removed from the main instrument 810. In some embodiments, the cassette 820 may be a non disposable cassette which can be permanently coupled to the main instrument 810.

Figure 25D:
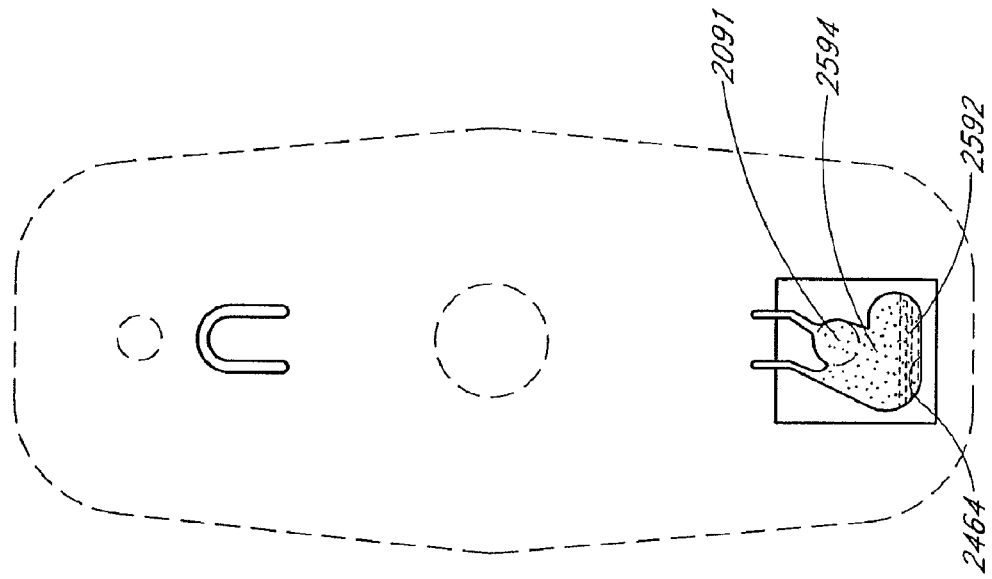
FIG. 25D is a front elevational view of the rotor of FIG. 25C after the sample fluid has been separated.

FIGS. 25A and 25B illustrate the centrifugal rotor 2020, which is capable of carrying a sample, such as bodily fluid. Thus, the illustrated centrifugal rotor 2020 can be considered a fluid handling element that can prepare a sample for analysis, as well as hold the sample during a spectroscopic analysis. The rotor 2020 preferably comprises an elongate body 2446, at least one sample element 2448, and at least one bypass element 2452. The sample element 2448 and bypass element 2452 can be located at opposing ends of the rotor 2020. The bypass element 2452 provides a bypass flow path that can be used to clean or flush fluid passageways of the fluid handling and analysis apparatus 140 without passing fluid through the sample element 2448.

The illustrated rotor body 2446 can be a generally planar member that defines a mounting aperture 2447 for coupling to the drive system 2030. The illustrated rotor 2020 has a somewhat rectangular shape. In alternative embodiments, the rotor 2020 is generally circular, polygonal, elliptical, or can have any other shape as desired. The illustrated shape can facilitate loading when positioned horizontally to accommodate the analyte detection system 1700.

With reference to FIG. 25B, a pair of opposing first and second fluid connectors 2027, 2029 extends outwardly from a front face of the rotor 2020, to facilitate fluid flow through the rotor body 2446 to the sample element 2448 and bypass element 2452, respectively. The first fluid connector 2027 defines an outlet port 2472 and an inlet port 2474 that are in fluid communication with the sample element 2448. In the illustrated embodiment, fluid channels 2510, 2512 extend from the outlet port 2472 and inlet port 2474, respectively, to the sample element 2448. (See FIGS. 25E and 25F.) As such, the ports 2472, 2474 and channels 2510, 2512 define input and return flow paths through the rotor 2020 to the sample element 2448 and back.

With continued reference to FIG. 25B, the rotor 2020 includes the bypass element 2452 which permits fluid flow therethrough from an outlet port 2572 to the inlet port 2574. A channel 2570 extends between the outlet port 2572 and the inlet port 2574 to facilitate this fluid flow. The channel 2570 thus defines a closed flow path through the rotor 2020 from one port 2572 to the other port 2574. In the illustrated embodiment, the outlet port 2572 and inlet port 2574 of the bypass element 2452 have generally the same spacing therebetween on the rotor 2020 as the outlet port 2472 and the inlet port 2474.

One or more windows 2460a, 2460b can be provided for optical access through the rotor 2020. A window 2460a proximate the bypass element 2452 can be a through-hole (see FIG. 25E) that permits the passage of electromagnetic radiation through the rotor 2020. A window 2460b proximate the sample element 2448 can also be a similar through-hole which permits the passage of electromagnetic radiation. Alternatively, one or both of the windows 2460a, 2460b can be a sheet constructed of calcium fluoride, barium fluoride, germanium, silicon, polypropylene, polyethylene, combinations thereof, or any material with suitable transmissivity (i.e., transmittance per unit thickness) in the relevant wavelength(s). The windows 2460a, 2460b are positioned so that one of the windows 2460a, 2460b is positioned in the slot 2074 when the rotor 2020 is in a vertically orientated position.

Various fabrication techniques can be used to form the rotor 2020. In some embodiments, the rotor 2020 can be formed by molding (e.g., compression or injection molding), machining, or a similar production process or combination of production processes. In some embodiments, the rotor 2020 is comprised of plastic. The compliance of the plastic material can be selected to create the seal with the ends of pins 2542, 2544 of a fluid interface 2028 (discussed in further detail below). Non-limiting exemplary plastics for forming the ports (e.g., ports 2572, 2574, 2472, 2474) can be relatively chemically inert and can be injection molded or machined. These plastics include, but are not limited to, PEEK and polyphenylenesulfide (PPS). Although both of these plastics have high modulus, a fluidic seal can be made if sealing surfaces are produced with smooth finish and the sealing zone is a small area where high contact pressure is created in a very small zone. Accordingly, the materials used to form the rotor 2020 and pins 2542, 2544 can be selected to achieve the desired interaction between the rotor 2020 and the pins 2542, 2544, as described in detail below.

The illustrated rotor assembly 2016 of FIG. 23A rotatably connects the rotor 2020 to the cassette housing 2400 via a rotor axle boss 2426 which is fixed with respect to the cassette housing and pivotally holds a rotor axle 2430 and the rotor 2020 attached thereto. The rotor axle 2430 extends outwardly from the rotor axle boss 2426 and is fixedly attached to a rotor bracket 2436, which is preferably securely coupled to a rear face of the rotor 2020. Accordingly, the rotor assembly 2016 and the drive system 2030 cooperate to ensure that the rotor 2020 rotates about the axis 2024, even at high speeds. The illustrated cassette 820 has a single rotor assembly 2016. In other embodiments, the cassette 820 can have more than one rotor assembly 2016. Multiple rotor assemblies 2016 can be used to prepare (preferably simultaneously) and test multiple samples.

With reference again to FIGS. 25A, 25B, 25E and 25F, the sample element 2448 is coupled to the rotor 2020 and can hold a sample of body fluid for processing with the centrifuge. The sample element 2448 can, in certain embodiments, be generally similar to other sample elements or cuvettes disclosed herein (e.g., sample elements 1730, 2112) except as further detailed below.

The sample element 2448 comprises a sample chamber 2464 that holds a sample for centrifuging, and fluid channels 2466, 2468, which provide fluid communication between the chamber 2464 and the channels 2512, 2510, respectively, of the rotor 2020. Thus, the fluid channels 2512, 2466 define a first flow path between the port 2474 and the chamber 2464, and the channels 2510, 2468 define a second flow path between the port 2472 and the chamber 2464. Depending on the direction of fluid flow into the sample element 2448, either of the first or second flow paths can serve as an input flow path, and the other can serve as a return flow path.

A portion of the sample chamber 2464 can be considered an interrogation region 2091, which is the portion of the sample chamber through which electromagnetic radiation passes during analysis by the detection system 1700 of fluid contained in the chamber 2464. Accordingly, the interrogation region 2091 is aligned with the window 2460b when the sample element 2448 is coupled to the rotor 2020. The illustrated interrogation region 2091 comprises a radially inward portion (i.e., relatively close to the axis of rotation 2024 of the rotor 2020) of the chamber 2464, to facilitate spectroscopic analysis of the lower density portion(s) of the body fluid sample (e.g., the plasma of a whole blood sample) after centrifuging, as will be discussed in greater detail below. Where the higher-density portions of the body fluid sample are of interest for spectroscopic analysis, the interrogation region 2091 can be located in a radially outward (i.e., further from the axis of rotation 2024 of the rotor 2020) portion of the chamber 2464.

Figure 25C:
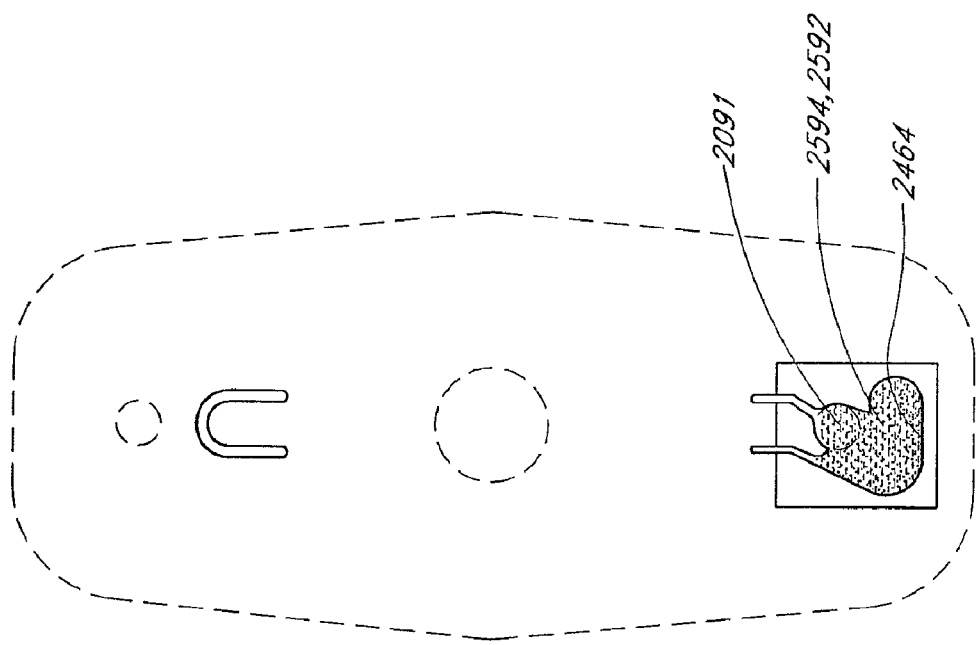
FIG. 25C is a front elevational view of the rotor of FIG. 25A with the sample element filled with a sample fluid.
Figures 25E, 25F:
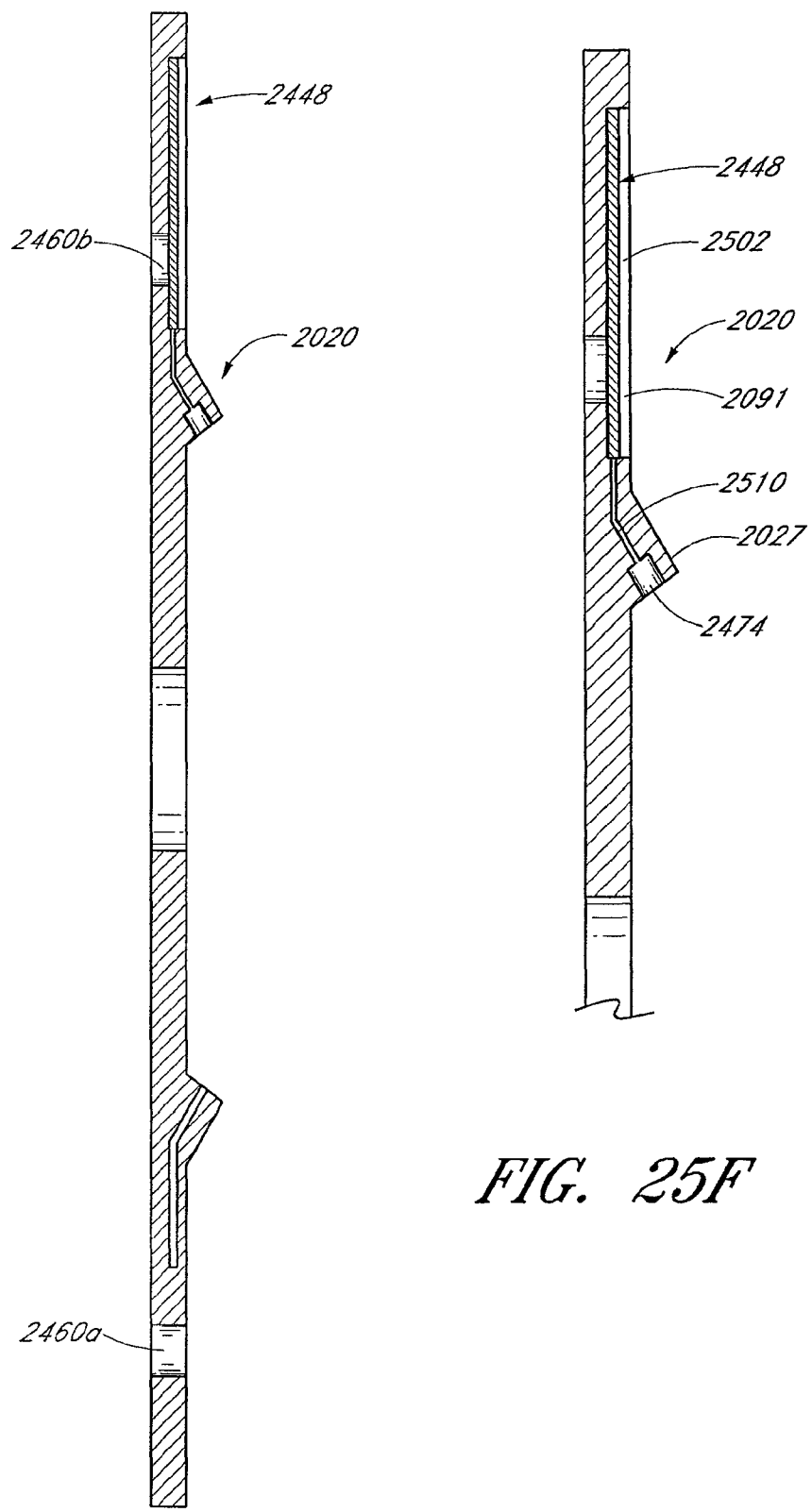
FIG. 25E is a cross-sectional view of the rotor taken along the line 25E-25E of FIG. 25A.
FIG. 25F is an enlarged sectional view of the rotor of FIG. 25E.

The rotor 2020 can temporarily or permanently hold the sample element 2448. As shown in FIG. 25F, the rotor 2020 forms a recess 2502 which receives the sample element 2448. The sample element 2448 can be held in the recess 2502 by frictional interaction, adhesives, or any other suitable coupling means. The illustrated sample element 2448 is recessed in the rotor 2020. However, the sample element 2448 can alternatively overlie or protrude from the rotor 2020.

The sample element 2448 can be used for a predetermined length of time, to prepare a predetermined amount of sample fluid, to perform a number of analyses, etc. If desired, the sample element 2448 can be removed from the rotor 2020 and then discarded. Another sample element 2448 can then be placed into the recess 2502. Thus, even if the cassette 820 is disposable, a plurality of disposable sample elements 2448 can be used with a single cassette 820. Accordingly, a single cassette 820 can be used with any number of sample elements as desired. Alternatively, the cassette 820 can have a sample element 2448 that is permanently coupled to the rotor 2020. In some embodiments, at least a portion of the sample element 2448 is integrally or monolithically formed with the rotor body 2446. Additionally or alternatively, the rotor 2020 can comprise a plurality of sample elements (e.g., with a record sample element in place of the bypass 2452). In this embodiment, a plurality of samples (e.g., bodily fluid) can be prepared simultaneously to reduce sample preparation time.

Figure 26B:
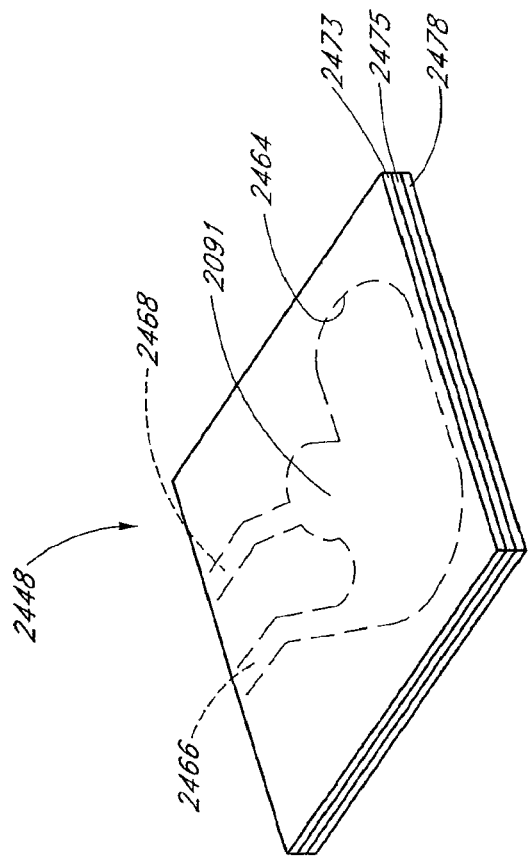
FIG. 26B is a perspective view of an assembled sample element.
Figure 26A:
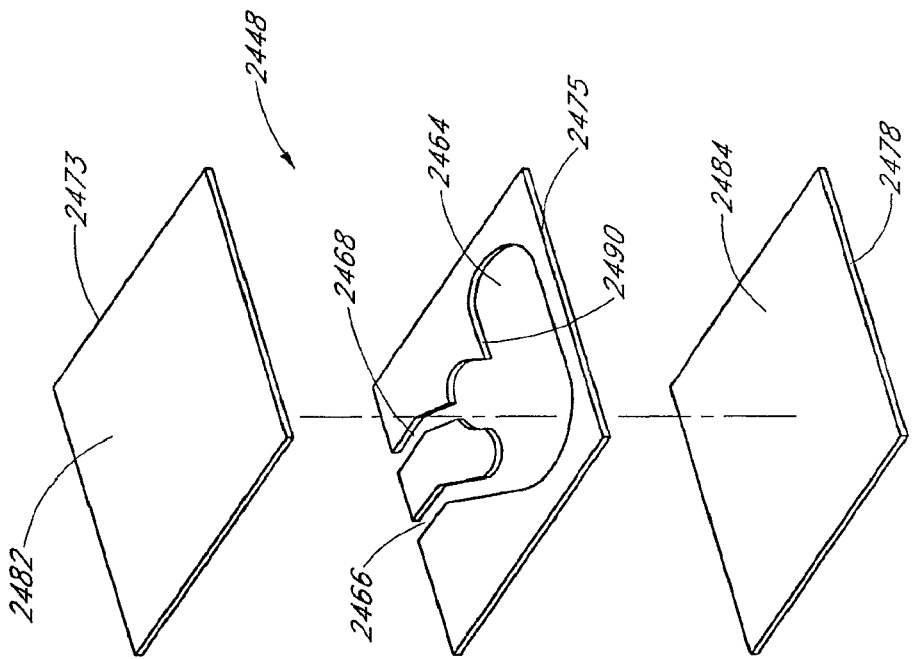
FIG. 26A is an exploded perspective view of a sample element for use with a rotor of a fluid handling and analysis apparatus.

FIGS. 26A and 26B illustrate a layered construction technique which can be employed when forming certain embodiments of the sample element 2448. The depicted layered sample element 2448 comprises a first layer 2473, a second layer 2475, and a third layer 2478. The second layer 2475 is preferably positioned between the first layer 2473 and the third layer 2478. The first layer 2473 forms an upper chamber wall 2482, and the third layer 2478 forms a lower chamber wall 2484. A lateral wall 2490 of the second layer 2475 defines the sides of the chamber 2464 and the fluid channels 2466, 2468.

The second layer 2475 can be formed by die-cutting a substantially uniform-thickness sheet of a material to form the lateral wall pattern shown in FIG. 26A. The second layer 2475 can comprise a layer of lightweight flexible material, such as a polymer material, with adhesive disposed on either side thereof to adhere the first and third layers 2473, 2478 to the second layer 2475 in "sandwich" fashion as shown in FIG. 26B. Alternatively, the second layer 2475 can comprise an "adhesive-only" layer formed from a uniform-thickness sheet of adhesive which has been die-cut to form the depicted lateral wall pattern.

However constructed, the second layer 2475 is preferably of uniform thickness to define a substantially uniform thickness or path length of the sample chamber 2464 and/or interrogation region 2091. This path length (and therefore the thickness of the second layer 2475 as well) is preferably between 10 microns and 100 microns, or is 20, 40, 50, 60, or 80 microns, in various embodiments.

The upper chamber wall 2482, lower chamber wall 2484, and lateral wall 2490 cooperate to form the chamber 2464. The upper chamber wall 2482 and/or the lower chamber wall 2484 can permit the passage of electromagnetic energy therethrough. Accordingly, one or both of the first and third layers 2473, 2478 comprises a sheet or layer of material which is relatively or highly transmissive of electromagnetic radiation (preferably infrared radiation or mid-infrared radiation) such as barium fluoride, silicon, polyethylene or polypropylene. If only one of the layers 2473, 2478 is so transmissive, the other of the layers is preferably reflective, to back-reflect the incoming radiation beam for detection on the same side of the sample element 2448 as it was emitted. Thus the upper chamber wall 2482 and/or lower chamber wall 2484 can be considered optical window(s). These window(s) are disposed on one or both sides of the interrogation region 2091 of the sample element 2448.

In one embodiment, sample element 2448 has opposing sides that are transmissive of infrared radiation and suitable for making optical measurements as described, for example, in U.S. patent application Publication No. 2005/0036146, published Feb. 17, 2005, titled SAMPLE ELEMENT QUALIFICATION, and hereby incorporated by reference and made a part of this specification. Except as further described herein, the embodiments, features, systems, devices, materials, methods and techniques described herein may, in some embodiments, be similar to any one or more of the embodiments, features, systems, devices, materials, methods and techniques described in U.S. patent application Publication No. 2003/0090649, published on May 15, 2003, titled REAGENT-LESS WHOLE-BLOOD GLUCOSE METER; or in U.S. patent application Publication No. 2003/

0086075, published on May 8, 2003, titled DEVICE AND METHOD FOR IN VITRO DETERMINATION OF ANALYTE CONCENTRATIONS WITHIN BODY FLUIDS; or in U.S. patent application Publication No. 2004/0019431, published on Jan. 29, 2004, titled METHOD OF DETERMINING AN ANALYTE CONCENTRATION IN A SAMPLE FROM AN ABSORPTION SPECTRUM, or in U.S. Pat. No. 6,652,136, issued on Nov. 25, 2003 to Marziali, titled METHOD OF SIMULTANEOUS MIXING OF SAMPLES. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned U.S. patent applications Publications Nos. 2003/0090649; 2003/0086075; 2004/0019431; or U.S. Pat. No. 6,652,136. All of the above-mentioned publications and patent are hereby incorporated by reference herein and made a part of this specification.

Figure 23B:
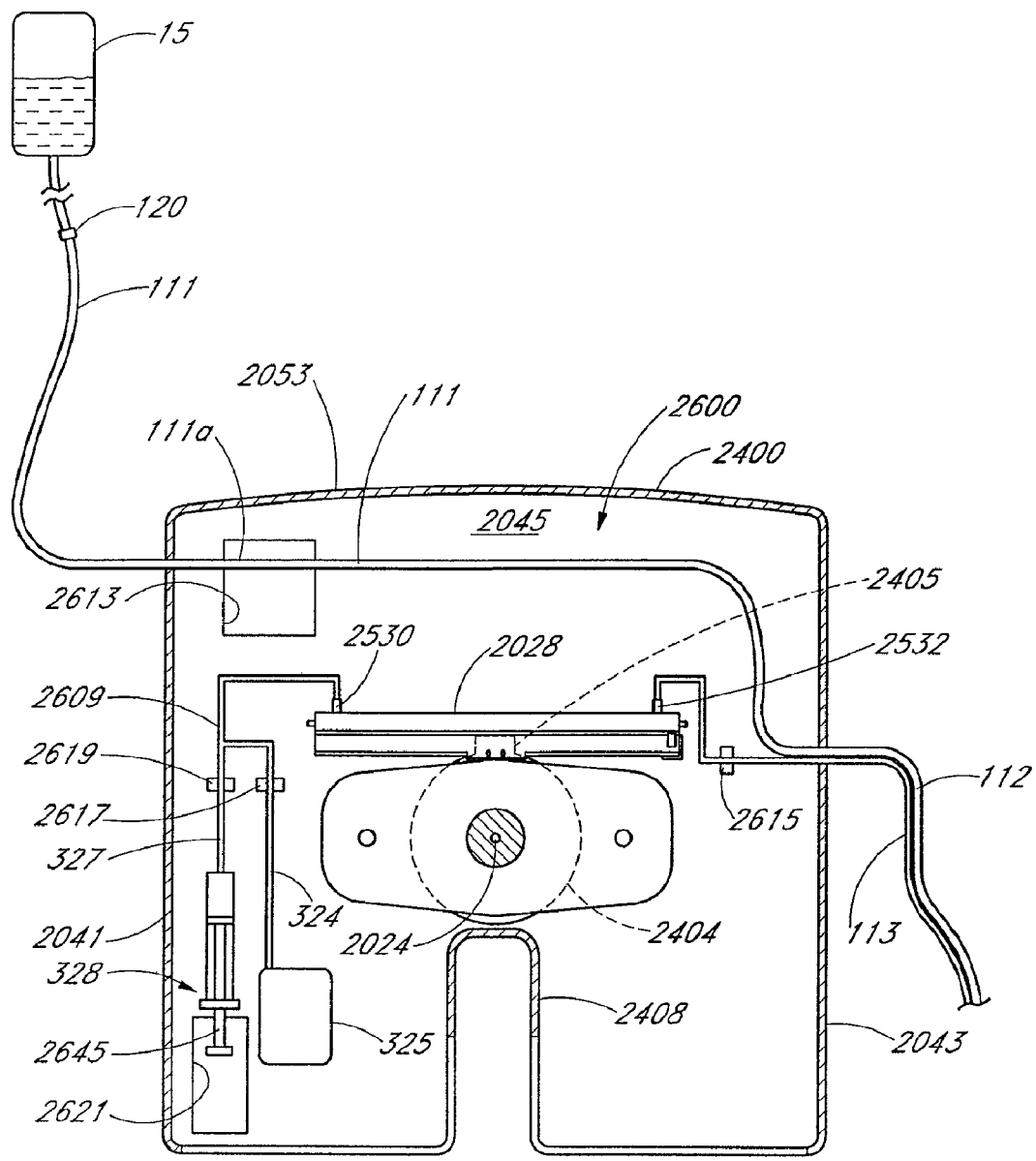
FIG. 23B is a cross-sectional view of the cassette of FIG. 23A taken along the line 23B-23B of FIG. 23A.
Figure 23C:
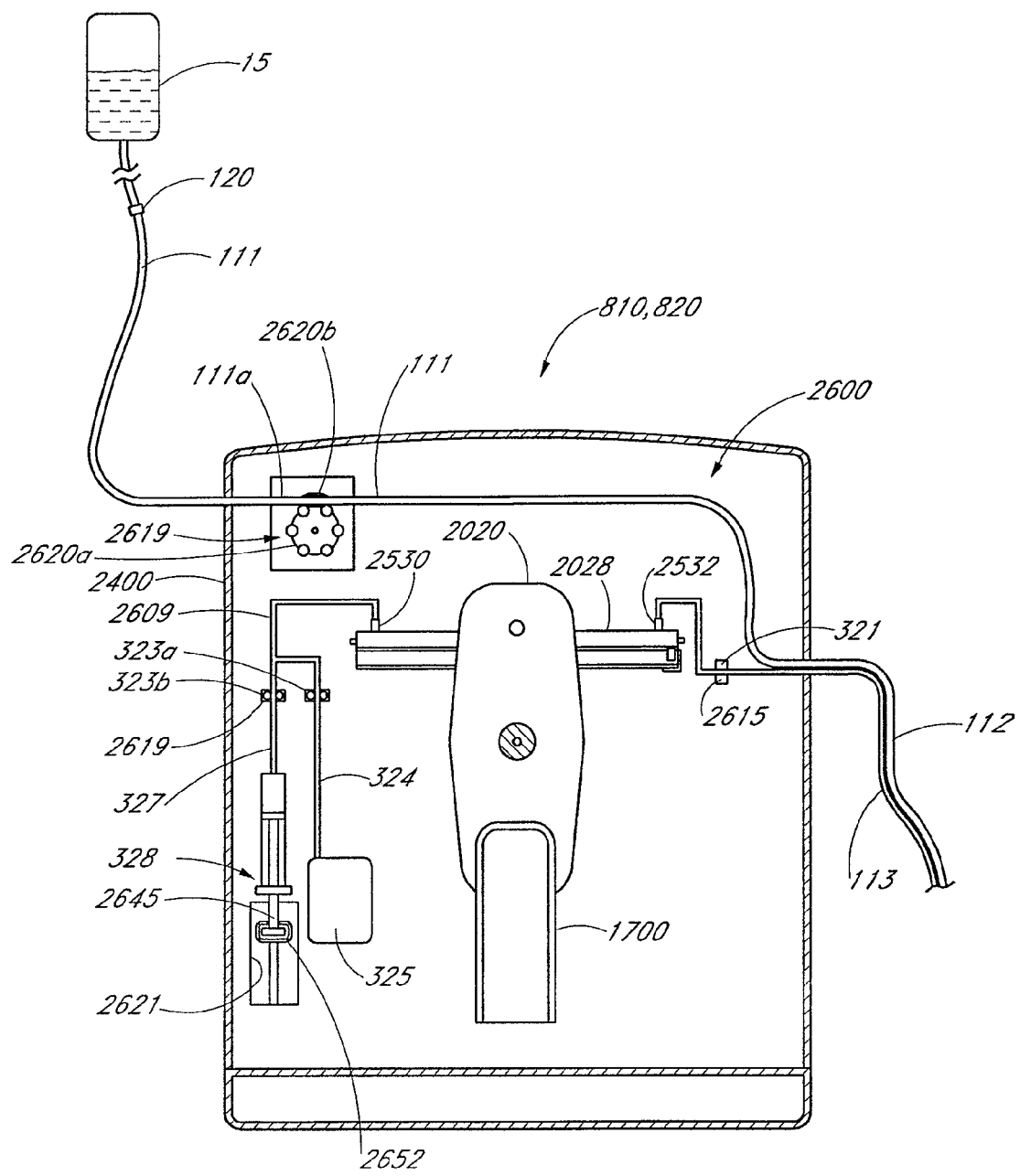
FIG. 23C is a cross-sectional view of the fluid handling and analysis apparatus having a fluid handling network, wherein a rotor of the cassette is in a generally vertical orientation.
Figure 23D:
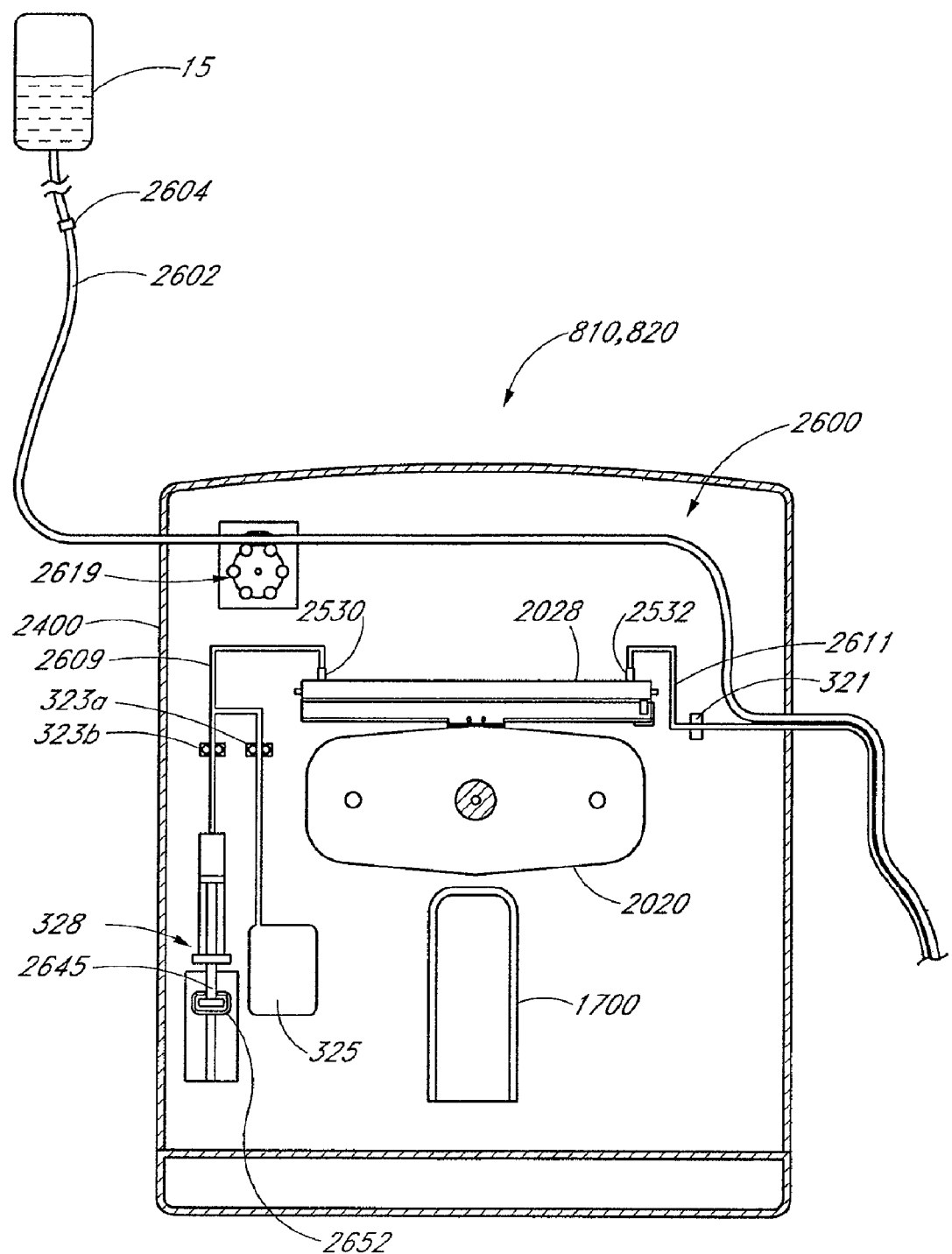
FIG. 23D is a cross-sectional view of the fluid handling and analysis apparatus, wherein the rotor of the cassette is in a generally horizontal orientation.

With reference to FIGS. 23B and 23C, the cassette 820 can further comprise the movable fluid interface 2028 for filling and/or removing sample liquid from the sample element 2448. In the depicted embodiment, the fluid interface 2028 is rotatably mounted to the housing 2400 of the cassette 820. The fluid interface 2028 can be actuated between a lowered position (FIG. 22C) and a raised or filling position (FIG. 27C). When the interface 2028 is in the lowered position, the rotor 2020 can freely rotate. To transfer sample fluid to the sample element 2448, the rotor 2020 can be held stationary and in a sample element loading position (see FIG. 22C) the fluid interface 2028 can be actuated, as indicated by the arrow 2590, upwardly to the filling position. When the fluid interface 2028 is in the filling position, the fluid interface 2028 can deliver sample fluid into the sample element 2448 and/or remove sample fluid from the sample element 2448.

Figure 27A:
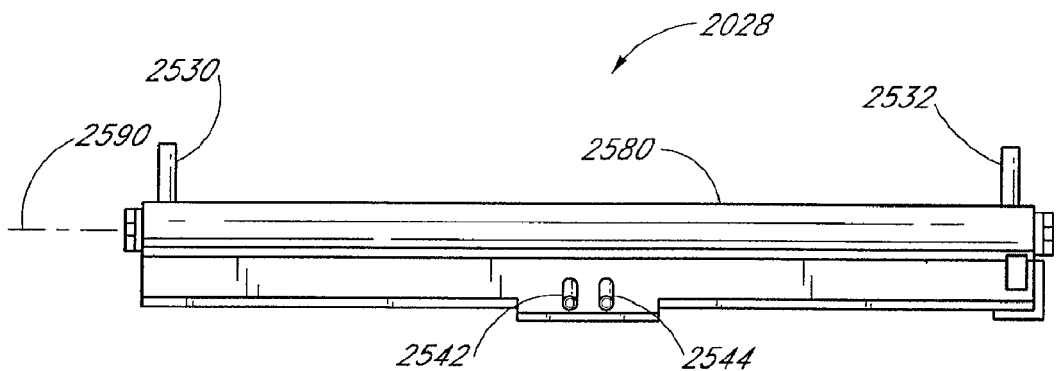
FIG. 27A is a front elevational view of a fluid interface for use with a cassette.
Figure 27B:
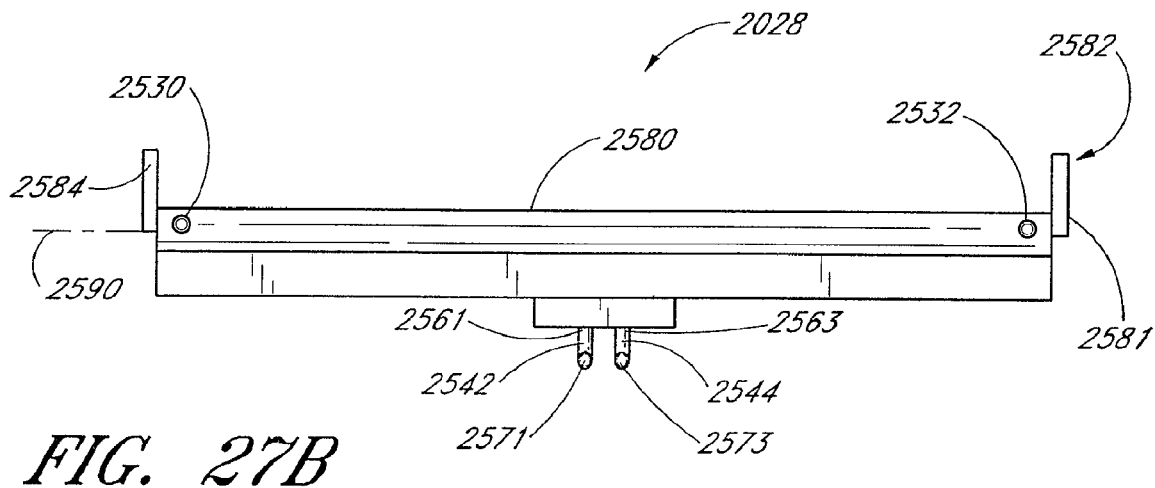
FIG. 27B is a top elevational view of the fluid interface of FIG. 27A.
Figure 27C:
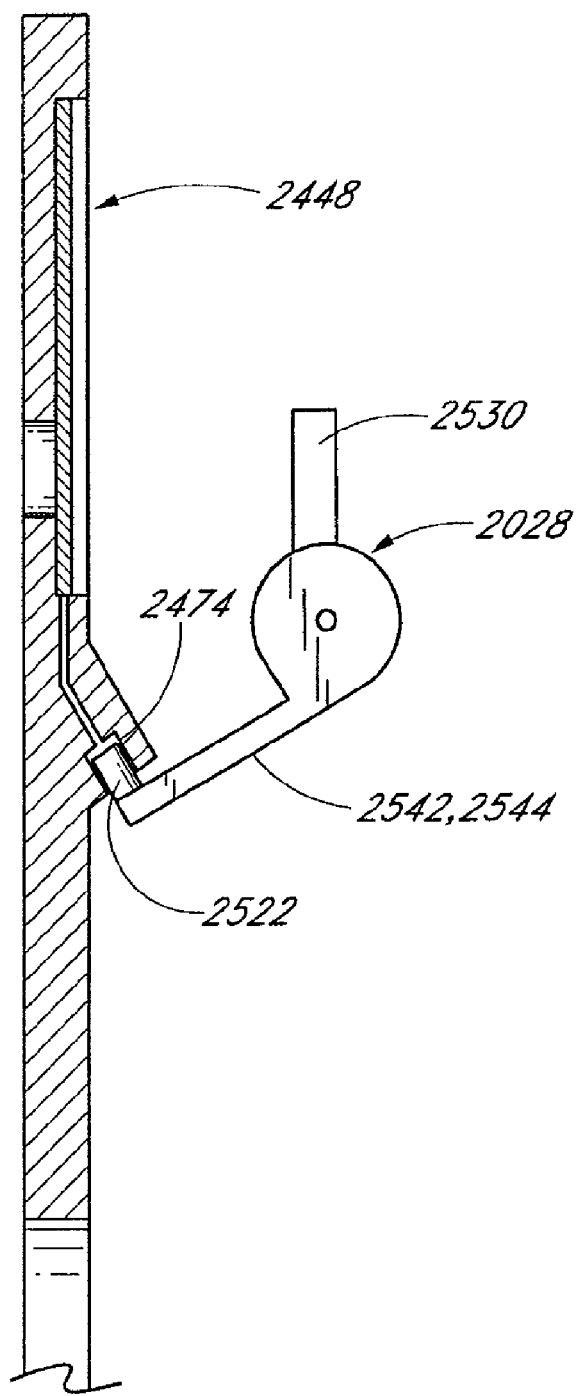
FIG. 27C is an enlarged side view of a fluid interface engaging a rotor.

With continued reference to FIGS. 27A and 27B, the fluid interface 2028 has a main body 2580 that is rotatably mounted to the housing 2400 of the cassette 820. Opposing brackets 2581, 2584 can be employed to rotatably couple the main body 2580 to the housing 2400 of the cassette 820, and permit rotation of the main body 2580 and the pins 2542, 2544 about an axis of rotation 2590 between the lowered position and the filling position. The main instrument 810 can include a horizontally moveable actuator (not shown) in the form of a solenoid, pneumatic actuator, etc. which is extendible through an opening 2404 in the cassette housing 2400 (see FIG. 23B). Upon extension, the actuator strikes the main body 2580 of the fluid interface 2028, causing the body 2580 to rotate to the filling position shown in FIG. 27C. The main body 2580 is preferably spring-biased towards the retracted position (shown in FIG. 23A) so that retraction of the actuator allows the main body to return to the retracted position. The fluid interface 2028 can thus be actuated for periodically placing fluid passageways of the pins 2542, 2544 in fluid communication with a sample element 2448 located on the rotor 2020.

The fluid interface 2028 of FIGS. 27A and 23B includes fluid connectors 2530, 2532 that can provide fluid communication between the interface 2028 and one or more of the fluid passageways of the apparatus 140 and/or sampling system 100/800, as will be discussed in further detail below. The illustrated connectors 2530, 2532 are in an upwardly extending orientation and positioned at opposing ends of the main body 2580. The connectors 2530, 2532 can be situated in other orientations and/or positioned at other locations along the main body 2580. The main body 2580 includes a first inner passageway (not shown) which provides fluid communication between the connector 2530 and the pin 2542, and a second inner passageway (not shown) which provides fluid communication between the connector 2532 and the pin 2544.

The fluid pins 2542, 2544 extend outwardly from the main body 2580 and can engage the rotor 2020 to deliver and/or remove sample fluid to or from the rotor 2020. The fluid pins 2542, 2544 have respective pin bodies 2561, 2563 and pin ends 2571, 2573. The pin ends 2571, 2573 are sized to fit within corresponding ports 2472, 2474 of the fluid connector 2027 and/or the ports 2572, 2574 of the fluid connector 2029, of the rotor 2020. The pin ends 2571, 2573 can be slightly chamfered at their tips to enhance the sealing between the pin ends 2571, 2573 and rotor ports. In some embodiments, the outer diameters of the pin ends 2573, 2571 are slightly larger than the inner diameters of the ports of the rotor 2020 to ensure a tight seal, and the inner diameters of the pins 2542, 2544 are preferably identical or very close to the inner diameters of the channels 2510, 2512 leading from the ports. In other embodiments, the outer diameter of the pin ends 2571, 2573 are equal to or less than the inner diameters of the ports of the rotor 2020.

The connections between the pins 2542, 2544 and the corresponding portions of the rotor 2020, either the ports 2472, 2474 leading to the sample element 2448 or the ports 2572, 2574 leading to the bypass element 2452, can be relatively simple and inexpensive. At least a portion of the rotor 2020 can be somewhat compliant to help ensure a seal is formed with the pins 2542, 2544. Alternatively or additionally, sealing members (e.g., gaskets, O-rings, and the like) can be used to inhibit leaking between the pin ends 2571, 2573 and corresponding ports 2472, 2474, 2572, 2574.

FIGS. 23A and 23B illustrate the cassette housing 2400 enclosing the rotor assembly 2016 and the fluid interface 2028. The housing 2400 can be a modular body that defines an aperture or opening 2404 dimensioned to receive a drive system housing 2050 when the cassette 820 is operatively coupled to the main instrument 810. The housing 2400 can protect the rotor 2020 from external forces and can also limit contamination of samples delivered to a sample element in the rotor 2020, when the cassette 820 is mounted to the main instrument 810.

The illustrated cassette 820 has a pair of opposing side walls 2041, 2043, top 2053, and a notch 2408 for mating with the detection system 1700. A front wall 2045 and rear wall 2047 extend between the side walls 2041, 2043. The rotor assembly 2016 is mounted to the inner surface of the rear wall 2047. The front wall 2045 is configured to mate with the main instrument 810 while providing the drive system 2030 with access to the rotor assembly 2016.

The illustrated front wall 2045 has the opening 2404 that provides access to the rotor assembly 2016. The drive system 2030 can be passed through the opening 2404 into the interior of the cassette 820 until it operatively engages the rotor assembly 2016. The opening 2404 of FIG. 23B is configured to mate and tightly surround the drive system 2030. The illustrated opening 2404 is generally circular and includes an upper notch 2405 to permit the fluid interface actuator of the main instrument 810 to access the fluid interface 2028, as discussed above. The opening 2404 can have other configurations suitable for admitting the drive system 2030 and actuator into the cassette 820.

The notch 2408 of the housing 2400 can at least partially surround the projecting portion of the analyte detection system 1700 when the cassette 820 is loaded onto the main instrument 810. The illustrated notch 2408 defines a cassette slot 2410 (FIG. 23A) that is aligned with elongate slot 2074 shown in FIG. 22C, upon loading of the cassette 820. The rotating rotor 2020 can thus pass through the aligned slots 2410, 2074. In some embodiments, the notch 2408 has a generally U-shaped axial cross section as shown. More generally, the configuration of the notch 2408 can be selected based on the design of the projecting portion of the detection system 1700.

Although not illustrated, fasteners, clips, mechanical fastening assemblies, snaps, or other coupling means can be used to ensure that the cassette 820 remains coupled to the main instrument 810 during operation. Alternatively, the interaction between the housing 2400 and the components of the main instrument 810 can secure the cassette 820 to the main instrument 810.

Figure 28:
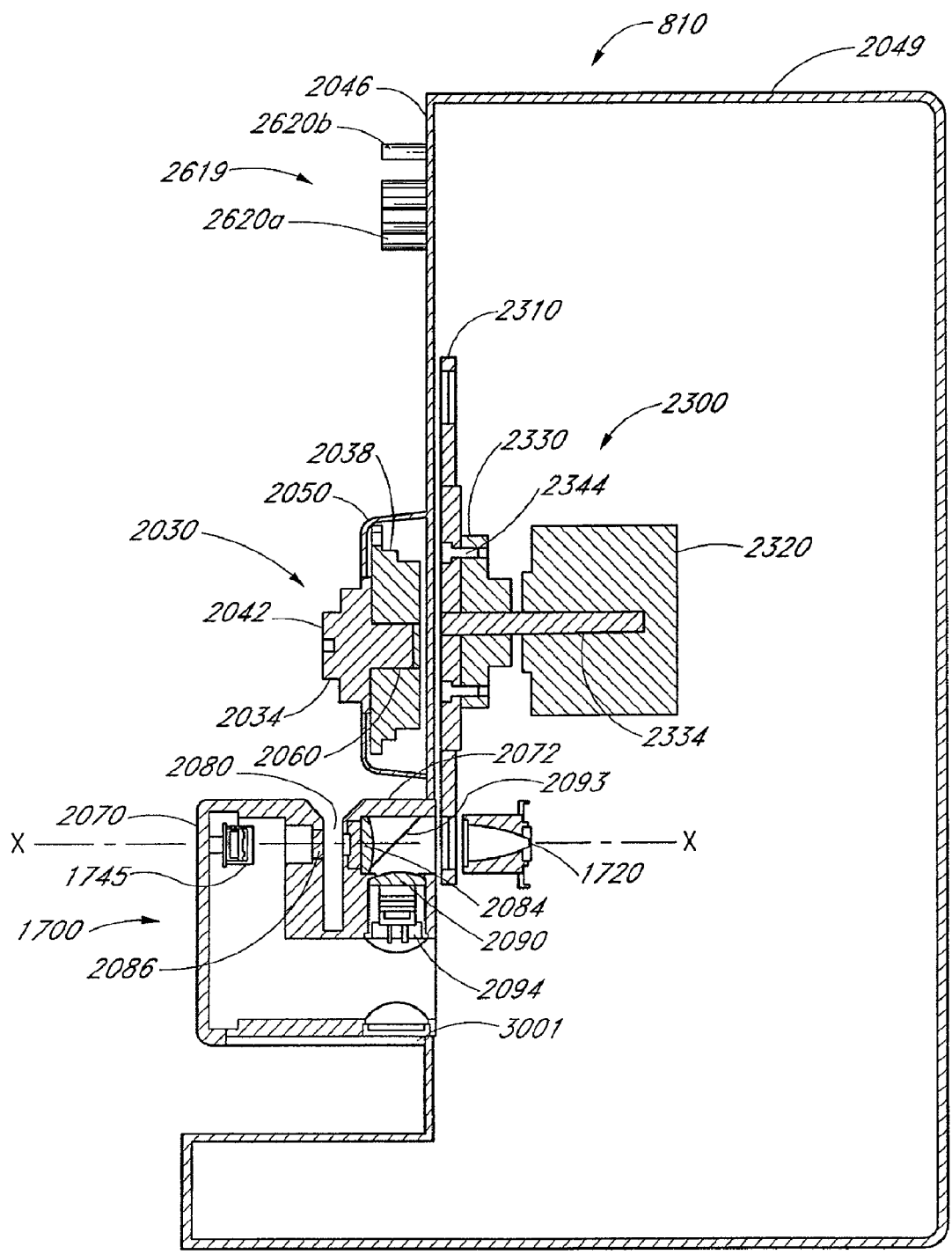
FIG. 28 is a cross-sectional view of the main instrument of the fluid handling and analysis apparatus of FIG. 22A taken along the line 28-28.

FIG. 28 is a cross-sectional view of the main instrument 810. The illustrated centrifuge drive system 2030 extends outwardly from a front face 2046 of the main instrument 810 so that it can be easily mated with the rotor assembly 2016 of the cassette 820. When the centrifuge drive system 2030 is energized, the drive system 2030 can rotate the rotor 2020 at a desired rotational speed.

Figure 23E:
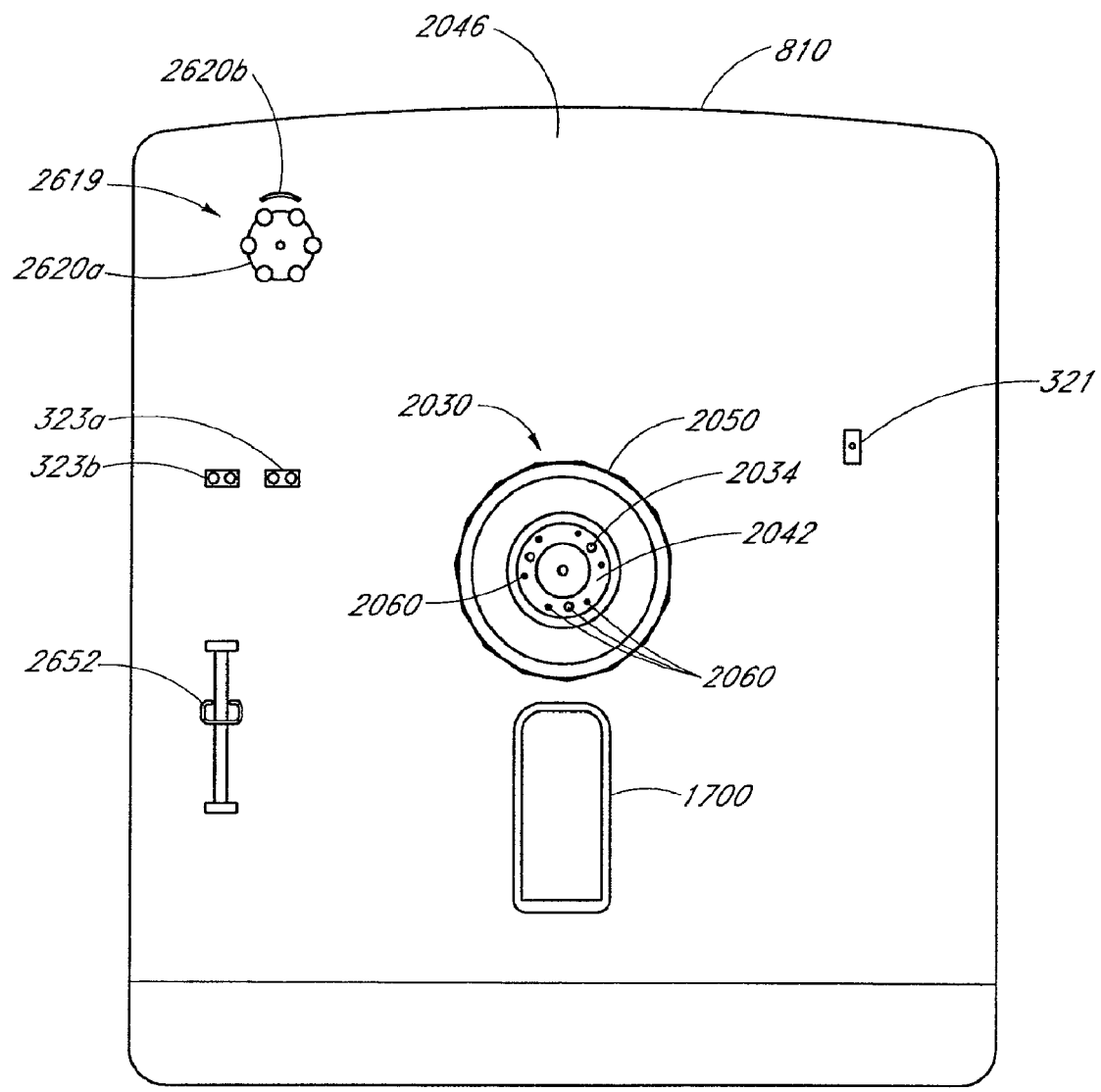
FIG. 23E is a front elevational view of the main instrument of the fluid handling and analysis apparatus of FIG. 23C.

The illustrated centrifuge drive system 2030 of FIGS. 23E and 28 includes a centrifuge drive motor 2038 and a drive spindle 2034 that is drivingly connected to the drive motor 2038. The drive spindle 2034 extends outwardly from the drive motor 2038 and forms a centrifuge interface 2042. The centrifuge interface 2042 extends outwardly from the drive system housing 2050, which houses the drive motor 2038. To impart rotary motion to the rotor 2020, the centrifuge interface 2042 can have keying members, protrusions, notches, detents, recesses, pins, or other types of structures that can engage the rotor 2020 such that the drive spindle 2034 and rotor 2020 are coupled together.

The centrifuge drive motor 2038 of FIG. 28 can be any suitable motor that can impart rotary motion to the rotor 2020. When the drive motor 2038 is energized, the drive motor 2038 can rotate the drive spindle 2034 at constant or varying speeds. Various types of motors, including, but not limited to, centrifuge motors, stepper motors, spindle motors, electric motors, or any other type of motor for outputting a torque can be utilized. The centrifuge drive motor 2038 is preferably fixedly secured to the drive system housing 2050 of the main instrument 810.

The drive motor 2038 can be the type of motor typically used in personal computer hard drives that is capable of rotating at about 7,200 RPM on precision bearings, such as a motor of a Seagate Model ST380011A hard drive (Seagate Technology, Scotts Valley, Calif.) or similar motor. In one embodiment, the drive spindle 2034 may be rotated at 6,000 rpm, which yields approximately 2,000 G's for a rotor having a 2.5 inch (64 millimeter) radius. In another embodiment, the drive spindle 2034 may be rotated at speeds of approximately 7,200 rpm. The rotational speed of the drive spindle 2034 can be selected to achieve the desired centrifugal force applied to a sample carried by the rotor 2020.

The main instrument 810 includes a main housing 2049 that defines a chamber sized to accommodate a filter wheel assembly 2300 including a filter drive motor 2320 and filter wheel 2310 of the analyte detection system 1700. The main housing 2049 defines a detection system opening 3001 configured to receive an analyte detection system housing 2070. The illustrated analyte detection system housing 2070 extends or projects outwardly from the housing 2049.

The main instrument 810 of FIGS. 23C and 23E includes a bubble sensor unit 321, a pump 2619 in the form of a peristaltic pump roller 2620a and a roller support 2620b, and valves 323a, 323b. The illustrated valves 323a, 323b are pincher pairs, although other types of valves can be used. When the cassette 820 is installed, these components can engage components of a fluid handling network 2600 of the cassette 820, as will be discussed in greater detail below.

With continued reference to FIG. 28, the analyte detection system housing 2070 surrounds and houses some of the internal components of the analyte detection system 1700. The elongate slot 2074 extends downwardly from an upper face 2072 of the housing 2070. The elongated slot 2074 is sized and dimensioned so as to receive a portion of the rotor 2020. When the rotor 2020 rotates, the rotor 2020 passes periodically through the elongated slot 2074. When a sample element of the rotor 2020 is in the detection region 2080 defined by the slot 2074, the analyte detection system 1700 can analyze material in the sample element.

The analyte detection system 1700 can be a spectroscopic bodily fluid analyzer that preferably comprises an energy source 1720. The energy source 1720 can generate an energy beam directed along a major optical axis X that passes through the slot 2074 towards a sample detector 1745. The slot 2074 thus permits at least a portion of the rotor (e.g., the interrogation region 2091 or sample chamber 2464 of the sample element 2448) to be positioned on the optical axis X. To analyze a sample carried by the sample element 2448, the sample element and sample can be positioned in the detection region 2080 on the optical axis X such that light emitted from the source 1720 passes through the slot 2074 and the sample disposed within the sample element 2448.

The analyte detection system 1700 can also comprise one or more lenses positioned to transmit energy outputted from the energy source 1720. The illustrated analyte detection system 1700 of FIG. 28 comprises a first lens 2084 and a second lens 2086. The first lens 2084 is configured to focus the energy from the source 1720 generally onto the sample element and material sample. The second lens 2086 is positioned between the sample element and the sample detector 1745. Energy from energy source 1720 passing through the sample element can subsequently pass through the second lens 2086. A third lens 2090 is preferably positioned between a beam splitter 2093 and a reference detector 2094. The reference detector 2094 is positioned to receive energy from the beam splitter 2093.

The analyte detection system 1700 can be used to determine the analyte concentration in the sample carried by the rotor 2020. Other types of detection or analysis systems can be used with the illustrated centrifuge apparatus or sample preparation unit. The fluid handling and analysis apparatus 140 is shown for illustrative purposes as being used in conjunction with the analyte detection system 1700, but neither the sample preparation unit nor analyte detection system are intended to be limited to the illustrated configuration, or to be limited to being used together.

To assemble the fluid handling and analysis apparatus 140, the cassette 820 can be moved towards and installed onto the main instrument 810, as indicated by the arrow 2007 in FIG. 22A. As the cassette 820 is installed, the drive system 2030 passes through the aperture 2040 so that the spindle 2034 mates with the rotor 2020. Simultaneously, the projecting portion of the detection system 1700 is received in the notch 2408 of the cassette 820. When the cassette 820 is installed on the main instrument 810, the slot 2410 of the notch 2048 and the slot 2074 of the detection system 1700 are aligned as shown in FIG. 22C. Accordingly, when the cassette 820 and main instrument 810 are assembled, the rotor 2020 can rotate about the axis 2024 and pass through the slots 2410, 2074.

After the cassette 820 is assembled with the main instrument 810, a sample can be added to the sample element 2448.

The cassette 820 can be connected to an infusion source and a patient to place the system in fluid communication with a bodily fluid to be analyzed. Once the cassette 820 is connected to a patient, a bodily fluid may be drawn from the patient into the cassette 820. The rotor 2020 is rotated to a vertical loading position wherein the sample element 2448 is near the fluid interface 2028 and the bypass element 2452 is positioned within the slot 2074 of the detection system 1700. Once the rotor 2020 is in the vertical loading position, the pins 2542, 2544 of the fluid interface 2028 are positioned to mate with the ports 2472, 2474 of the rotor 2020. The fluid interface 2028 is then rotated upwardly until the ends 2571, 2573 of the pins 2542, 2544 are inserted into the ports 2472, 2474.

When the fluid interface 2028 and the sample element 2448 are thus engaged, sample fluid (e.g., whole blood) is pumped into the sample element 2448. The sample can flow through the pin 2544 into and through the rotor channel 2512 and the sample element channel 2466, and into the sample chamber 2464. As shown in FIG. 25C, the sample chamber 2464 can be partially or completely filled with sample fluid. In some embodiments, the sample fills at least the sample chamber 2464 and the interrogation region 2091 of the sample element 2448. The sample can optionally fill at least a portion of the sample element channels 2466, 2468. The illustrated sample chamber 2464 is filled with whole blood, although the sample chamber 2464 can be filled with other substances. After the sample element 2448 is filled with a desired amount of fluid, the fluid interface 2028 can be moved to a lowered position to permit rotation of the rotor 2020.

The centrifuge drive system 2030 can then spin the rotor 2020 and associated sample element 2448 as needed to separate one or more components of the sample. The separated component(s) of the sample may collect or be segregated in a section of the sample element for analysis. In the illustrated embodiment, the sample element 2448 of FIG. 25C is filled with whole blood prior to centrifuging. The centrifugal forces can be applied to the whole blood until plasma 2594 is separated from the blood cells 2592. After centrifuging, the plasma 2594 is preferably located in a radially inward portion of the sample element 2448, including the interrogation region 2091. The blood cells 2592 collect in a portion of the sample chamber 2464 which is radially outward of the plasma 2594 and interrogation region 2091.

The rotor 2020 can then be moved to a vertical analysis position wherein the sample element 2448 is disposed within the slot 2074 and aligned with the source 1720 and the sample detector 1745 on the major optical axis X. When the rotor 2020 is in the analysis position, the interrogation portion 2091 is preferably aligned with the major optical axis X of the detection system 1700. The analyte detection system 1700 can analyze the sample in the sample element 2448 using spectroscopic analysis techniques as discussed elsewhere herein.

After the sample has been analyzed, the sample can be removed from the sample element 2448. The sample may be transported to a waste receptacle so that the sample element 2448 can be reused for successive sample draws and analyses. The rotor 2020 is rotated from the analysis position back to the vertical loading position. To empty the sample element 2448, the fluid interface 2028 can again engage the sample element 2448 to flush the sample element 2448 with fresh fluid (either a new sample of body fluid, or infusion fluid). The fluid interface 2028 can be rotated to mate the pins 2542, 2544 with the ports 2472, 2474 of the rotor 2020. The fluid interface 2028 can pump a fluid through one of the pins 2542, 2544 until the sample is flushed from the sample element 2448. Various types of fluids, such as infusion liquid, air, water, and the like, can be used to flush the sample element 2448. After the sample element 2448 has been flushed, the sample element 2448 can once again be filled with another sample.

In an alternative embodiment, the sample element 2448 may be removed from the rotor 2020 and replaced after each separate analysis, or after a certain number of analyses. Once the patient care has terminated, the fluid passageways or conduits may be disconnected from the patient and the sample cassette 820 which has come into fluid contact with the patient's bodily fluid may be disposed of or sterilized for reuse. The main instrument 810, however, has not come into contact with the patient's bodily fluid at any point during the analysis and therefore can readily be connected to a new fluid handling cassette 820 and used for the analysis of a subsequent patient.

The rotor 2020 can be used to provide a fluid flow bypass. To facilitate a bypass flow, the rotor 2020 is first rotated to the vertical analysis/bypass position wherein the bypass element 2452 is near the fluid interface 2028 and the sample element 2448 is in the slot 2074 of the analyte detection system 1700. Once the rotor 2020 is in the vertical analysis/bypass position, the pins 2542, 2544 can mate with the ports 2572, 2574 of the rotor 2020. In the illustrated embodiment, the fluid interface 2028 is rotated upwardly until the ends 2571, 2573 of the pins 2542, 2544 are inserted into the ports 2572, 2574. The bypass element 2452 can then provide a completed fluid circuit so that fluid can flow through one of the pins 2542, 2544 into the bypass element 2452, through the bypass element 2452, and then through the other pin 2542, 2544. The bypass element 2452 can be utilized in this manner to facilitate the flushing or sterilizing of a fluid system connected to the cassette 820.

As shown in FIG. 23B, the cassette 820 preferably includes the fluid handling network 2600 which can be employed to deliver fluid to the sample element 2448 in the rotor 2020 for analysis. The main instrument 810 has a number of components that can, upon installation of the cassette 820 on the main instrument 810, extend through openings in the front face 2045 of cassette 820 to engage and interact with components of the fluid handling network 2600, as detailed below.

The fluid handling network 2600 of the fluid handling and analysis apparatus 140 includes the passageway 111 which extends from the connector 120 toward and through the cassette 820 until it becomes the passageway 112, which extends from the cassette 820 to the patient connector 110. A portion 111a of the passageway 111 extends across an opening 2613 in the front face 2045 of the cassette 820. When the cassette 820 is installed on the main instrument 810, the roller pump 2619 engages the portion 111a, which becomes situated between the impeller 2620a and the impeller support 2620b (see FIG. 23C).

The fluid handling network 2600 also includes passageway 113 which extends from the patient connector 110 towards and into the cassette 820. After entering the cassette 820, the passageway 113 extends across an opening 2615 in the front face 2045 to allow engagement of the passageway 113 with a bubble sensor 321 of the main instrument 810, when the cassette 820 is installed on the main instrument 810. The passageway 113 then proceeds to the connector 2532 of the fluid interface 2028, which extends the passageway 113 to the pin 2544. Fluid drawn from the patient into the passageway 113 can thus flow into and through the fluid interface 2028, to the pin 2544. The drawn body fluid can further flow from the pin 2544 and into the sample element 2448, as detailed above.

A passageway 2609 extends from the connector 2530 of the fluid interface 2028 and is thus in fluid communication with the pin 2542. The passageway 2609 branches to form the waste line 324 and the pump line 327. The waste line 324 passes across an opening 2617 in the front face 2045 and extends to the waste receptacle 325. The pump line 327 passes across an opening 2619 in the front face 2045 and extends to the pump 328. When the cassette 820 is installed on the main instrument 810, the pinch valves 323a, 323b extend through the openings 2617, 2619 to engage the lines 324, 327, respectively.

The waste receptacle 325 is mounted to the front face 2045. Waste fluid passing from the fluid interface 2028 can flow through the passageways 2609, 324 and into the waste receptacle 325. Once the waste receptacle 325 is filled, the cassette 820 can be removed from the main instrument 810 and discarded. Alternatively, the filled waste receptacle 325 can be replaced with an empty waste receptacle 325.

The pump 328 can be a displacement pump (e.g., a syringe pump). A piston control 2645 can extend over at least a portion of an opening 2621 in the cassette face 2045 to allow engagement with an actuator 2652 when the cassette 820 is installed on the main instrument 810. When the cassette 820 is installed, the actuator 2652 (FIG. 23E) of the main instrument 810 engages the piston control 2645 of the pump 328 and can displace the piston control 2645 for a desired fluid flow.

It will be appreciated that, upon installing the cassette 820 of FIG. 23A on the main instrument 810 of FIG. 23E, there is formed (as shown in FIG. 23E) a fluid circuit similar to that shown in the sampling unit 200 in FIG. 3. This fluid circuit can be operated in a manner similar to that described above in connection with the apparatus of FIG. 3 (e.g., in accordance with the methodology illustrated in FIGS. 7A-7J and Table 1).

Figure 24A:
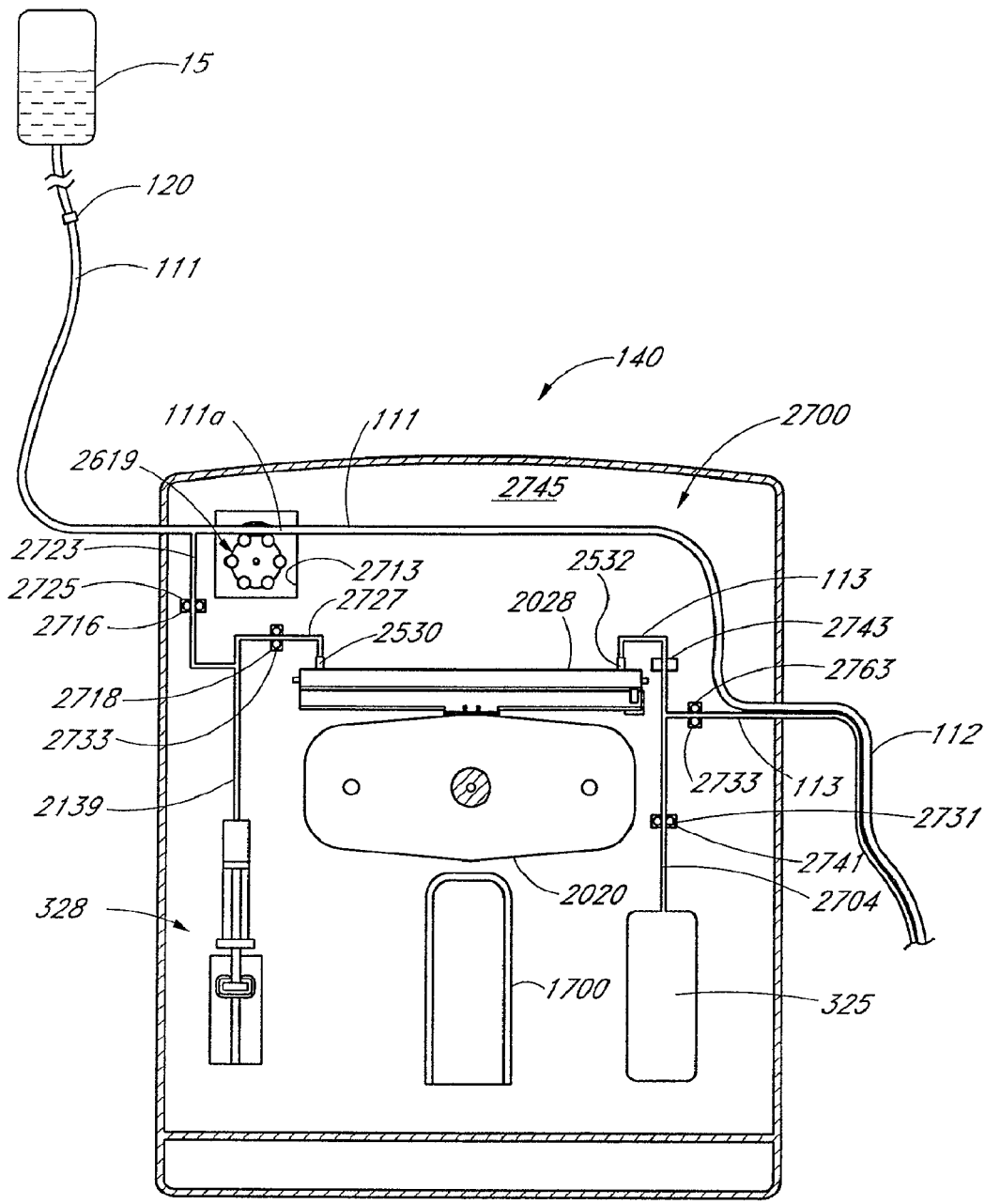
FIG. 24A is a cross-sectional view of the fluid handling and analysis apparatus having a fluid handling network in accordance with another embodiment.

FIG. 24A depicts another embodiment of a fluid handling network 2700 that can be employed in the cassette 820. The fluid handling network 2700 can be generally similar in structure and function to the network 2600 of FIG. 23B, except as detailed below. The network 2700 includes the passageway 111 which extends from the connector 120 toward and through the cassette 820 until it becomes the passageway 112, which extends from the cassette 820 to the patient connector 110. A portion 111a of the passageway 111 extends across an opening 2713 in the front face 2745 of the cassette 820. When the cassette 820 is installed on the main instrument 810, a roller pump 2619 of the main instrument 810 of FIG. 24B can engage the portion 111a in a manner similar to that described above with respect to FIGS. 23B-23C. The passageway 113 extends from the patient connector 110 towards and into the cassette 820. After entering the cassette 820, the passageway 113 extends across an opening 2763 in the front face 2745 to allow engagement with a valve 2733 of the main instrument 810. A waste line 2704 extends from the passageway 113 to the waste receptacle 325 and across an opening 2741 in the front face 2745. The passageway 113 proceeds to the connector 2532 of the fluid interface 2028, which extends the passageway 113 to the pin 2544. The passageway 113 crosses an opening 2743 in the front face 2745 to allow engagement of the passageway 113 with a bubble sensor 2741 of the main instrument 810 of FIG. 24B. When the cassette 820 is installed on the main instrument 810, the pinch valves 2732, 2733 extend through the openings 2731, 2743 to engage the passageways 113, 2704, respectively.

The illustrated fluid handling network 2700 also includes a passageway 2723 which extends between the passageway 111 and a passageway 2727, which in turn extends between the passageway 2723 and the fluid interface 2028. The passageway 2727 extends across an opening 2733 in the front face 2745. A pump line 2139 extends from a pump 328 to the passageways 2723, 2727. When the cassette 820 is installed on the main instrument 810, the pinch valves 2716, 2718 extend through the openings 2725, 2733 in the front face 2745 to engage the passageways 2723, 2727, respectively.

It will be appreciated that, upon installing the cassette 820 on the main instrument 810 (as shown in FIG. 24A), there is formed a fluid circuit that can be operated in a manner similar to that described above, in connection with the apparatus of FIGS. 9-10.

In view of the foregoing, it will be further appreciated that the various embodiments of the fluid handling and analysis apparatus 140 (comprising a main instrument 810 and cassette 820) depicted in FIGS. 22A-28 can serve as the fluid handling and analysis apparatus 140 of any of the sampling systems 100/300/500, or the fluid handling system 10, depicted in FIGS. 1-5 herein. In addition, the fluid handling and analysis apparatus 140 of FIGS. 22A-28 can, in certain embodiments, be similar to the apparatus 140 of FIGS. 1-2 or 8-10, except as further described above.

Section V—Methods for Determining Analyte Concentrations from Sample Spectra

This section discusses a number of computational methods or algorithms which may be used to calculate the concentration of the analyte(s) of interest in the sample S, and/or to compute other measures that may be used in support of calculations of analyte concentrations. Any one or combination of the algorithms disclosed in this section may reside as program instructions stored in the memory 212 so as to be accessible for execution by the processor 210 of the fluid handling and analysis apparatus 140 or analyte detection system 334 to compute the concentration of the analyte(s) of interest in the sample, or other relevant measures.

Several disclosed embodiments are devices and methods for analyzing material sample measurements and for quantifying one or more analytes in the presence of interferents. Interferents can comprise components of a material sample being analyzed for an analyte, where the presence of the interferent affects the quantification of the analyte. Thus, for example, in the spectroscopic analysis of a sample to determine an analyte concentration, an interferent could be a compound having spectroscopic features that overlap with those of the analyte. The presence of such an interferent can introduce errors in the quantification of the analyte. More specifically, the presence of interferents can affect the sensitivity of a measurement technique to the concentration of analytes of interest in a material sample, especially when the system is calibrated in the absence of, or with an unknown amount of, the interferent.

Independently of or in combination with the attributes of interferents described above, interferents can be classified as being endogenous (i.e., originating within the body) or exogenous (i.e., introduced from or produced outside the body). As example of these classes of interferents, consider the analysis of a blood sample (or a blood component sample or a blood plasma sample) for the analyte glucose. Endogenous interferents include those blood components having origins within the body that affect the quantification of glucose, and may include water, hemoglobin, blood cells, and any other component that naturally occurs in blood. Exogenous interferents include those blood components having origins outside of the body that affect the quantification of glucose, and can include items administered to a person, such as medicaments, drugs, foods or herbs, whether administered orally, intravenously, topically, etc.

Independently of or in combination with the attributes of interferents described above, interferents can comprise components which are possibly but not necessarily present in the sample type under analysis. In the example of analyzing samples of blood or blood plasma drawn from patients who are receiving medical treatment, a medicament such as acetaminophen is possibly, but not necessarily present in this sample type. In contrast, water is necessarily present in such blood or plasma samples.

To facilitate an understanding of the inventions, embodiments are discussed herein where one or more analyte concentrations are obtained using spectroscopic measurements of a sample at wavelengths including one or more wavelengths that are identified with the analyte(s). The embodiments disclosed herein are not meant to limit, except as claimed, the scope of certain disclosed inventions which are directed to the analysis of measurements in general.

As an example, certain disclosed methods are used to quantitatively estimate the concentration of one specific compound (an analyte) in a mixture from a measurement, where the mixture contains compounds (interferents) that affect the measurement. Certain disclosed embodiments are particularly effective if each analyte and interferent component has a characteristic signature in the measurement, and if the measurement is approximately affine (i.e., includes a linear component and an offset) with respect to the concentration of each analyte and interferent. In one embodiment, a method includes a calibration process including an algorithm for estimating a set of coefficients and an offset value that permits the quantitative estimation of an analyte. In another embodiment, there is provided a method for modifying hybrid linear algorithm (HLA) methods to accommodate a random set of interferents, while retaining a high degree of sensitivity to the desired component. The data employed to accommodate the random set of interferents are (a) the signatures of each of the members of the family of potential additional components and (b) the typical quantitative level at which each additional component, if present, is likely to appear.

Certain methods disclosed herein are directed to the estimation of analyte concentrations in a material sample in the possible presence of an interferent. In certain embodiments, any one or combination of the methods disclosed herein may be accessible and executable processor 210 of system 334. Processor 210 may be connected to a computer network, and data obtained from system 334 can be transmitted over the network to one or more separate computers that implement the methods. The disclosed methods can include the manipulation of data related to sample measurements and other information supplied to the methods (including, but not limited to, interferent spectra, sample population models, and threshold values, as described subsequently). Any or all of this information, as well as specific algorithms, may be updated or changed to improve the method or provide additional information, such as additional analytes or interferents.

Certain disclosed methods generate a "calibration constant" that, when multiplied by a measurement, produces an estimate of an analyte concentration. Both the calibration constant and measurement can comprise arrays of numbers. The calibration constant is calculated to minimize or reduce the sensitivity of the calibration to the presence of interferents that are identified as possibly being present in the sample. Certain methods described herein generate a calibration constant by: 1) identifying the presence of possible interferents; and 2) using information related to the identified interferents to generate the calibration constant. These certain methods do not require that the information related to the interferents includes an estimate of the interferent concentration—they merely require that the interferents be identified as possibly present. In one embodiment, the method uses a set of training spectra each having known analyte concentration(s) and produces a calibration that minimizes the variation in estimated analyte concentration with interferent concentration. The resulting calibration constant is proportional to analyte concentration(s) and, on average, is not responsive to interferent concentrations.

In one embodiment, it is not required (though not prohibited either) that the training spectra include any spectrum from the individual whose analyte concentration is to be determined. That is, the term "training" when used in reference to the disclosed methods does not require training using measurements from the individual whose analyte concentration will be estimated (e.g., by analyzing a bodily fluid sample drawn from the individual).

Several terms are used herein to describe the estimation process. As used herein, the term "Sample Population" is a broad term and includes, without limitation, a large number of samples having measurements that are used in the computation of a calibration—in other words, used to train the method of generating a calibration. For an embodiment involving the spectroscopic determination of glucose concentration, the Sample Population measurements can each include a spectrum (analysis measurement) and a glucose concentration (analyte measurement). In one embodiment, the Sample Population measurements are stored in a database, referred to herein as a "Population Database."

The Sample Population may or may not be derived from measurements of material samples that contain interferents to the measurement of the analyte(s) of interest. One distinction made herein between different interferents is based on whether the interferent is present in both the Sample Population and the sample being measured, or only in the sample. As used herein, the term "Type-A interferent" refers to an interferent that is present in both the Sample Population and in the material sample being measured to determine an analyte concentration. In certain methods it is assumed that the Sample Population includes only interferents that are endogenous, and does not include any exogenous interferents, and thus Type-A interferents are endogenous. The number of Type-A interferents depends on the measurement and analyte(s) of interest, and may number, in general, from zero to a very large number. The material sample being measured, for example sample S, may also include interferents that are not present in the Sample Population. As used herein, the term "Type-B interferent" refers to an interferent that is either: 1) not found in the Sample Population but that is found in the material sample being measured (e.g., an exogenous interferent), or 2) is found naturally in the Sample Population, but is at abnormally high concentrations in the material sample (e.g., an endogenous interferent). Examples of a Type-B exogenous interferent may include medications, and examples of Type-B endogenous interferents may include urea in persons suffering from renal failure. In the example of mid-IR spectroscopic absorption measurement of glucose in blood, water is found in all blood samples, and is thus a Type-A interferent. For a Sample Population made up of individuals who are not taking intravenous drugs, and a material sample taken from a hospital patient who is being administered a selected intravenous drug, the selected drug is a Type-B interferent.

In one embodiment, a list of one or more possible Type-B Interferents is referred to herein as forming a "Library of Interferents," and each interferent in the library is referred to as a "Library Interferent." The Library Interferents include exogenous interferents and endogenous interferents that may be present in a material sample due, for example, to a medical condition causing abnormally high concentrations of the endogenous interferent.

Figure 29:
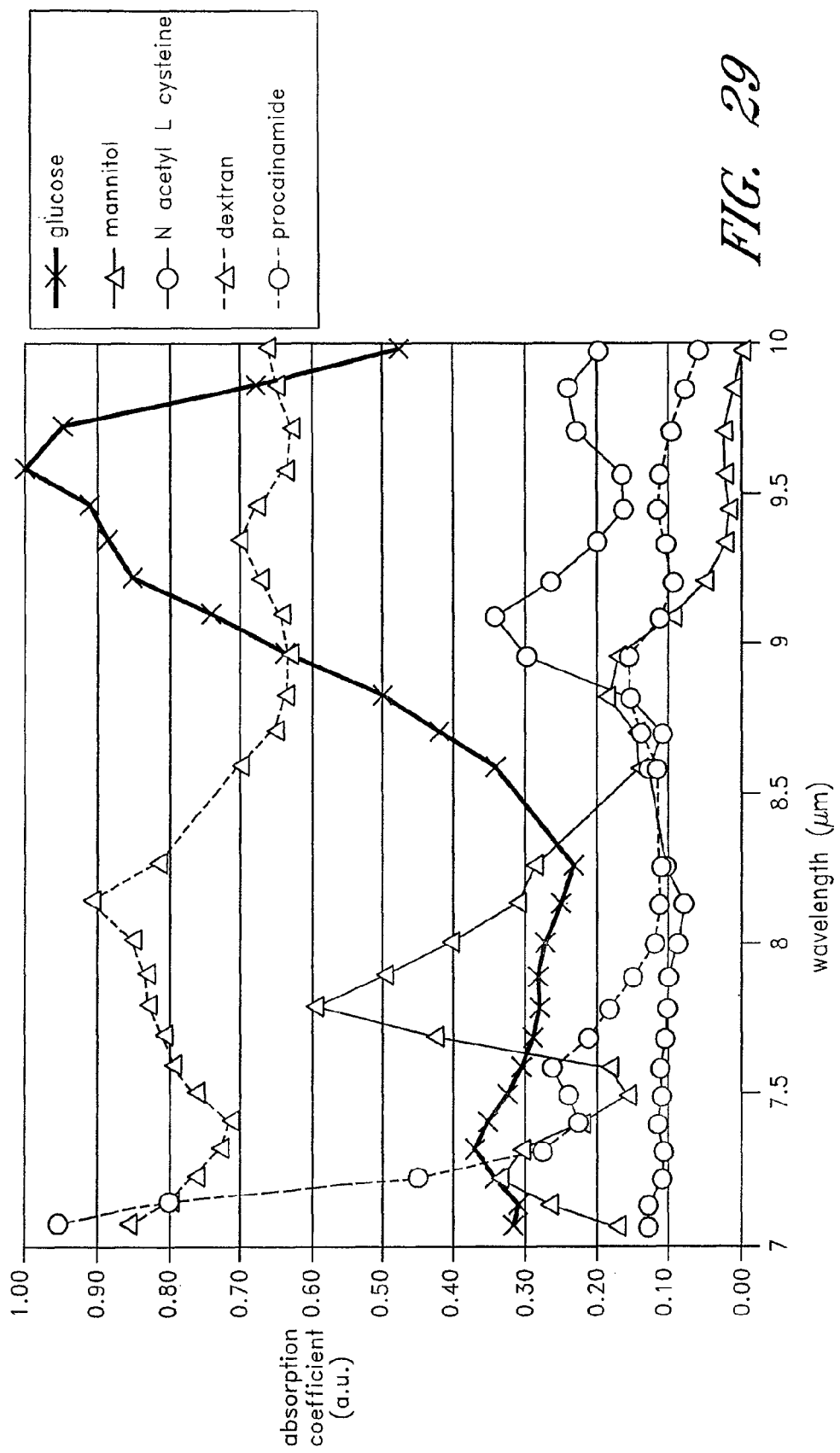
FIG. 29 is a graph illustrating the absorption spectra of various components that may be present in a blood sample.
Figure 30:
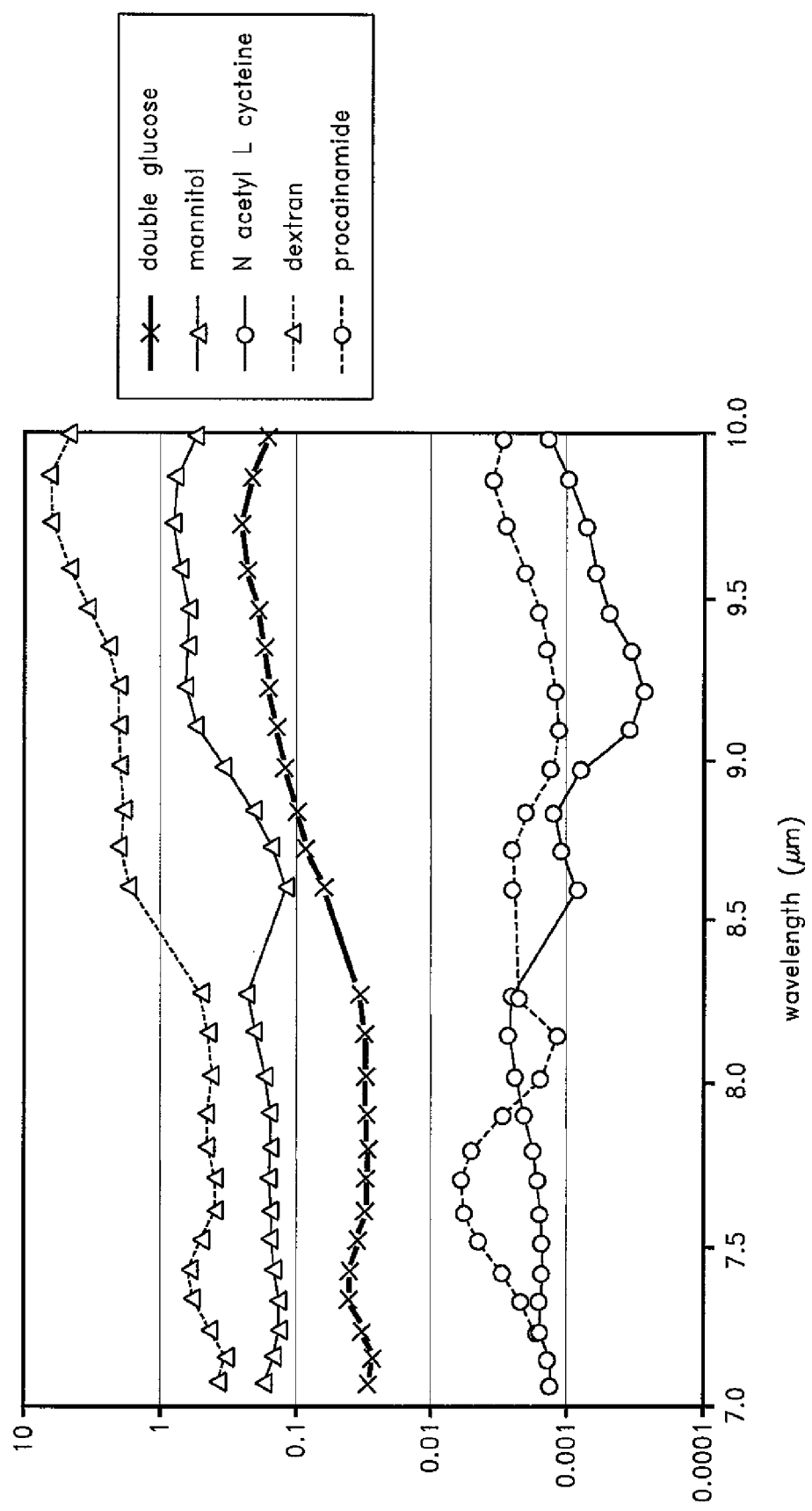
FIG. 30 is a graph illustrating the change in the absorption spectra of blood having the indicated additional components of FIG. 29 relative to a Sample Population blood and glucose concentration, where the contribution due to water has been numerically subtracted from the spectra.

In addition to components naturally found in the blood, the ingestion or injection of some medicines or illicit drugs can result in very high and rapidly changing concentrations of exogenous interferents. This results in problems in measuring analytes in blood of hospital or emergency room patients. An example of overlapping spectra of blood components and medicines is illustrated in FIG. 29 as the absorption coefficient at the same concentration and optical pathlength of pure glucose and three spectral interferents, specifically mannitol (chemical formula: hexane-1,2,3,4,5,6-hexaol), N acetyl L cysteine, dextran, and procainamide (chemical formula: 4-amino-N-(2-diethylaminoethyl)benzamid). FIG. 30 shows the logarithm of the change in absorption spectra from a Sample Population blood composition as a function of wavelength for blood containing additional likely concentrations of components, specifically, twice the glucose concentration of the Sample Population and various amounts of mannitol, N acetyl L cysteine, dextran, and procainamide. The presence of these components is seen to affect absorption over a wide range of wavelengths. It can be appreciated that the determination of the concentration of one species without a priori knowledge or independent measurement of the concentration of other species is problematic.

Figure 31:
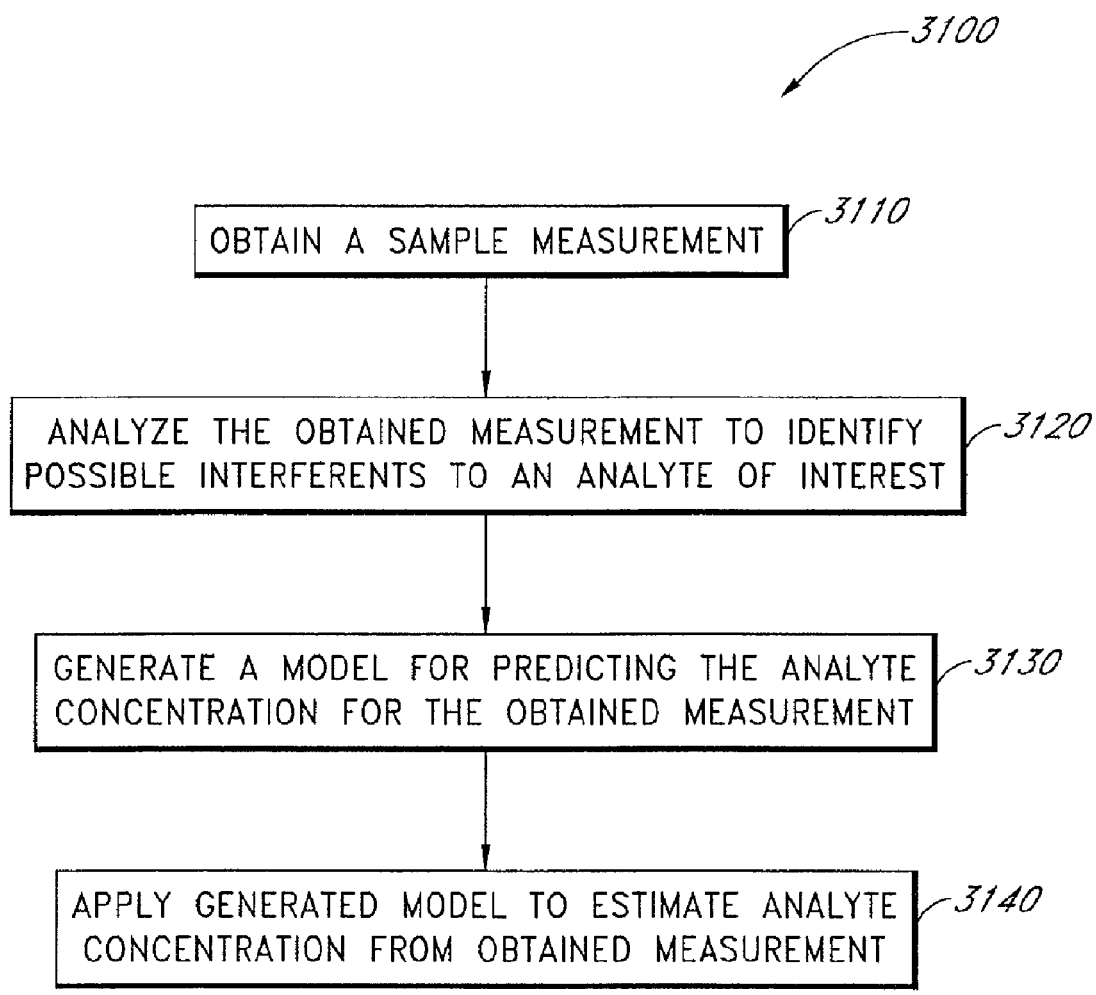
FIG. 31 is an embodiment of an analysis method for determining the concentration of an analyte in the presence of possible interferents.

One method for estimating the concentration of an analyte in the presence of interferents is presented in flowchart 3100 of FIG. 31 as a first step (Block 3110) where a measurement of a sample is obtained, a second step (Block 3120), where the obtained measurement data is analyzed to identify possible interferents to the analyte, a third step (Block 3130) where a model is generated for predicting the analyte concentration in the presence of the identified possible interferents, and a fourth step (Block 3140) where the model is used to estimate the analyte concentration in the sample from the measurement. Preferably the step of Block 3130 generates a model where the error is minimized for the presence of the identified interferents that are not present in a general population of which the sample is a member.

The method Blocks 3110, 3120, 3130, and 3140 may be repeatedly performed for each analyte whose concentration is required. If one measurement is sensitive to two or more analytes, then the methods of Blocks 3120, 3130, and 3140 may be repeated for each analyte. If each analyte has a separate measurement, then the methods of Blocks 3110, 3120, 3130, and 3140 may be repeated for each analyte.

An embodiment of the method of flowchart 3100 for the determination of an analyte from spectroscopic measurements will now be discussed. Further, this embodiment will estimate the amount of glucose concentration in blood sample S, without limit to the scope of the invention disclosed herein. In one embodiment, the measurement of Block 3110 is an absorbance spectrum, $C_s(\lambda_i)$, of a measurement sample S that has, in general, one analyte of interest, glucose, and one or more interferents. In one embodiment, the methods include generating a calibration constant $\kappa(\lambda_i)$ that, when multiplied by the absorbance spectrum $C_s(\lambda_i)$, provides an estimate, $g_{est}$, of the glucose concentration $g_s$.

As described subsequently, one embodiment of Block 3120 includes a statistical comparison of the absorbance spectrum of sample S with a spectrum of the Sample Population and combinations of individual Library Interferent spectra. After the analysis of Block 3120, a list of Library Interferents that are possibly contained in sample S has been identified and includes, depending on the outcome of the analysis of Block 3120, either no Library Interferents, or one or more Library Interferents. Block 3130 then generates a large number of spectra using the large number of spectra of the Sample Population and their respective known analyte concentrations and known spectra of the identified Library Interferents. Block 3130 then uses the generated spectra to generate a calibration constant matrix to convert a measured spectrum to an analyte concentration that is the least sensitive to the presence of the identified Library Interferents. Block 3140 then applies the generated calibration constant to predict the glucose concentration in sample S.

As indicated in Block 3110, a measurement of a sample is obtained. For illustrative purposes, the measurement, $C_s(\lambda_i)$, is assumed to be a plurality of measurements at different wavelengths, or analyzed measurements, on a sample indicating the intensity of light that is absorbed by sample S. It is to be understood that spectroscopic measurements and computations may be performed in one or more domains including, but not limited to, the transmittance, absorbance and/or optical density domains. The measurement $C_s(\lambda_i)$ is an absorption, transmittance, optical density or other spectroscopic measurement of the sample at selected wavelength or wavelength bands. Such measurements may be obtained, for example, using analyte detection system 334. In general, sample S contains Type-A interferents, at concentrations preferably within the range of those found in the Sample Population.

In one embodiment, absorbance measurements are converted to pathlength normalized measurements. Thus, for example, the absorbance is converted to optical density by dividing the absorbance by the optical pathlength, L, of the measurement. In one embodiment, the pathlength L is measured from one or more absorption measurements on known compounds. Thus, in one embodiment, one or more measurements of the absorption through a sample S of water or saline solutions of known concentration are made and the pathlength, L, is computed from the resulting absorption measurement(s). In another embodiment, absorption measurements are also obtained at portions of the spectrum that are not appreciably affected by the analytes and interferents, and the analyte measurement is supplemented with an absorption measurement at those wavelengths.

Some methods are "pathlength insensitive," in that they can be used even when the precise pathlength is not known beforehand. The sample can be placed in the sample chamber 903 or 2464, sample element 1730 or 2448, or in a cuvette or other sample container. Electromagnetic radiation (in the mid-infrared range, for example) can be emitted from a radiation source so that the radiation travels through the sample chamber. A detector can be positioned where the radiation emerges, on the other side of the sample chamber from the radiation source, for example. The distance the radiation travels through the sample can be referred to as a "pathlength." In some embodiments, the radiation detector can be located on the same side of the sample chamber as the radiation source, and the radiation can reflect off one or more internal walls of the sample chamber before reaching the detector.

As discussed above, various substances can be inserted into the sample chamber. For example, a reference fluid such as water or saline solution can be inserted, in addition to a sample or samples containing an analyte or analytes. In some embodiments, a saline reference fluid is inserted into the sample chamber and radiation is emitted through that reference fluid. The detector measures the amount and/or characteristics of the radiation that passes through the sample chamber and reference fluid without being absorbed or reflected. The measurement taken using the reference fluid can provide information relating to the pathlength traveled by the radiation. For example, data may already exist from previous measurements that have been taken under similar circumstances. That is, radiation can be emitted previously through sample chambers with various known pathlengths to establish reference data that can be arranged in a "look-up table," for example. With reference fluid in the sample chamber, a oneto-one correspondence can be experimentally established between various detector readings and various pathlengths, respectively. This correspondence can be recorded in the look-up table, which can be recorded in a computer database or in electronic memory, for example.

One method of determining the radiation pathlength can be accomplished with a thin, empty sample chamber. In particular, this approach can determine the thickness of a narrow sample chamber or cell with two reflective walls. (Because the chamber will be filled with a sample, this same thickness corresponds to the "pathlength" radiation will travel through the sample). A range of radiation wavelengths can be emitted in a continuous manner through the cell or sample chamber. The radiation can enter the cell and reflect off the interior cell walls, bouncing back and forth between those walls one or multiple times before exiting the cell and passing into the radiation detector. This can create a periodic interference pattern or "fringe" with repeating maxima and minima. This periodic pattern can be plotted where the horizontal axis is a range of wavelengths and the vertical axis is a range of transmittance, measured as a percentage of total transmittance, for example. The maxima occur when the radiation reflected off of the two internal surfaces of the cell has traveled a distance that is an integral multiple N of the wavelength of the radiation that was transmitted without reflection. Constructive interference occurs whenever the wavelength is equal to 2b/N, where "b" is the thickness (or pathlength) of the cell. Thus, if $\Delta N$ is the number of maxima in this fringe pattern for a given range of wavelengths $\lambda_1$-$\lambda_2$, then the thickness of the cell b is provided by the following relation: $b=\Delta N/2(\lambda_1-\lambda_2)$. This approach can be especially useful when the refractive index of the material within the sample chamber or fluid cell is not the same as the refractive index of the walls of the cell, because this condition improves reflection.

Once the pathlength has been determined, it can be used to calculate or determine a reference value or a reference spectrum for the interferents (such as protein or water) that may be present in a sample. For example, both an analyte such as glucose and an interferent such as water may absorb radiation at a given wavelength. When the source emits radiation of that wavelength and the radiation passes through a sample containing both the analyte and the interferent, both the analyte and the interferent absorb the radiation. The total absorption reading of the detector is thus fully attributable to neither the analyte nor the interferent, but a combination of the two. However, if data exists relating to how much radiation of a given wavelength is absorbed by a given interferent when the radiation passes through a sample with a given pathlength, the contribution of the interferent can be subtracted from the total reading of the detector and the remaining value can provide information regarding concentration of the analyte in the sample. A similar approach can be taken for a whole spectrum of wavelengths. If data exists relating to how much radiation is absorbed by an interferent over a range of wavelengths when the radiation passes through a sample with a given pathlength, the interferent absorbance spectrum can be subtracted from the total absorbance spectrum, leaving only the analyte's absorbance spectrum for that range of wavelengths. If the interferent absorption data is taken for a range of possible pathlengths, it can be helpful to determine the pathlength of a particular sample chamber first so that the correct data can be found for samples measured in that sample chamber.

This same process can be applied iteratively or simultaneously for multiple interferents and/or multiple analytes. For example, the water absorbance spectrum and the protein absorbance spectrum can both be subtracted to leave behind the glucose absorbance spectrum.

The pathlength can also be calculated using an isosbestic wavelength. An isosbestic wavelength is one at which all components of a sample have the same absorbance. If the components (and their absorption coefficients) in a particular sample are known, and one or multiple isosbestic wavelengths are known for those particular components, the absorption data collected by the radiation detector at those isosbestic wavelengths can be used to calculate the pathlength. This can be advantageous because the needed information can be obtained from multiple readings of the absorption detector that are taken at approximately the same time, with the same sample in place in the sample chamber. The isosbestic wavelength readings are used to determine pathlength, and other selected wavelength readings are used to determine interferent and/or analyte concentration. Thus, this approach is efficient and does not require insertion of a reference fluid in the sample chamber.

In some embodiments, a method of determining concentration of an analyte in a sample can include inserting a fluid sample into a sample container, emitting radiation from a source through the container and the fluid sample, obtaining total sample absorbance data by measuring the amount of radiation that reaches the detector, subtracting the correct interferent absorbance value or spectrum from the total sample absorbance data, and using the remaining absorbance value or spectrum to determine concentration of an analyte in the fluid sample. The correct interferent absorbance value can be determined using the calculated pathlength.

The concentration of an analyte in a sample can be calculated using the Beer-Lambert law (or Beer's Law) as follows: If T is transmittance, A is absorbance, $P_0$ is initial radiant power directed toward a sample, and P is the power that emerges from the sample and reaches a detector, then $T=P/P_0$, and $A=-\log T=\log(P_0/P)$. Absorbance is directly proportional to the concentration (c) of the light-absorbing species in the sample, also known as an analyte or an interferent. Thus, if e is the molar absorptivity (1/M 1/cm), b is the path length (cm), and c is the concentration (M), Beer's Law can be expressed as follows: $A=ebc$. Thus, $c=A/(eb)$.

Referring once again to flowchart 3100, the next step is to determine which Library Interferents are present in the sample. In particular, Block 3120 indicates that the measurements are analyzed to identify possible interferents. For spectroscopic measurements, it is preferred that the determination is made by comparing the obtained measurement to interferent spectra in the optical density domain. The results of this step provide a list of interferents that may, or are likely to, be present in the sample. In one embodiment, several input parameters are used to estimate a glucose concentration $g_{est}$ from a measured spectrum, $C_s$. The input parameters include previously gathered spectrum measurement of samples that, like the measurement sample, include the analyte and combinations of possible interferents from the interferent library; and spectrum and concentration ranges for each possible interferent. More specifically, the input parameters are:

Library of Interferent Data: Library of Interferent Data includes, for each of "M" interferents, the absorption spectrum of each interferent, $IF=\{IF_1, IF_2, \ldots, IF_M\}$, where $m=1, 2, \ldots, M$; and a maximum concentration for each interferent, $Tmax=\{Tmax_1, Tmax_2, \ldots, Tmax_M\}$; and Sample Population Data: Sample Population Data includes individual spectra of a statistically large population taken over the same wavelength range as the sample spectrum, $Cs_i$, and an analyte concentration corresponding to each spectrum. As an example, if there are N Sample Population spectra, then the spectra can be represented as $C=\{C_1, C_2, \ldots, C_N\}$, where $n=1, 2, \ldots, N$, and the analyte concentration corresponding to each spectrum can be represented as $g=\{g_1, g_2, \ldots, g_N\}$.

Preferably, the Sample Population does not have any of the M interferents present, and the material sample has interferents contained in the Sample Population and none or more of the Library Interferents. Stated in terms of Type-A and Type-B interferents, the Sample Population has Type-A interferents and the material sample has Type-A and may have Type-B interferents. The Sample Population Data are used to statistically quantify an expected range of spectra and analyte concentrations. Thus, for example, for a system 10 or 334 used to determine glucose in blood of a person having unknown spectral characteristics, the spectral measurements are preferably obtained from a statistical sample of the population.

The following discussion, which is not meant to limit the scope of the present disclosure, illustrates embodiments for measuring more than one analyte using spectroscopic techniques. If two or more analytes have non-overlapping spectral features, then a first embodiment is to obtain a spectrum corresponding to each analyte. The measurements may then be analyzed for each analyte according to the method of flowchart 3100. An alternative embodiment for analytes having non-overlapping features, or an embodiment for analytes having overlapping features, is to make one measurement comprising the spectral features of the two or more analytes. The measurement may then be analyzed for each analyte according to the method of flowchart 3100. That is, the measurement is analyzed for each analyte, with the other analytes considered to be interferents to the analyte being analyzed for.

Interferent Determination

Figure 32:
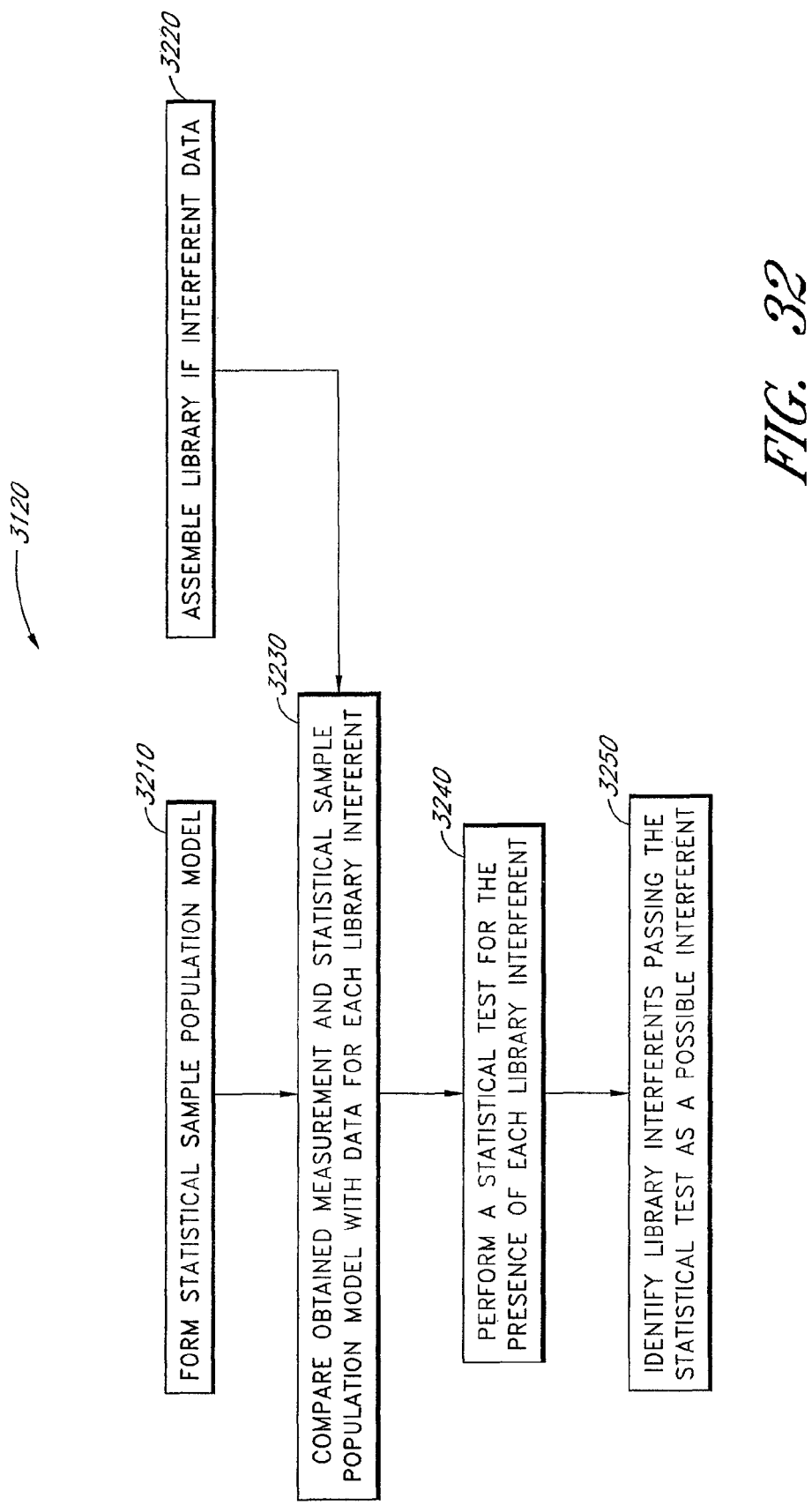
FIG. 32 is one embodiment of a method for identifying interferents in a sample for use with the embodiment of FIG. 31.

One embodiment of the method of Block 3120 is shown in greater detail with reference to the flowchart of FIG. 32. The method includes forming a statistical Sample Population model (Block 3210), assembling a library of interferent data (Block 3220), comparing the obtained measurement and statistical Sample Population model with data for each interferent from an interferent library (Block 3230), performing a statistical test for the presence of each interferent from the interferent library (Block 3240), and identifying each interferent passing the statistical test as a possible Library Interferent (Block 3250). The steps of Block 3220 can be performed once or can be updated as necessary. The steps of Blocks 3230, 3240, and 3250 can either be performed sequentially for all interferents of the library, as shown, or alternatively, be repeated sequentially for each interferent.

One embodiment of each of the methods of Blocks 3210, 3220, 3230, 3240, and 3250 are now described for the example of identifying Library Interferents in a sample from a spectroscopic measurement using Sample Population Data and a Library of Interferent Data, as discussed previously. Each Sample Population spectrum includes measurements (e.g., of optical density) taken on a sample in the absence of any Library Interferents and has an associated known analyte concentration. A statistical Sample Population model is formed (Block 3210) for the range of analyte concentrations by combining all Sample Population spectra to obtain a mean matrix and a covariance matrix for the Sample Population. Thus, for example, if each spectrum at n different wavelengths is represented by an $n \times 1$ matrix, $C$, then the mean spectrum, $\mu$, is a $n \times 1$ matrix with the (e.g., optical density) value at each wavelength averaged over the range of spectra, and the covariance matrix, $V$, is the expected value of the deviation between $C$ and $\mu$ as $V = E((C-\mu)(C-\mu)^T)$. The matrices $\mu$ and $V$ are one model that describes the statistical distribution of the Sample Population spectra.

In another step, Library Interferent information is assembled (Block 3220). A number of possible interferents are identified, for example as a list of possible medications or foods that might be ingested by the population of patients at issue or measured by system 10 or 334, and their spectra (in the absorbance, optical density, or transmission domains) are obtained. In addition, a range of expected interferent concentrations in the blood, or other expected sample material, are estimated. Thus, each of M interferents has spectrum IF and maximum concentration Tmax. This information is preferably assembled once and is accessed as needed.

The obtained measurement data and statistical Sample Population model are next compared with data for each interferent from the interferent library (Block 3230) to perform a statistical test (Block 3240) to determine the identity of any interferent in the mixture (Block 3250). This interferent test will first be shown in a rigorous mathematical formulation, followed by a discussion of FIGS. 33A and 33B which illustrates the method.

Mathematically, the test of the presence of an interferent in a measurement proceeds as follows. The measured optical density spectrum, $C_s$, is modified for each interferent of the library by analytically subtracting the effect of the interferent, if present, on the measured spectrum. More specifically, the measured optical density spectrum, $C_s$, is modified, wavelength-by-wavelength, by subtracting an interferent optical density spectrum. For an interferent, M, having an absorption spectrum per unit of interferent concentration, $IF_M$, a modified spectrum is given by $C'_s(T) = C_s - IF_M T$, where T is the interferent concentration, which ranges from a minimum value, Tmin, to a maximum value Tmax. The value of Tmin may be zero or, alternatively, be a value between zero and Tmax, such as some fraction of Tmax.

Next, the Mahalanobis distance (MD) between the modified spectrum $C'_s(T)$ and the statistical model ($\mu$, V) of the Sample Population spectra is calculated as:

$$MD^2(C_s-(Tt),\mu;\rho_s) = (C_s-(TIF_m)-\mu)^T V^{-1}(C_s-(TIF_m)-\mu)$$  Eq. (1)

The test for the presence of interferent IF is to vary T from Tmin to Tmax (i.e., evaluate $C'_s(T)$ over a range of values of T) and determine whether the minimum MD in this interval is in a predetermined range. Thus for example, one could determine whether the minimum MD in the interval is sufficiently small relative to the quantiles of a $\chi^2$ random variable with L degrees of freedom (L=number of wavelengths).

Figure 33A:
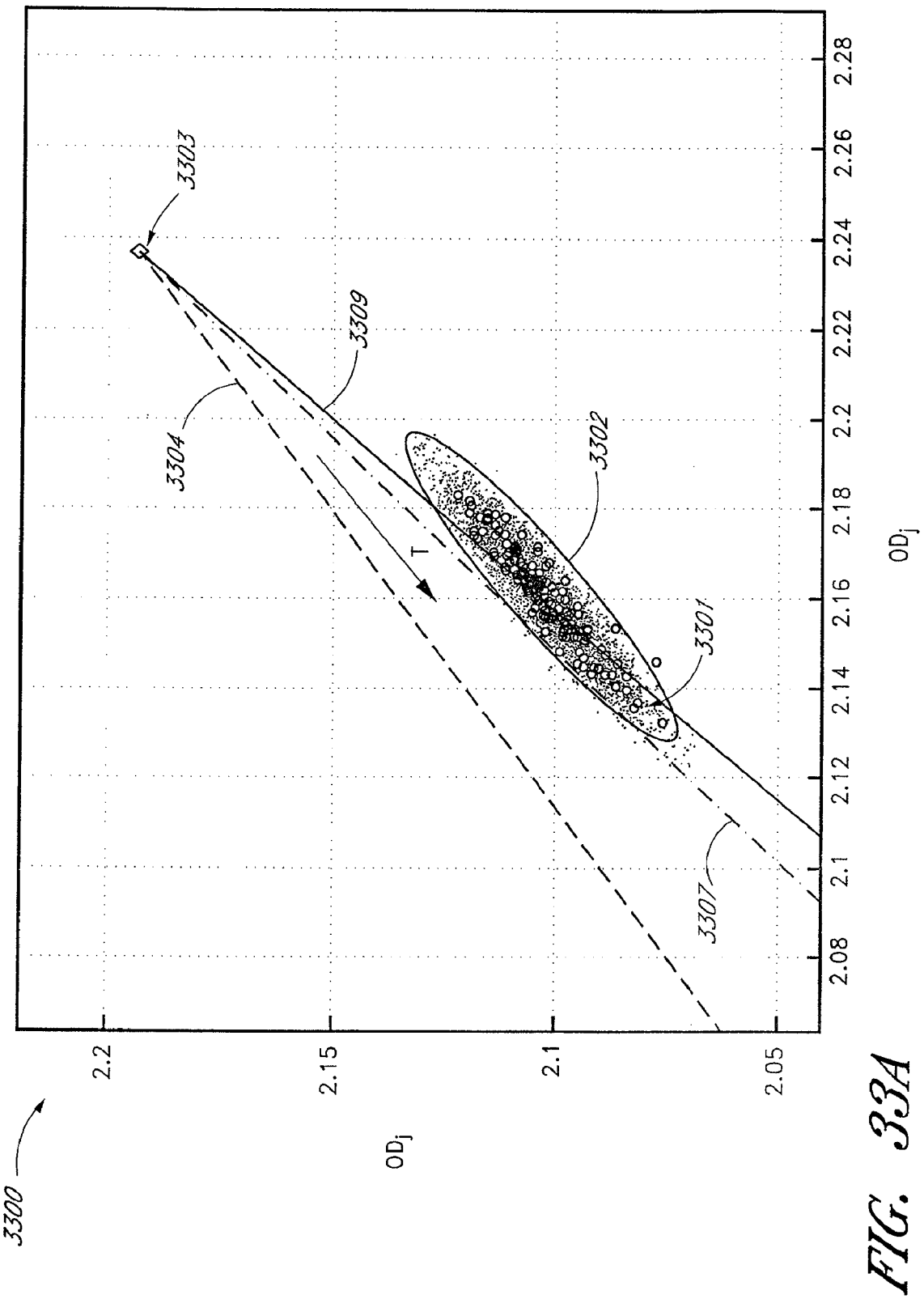
FIG. 33A is a graph illustrating one embodiment of the method of FIG. 32.

FIG. 33A is a graph 3300 illustrating the steps of Blocks 3230 and 3240. The axes of graph 3300, $OD_i$ and $OD_j$, are used to plot optical densities at two of the many wavelengths at which measurements are obtained. The points 3301 are the measurements in the Sample Population distribution. Points 3301 are clustered within an ellipse that has been drawn to encircle the majority of points. Points 3301 inside ellipse 3302 represent measurements in the absence of Library Interferents. Point 3303 is the sample measurement. Presumably, point 3303 is outside of the spread of points 3301 due the presence of one or more Library Interferents. Lines 3304, 3307, and 3309 indicate the measurement of point 3303 as corrected for increasing concentration, T, of three different Library Interferents over the range from Tmin to Tmax. The three interferents of this example are referred to as interferent #1, interferent #2, and interferent #3. Specifically, lines 3304, 3307, and 3309 are obtained by subtracting from the sample measurement an amount T of a Library Interferent (interferent #1, interferent #2, and interferent #3, respectively), and plotting the corrected sample measurement for increasing T.

Figure 33B:
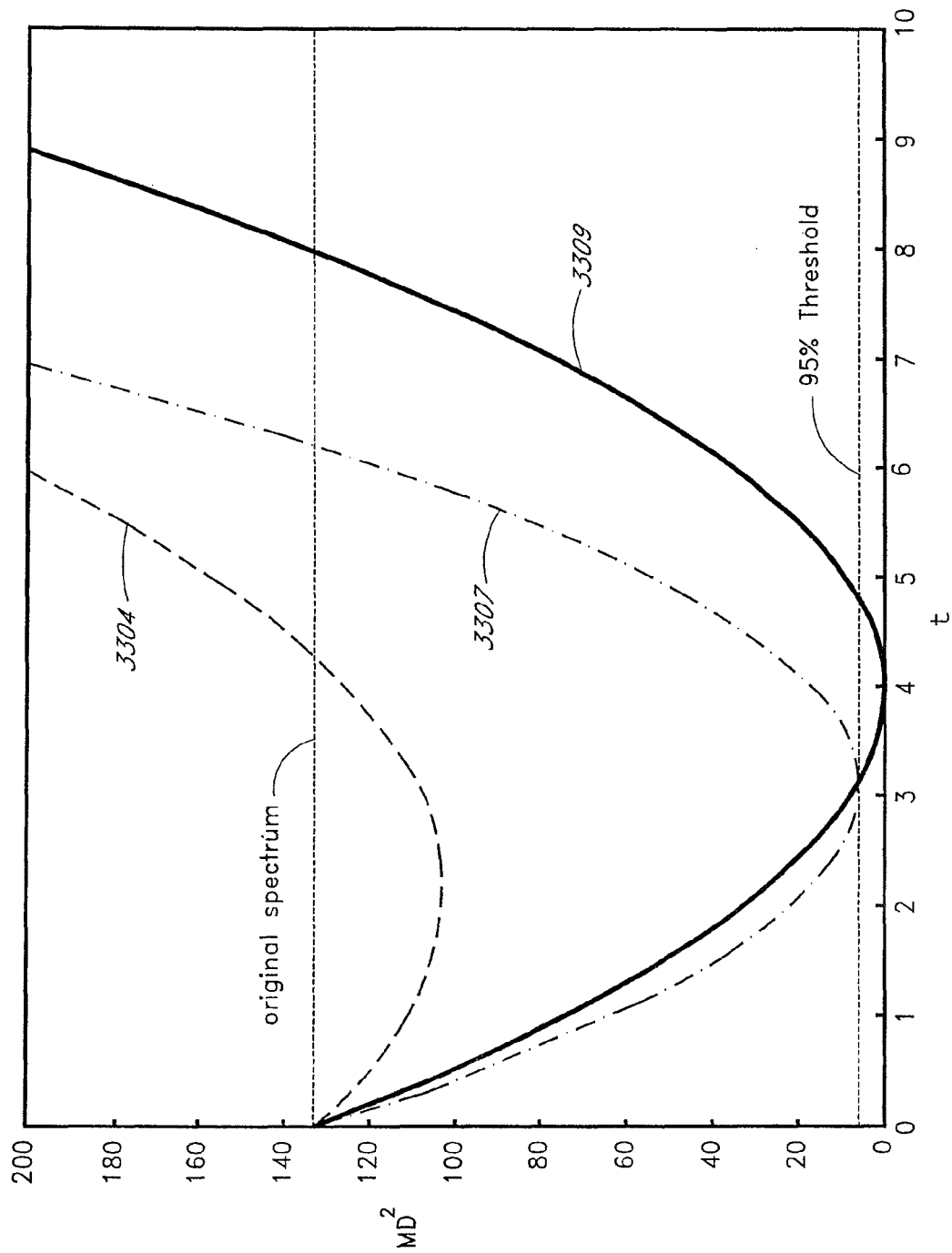
FIG. 33B is a graph further illustrating the method of FIG. 32.

FIG. 33B is a graph further illustrating the method of FIG. 32. In the graph of FIG. 33B, the squared Mahalanobis distance, $MD^2$ has been calculated and plotted as a function of t for lines 3304, 3307, and 3309. Referring to FIG. 33A, line 3304 reflects decreasing concentrations of interferent #1 and only slightly approaches points 3301. The value of $MD^2$ of line 3304, as shown in FIG. 33B, decreases slightly and then increases with decreasing interferent #1 concentration.

Referring to FIG. 33A, line 3307 reflects decreasing concentrations of interferent #2 and approaches or passes through many points 3301. The value of $MD^2$ of line 3307, as shown in FIG. 33B, shows a large decrease at some interferent #2 concentration, then increases. Referring to FIG. 33A, line 3309 has decreasing concentrations of interferent #3 and approaches or passes through even more points 3303. The value of $MD^2$ of line 3309, as shown in FIG. 33B, shows a still larger decrease at some interferent #3 concentration.

In one embodiment, a threshold level of $MD^2$ is set as an indication of the presence of a particular interferent. Thus, for example, FIG. 33B shows a line labeled "original spectrum" indicating $MD^2$ when no interferents are subtracted from the spectrum, and a line labeled "95% Threshold", indicating the 95% quantile for the $chi^2$ distribution with L degrees of freedom (where L is the number of wavelengths represented in the spectra). This level is the value which should exceed 95% of the values of the $MD^2$ metric; in other words, values at this level are uncommon, and those far above it should be quite rare. Of the three interferents represented in FIGS. 33A and 33B, only interferent #3 has a value of $MD^2$ below the threshold. Thus, this analysis of the sample indicates that interferent #3 is the most likely interferent present in the sample. Interferent #1 has its minimum far above the threshold level and is extremely unlikely to be present; interferent #2 barely crosses the threshold, making its presence more likely than interferent #1, but still far less likely to be present than interferent #1.

As described subsequently, information related to the identified interferents is used in generating a calibration constant that is relatively insensitive to a likely range of concentration of the identified interferents. In addition to being used in certain methods described subsequently, the identification of the interferents may be of interest and may be provided in a manner that would be useful. Thus, for example, for a hospital based glucose monitor, identified interferents may be reported on display 141 or be transmitted to a hospital computer via communications link 216.

Calibration Constant Generation Embodiments

Figure 34:
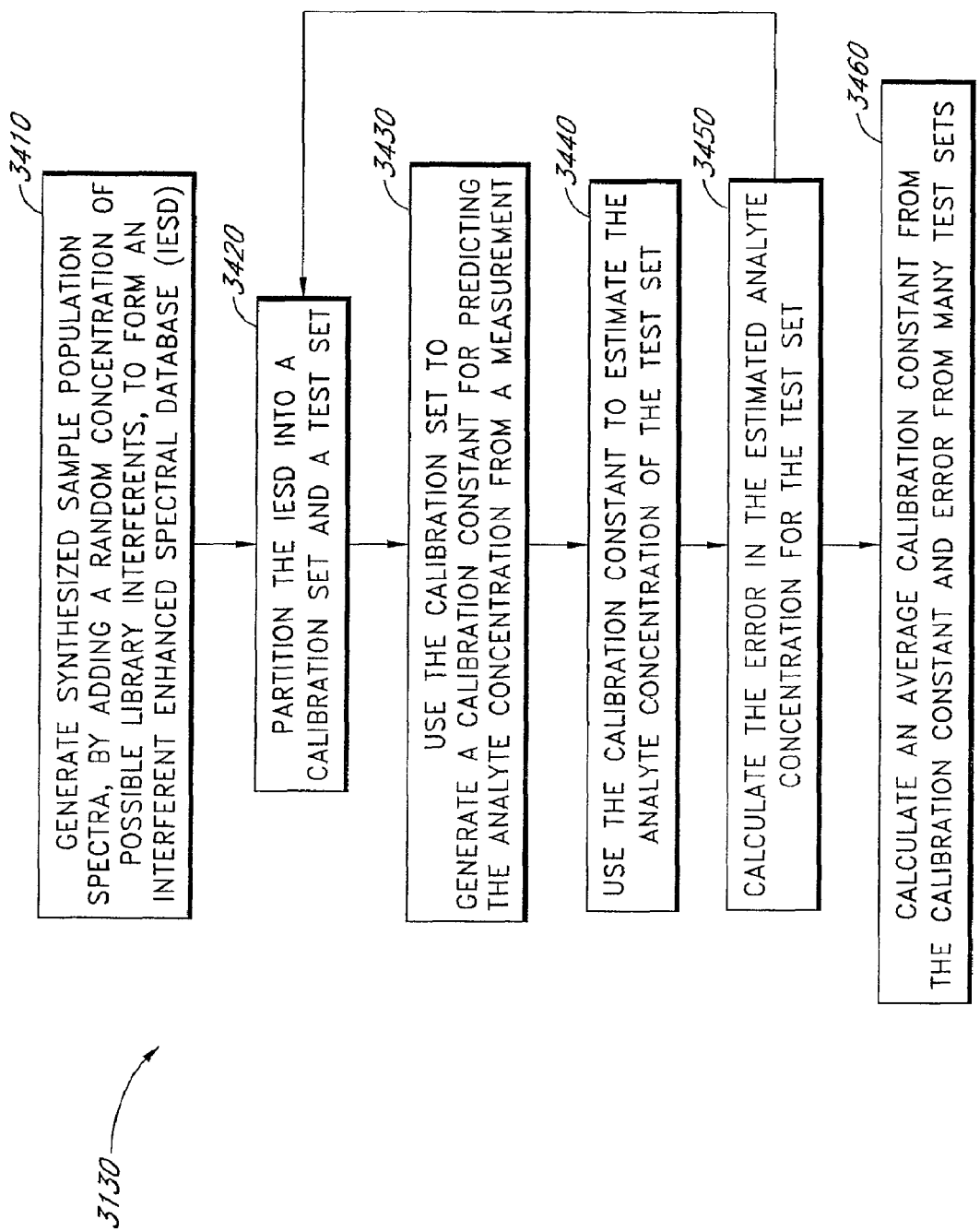
FIG. 34 is a one embodiment of a method for generating a model for identifying possible interferents in a sample for use with an embodiment of FIG. 31.

Once Library Interferents are identified as being possibly present in the sample under analysis, a calibration constant for estimating the concentration of analytes in the presence of the identified interferents is generated (Block 3130). More specifically, after Block 3120, a list of possible Library Interferents is identified as being present. One embodiment of the steps of Block 3120 are shown in the flowchart of FIG. 34 as Block 3410, where synthesized Sample Population measurements are generated, Block 3420, where the synthesized Sample Population measurements are partitioned in to calibration and test sets, Block 3430, where the calibration are is used to generate a calibration constant, Block 3440, where the calibration set is used to estimate the analyte concentration of the test set, Block 3450 where the errors in the estimated analyte concentration of the test set is calculated, and Block 3460 where an average calibration constant is calculated.

Figure 35:
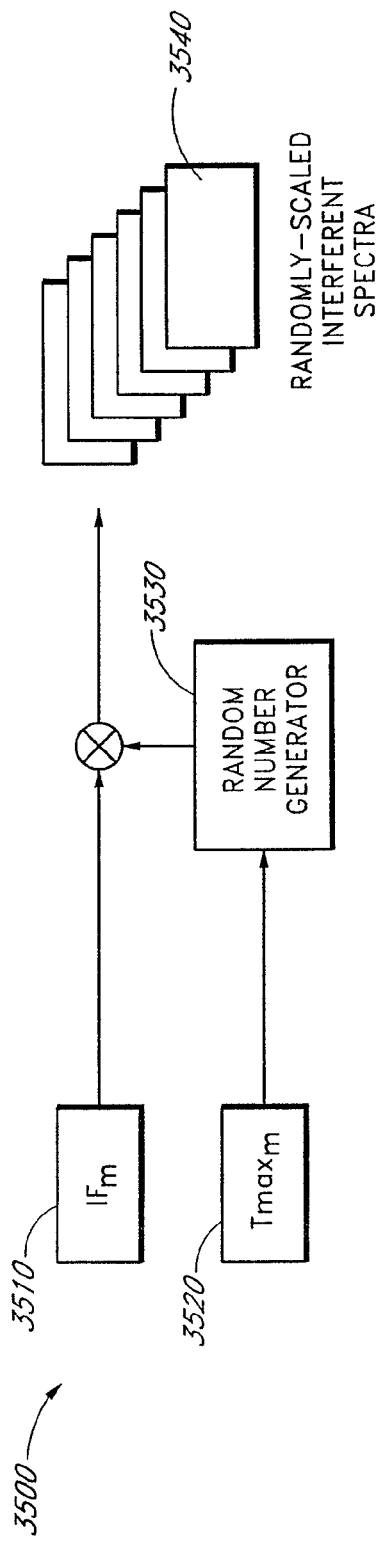
FIG. 35 is a schematic of one embodiment of a method for generating randomly-scaled interferent spectra.
Figure 36:
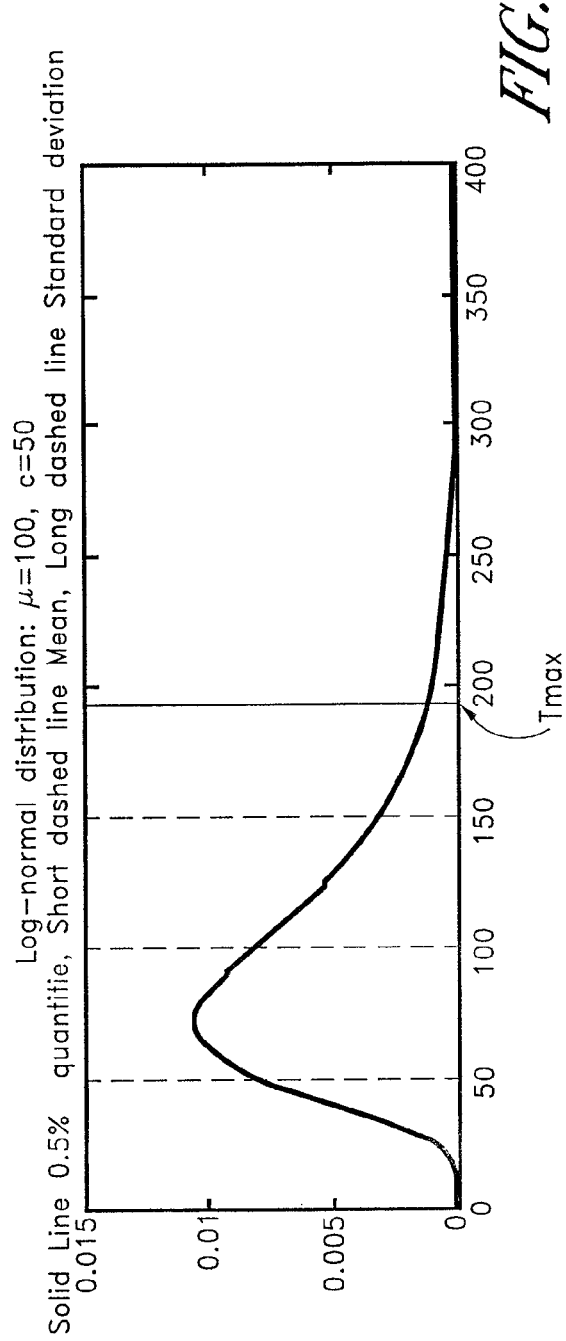
FIG. 36 is one embodiment of a distribution of interferent concentrations for use with the embodiment of FIG. 35.
Figure 37:
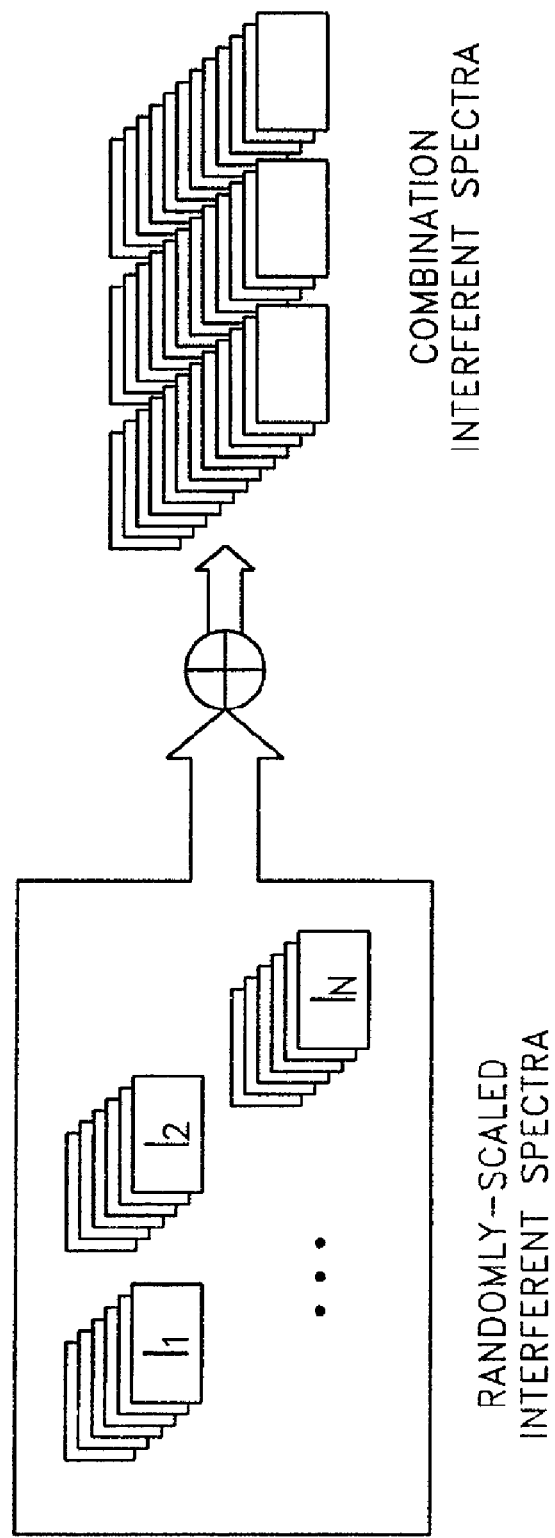
FIG. 37 is a schematic of one embodiment of a method for generating combination interferent spectra.

One embodiment of each of the methods of Blocks 3410, 3420, 3430, 3440, 3450, and 3460 are now described for the example of using identifying interferents in a sample for generating an average calibration constant. As indicated in Block 3410, one step is to generate synthesized Sample Population spectra, by adding a random concentration of possible Library Interferents to each Sample Population spectrum. The spectra generated by the method of Block 3410 are referred to herein as an Interferent-Enhanced Spectral Database, or IESD. The IESD can be formed by the steps illustrated in FIGS. 35-38, where FIG. 35 is a schematic diagram 3500 illustrating the generation of Randomly-Scaled Single Interferent Spectra, or RSIS; FIG. 36 is a graph 3600 of the interferent scaling; FIG. 37 is a schematic diagram illustrating the combination of RSIS into Combination Interferent Spectra, or CIS; and FIG. 38 is a schematic diagram illustrating the combination of CIS and the Sample Population spectra into an IESD.

The first step in Block 3410 is shown in FIGS. 35 and 36. As shown schematically in flowchart 3500 in FIG. 35, and in graph 3600 in FIG. 36, a plurality of RSIS (Block 3540) are formed by combinations of each previously identified Library Interferent having spectrum $IF_m$ (Block 3510), multiplied by the maximum concentration $Tmax_m$ (Block 3520) that is scaled by a random factor between zero and one (Block 3530), as indicated by the distribution of the random number indicated in graph 3600. In one embodiment, the scaling places the maximum concentration at the $95^{th}$ percentile of a log-normal distribution to produce a wide range of concentrations with the distribution having a standard deviation equal to half of its mean value. The distribution of the random numbers in graph 3600 are a log-normal distribution of $\mu t=100$, $\sigma 50$.

Once the individual Library Interferent spectra have been multiplied by the random concentrations to produce the RSIS, the RSIS are combined to produce a large population of interferent-only spectra, the CIS, as illustrated in FIG. 37. The individual RSIS are combined independently and in random combinations, to produce a large family of CIS, with each spectrum within the CIS consisting of a random combination of RSIS, selected from the full set of identified Library Interferents. The method illustrated in FIG. 37 produces adequate variability with respect to each interferent, independently across separate interferents.

Figure 38:
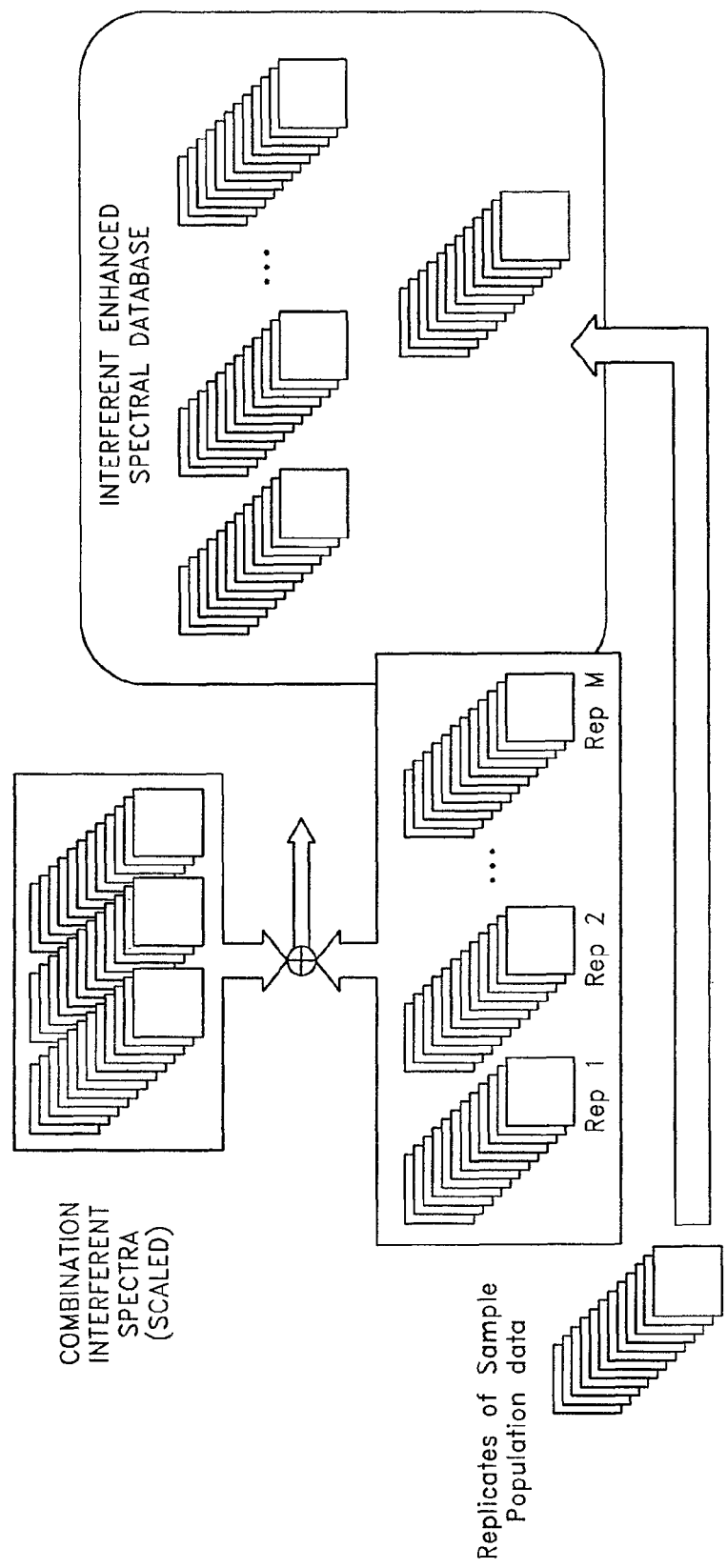
FIG. 38 is a schematic of one embodiment of a method for generating an interferent-enhanced spectral database.

The next step combines the CIS and replicates of the Sample Population spectra to form the IESD, as illustrated in FIG. 38. Since the Interferent Data and Sample Population spectra may have been obtained at different pathlengths, the CIS are first scaled (i.e., multiplied) to the same pathlength. The Sample Population database is then replicated M times, where M depends on the size of the database, as well as the number of interferents to be treated. The IESD includes M copies of each of the Sample Population spectra, where one copy is the original Sample Population Data, and the remaining M−1 copies each have an added random one of the CIS spectra. Each of the IESD spectra has an associated analyte concentration from the Sample Population spectra used to form the particular IESD spectrum.

In one embodiment, a 10-fold replication of the Sample Population database is used for 130 Sample Population spectra obtained from 58 different individuals and 18 Library Interferents. Greater spectral variety among the Library Interferent spectra requires a smaller replication factor, and a greater number of Library Interferents requires a larger replication factor.

The steps of Blocks 3420, 3430, 3440, and 3450 are executed to repeatedly combine different ones of the spectra of the IESD to statistically average out the effect of the identified Library Interferents. First, as noted in Block 3420, the IESD is partitioned into two subsets: a calibration set and a test set. As described subsequently, the repeated partitioning of the IESD into different calibration and test sets improves the statistical significance of the calibration constant. In one embodiment, the calibration set is a random selection of some of the IESD spectra and the test set are the unselected IESD spectra. In a preferred embodiment, the calibration set includes approximately two-thirds of the IESD spectra.

In an alternative embodiment, the steps of Blocks 3420, 3430, 3440, and 3450 are replaced with a single calculation of an average calibration constant using all available data.

Next, as indicted in Block 3430, the calibration set is used to generate a calibration constant for predicting the analyte concentration from a sample measurement. First an analyte spectrum is obtained. For the embodiment of glucose determined from absorption measurements, a glucose absorption spectrum is indicated as $a_G$. The calibration constant is then generated as follows. Using the calibration set having calibration spectra $\mathbf{C}=\{c_1, c_2, \ldots, c_n\}$ and corresponding glucose concentration values $\mathbf{G}=\{g_1, g_2, \ldots, g_n\}$, then glucose-free spectra $\mathbf{C}'=\{c'_1, c'_2, \ldots, c'_n\}$ can be calculated as: $c'_j = c_j - a_G g_j$. Next, the calibration constant, $\kappa$, is calculated from $\mathbf{C}'$ and $a_G$, according to the following 5 steps:

1) $\mathbf{C}'$ is decomposed into $\mathbf{C}' = A_{\mathbf{C}'} \Delta_{\mathbf{C}'} B_{\mathbf{C}'}$, that is, a singular value decomposition, where the A-factor is an orthonormal basis of column space, or span, of $\mathbf{C}'$;
2) $A_{\mathbf{C}'}$ is truncated to avoid overfitting to a particular column rank r, based on the sizes of the diagonal entries of $\Delta$ (the singular values of $\mathbf{C}'$). The selection of r involves a trade-off between the precision and stability of the calibration, with a larger r resulting in a more precise but less stable solution. In one embodiment, each spectrum C includes 25 wavelengths, and r ranges from 15 to 19;
3) The first r columns of $A_{\mathbf{C}'}$ are taken as an orthonormal basis of span($\mathbf{C}'$);
4) The projection from the background is found as the product $P_{\mathbf{C}'} = A_{\mathbf{C}'} A_{\mathbf{C}'}^T$, that is the orthogonal projection onto the span of $\mathbf{C}'$, and the complementary, or nulling projection $P_{\mathbf{C}'}^\perp = 1 - P_{\mathbf{C}'}$, which forms the projection onto the complementary subspace $\mathbf{C}'^\perp$, is calculated; and
5) The calibration vector $\kappa$ is then found by applying the nulling projection to the absorption spectrum of the analyte of interest: $\kappa_{RAW} = P_{\mathbf{C}'}^\perp a_G$, and normalizing: $\kappa = \kappa_{RAW} / \langle \kappa_{RAW}, a_G \rangle$, where the angle brackets $\langle , \rangle$ denote the standard inner (or dot) product of vectors. The normalized calibration constant produces a unit response for a unit $a_G$ spectral input for one particular calibration set.

Next, the calibration constant is used to estimate the analyte concentration in the test set (Block 3440). Specifically, each spectrum of the test set (each spectrum having an associated glucose concentration from the Sample Population spectra used to generate the test set) is multiplied by the calibration vector $\kappa$ from Block 3430 to calculate an estimated glucose concentration. The error between the calculated and known glucose concentration is then calculated (Block 3450). Specifically, the measure of the error can include a weighted value averaged over the entire test set according to $1/\text{rms}^2$.

Blocks 3420, 3430, 3440, and 3450 are repeated for many different random combinations of calibration sets. Preferably, Blocks 3420, 3430, 3440, and 3450 are repeated are repeated hundreds to thousands of times. Finally, an average calibration constant is calculated from the calibration and error from the many calibration and test sets (Block 3460). Specifically, the average calibration is computed as weighted average calibration vector. In one embodiment the weighting is in proportion to a normalized rms, such as the $\kappa_{ave} = \kappa * \text{rms}^2 / \Sigma(\text{rms}^2)$ for all tests.

With the last of Block 3130 executed according to FIG. 34, the average calibration constant $\kappa_{ave}$ is applied to the obtained spectrum (Block 3140).

Accordingly, one embodiment of a method of computing a calibration constant based on identified interferents can be summarized as follows:

1. Generate synthesized Sample Population spectra by adding the RSIS to raw (interferent-free) Sample Population spectra, thus forming an Interferent Enhanced Spectral Database (IESD)—each spectrum of the IESD is synthesized from one spectrum of the Sample Population, and thus each spectrum of the IESD has at least one associated known analyte concentration
2. Separate the spectra of the IESD into a calibration set of spectra and a test set of spectra
3. Generate a calibration constant for the calibration set based on the calibration set spectra and their associated known correct analyte concentrations (e.g., using the matrix manipulation outlined in five steps above)
4. Use the calibration constant generated in step 3 to calculate the error in the corresponding test set as follows (repeat for each spectrum in the test set):
   a. Multiply (the selected test set spectrum)×(average calibration constant generated in step 3) to generate an estimated glucose concentration
   b. Evaluate the difference between this estimated glucose concentration and the known, correct glucose concentration associated with the selected test spectrum to generate an error associated with the selected test spectrum
5. Average the errors calculated in step 4 to arrive at a weighted or average error for the current calibration set–test set pair
6. Repeat steps 2 through 5 n times, resulting in n calibration constants and n average errors
7. Compute a "grand average" error from the n average errors and an average calibration constant from the n calibration constants (preferably weighted averages wherein the largest average errors and calibration constants are discounted), to arrive at a calibration constant which is minimally sensitive to the effect of the identified interferents

EXAMPLE 1

One example of certain methods disclosed herein is illustrated with reference to the detection of glucose in blood using mid-IR absorption spectroscopy. Table 2 lists 10 Library Interferents (each having absorption features that overlap with glucose) and the corresponding maximum concentration of each Library Interferent. Table 2 also lists a Glucose Sensitivity to Interferent without and with training. The Glucose Sensitivity to Interferent is the calculated change in estimated glucose concentration for a unit change in interferent concentration. For a highly glucose selective analyte detection technique, this value is zero. The Glucose Sensitivity to Interferent without training is the Glucose Sensitivity to Interferent where the calibration has been determined using the methods above without any identified interferents. The Glucose Sensitivity to Interferent with training is the Glucose Sensitivity to Interferent where the calibration has been determined using the methods above with the appropriately identified interferents. In this case, least improvement (in terms of reduction in sensitivity to an interferent)

occurs for urea, seeing a factor of 6.4 lower sensitivity, followed by three with ratios from 60 to 80 in improvement. The remaining six all have seen sensitivity factors reduced by over 100, up to over 1600. The decreased Glucose Sensitivity to Interferent with training indicates that the methods are effective at producing a calibration constant that is selective to glucose in the presence of interferents.

TABLE 2

Rejection of 10 interfering substances

| Library Interferent | Maximum Concentration | Glucose Sensitivity to Interferent w/o training | Glucose Sensitivity to Interferent w/ training |
|---|---|---|---|
| Sodium Bicarbonate | 103 | 0.330 | 0.0002 |
| Urea | 100 | −0.132 | 0.0206 |
| Magnesium Sulfate | 0.7 | 1.056 | −0.0016 |
| Naproxen | 10 | 0.600 | −0.0091 |
| Uric Acid | 12 | −0.557 | 0.0108 |
| Salicylate | 10 | 0.411 | −0.0050 |
| Glutathione | 100 | 0.041 | 0.0003 |
| Niacin | 1.8 | 1.594 | −0.0086 |
| Nicotinamide | 12.2 | 0.452 | −0.0026 |
| Chlorpropamide | 18.3 | 0.334 | 0.0012 |

EXAMPLE 2

Figure 39:
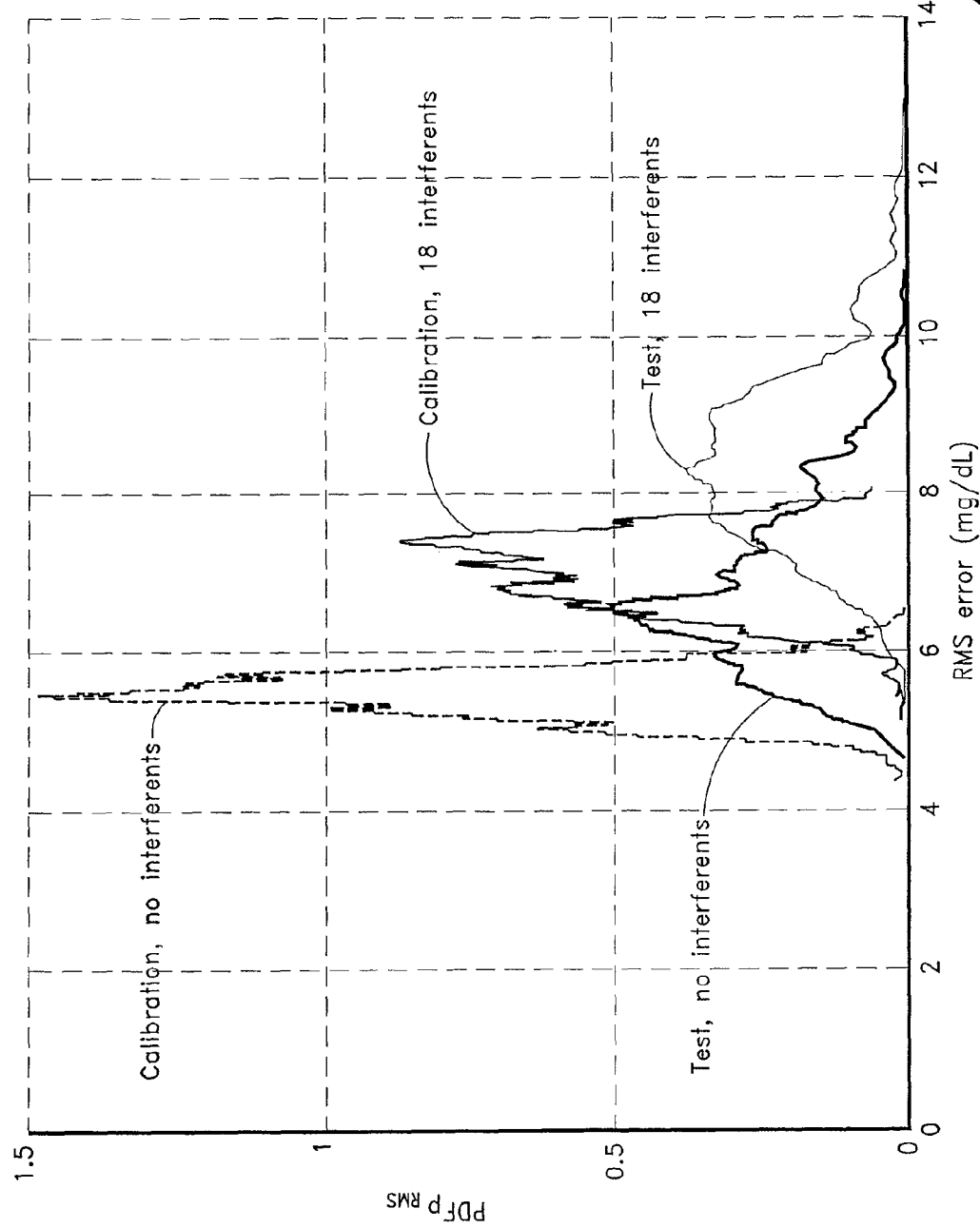
FIG. 39 is a graph illustrating the effect of interferents on the error of glucose estimation.
Figure 40A:
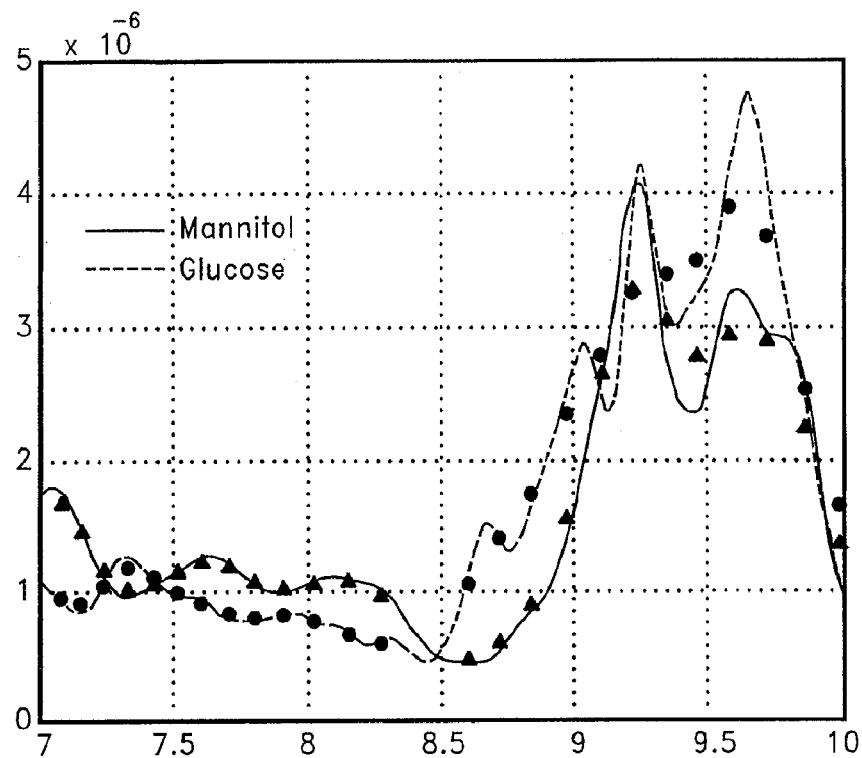
FIGS. 40A, 40B, 40C, and 40D each have a graph showing a comparison of the absorption spectrum of glucose with different interferents taken using two different techniques: a Fourier Transform Infrared (FTIR) spectrometer having an interpolated resolution of 1 $cm^{-1}$ (solid lines with triangles); and by 25 finite-bandwidth IR filters having a Gaussian profile and full-width half-maximum (FWHM) bandwidth of 28 $cm^{-1}$ corresponding to a bandwidth that varies from 140 nm at 7.08 μm, up to 279 nm at 10 μm (dashed lines with circles). The Figures show a comparison of glucose with mannitol (FIG. 40A), dextran (FIG. 40B), n-acetyl L cysteine (FIG. 40C), and procainamide (FIG. 40D), at a concentration level of 1 mg/dL and path length of 1 μm.
Figure 40B:
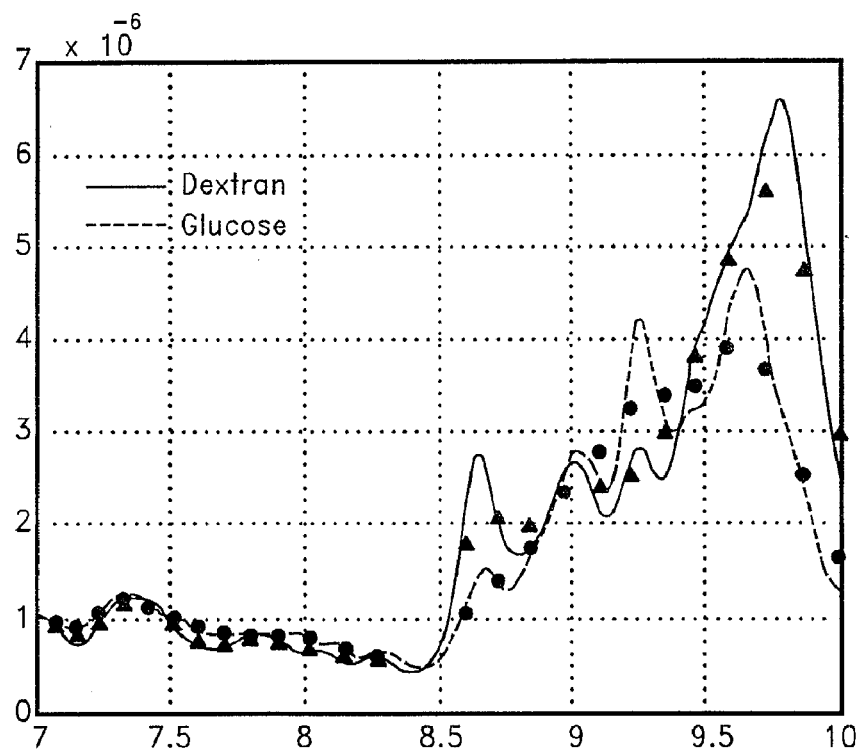
Figure 40C:
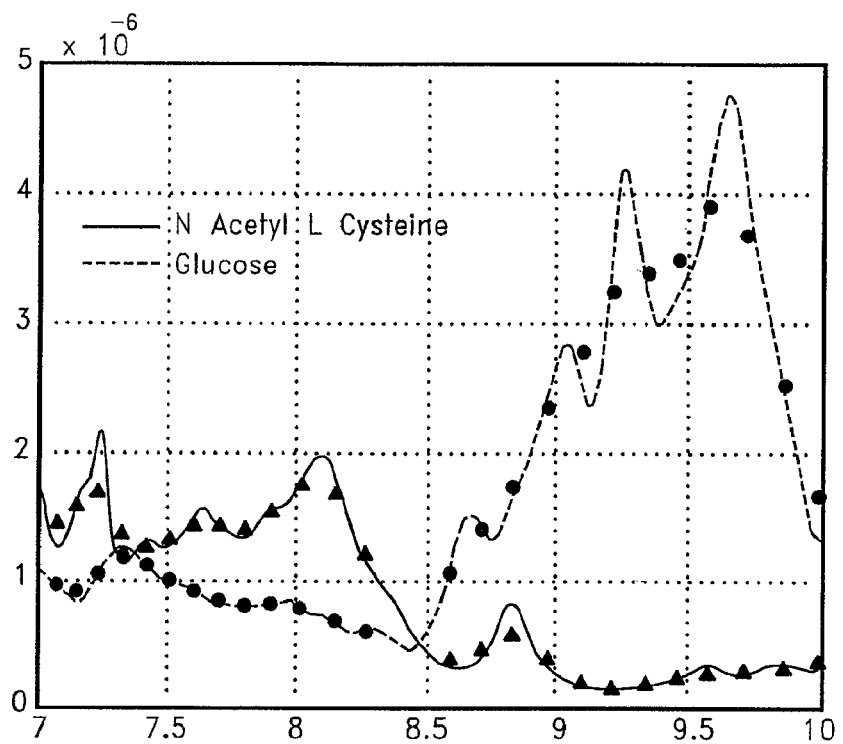
Figure 40D:
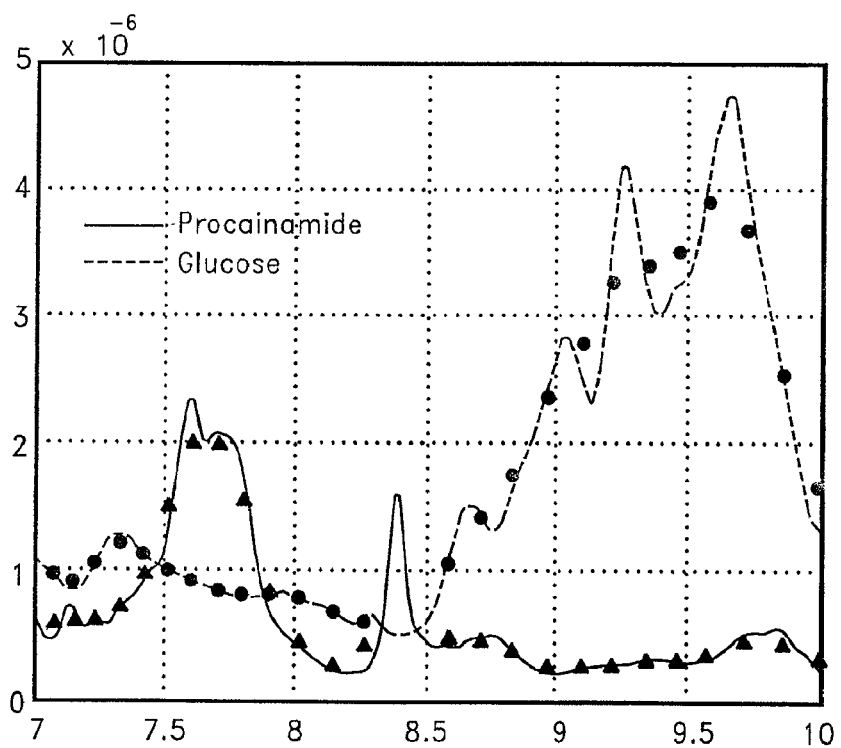

Another example illustrates the effect of the methods for 18 interferents. Table 3 lists of 18 interferents and maximum concentrations that were modeled for this example, and the glucose sensitivity to the interferent without and with training. The table summarizes the results of a series of 1000 calibration and test simulations that were performed both in the absence of the interferents, and with all interferents present. FIG. 39 shows the distribution of the R.M.S. error in the glucose concentration estimation for 1000 trials. While a number of substances show significantly less sensitivity (sodium bicarbonate, magnesium sulfate, tolbutamide), others show increased sensitivity (ethanol, acetoacetate), as listed in Table 3. The curves in FIG. 39 are for calibration set and the test set both without any interferents and with all 18 interferents. The interferent produces a degradation of performance, as can be seen by comparing the calibration or test curves of FIG. 39. Thus, for example, the peaks appear to be shifted by about 2 mg/dL, and the width of the distributions is increased slightly. The reduction in height of the peaks is due to the spreading of the distributions, resulting in a modest degradation in performance.

TABLE 3

List of 18 Interfering Substances with maximum concentrations and Sensitivity with respect to interferents, with/without training

| | Library Interferent | Conc. (mg/dL) | Glucose Sensitivity to Interferent w/o training | Glucose Sensitivity to Interferent w/ training |
|---|---|---|---|---|
| 1 | Urea | 300 | −0.167 | −0.100 |
| 2 | Ethanol | 400.15 | −0.007 | −0.044 |
| 3 | Sodium Bicarbonate | 489 | 0.157 | −0.093 |
| 4 | Acetoacetate Li | 96 | 0.387 | 0.601 |
| 5 | Hydroxybutyric Acid | 465 | −0.252 | −0.101 |
| 6 | Magnesium Sulfate | 29.1 | 2.479 | 0.023 |
| 7 | Naproxen | 49.91 | 0.442 | 0.564 |
| 8 | Salicylate | 59.94 | 0.252 | 0.283 |
| 9 | Ticarcillin Disodium | 102 | −0.038 | −0.086 |
| 10 | Cefazolin | 119.99 | −0.087 | −0.006 |

TABLE 3-continued

List of 18 Interfering Substances with maximum concentrations and Sensitivity with respect to interferents, with/without training

| | Library Interferent | Conc. (mg/dL) | Glucose Sensitivity to Interferent w/o training | Glucose Sensitivity to Interferent w/ training |
|---|---|---|---|---|
| 11 | Chlorpropamide | 27.7 | 0.387 | 0.231 |
| 12 | Nicotinamide | 36.6 | 0.265 | 0.366 |
| 13 | Uric Acid | 36 | −0.641 | −0.712 |
| 14 | Ibuprofen | 49.96 | −0.172 | −0.125 |
| 15 | Tolbutamide | 63.99 | 0.132 | 0.004 |
| 16 | Tolazamide | 9.9 | 0.196 | 0.091 |
| 17 | Bilirubin | 3 | −0.391 | −0.266 |
| 18 | Acetaminophen | 25.07 | 0.169 | 0.126 |

EXAMPLE 3

In a third example, certain methods disclosed herein were tested for measuring glucose in blood using mid-IR absorption spectroscopy in the presence of four interferents not normally found in blood (Type-B interferents) and that may be common for patients in hospital intensive care units (ICUs). The four Type-B interferents are mannitol, dextran, n-acetyl L cysteine, and procainamide.

Of the four Type-B interferents, mannitol and dextran have the potential to interfere substantially with the estimation of glucose: both are spectrally similar to glucose (see FIG. 1), and the dosages employed in ICUs are very large in comparison to typical glucose levels. Mannitol, for example, may be present in the blood at concentrations of 2500 mg/dL, and dextran may be present at concentrations in excess of 5000 mg/dL. For comparison, typical plasma glucose levels are on the order of 100-200 mg/dL. The other Type-B interferents, n-acetyl L cysteine and procainamide, have spectra that are quite unlike the glucose spectrum.

FIGS. 40A, 40B, 40C, and 40D each have a graph showing a comparison of the absorption spectrum of glucose with different interferents taken using two different techniques: a Fourier Transform Infrared (FTIR) spectrometer having an interpolated resolution of 1 $cm^{-1}$ (solid lines with triangles); and by 25 finite-bandwidth IR filters having a Gaussian profile and full-width half-maximum (FWHM) bandwidth of 28 $cm^{-1}$ corresponding to a bandwidth that varies from 140 nm at 7.08 μm, up to 279 nm at 10 μm (dashed lines with circles). Specifically, the figures show a comparison of glucose with mannitol (FIG. 40A), with dextran (FIG. 40B), with n-acetyl L cysteine (FIG. 40C), and with procainamide (FIG. 40D), at a concentration level of 1 mg/dL and path length of 1 μm. The horizontal axis in FIGS. 40A-40D has units of wavelength in microns (μm), ranging from 7 μm to 10 μm, and the vertical axis has arbitrary units.

The central wavelength of the data obtained using filter is indicated in FIGS. 40A, 40B, 40C, and 40D by the circles along each dashed curve, and corresponds to the following wavelengths, in microns: 7.082, 7.158, 7.241, 7.331, 7.424, 7.513, 7.605, 7.704, 7.800, 7.905, 8.019, 8.150, 8.271, 8.598, 8.718, 8.834, 8.969, 9.099, 9.217, 9.346, 9.461, 9.579, 9.718, 9.862, and 9.990. The effect of the bandwidth of the filters on the spectral features can be seen in FIGS. 40A-40D as the decrease in the sharpness of spectral features on the solid curves and the relative absence of sharp features on the dashed curves.

Figure 41:
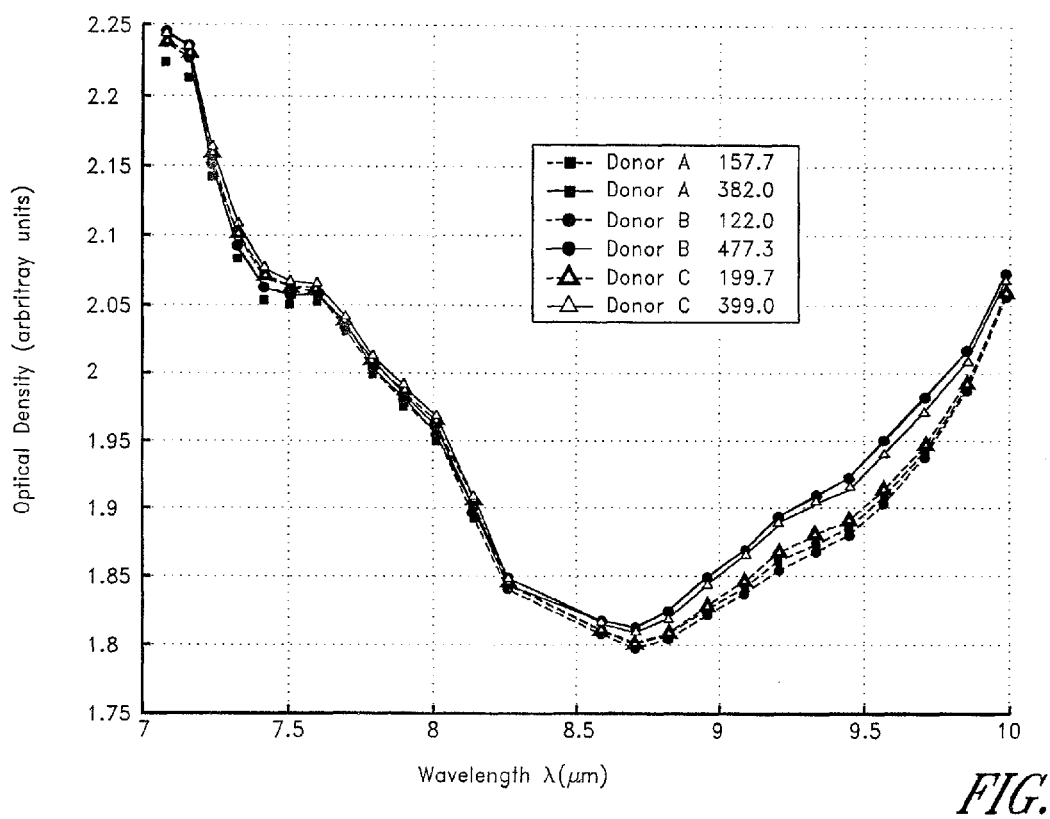
FIG. 41 shows a graph of the blood plasma spectra for 6 blood sample taken from three donors in arbitrary units for a wavelength range from 7 µm to 10 µm, where the symbols on the curves indicate the central wavelengths of the 25 filters.
Figure 42A:
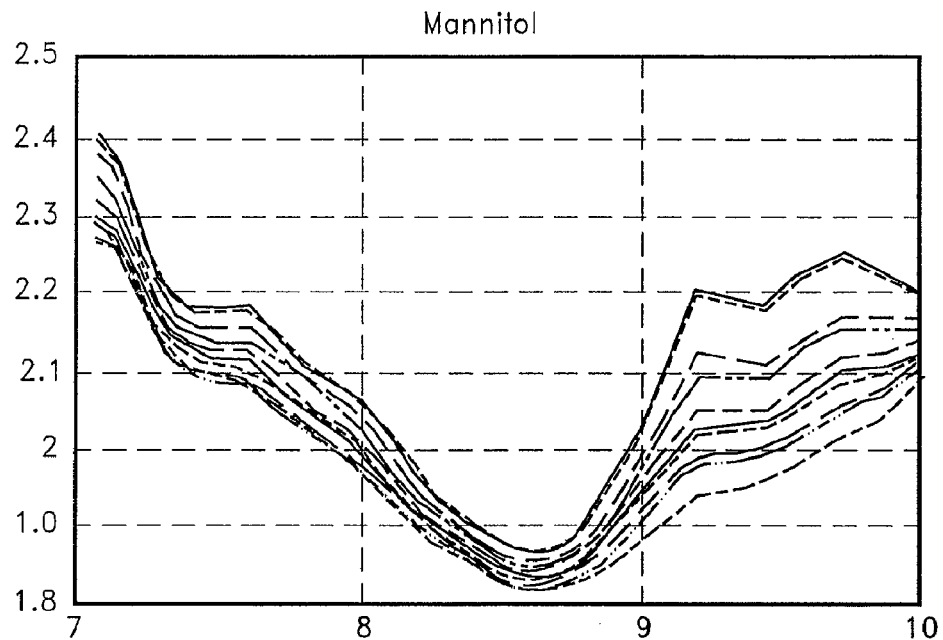
FIGS. 42A, 42B, 42C, and 42D contain spectra of the Sample Population of 6 samples having random amounts of mannitol (FIG. 42A), dextran (FIG. 42B), n-acetyl L cysteine (FIG. 42C), and procainamide (FIG. 42D), at a concentration levels of 1 mg/dL and path lengths of 1 µm.
Figure 42B:
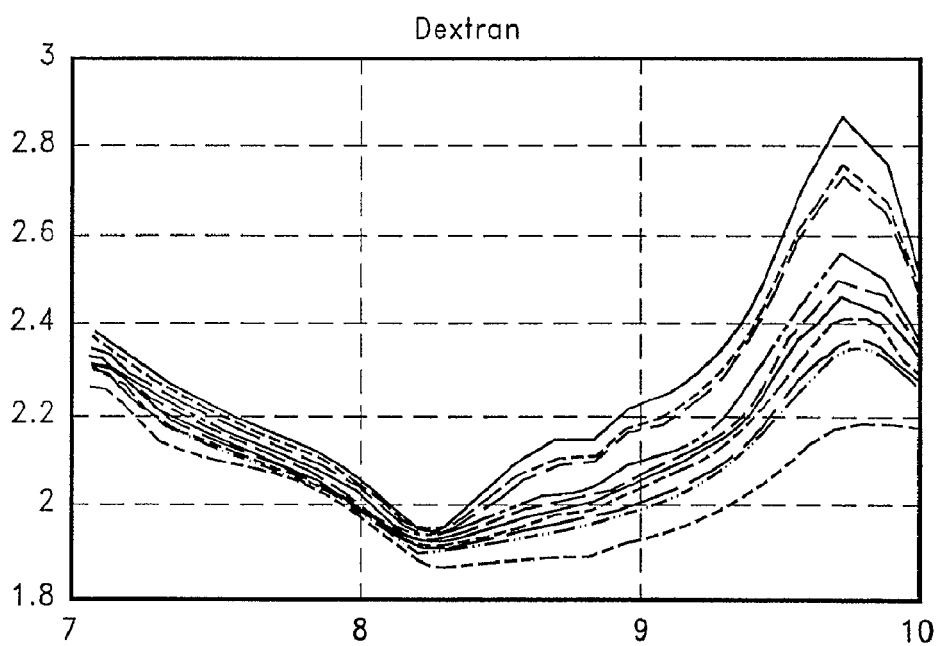
Figure 42C:
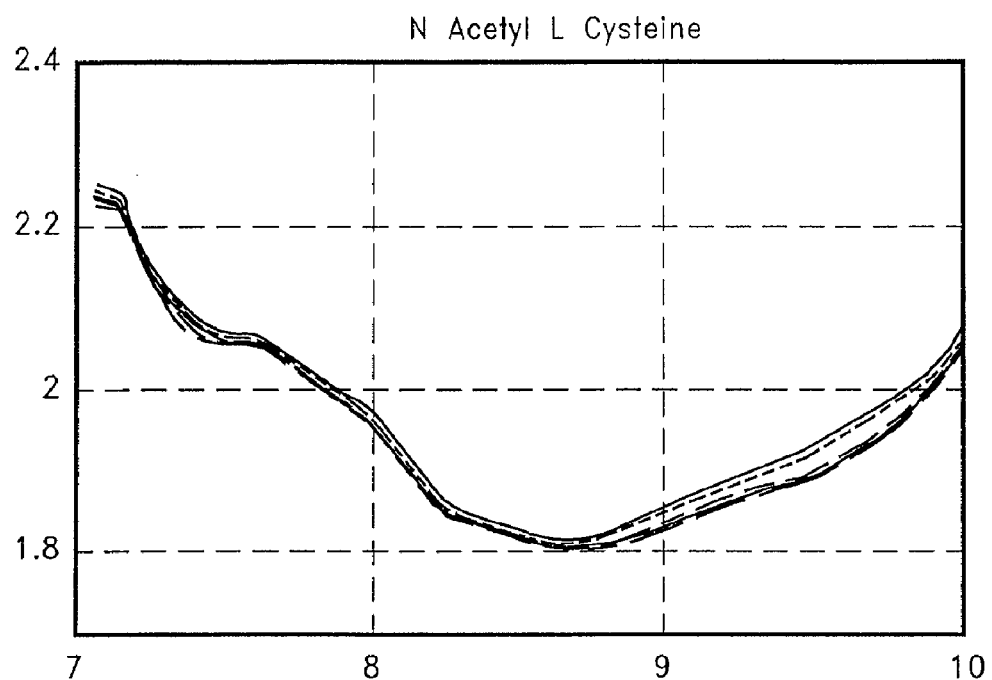
Figure 42D:
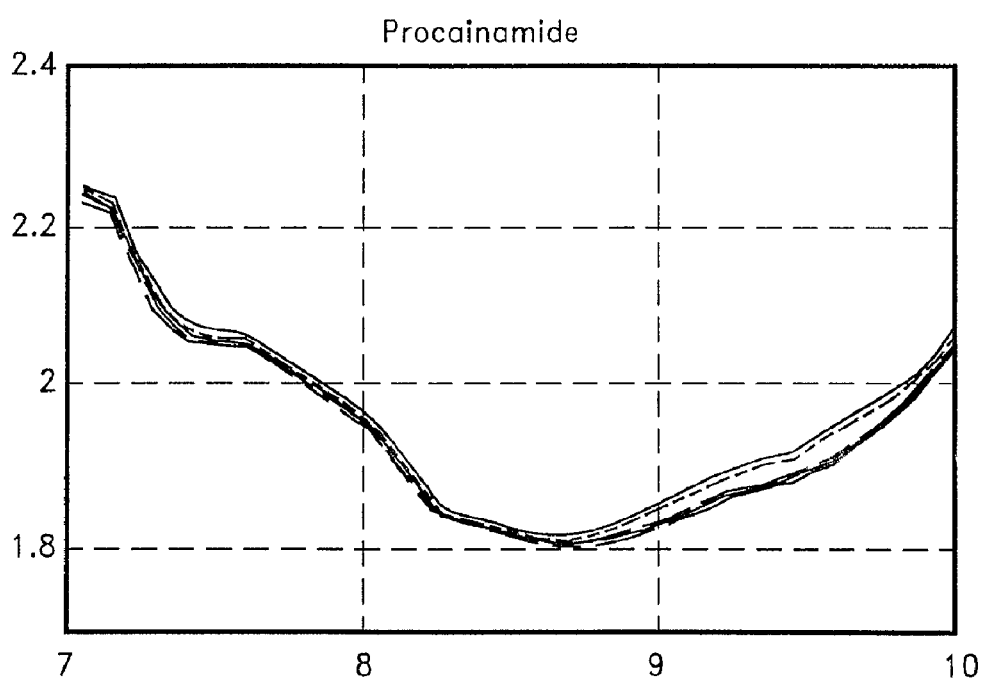
Figure 43A:
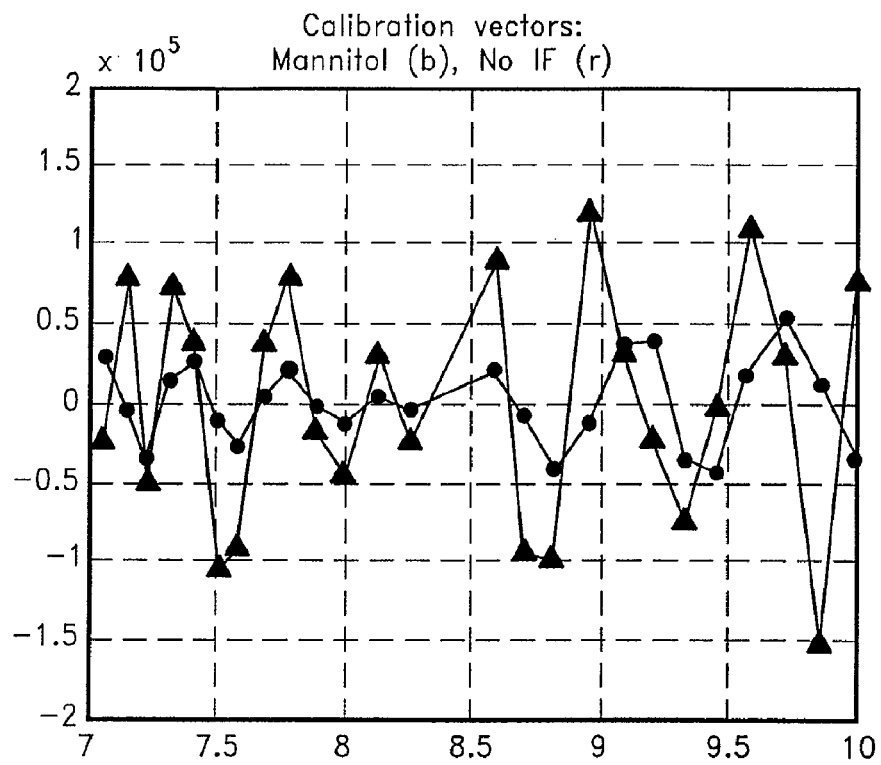
FIGS. 43A-43D are graphs comparing calibration vectors obtained by training in the presence of an interferent, to the calibration vector obtained by training on clean plasma spectra for mannitol (FIG. 43A), dextran (FIG. 43B), n-acetyl L cysteine (FIG. 43C), and procainamide (FIG. 43D) for water-free spectra.
Figure 43B:
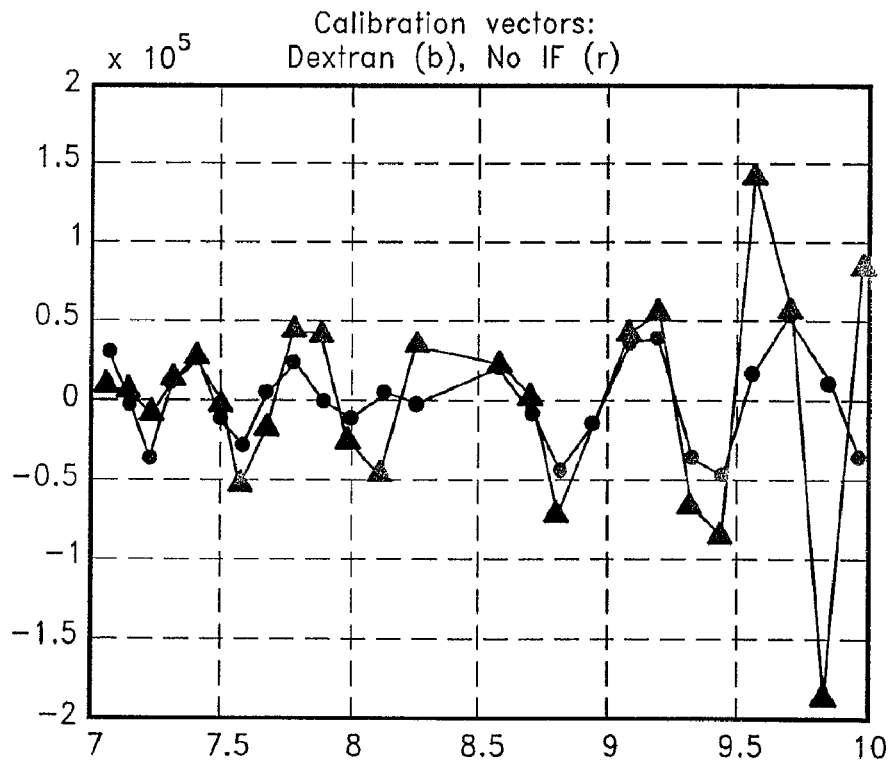
Figure 43C:
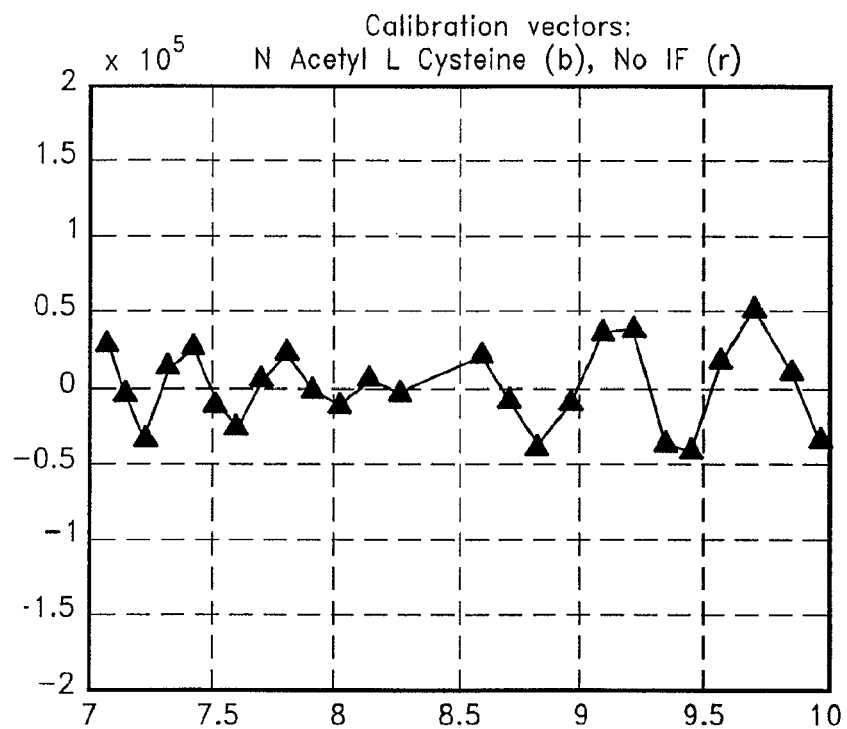
Figure 43D:
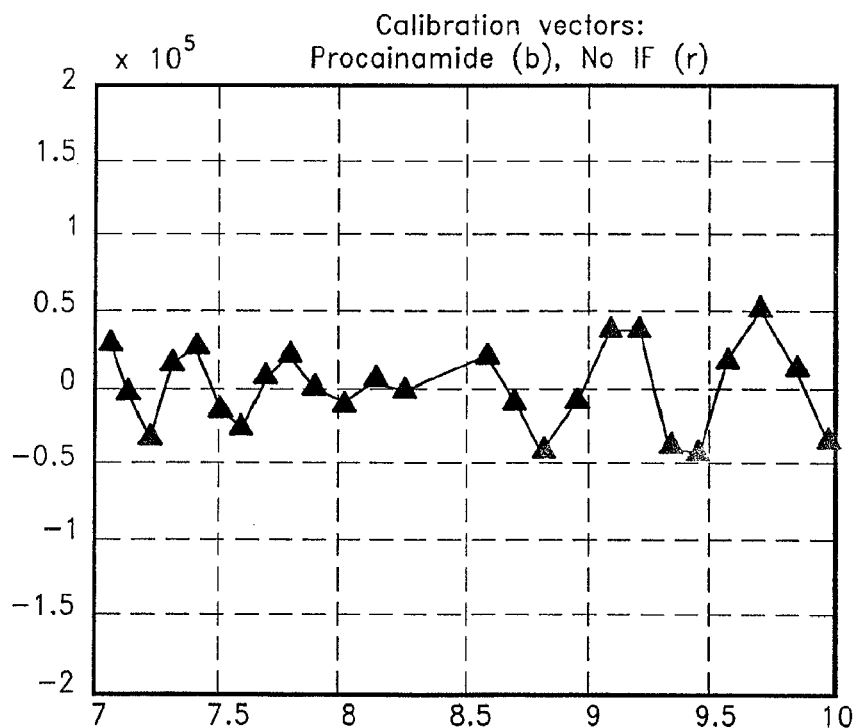

FIG. 41 shows a graph of the blood plasma spectra for 6 blood samples taken from three donors in arbitrary units for a wavelength range from 7 μm to 10 μm, where the symbols on the curves indicate the central wavelengths of the 25 filters. The 6 blood samples do not contain any mannitol, dextran, n-acetyl L cysteine, and procainamide—the Type-B interferents of this Example, and are thus a Sample Population. Three donors (indicated as donor A, B, and C) provided blood at different times, resulting in different blood glucose levels, shown in the graph legend in mg/dL as measured using a YSI Biochemistry Analyzer (YSI Incorporated, Yellow Springs, Ohio). The path length of these samples, estimated at 36.3 µm by analysis of the spectrum of a reference scan of saline in the same cell immediately prior to each sample spectrum, was used to normalize these measurements. This quantity was taken into account in the computation of the calibration vectors provided, and the application of these vectors to spectra obtained from other equipment would require a similar path-length estimation and normalization process to obtain valid results.

Next, random amounts of each Type-B interferent of this Example are added to the spectra to produce mixtures that, for example could make up an Interferent Enhanced Spectral. Each of the Sample Population spectra was combined with a random amount of a single interferent added, as indicated in Table 4, which lists an index number N, the Donor, the glucose concentration (GLU), interferent concentration (conc (IF)), and the interferent for each of 54 spectra. The conditions of Table 4 were used to form combined spectra including each of the 6 plasma spectra was combined with 2 levels of each of the 4 interferents.

TABLE 4

Interferent Enhanced Spectral Database for Example 3.

| N | Donor | GLU | conc(IF) | IF |
|---|---|---|---|---|
| 1 | A | 157.7 | | N/A |
| 2 | A | 382 | | N/A |
| 3 | B | 122 | | N/A |
| 4 | B | 477.3 | | N/A |
| 5 | C | 199.7 | | N/A |
| 6 | C | 399 | | N/A |
| 7 | A | 157.7 | 1001.2 | Mannitol |
| 8 | A | 382 | 2716.5 | Mannitol |
| 9 | A | 157.7 | 1107.7 | Mannitol |
| 10 | A | 382 | 1394.2 | Mannitol |
| 11 | B | 122 | 2280.6 | Mannitol |
| 12 | B | 477.3 | 1669.3 | Mannitol |
| 13 | B | 122 | 1710.2 | Mannitol |
| 14 | B | 477.3 | 1113.0 | Mannitol |
| 15 | C | 199.7 | 1316.4 | Mannitol |
| 16 | C | 399 | 399.1 | Mannitol |
| 17 | C | 199.7 | 969.8 | Mannitol |
| 18 | C | 399 | 2607.7 | Mannitol |
| 19 | A | 157.7 | 8.8 | N Acetyl L Cysteine |
| 20 | A | 382 | 2.3 | N Acetyl L Cysteine |
| 21 | A | 157.7 | 3.7 | N Acetyl L Cysteine |
| 22 | A | 382 | 8.0 | N Acetyl L Cysteine |
| 23 | B | 122 | 3.0 | N Acetyl L Cysteine |
| 24 | B | 477.3 | 4.3 | N Acetyl L Cysteine |
| 25 | B | 122 | 8.4 | N Acetyl L Cysteine |
| 26 | B | 477.3 | 5.8 | N Acetyl L Cysteine |
| 27 | C | 199.7 | 7.1 | N Acetyl L Cysteine |
| 28 | C | 399 | 8.5 | N Acetyl L Cysteine |
| 29 | C | 199.7 | 4.4 | N Acetyl L Cysteine |
| 30 | C | 399 | 4.3 | N Acetyl L Cysteine |
| 31 | A | 157.7 | 4089.2 | Dextran |
| 32 | A | 382 | 1023.7 | Dextran |
| 33 | A | 157.7 | 1171.8 | Dextran |
| 34 | A | 382 | 4436.9 | Dextran |
| 35 | B | 122 | 2050.6 | Dextran |
| 36 | B | 477.3 | 2093.3 | Dextran |
| 37 | B | 122 | 2183.3 | Dextran |
| 38 | B | 477.3 | 3750.4 | Dextran |
| 39 | C | 199.7 | 2598.1 | Dextran |
| 40 | C | 399 | 2226.3 | Dextran |
| 41 | C | 199.7 | 2793.0 | Dextran |
| 42 | C | 399 | 2941.8 | Dextran |
| 43 | A | 157.7 | 22.5 | Procainamide |
| 44 | A | 382 | 35.3 | Procainamide |
| 45 | A | 157.7 | 5.5 | Procainamide |
| 46 | A | 382 | 7.7 | Procainamide |
| 47 | B | 122 | 18.5 | Procainamide |
| 48 | B | 477.3 | 5.6 | Procainamide |
| 49 | B | 122 | 31.8 | Procainamide |
| 50 | B | 477.3 | 8.2 | Procainamide |
| 51 | C | 199.7 | 22.0 | Procainamide |
| 52 | C | 399 | 9.3 | Procainamide |
| 53 | C | 199.7 | 19.7 | Procainamide |
| 54 | C | 399 | 12.5 | Procainamide |

FIGS. 42A, 42B, 42C, and 42D contain spectra formed from the conditions of Table 4. Specifically, the figures show spectra of the Sample Population of 6 samples having random amounts of mannitol (FIG. 42A), dextran (FIG. 42B), n-acetyl L cysteine (FIG. 42C), and procainamide (FIG. 42D), at a concentration levels of 1 mg/dL and path lengths of 1 µm.

Next, calibration vectors were generated using the spectra of FIGS. 42A-42D, in effect reproducing the steps of Block 3120. The next step of this Example is the spectral subtraction of water that is present in the sample to produce water-free spectra. As discussed above, certain methods disclosed herein provide for the estimation of an analyte concentration in the presence of interferents that are present in both a sample population and the measurement sample (Type-A interferents), and it is not necessary to remove the spectra for interferents present in Sample Population and sample being measured. The step of removing water from the spectrum is thus an alternative embodiment of the disclosed methods.

The calibration vectors are shown in FIGS. 43A-43D for mannitol (FIG. 43A), dextran (FIG. 43B), n-acetyl L cysteine (FIG. 43C), and procainamide (FIG. 43D) for water-free spectra. Specifically each one of FIGS. 43A-43D compares calibration vectors obtained by training in the presence of an interferent, to the calibration vector obtained by training on clean plasma spectra alone. The calibration vector is used by computing its dot-product with the vector representing (path-length-normalized) spectral absorption values for the filters used in processing the reference spectra. Large values (whether positive or negative) typically represent wavelengths for which the corresponding spectral absorbance is sensitive to the presence of glucose, while small values generally represent wavelengths for which the spectral absorbance is insensitive to the presence of glucose. In the presence of an interfering substance, this correspondence is somewhat less transparent, being modified by the tendency of interfering substances to mask the presence of glucose.

The similarity of the calibration vectors obtained for minimizing the effects of the two interferents n-acetyl L cysteine and procainamide, to that obtained for pure plasma, is a reflection of the fact that these two interferents are spectrally quite distinct from the glucose spectrum; the large differences seen between the calibration vectors for minimizing the effects of dextran and mannitol, and the calibration obtained for pure plasma, are conversely representative of the large degree of similarity between the spectra of these substances and that of glucose. For those cases in which the interfering spectrum is similar to the glucose spectrum (that is, mannitol and dextran), the greatest change in the calibration vector. For those cases in which the interfering spectrum is different from the glucose spectrum (that is, n-acetyl L cysteine and procainamide), it is difficult to detect the difference between the calibration vectors obtained with and without the interferent.

It will be understood that the steps of methods discussed are performed in one embodiment by an appropriate processor (or processors) of a processing (i.e., computer) system executing instructions (code segments) stored in appropriate storage. It will also be understood that the disclosed methods and apparatus are not limited to any particular implementation or programming technique and that the methods and apparatus may be implemented using any appropriate techniques for implementing the functionality described herein. The methods and apparatus are not limited to any particular programming language or operating system. In addition, the various components of the apparatus may be included in a single housing or in multiple housings that communication by wire or wireless communication.

Further, the interferent, analyte, or population data used in the method may be updated, changed, added, removed, or otherwise modified as needed. Thus, for example, spectral information and/or concentrations of interferents that are accessible to the methods may be updated or changed by updating or changing a database of a program implementing the method. The updating may occur by providing new computer readable media or over a computer network. Other changes that may be made to the methods or apparatus include, but are not limited to, the adding of additional analytes or the changing of population spectral information.

One embodiment of each of the methods described herein may include a computer program accessible to and/or executable by a processing system, e.g., a one or more processors and memories that are part of an embedded system. Thus, as will be appreciated by those skilled in the art, embodiments of the disclosed inventions may be embodied as a method, an apparatus such as a special purpose apparatus, an apparatus such as a data processing system, or a carrier medium, e.g., a computer program product. The carrier medium carries one or more computer readable code segments for controlling a processing system to implement a method. Accordingly, various ones of the disclosed inventions may take the form of a method, an entirely hardware embodiment, an entirely software embodiment or an embodiment combining software and hardware aspects. Furthermore, any one or more of the disclosed methods (including but not limited to the disclosed methods of measurement analysis, interferent determination, and/or calibration constant generation) may be stored as one or more computer readable code segments or data compilations on a carrier medium. Any suitable computer readable carrier medium may be used including a magnetic storage device such as a diskette or a hard disk; a memory cartridge, module, card or chip (either alone or installed within a larger device); or an optical storage device such as a CD or DVD.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly, it should be appreciated that in the above description of embodiments, various features of the inventions are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

Further information on analyte detection systems, sample elements, algorithms and methods for computing analyte concentrations, and other related apparatus and methods can be found in U.S. patent application Publication No. 2003/0090649, published May 15, 2003, titled REAGENT-LESS WHOLE BLOOD GLUCOSE METER; U.S. patent application Publication No. 2003/0178569, published Sep. 25, 2003, titled PATHLENGTH-INDEPENDENT METHODS FOR OPTICALLY DETERMINING MATERIAL COMPOSITION; U.S. patent application Publication No. 2004/0019431, published Jan. 29, 2004, titled METHOD OF DETERMINING AN ANALYTE CONCENTRATION IN A SAMPLE FROM AN ABSORPTION SPECTRUM; U.S. patent application Publication No. 2005/0036147, published Feb. 17, 2005, titled METHOD OF DETERMINING ANALYTE CONCENTRATION IN A SAMPLE USING INFRARED TRANSMISSION DATA; and U.S. patent application Publication No. 2005/0038357, published on Feb. 17, 2005, titled SAMPLE ELEMENT WITH BARRIER MATERIAL. The entire contents of each of the above-mentioned publications are hereby incorporated by reference herein and are made a part of this specification.

A number of applications, publications and external documents are incorporated by reference herein. Any conflict or contradiction between a statement in the bodily text of this specification and a statement in any of the incorporated documents is to be resolved in favor of the statement in the bodily text.

Figure 49:
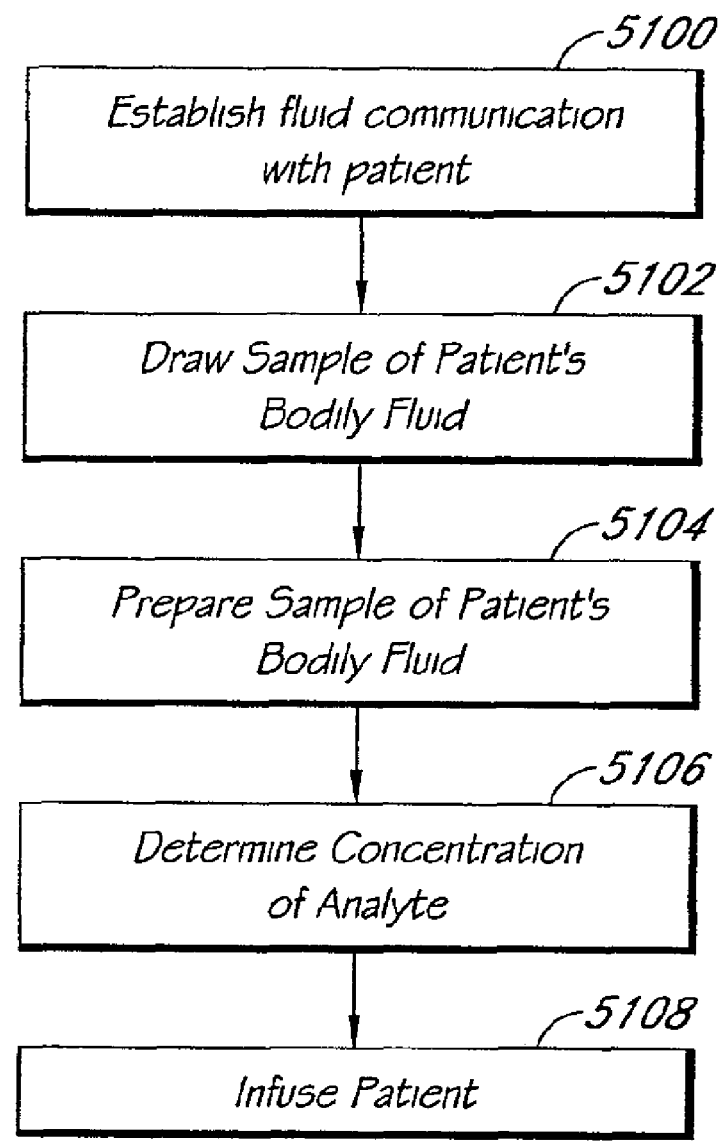
FIG. 49 is an embodiment of an analysis method for analyzing a sample.

In certain embodiments, the extraction and analysis of a patient's bodily fluid, for example blood plasma, may be performed entirely at the patient's point of care or bedside, and/or with a device attached or connected to a patient. Prior art methods of analyzing bodily fluid from a hospital patient involved taking a sample of a bodily fluid, transporting the sample to a central processing and analysis lab and periodically batch processing a group of samples collected from several patients using a common, central device, for example a centrifuge and bodily fluid analyzer. Here, as depicted in FIG. 49, methods of analysis are disclosed wherein a fluid handling system or sampling system is attached to a single patient, for example at the patients bedside or point of care, and is capable of extracting a bodily fluid sample from the patient, preparing the sample for analysis and analyzing the sample all at the patient's bedside.

At step 5100, a fluid handling system, sampling system, analyte detection system or other suitable apparatus is connected to a patient so that the system is placed in fluid communication with a bodily fluid of the patient. Since the system is only associated with a single patient, the connector between the system and patient may be of a type to establish a sustained connection to the patient such as through an IV tube or a catheter inserted into the patient's vasculature.

At step 5102, once fluid communication has been established with the patient's bodily fluid, a sample of the bodily fluid may be drawn into the system. The sample may then be transported through one or more passageways in the system to a sample preparation unit located with in the system. At step 5104, the sample preparation unit prepares the sample for analysis. Depending on the bodily fluid to be analyzed, the preparation of the sample may involve diverting or isolating of a fraction of the drawn portion of fluid for analysis, filtering the sample through a filter or membrane to remove impurities, or separating a first component from the whole sample, for example separating plasma from a sample of whole blood, to analyze only the first component. Since the sample preparation unit is co-located with the sample draw apparatus, the sample may be analyzed almost immediately after it has been drawn. Once the sample has been prepared, it may be transferred to a chamber, a sample cell or any other location accessible by an analyte detection system for analysis. Alternatively, the sample preparation unit itself may be configured to hold the sample of component for analysis by the analyte detection system.

At step 5106, after the sample has been prepared, the analyte detection system which is preferably located within the fluid handling system or sampling system connected to the patient determines the concentration of one or more analytes based on or within the prepared sample. The concentration of the measured analyte(s) may then be reported to a display or operator's console located at the patient's bedside or point of care, and/or uploaded to a data network such as a Hospital Information system (HIS), shortly after the sample was drawn from said patient.

At step 5108, once the sample has been drawn, prepared, and analyzed the fluid handling system or sampling system may shift to infusing the patient with an infusion fluid, such as saline, lactated Ringer's solution, water or any other suitable infusion liquid. In shifting to the infusion mode, the system may return at least a portion of the drawn portion or sample of bodily fluid to the patient. In addition, since the system is dedicated to a single patient use and continuously connected to the patient, the system may further be automated to periodically draw, prepare, and measure a sample of bodily fluid from the patient. In an alternative embodiment where the fluid handling system or sampling system includes an alarm system, the determined analyte concentration(s) may then be compared to a predetermined range of acceptable concentrations and if the determined concentration(s) fall outside said range, an indicator may be triggered, for example an alarm may be sounded, to alert the hospital staff.

Embodiments of the above described method and apparatus as used to prepare a plasma sample from a patient's whole blood and analyze the plasma sample at the patient's bedside or point of care are further described below in reference to FIGS. 1-3. However, it is envisioned that the presently-described methods and apparatus could be used to prepare and analyze a sample of any one of a number of bodily fluids extracted from the patient at the point of care, for example interstitial fluid, intercellular fluid, saliva, urine, sweat and/or other organic or inorganic materials.

In use, the patient sampling system 100 may be connected to a patient via the patient connector 110 and passageway 112. Since the sampling system is associated with only a single patient, the patient connector 110 may be configured to allow a sustained connection to the patient, for example through IV tubing or the catheter 11 inserted into the patient's vasculature. The sampling system further includes a fluid handling and analysis apparatus 140 which is connected to the patient in part via passageway 112. The fluid handling and analysis apparatus 140 is thus also located at the patient's bedside or point of care and dedicated to a single patient via connector 110 and passageway 112. As shown in FIG. 3, the fluid handling system or sampling system 300 may further include a fluid component separator, such as the sample preparation unit 332, and an analyte detection system 334 for preparing the sample for analysis and determining the concentration of an analyte based on analysis of the prepared sample. In an alternative embodiment, the fluid handling system or sampling system 100 may be further associated to the patient for example, via manual input of patient data or a patient code into the sampling system.

Once the system 100 is connected to a patient, a sample of whole blood from the patient may be periodically withdrawn from the patient's vasculature through connector 110 and passageway 112. The whole blood sample may then be transported to the co-located fluid handling and analysis apparatus 140 where it may be processed and analyzed. Such a system and method of analysis is advantageous over the prior methods because it permits the sample to be processed in a much shorter timeframe. Since the sample does not have to be transported to a central facility and is not batch processed with a group of samples from other hospital patients, but rather is drawn and analyzed at the patient's bedside via a dedicated machine, the sample can be processed and analyzed almost without delay. In addition, such a system and method of analysis permits the system to use a smaller sample size to perform the analysis, since multiple transfers (and the associated incidental fluid loss) from a separate sampling device to a separate processing device to a separate analysis device are no longer necessary.

Once the sample of whole blood has been drawn from the patient, at least a portion of the sample may be transported through passageway 112 to the fluid component separator or sample preparation unit 332, for example a centrifuge or filter membrane, located in the fluid handling and analysis apparatus 140. Here, the sample may be separated into at least one component for analysis and a remainder portion, for example a whole blood sample may be separated into a plasma sample and a remainder. Again, because the fluid component separator is co-located with the sampling system at the patient's bedside, the sample may be separated almost without delay, for example in less than 5 minutes from drawing, alternatively less than 2 minutes from drawing, alternatively immediately after drawing from the patient. In an alternative embodiment, for example analysis of whole blood, separation into components may not be required and the sample may simply be filtered to remove impurities. Once the sample has been processed into a first component, the first component may then be almost immediately analyzed by the analyte detection system 334 co-located in the fluid handling and analysis apparatus 140.

This is especially advantageous when the sample is whole blood and the component desired is blood plasma. For example, the glucose levels in plasma are an important indicator of patient health. However, since blood typically clots in less than two minutes, the delay in prior art systems where the samples were transported to a central lab for batch processing often precluded separation of plasma from whole blood. Under these prior art methods, either an anticoagulant was added to the blood sample to prevent clotting prior to processing and separation of the plasma, or conversely a coagulant was added to the sample and a serum was generated from the whole blood which was then analyzed and the blood glucose level in the plasma extrapolated from the levels in the serum. With regard to certain embodiments of the presently disclosed method and apparatus, because the samples are processed shortly after they are drawn, it is possible to separate the plasma from the whole blood without the addition of anti-coagulants and thus it is possible to get an accurate measurement of the plasma glucose level.

In addition, as shown in FIG. 1, the sampling system may further include a connector 120 for attaching an infusion source 15 containing an infusion liquid to 14 to the system. In use, connector 120 may connect the infusion source 15 to a passageway 111 that is in fluid communication with the patient via passageway 112 and patient connector 110. In use, the infusion liquid may then be delivered to the patient in between periodic draws of a sample of bodily fluid. Infusing the patient's vasculature with a fluid such as saline, lactated ringer's solution, water or any other suitable infusion fluid, may keep the patient's vascular line from constricting or clotting and preventing periodic future extraction of additional samples of bodily fluid. To keep the patient's vascular line open between extractions of bodily fluid samples, the infusion fluid may be delivered at a rate ranging from 1-5 ml/hr. Here, the system may alternate between drawing a bodily fluid sample from the patient's vasculature through passageway 112 and into the fluid handling and analysis apparatus 140 and delivering an infusion liquid via passageways 111 and 112 to the patient's vasculature. Since the system is dedicated to the patient and is continuously attached to the patient, this process may be automatically cycled according to a preset schedule to periodically sample a patient's bodily fluid, measure the levels of an analyte in the sample and update the results on a display 141 at the patient's bedside. In addition, in an alternate embodiment, the system may further include an indicator which may be set to sound an alarm if the levels of the analyte fall outside a preset range.

Certain alternative embodiments, shown in FIGS. 5 and 8, are generally similar to the sampling systems 100 and 300 as described herein. For example, FIG. 5 depicts a sampling system 500, configured to perform the methods described herein and further including a return line 503 connected to the sample analysis device 330 and passageway 111. Here, once the sample has been prepared and analyzed, as described above, the remainder of the sample may be transported to passageway 111 where it may be reintroduced to the patient's vasculature along with the infusion liquid. FIG. 8 depicts an alternative embodiment of a sampling system 800 wherein a fluid handling and analysis apparatus 140 comprises two modules, a main instrument 810 and a disposable cassette 820, that have been configured to be connected at a patient's bedside or point of care and interface to perform the fluid handling and analysis functions described herein. Thus, it should be understood that sampling systems 100, 300, 500 and 800 as shown in FIGS. 1-8 each represent variations of an apparatus configured to carry out the above described method for extracting and analyzing a bodily fluid from a hospital patients at the patient's bedside or point of care.

In view of the foregoing, certain disclosed embodiments can comprise an apparatus for extracting and analyzing a patient's bodily fluid, for example blood, at the patient's point of care or bedside, and/or with a device attached or connected to a patient. A bodily fluid sampling and analysis system generally comprises at least a first fluid passageway configured to be connected to a patient's bodily fluid, a sample analysis chamber for holding a sample of bodily fluid, at least one pump for directing fluid flow through the passageway to the sample analysis chamber, and an analyte detection system for determining the concentration of an analyte in the of bodily fluid. In certain embodiments, wherein only a component of the bodily fluid is to be analyzed, for example blood plasma, the system may further comprise a fluid separator for separating a component such as plasma from the sample. Certain embodiments of the sampling systems 100, 300, 500, 800, and 2000, as shown in FIGS. 1-10 and 22-25, represent variations of the general apparatus described above and will be referenced herein to describe the various features of such an apparatus.

As shown in FIG. 1, a first fluid passageway 112 may be connected to a patient via a releasable patient connector 110 to place the fluid handling and analysis apparatus 140 in fluid communication with the patient's bodily fluid. As previously disclosed, since the system is preferably associated with only a single patient, the patient connector 110 may be configured to allow a sustained connection to the patient, for example through IV tubing or the catheter 11 inserted into the patient's vasculature. In certain embodiments, as shown in FIGS. 1, 2, 3, 5, 23B-23D and 24A, the first fluid passageway may be comprised of one or more sections, including but not limited to passageways or sections 111, 112, 113, 2602, 2611, 2704, and 2710 such that another end of the passageway may be connected to an infusion source via connector 120.

With reference to FIG. 2, the first fluid passageway, comprised of sections 111 and 112, is further engaged by at least one pump 203 for facilitating fluid flow in the fluid passageway. In general, one or more pumps may engage or otherwise communicate with the first fluid passageway to infuse a patient, to draw a sample of bodily fluid from a patient and/or to transport the bodily fluid through the first fluid passageway to an analyzer. For example, the pump may be operated to draw a bodily fluid from the patient into passageway 112 and towards a sample assembly 220.

In certain embodiments, one or more pumps, such as pump 203, may be operated in multiple modes to control the direction of fluid flow through the various passageways. For example, as depicted in FIG. 2, the pump 203 may be operated in a forward direction to deliver an infusion liquid from an infusion source 15 connected to connector 120 through passageways 111 and 112 to the patient via connector 230. Alternately, the pump 203 may be operated in a reverse direction to draw a sample of bodily fluid from the patient through connector 230 and into sampling assembly 220 via passageway 112. It is envisioned that the pump may comprise any of the pumps disclosed herein, including pumps 203 and 328, roller pumps 1005a and 2619 and displacement pump 905. It is further envisioned that the one or more pumps may comprise one or more multi-directional pumps as described above with reference to FIG. 2, or two or more unidirectional pumps wherein one pump provides the infusion mode and one pump provides the sample mode. The one or more pumps may be considered to comprise a pump unit of the system or apparatus.

As shown in FIGS. 2, 3, 5, and 22A-24B, an embodiment of a bodily fluid sampling and analysis system may further include one or more additional passageways, such as passageways 113, 2609, 2611, 2704 or 2710, and one or more valves for directing the fluid flow through the fluid transport network of the system. For example, in one embodiment, as depicted in FIG. 3, the fluid transport network includes a second branch or passageway 113 connecting the first passageway 112 to the sample preparation unit 332 and analyte detection system 334. In addition, valves 316, 323a and 323b are located along the passageway 113 for regulating the fluid communication from passageway 112 through passageway 113. Valves 316, 323a and 323b may be opened and closed in coordination with operation of the pumps 203 and/or 328 to regulate fluid communication along passageway 113 and to control fluid flow direction.

The addition of a branch passageway 113 for diverting a drawn sample toward the sample preparation unit and analysis system and the ability to selectively control fluid communication between passageways 112, 113 and 111 permits the system to alternate fluid flow in said passageways between a forward direction for delivering an infusion liquid to the patient via patient connector 230 and a reverse direction for drawing a sample of a patient's bodily fluid through connector 230 and towards the sample preparation unit 332 via passageway 113. Specifically, pump 328 may be operated to draw a sample of bodily fluid from a patient through connector 230. Once the sample has been drawn through passageway 112 into passageway 113, valve 316 may be closed and the fluid flow through passageways 112 and 111 may be returned to a forward direction to permit the system immediately re-initiate infusion of the patient's vasculature after the sample has been drawn.

While FIG. 3 depicts an example of a combination of valves 316, 323a and 323b and a pump 328 used to selectively control fluid communication along the fluid passageways 111, 112 and 113, it is further envisioned that any other combination of valve(s) and pump(s), for example as depicted in FIG. 4, 5, 7, 9, 10, or 22A-24B may be used to selectively control fluid communication within fluid passageways of the system. For example, as depicted in FIG. 5, a series of pumps and valves may be engaged to control fluid flow along passageways 111, 112 and 113. Here, pump 203 may be operated to control fluid flow along passageways 111 and 112 while pump 328 may be engaged to draw fluid from passageway 112 into passageway 113 and into sample analysis device 330. Valves 501, 326a and 326b may also be opened and closed to provide selective fluid communication between passageway 113 and passageways 111, 112, 503, etc.

In addition, the pump unit or one or more pumps may be further operably positioned to draw the sample into a sample analysis device 330 including a sample preparation unit 332, a sample cell 903 or 2464 and an analyte detection system 334. As shown in FIG. 3, pump 328 may further draw at least a portion of the sample through passageway 112 and passageway 113 to the sample analysis device 330 located in the fluid handling and analysis apparatus 140. Here, the fluid component separator or sample preparation unit 332, for example a centrifuge or filter membrane, prepares the sample for analysis by the analyte detection system 334. The sample preparation unit 332 may comprise any one of the fluid component separators discussed herein, including the centrifuge formed by installation of the cassette 820 on the main instrument 810 as depicted in FIGS. 5 and 22-23, filter 1500, or any other suitable separator. The sample preparation unit 332 may separate the sample into at least one component for analysis and a remainder portion, such as separating plasma from a whole blood sample, and then transfer the component to a sample analysis chamber 903 or 2464 for analysis, or in the case of cassette 820 in FIGS. 22A-24B, perform the separation while the sample is in the sample chamber 2464.

In an alternative embodiment, for example analysis of whole blood, separation of the sample into components may not be required and the sample may simply be transferred directly from the patient to a sample analysis cell 903 or 2464 for analysis by the analyte detection system 334. In certain embodiments, one or more pumps may be engaged to separate and divert a smaller volume of the sample for transport to the sample cell and to return excess fluid drawn to the patient. For example, as depicted in FIG. 5, pump 328 may be configured to divert into passageway 113 and to sample cell 903 or 2464 a portion of the initial volume of fluid drawn into passageway 112. Here, remaining portion of blood may be transported to passageway 112 via a return line 503 where it may be reintroduced to the patient's vasculature along with the infusion liquid.

The bodily fluid analyzer, for example analyte detection systems 334 or 1700 described herein or any other suitable optical or spectroscopic bodily fluid analyzer, is preferably configured to optically engage the sample analysis cell and determine the concentration of an analyte within the sample contained in the sample cell. For example, with reference to FIGS. 18-19, the sample cell 903 may comprise a spectroscopic sample cell having at least one optical window which is transmissive of the wavelength(s) of electromagnetic radiation employed by the analyte detection system 334. Thus, when the optical window(s) of the sample cell is/are properly aligned with the analyte detection system, the analyte detection system will be able to analyze the fluid component contained within the sample cell and determine the concentration of an analyte for that component.

In addition, certain embodiments may include a waste receptacle for discarding the sample once it has been analyzed. For example as depicted in FIGS. 3, 5, 23C-23D and 24A, a waste receptacle 325 is connected to passageway 113 or 2609 and placed in selective fluid communication via a valve 323, 323a, 326a or 2731. Here, once the sample has been prepared and analyzed, valves 323a and 323b may be opened and pump 328 operated to direct flow of the sample towards the waste receptacle 325. In such embodiments, the sample analysis cell may then be flushed, for example with liquid from the attached infusion source and reused to prepare and analyze subsequent samples.

In use, a first fluid passageway such as passageway 112 may be connected to a patient via a releasable patient connector 110 to establish fluid communication between the patient's bodily fluid and the fluid transport network of the system. The fluid passageway 112 may be connected to the patient via an IV tubing or catheter for example to facilitate sustained access to the patient's bodily fluid. In certain embodiments, the fluid transport network may further include additional passageway portions or branch passageway such as 111 or 113, a fluid interface component 2028 and a fluid component separator such as centrifuge combination 2020 and 2030 or filter membrane 1500.

Once connected, one or more pumps, including any of the pumps 203, 328, 905, 1005, 2619 depicted in FIGS. 4, 5, 7, 9, 10, and 22-24, positioned along the fluid transport network, including for example passageway portions 111, 112 and 113, may be operated alone or in combination to draw a volume of bodily fluid from the patient into passageway 112.

The one or more pumps may then be further engaged to transport at least a portion of the volume of drawn bodily fluid into a sample cell such as sample cell 903 or 2464 for analysis with an analyte detection system. In certain embodiments, wherein the whole sample of bodily fluid, for example whole blood, is to be analyzed, the fluid passageway may be directly connected to the sample analysis cell 903 and the pump(s) simply diverts a portion of the drawn sample from the passageway 112 into passageway 113 and transfers the diverted portion through passageway 113 directly to the sample analysis chamber 903 for analysis by a bodily fluid analyzer.

Alternatively, wherein the fluid transport network includes a fluid component separator, such as centrifuge combination 2020 and 2030 or filter membrane 1500, the drawn volume of bodily fluid may first be transported through the fluid component separator, such as filter membrane 1500, to separate a first component from the volume. Then, as depicted in FIGS. 3 and 5, the one or more pumps may be further engaged to transfer the separated component to sample cell 903 or 2464 for analysis. In other embodiments, as depicted in FIGS. 22-24, wherein the fluid component separator includes centrifuge combination 2020 and 2030, the one or more pumps transport the drawn sample to sample cell 2464 located on centrifuge rotor 2020 and then the centrifuge 2020/2030 may be engaged to separate a component from the sample within the sample cell 2464.

In certain embodiments, as shown in FIGS. 3, 4, 5, 9, and 22-24, once the fluid in the sample cell 903 or 2464 has been analyzed by the analyte detection system, valves 323, 323a, 326, or 326a may be opened to place the sample cell in fluid communication with a waste receptacle, for example the receptacle 325 and pumps 203, 328, 905 may be further operated to draw the fluid in sample cell 903 or 2464 into waste receptacle 325.

In certain embodiments, the fluid handling network may be further connected to an infusion source 15. Preferably, infusion source 15 is in fluid communication with the patient, for example via a passageway portion such as 111 connected to passageway 112. Here, once a volume of bodily fluid has been drawn from the patient into passageway 112 for transport and processing by the system, the combination of pumps and valves may be engaged to reverse fluid flow along passageway 111 and 112 such that the infusion liquid may be transported through the first fluid passageway into the patient's vasculature. It is further envisioned that the pump(s) may be engaged to alternately draw a sample of bodily fluid into the first passageway and transport an infusion liquid through the first passageway to the patient's vasculature.

As described elsewhere herein, it is contemplated that the bodily fluid sampling and analysis system may be separated into a disposable fluid handling cassette and a reusable main analysis instrument that are configured to be attached at the patient's bedside to form a complete working system. In such an embodiment, the disposable fluid handling cassette may include the "wet" fluid transport passageways making up the fluid handling network and an optical interface with the bodily fluid analyzer, such that the main instrument, including the bodily fluid analyzer, does not come in contact with the patient's bodily fluid. This would be advantageous in that the costly analysis system, while located at the patient's bedside and dedicated to the patient throughout the duration of the patient's care, would not have to be disposed of or sterilized before reuse.

For example, as shown in FIGS. 8-9, a fluid handling cassette 820 is configured to interface with a main instrument 810. The fluid handling cassette includes an infusion fluid passageway comprising passageway 112 extending from the cassette body toward the patient connector 110 and passageway 111 extending from the cassette body toward the infusion connector 120. Passageways 111 and 112 are connected within the fluid handling cassette to provide fluid communication from an infusion source attached to connector 120 to a patient attached to connector 230. Sample fluid passageway 113 also extends from the fluid handling cassette and is in fluid communication with the infusion passageway at a junction 615 with passageway 112. Sample fluid passageway 113 is further connected to a sample preparation unit 332, for example a fluid component separator, housed in the fluid handling cassette. In addition, as shown here, the sample fluid passageway 113 may also be connected to a sample analysis cell 903 and a waste receptacle 325 also housed in the fluid handling cassette 820. In an alternative embodiment, wherein a whole sample, for example whole blood, is analyzed, a sample preparation unit may not be necessary and the sample fluid passageway 113 may be directly connected to a sample analysis cell 903.

The sample preparation unit 332 may include a filter, a centrifuge or a centrifuge rotor for separating a component from a sample of bodily fluid drawn from the attached patient. For example, in one embodiment, a filter membrane may be placed in the sample fluid passageway to permit only a first component to pass through to the sample analysis cell 903. In an alternative embodiment, a centrifuge may be used to separate a component for analysis from the bodily fluid sample. In such an embodiment, as depicted in FIGS. 22A-28, the sample analysis cell 2464 may be located on the centrifuge rotor 2020 and the entire sample may be transferred to the sample analysis cell 2464. Here, the sample analysis cell 2464 may be designed so that during operation of the centrifuge rotor 2020, a component of the sample may be segregated in a section of the sample analysis cell 2464 for analysis. In one embodiment, the centrifuge, including a centrifuge motor may be wholly located on the fluid handling cassette. In an alternative embodiment, as depicted in FIGS. 22A-24, the centrifuge rotor 2020 may be rotatably mounted in the fluid handling cassette 820 and driven by a centrifuge motor 2320 located on the main instrument 810. In such an embodiment, the centrifuge rotor 2020 includes an interface 2051 for attaching to a centrifuge drive 2030 which is located on the main instrument 810.

Once the component is separated from the sample, the component may be transferred to a sample analysis cell 903 for analysis by the main instrument 810. The sample analysis cell 903 includes an interface for interfacing with the bodily fluid analyzer on the main instrument. Several embodiments are discussed herein where one or more analyte concentrations are obtained using spectroscopic measurements of a sample at wavelengths including one or more wavelengths that are identified with the analyte(s). In such an embodiment, the sample analysis cell 903 may be a spectroscopic sample analysis cell capable of permitting spectroscopic measurement of the contents of the sample analysis cell. For example, in one method of operation, the bodily fluid analyzer measures the concentration of one or more analytes in the component, in part, by comparing the electromagnetic radiation detected by the sample and reference detectors. Here, the sample analysis cell 903 may include one or more optical windows which are constructed of a material that allows electromagnetic radiation to pass through. Thus, when the sample analysis cell is properly aligned with a bodily fluid analyzer on the main instrument, such that the sample analysis cell is placed between the source of electromagnetic radiation and a detector, the bodily fluid analyzer may analyze the component of bodily fluid contained in the sample analysis cell via the optical window(s).

For example, as depicted in FIG. 18, the sample chamber 903 may be defined by first and second lateral chamber walls 1802a, 1802b and upper and lower chamber walls 1802c, 1802d wherein the upper and lower chamber walls 1802c, 1802d are formed from a material which is sufficiently transmissive of the wavelength(s) of electromagnetic radiation that are employed by the sample analysis. In another embodiment, only one of the upper and lower chamber walls 1802c, 1802d comprises a window; in such an embodiment, the other of the upper and lower chamber walls may comprise a reflective surface configured to back-reflect any electromagnetic energy emitted into the sample chamber 903 by the bodily fluid analyzer. Accordingly, this embodiment is well suited for use with a bodily fluid analyzer in which a source and a detector of electromagnetic energy are located on the same side of the sample chamber In use, the fluid handling cassette 820 may be connected to a main instrument 810 located at a patient's bedside. The fluid passageways 111 and 112 extending into and/or from the fluid handling cassette 810 may then be attached to a patient via connector 110 and to an infusion source via connector 120.

The fluid passageway may be connected to the patient via an IV tubing or catheter for example to facilitate sustained access to the patient's bodily fluid. Once the passageways are connected, a sample of the patient's bodily fluid, for example blood, may be drawn into passageway 112 and transferred through sample passageway 113 toward sample preparation unit 332. If only a component of the bodily fluid is to be analyzed, sample preparation unit 332 may include a fluid component separator, such as a filter or a centrifuge. Here, a component may be separated from the sample of bodily fluid and only the component transferred to the sample analysis cell 903. Alternatively, for example wherein the sample analysis cell is located on the fluid component separator, the entire sample may be transferred to the sample analysis cell and subsequently a component isolated and segregated within the sample analysis cell 903 for analysis.

Once the component of bodily fluid has been transferred to the sample analysis cell 903 for analysis, the bodily fluid analyzer 1002 located on the main instrument 820 may analyze the component of bodily fluid to determine the concentration of an analyte within the component. In several embodiments, for example as depicted in FIGS. 9-10, the sample analysis cell 903 is permanently positioned on the fluid handling cassette 820 so that when the fluid handling cassette 820 is connected to the main instrument 810, the sample analysis cell 903 is accessible by the bodily fluid analyzer 1002. In an alternative embodiment, for example where the sample analysis cell 2464 is located on the centrifuge rotor 2020 as depicted in FIGS. 22-25, the centrifuge rotor 2020 must be rotated to bring the sample analysis cell 2464 to a position where it is accessible by the bodily fluid analyzer 1700 though slot 2074. For example, slot 2074 may by positioned to provide access to the sample analysis cell 2464 when the centrifuge rotor is rotated to a position which places the sample analysis cell 2464 on the optical axis X-X of the bodily fluid analyzer 1700. Once the component has been analyzed, it may be transferred to the waste receptacle 325 via the sample fluid passageway 113 for storage and removal.

An alternative embodiment of a system comprising a disposable fluid handling cassette including a centrifuge rotor and a reusable main analysis instrument is shown in FIGS. 22A-28. FIG. 22A depicts a bodily fluid sampling and analysis system 140 including a reusable main instrument 810 and a disposable cassette 820 configured to interface with the main instrument 810. As shown in FIGS. 22A-22B the reusable main instrument 810, includes a bodily fluid analyzer 1700 and a centrifuge drive 2030 connected to a motor for driving a centrifuge rotor 2020 located on the fluid handling cassette 820.

FIGS. 23A-24B show embodiments of the disposable cassette 820. Fluid handling cassette 820 includes a cassette housing 2400 enclosing a centrifuge rotor 2020. Passageways 111, 112 extend from the housing 2400 and are preferably configured to be connected a patient at one end and an infusion source 15 via connector 120 at the opposite end. A sample fluid passageway 113 also extends from the cassette housing 2400 and includes a fluid interface 2028 for periodically placing the sample fluid passageway 113 in fluid communication with a sample analysis chamber 2464 located on the centrifuge rotor 2020. Sample fluid passageway 113 is configured to intersect the patient connection passageway 112 near the patient end thereof so that the sample fluid passageway 113 may be placed in fluid communication with a patient via the patient connection passageway 112 when the passageway 112 is connected to the patient via the patient connector. In one embodiment, a passageway 2609 may be provided between the fluid interface 2028 and the waste receptacle 325 for transporting the bodily fluid from the sample cell 2464 to the waste receptacle 325 for storage and disposal after it has been analyzed.

As shown in FIG. 23B, the cassette housing 2400 includes a centrifuge interface 2051 configured to interface with a centrifuge drive 2030 located on the main device 2004 and facilitate the operation of the centrifuge. As shown in FIG. 25A, the cassette housing 2400 may also include an opening 2404 providing physical access to the centrifuge rotor 2020 and the sample analysis cell 2464 located on the centrifuge rotor 2020 such that the centrifuge drive 2030 and the bodily fluid analyzer 1700 of the main instrument 810 may access and interface with the centrifuge rotor 2020 and sample cell 2464, respectively.

In use, the fluid handling cassette 820 is connected to a main analysis instrument 810 as depicted in FIG. 22C. The centrifuge interface 2051 is connected to the centrifuge drive 2030 for rotating the centrifuge rotor 2020. Fluid passageways 111 and 112 may be connected with an infusion source 15 and a patient, to place the system in fluid communication with a bodily fluid to be analyzed. Once connected to a patient, a bodily fluid may be drawn from the patient into the fluid interface 2028 in the fluid handling cassette 820. When the centrifuge rotor 2020 is rotated vertical, as depicted in FIG. 22C, so that the sample analysis cell 2464 is aligned with the fluid passageway interface 2028, a portion of the drawn bodily fluid may flow into the sample analysis cell 2464 via the fluid passageway interface 2028. Then, the centrifuge rotor 2020 may be further rotated at a relatively high speed to separate a first component from the sample of bodily fluid. As described above, the sample analysis cell 2464 may be configured to isolate the separated first component from the remainder of the sample. Once the component has been separated, the centrifuge rotor 2020 may be further rotated to align sample analysis cell 2464 with the slot in bodily fluid analyzer 1700 such that the sample analysis cell 2464 (or at least the interrogation region 2091 thereof) will be accessible by the bodily fluid analyzer 1700. In this alignment, the cell 2464/region 2091 is located on the optical axis X-X of the analyzer 1700.

In an embodiment, depicted in FIG. 22C, wherein the bodily fluid analyzer uses electromagnetic radiation to determine the concentration of an analyte in the component sample, the sample analysis cell 2464 (or at least the interrogation region 2091 thereof) may be aligned with the bodily fluid analyzer 1700 so that the sample analysis cell 2464 is placed in between a source of electromagnetic radiation 1720 and a detector 1745. Here, as described above, the sample analysis cell 2464 may be a spectroscopic cell including one or more optical windows capable of permitting spectroscopic measurement of the contents of the sample analysis cell 2464.

Once the sample analysis cell has been aligned, or otherwise interfaced, with the bodily fluid analyzer 1700, the bodily fluid analyzer may operatively engage the sample analysis cell to measure the concentration of an analyte in the component of bodily fluid contained in the interrogation region 2091 of sample analysis cell 2464. Once analyzed, the component of bodily fluid in the interrogation region 2091 and the remainder of the sample may be transported to the waste receptacle 325 and the sample analysis cell 2464 may be reused for successive sample draws and analysis. In an alternative embodiment, the sample element 2448 may be removed from the rotor 2020 and replaced after each separate analysis. Once the patient care has terminated, the fluid passageway 112 may be disconnected from the patient and the fluid handling cassette 820 which has come into fluid contact with the patient's bodily fluid may be disposed of or sterilized for reuse. The main instrument portion 810, however, has preferably not come into contact with the patient's bodily fluid at any point during the analysis and therefore can readily be connected to a new fluid handling cassette 820 and used for the analysis of a subsequent patient.

As described above, it is contemplated that the bodily fluid sampling and analysis system may be separated into a disposable fluid handling cassette and a reusable main analysis instrument that are configured to be attached at the patient's bedside to form a complete working system. In such an embodiment, the disposable fluid handling cassette may include all of the fluid handling elements, such as the fluid passageways, a sample analysis cell and/or a fluid component separator, that would comprise the fluid handling network, such that the main instrument, including the bodily fluid analyzer, is not required to have contact with the patient's bodily fluid. The main instrument, however may include control elements, for example a valve actuator, a pump actuator, a centrifuge motor, and/or a syringe or pump actuator, which are operably positioned on the main instrument to be able to interface with the fluid handling elements of the cassette. In such an embodiment, some or all of the fluid handling elements include a control element interface which is operatively positioned such that when the cassette and main instrument are connected, the control elements may engage their respective fluid handling elements and thereby control fluid flow though the fluid network within the cassette. This is advantageous in that the costly analysis system, which is preferably located at the patient's bedside and dedicated to the patient throughout the duration of the patient's care, need not be disposed of or sterilized before reuse.

In one embodiment, depicted in FIG. 8, the fluid handling cassette 820 includes a fluid handling network comprised of multiple fluid handling elements including for example passageways 111, 112 and 113, a fluid component separator 332 and displacement pump 905. A sample cell 903 is accessible by the fluid handling network via passageway 113. In addition, as shown here, the sample fluid passageway 113 may also be connected to, or otherwise facilitate access to, a sample analysis cell 903 and a waste receptacle 325 also housed in the fluid handling cassette 820. In certain embodiments, a sample preparation unit, for example a filter or centrifuge, may be connected to the sample analysis cell 903. In an alternative embodiment, where a whole sample, for example whole blood will be analyzed, a sample preparation unit may not be necessary and the sample fluid passageway 113 may be directly connected to a sample analysis cell 903.

The fluid cassette housing interface 821 is constructed such that a portion of some or all of the fluid handling elements is accessible by the main instrument 810 when the main instrument 810 and the fluid handling cassette 820 are connected. The main instrument includes one or more control elements for controlling fluid flow and direction through the fluid network of the cassette to direct drawing of a sample of a patient's bodily fluid, transporting the sample through the network, separating a component from the sample for analysis. For example, as shown in FIG. 9, the main instrument may include the following control elements: a roller pump impeller 1005*a* and support 1005*b*, one or more valve actuators 1007*a*, 1007*b*, 1007*c*, 1007*d* and a syringe actuator or pump actuator 1009 for controlling fluid flow through passageways 111 and 113 on the fluid handling cassette 820.

When the cassette interface 821 is connected to the main instrument interface 811, the fluid handling elements are aligned with their respective control elements such that the control element can access and engage and control the respective fluid handling elements. Each fluid handling element further includes a control element interface for interfacing with the control element. For example, FIG. 8 shows openings in the cassette housing operably positioned to allow access to passageway portions 111*a*, 113*a*, 113*b*, 113*c*, 113*d* and 113*e*, which comprise control element interfaces of the respective passageways (fluid handling elements) 111 and 113. When the main instrument 810 is connected to the cassette 820, the valve actuators 1007*a*, 1007*b*, 1007*c* and 1007*d*, are operably positioned to engage a portion of a passageway and alternately permit or block fluid flow therethrough. In one embodiment, the respective passageway portions 111*a*, 113*a*, 113*b*, 113*c*, 113*d* and 113*e* which the valves on the main instrument are positioned to engage are flexible tubes, and valves 1007*a*, 1007*b*, 1007*c* and 1007*d* are "pinch valves." The pinch valves 1007*a*, 1007*b*, 1007*c* and 1007*d* include one or more moving surfaces that are actuated to move together and "pinch" a flexible passageway to stop flow therethrough. Examples of a pinch valve include, for example, Model PV256 Low Power Pinch Valve (Instech Laboratories, Inc., Plymouth Meeting, Pa.). Alternatively, one or more of valves 1007*a*, 1007*b*, 1007*c*, and 1007*d* may be other valve types for controlling the flow through their respective passageways.

In addition, roller pump 1005 is configured to engage passageway portion 111*a* to move fluid though passageway 111 and actuator 1009 is configured to engage piston 907 and thus control displacement pump 905. Thus, when the main instrument 810 and the fluid handling cassette 820 are connected, the combination of one or more control elements on the main instrument 810, including one or more valves, and/or one or more pumps or pump actuators, may engage one or more fluid handling elements within the fluid handling network of the cassette to control fluid flow though fluid passageways 111 and 113. Fluid passageway 113 may be further connected to a sample preparation unit 332, for example a fluid component separator, and a sample analysis cell 903. Fluid communication with the sample preparation unit 332 and the sample analysis cell 903 may also be controlled by the combination of one or more control elements on the main instrument engaging fluid passageway 113 and controlling fluid flow therethrough.

In use, the fluid handling cassette 820 may be connected to a main instrument 810 located at a patient's bedside. The fluid passageway portions 111 and 112 extending from the fluid handling cassette 810 may then be attached to a patient via patient connector 230 and to an infusion source via connector 120. The fluid passageway 112 may be connected to the patient via an IV tubing or catheter for example to facilitate sustained access to the patient's bodily fluid. Once connected, pump 905 may be activated by actuator 1009 engaging piston 907. Pumps 905 and/or 1005 may then be controlled to draw a sample of the patient's bodily fluid, for example blood, into passageway 112 and through sample passageway 113 toward sample preparation unit 332. Valves 1007*a* on passageway 113*a* and 1007*h* located on the patient connector are moved to an open position to allow fluid flow though passageway 113 while valve 1007*h* is moved to a closed position to prohibit fluid flow though passageway 112.

If only component(s) of the bodily fluid is/are to be analyzed, sample preparation unit 332 may include a fluid component separator, such as a filter or a centrifuge. Here, one or more components may be separated from the sample of bodily fluid and only the component(s) transferred to the sample analysis cell 903. Alternatively, for example wherein the sample analysis cell 903 is located on the fluid component separator, the entire sample may be transferred to the sample analysis cell 903 and subsequently a component isolated and segregated within the sample analysis cell 903 for analysis.

Once the component in the sample analysis cell 903 has been analyzed by the bodily fluid analyzer 1700 on the main instrument, the actuator 1009 may again engage piston 907 to cause a reverse flow in passageway 113 and transfer the component in sample cell 903 to a waste receptacle 325. Valve 1007b controlling fluid communication with waste receptacle 325 via passageway portion 113c may be moved to an open position to permit the analyzed component to be delivered to the waste receptacle.

Once a sample of bodily fluid has been drawn from the patient, the control elements on the main instrument may be engaged to prohibit access to fluid passageway 113 and reverse fluid flow in passageway 112. For example, roller pump 1005a may be activated to initiate fluid flow from an attached infusion source through passageways 111 and 112 into the patient's vasculature.

In an alternative embodiment, as shown in FIGS. 22-23E, the fluid handling network of the cassette 820 includes a fluid handling and transport network comprising a plurality of fluid handling elements including: a centrifuge rotor 2020 and fluid passageways 111, 112, 113, 324, 327 and 2609. As shown in FIGS. 22C and 23B, the main instrument 810 includes a roller pump impeller 2619 and pincher valves 323a and 323b as control elements for engaging fluid passageways 111, 327 and 324, respectively, of the cassette 820; centrifuge drive 2030 as a control element for engaging and operating the centrifuge rotor 2020; and syringe actuator or pump actuator 2652 as a control element for engaging and operating the syringe pump 328.

When the cassette 820 is connected to the main instrument 810, the fluid handling elements 2020, 111, 327, 324 and 328 are aligned with their respective control element 2030, 2619, 323a, 323b and 2652 such that the control elements can access and engage the fluid handling element to control fluid transport therethrough. Each fluid handling element further includes a control element interface for interfacing with the control element. For passageways 111, 327 and 324, the control element interface can comprise a section (e.g., portion 111a) of the passageway in question that extends into, across or adjacent an opening or window in the cassette housing which allows the corresponding control element to access the passageway 111/327/324. For this purpose, openings 2613, 2619 and 2617 are provided in the front wall 2045 of the cassette housing 2400. Alternatively the cassette 820 may include a single opening dimensioned such that when the cassette 820 and main instrument 810 are connected the fluid handling elements 111, 327 and 324 will be accessible by their respective control elements.

A opening 2621 is provided in the front wall 2045 of the cassette housing 2400 to permit the pump actuator 2652 to engage the piston control 2645 of the syringe pump 328 upon loading of the cassette 820 onto the main instrument 810. Accordingly the piston control 2645 can be considered the control element interface of the pump 328, as it coacts with the pump actuator (control element) 2652 to facilitate operation of the pump 328 by the main instrument 810.

As shown in FIG. 22C, the centrifuge rotor 2020 includes a centrifuge interface 2061 configured to interface with the centrifuge drive 2030 located on the main device and facilitate the operation of the centrifuge. With reference to FIG. 23B, the cassette housing opening 2404 may also provide physical and/or optical access to the centrifuge rotor 2020 and a sample analysis cell 2464 located on the centrifuge rotor 2002 such that the centrifuge drive 2030 on the main instrument 810 may access and engage the centrifuge rotor 2020 when the cassette 820 and main instrument 810 are connected.

In use, the fluid handling cassette 820 is connected to a main analysis instrument 810 as depicted in FIG. 22C. Once the cassette and instrument are connected, the control elements including centrifuge drive motor 2030, roller pump 2619, valves 323a and 323b, and pump actuator 2652 located on the main instrument 810 may access the fluid handling elements via the openings provided in the cassette housing 2400 to control fluid flow through fluid passageways 111, 327 and 324 and to engage centrifuge rotor 2020 and piston control 2645. The centrifuge rotor interface 2051 is connected to a centrifuge interface 2042 of centrifuge drive 2030 (see FIG. 28) which is further connected to a drive motor for rotating the centrifuge rotor 2020. Once engaged, the centrifuge drive 2030 may then control rotation of the centrifuge rotor 2020 about its axis to separate a component from a sample contained in a sample cell 2464 located on the rotor 2020 and to position the sample cell 2464 in the slot 2074 of the bodily fluid analyzer 1700 as further discussed elsewhere herein.

Fluid passageway portions 111 and 112 may be connected with an infusion source 15 and a patient, respectively, to place the system in fluid communication with a bodily fluid to be analyzed. Once the passageway portions are connected to a patient, rotary pump 2619 may be operated in a reverse direction to draw a bodily fluid from the patient into the fluid passageway 112. From there the bodily fluid can be drawn into the fluid handling cassette 820 via the passageway 113 as described elsewhere herein. When the centrifuge rotor 2020 is rotated vertical, as depicted in FIG. 22C, so that the sample analysis cell 2464 is aligned with the fluid passageway interface 2028, a portion of the drawn bodily fluid may flow into the sample analysis cell 2464 via the fluid passageway interface 2028. Then, the centrifuge rotor 2020 may be further rotated at a relatively high speed to separate a first component from the sample of bodily fluid.

As described herein in reference to FIGS. 25A-D, the sample analysis cell 2464 may be configured to isolate the separated first component from the remainder of the sample. Once the component has been separated, the centrifuge rotor 2020 may be further rotated to align sample cell 2464 (or at least the interrogation region 2091 thereof) with the slot 2074 in the bodily fluid analyzer 1700. The slot 2074 is configured such that when the centrifuge rotor is rotated to a measurement position, the sample analysis cell 2464 (or at least the interrogation region 2091 thereof) is positioned in slot 2074 and thus optically accessible by the bodily fluid analyzer 1700. Where the bodily fluid analyzer uses electromagnetic radiation to determine the concentration of an analyte in the component sample, the sample analysis cell 2464 or region 2091 may be aligned with the bodily fluid analyzer 1700 so that the cell 2464 or region 2091 is on the optical axis X-X, between a source of electromagnetic radiation 1720 and a detector 1745. Here, as depicted in FIGS. 25A-D, the sample analysis cell 2464 may be a spectroscopic cell including one or more optical windows capable of permitting spectroscopic measurement of the contents of the sample analysis cell 2464.

Once the sample analysis cell 2464 has been aligned, or otherwise interfaced, with the bodily fluid analyzer 1700, the bodily fluid analyzer 1700 may operatively engage the sample analysis cell 2464 to determine the concentration of an analyte in the component of bodily fluid contained in the sample analysis cell 2464 or region 2091. Once the sample has been analyzed, valve 323a positioned on passageway 324 may be opened and the used component of bodily fluid in the sample cell 2464 may be transported to the waste receptacle 325 for storage and disposal. Sample analysis cell 2464 may then be reused for successive sample draws and analysis. In an alternative embodiment, the sample cell 2464 may be removed from the rotor 2020 and replaced after each separate analysis. Once the patient care has terminated, the fluid passageway 112 may be disconnected from the patient and the fluid handling module 820 which has come into fluid contact with the patient's bodily fluid may be disposed of or sterilized for reuse. The main instrument portion 810, however, has preferably not come into contact with the patient's bodily fluid during the analysis and therefore can readily be connected to a new fluid handling cassette 820 and used for the analysis of a subsequent patient.

Figure 24B:
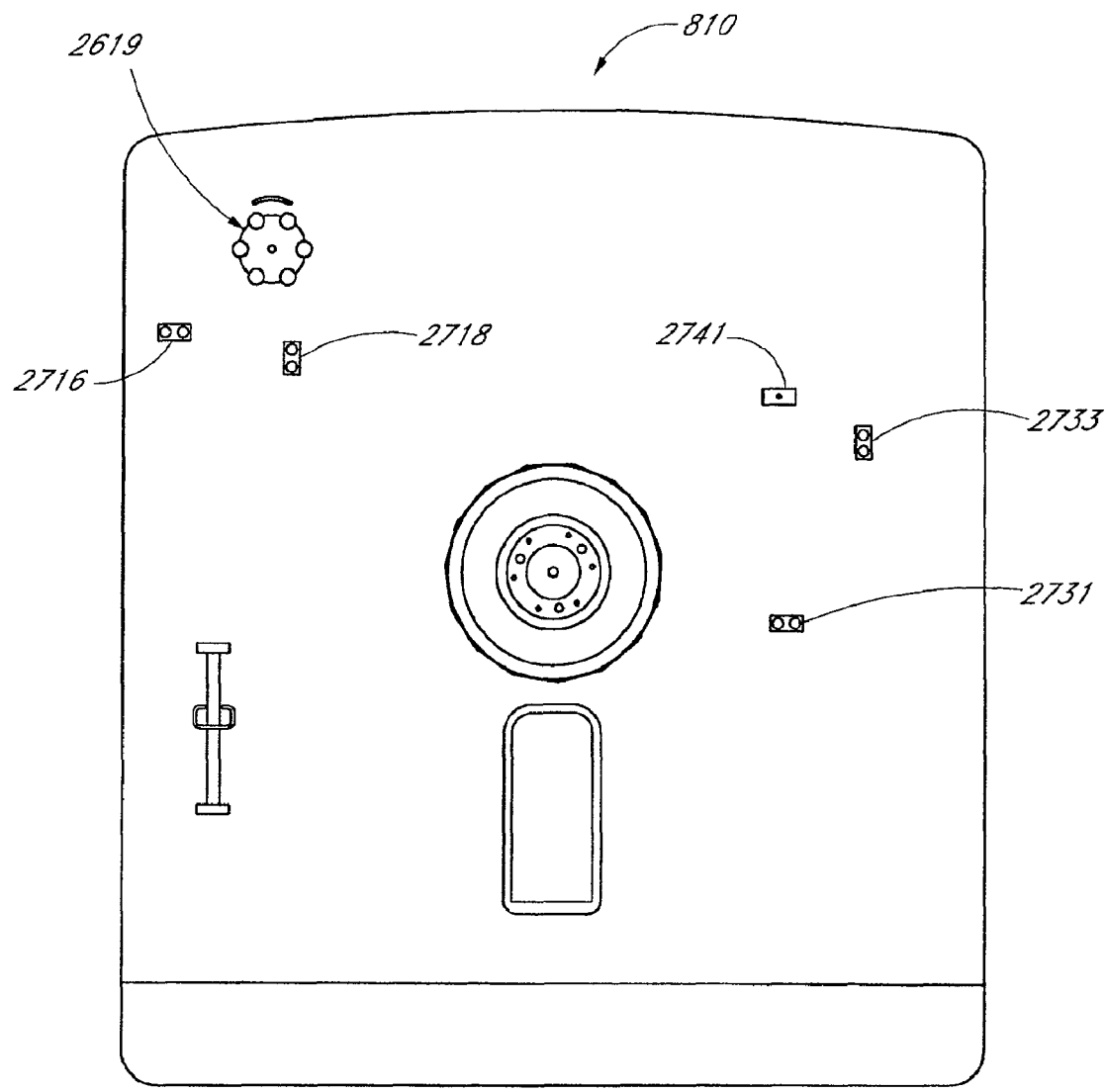
FIG. 24B is a front elevational view of the main instrument of the fluid handling and analysis apparatus of FIG. 24A.

As may be appreciated, the foregoing discussion of the cassette 820 equipped with the fluid handling network 2600 applies as well to the cassette 820 equipped with the fluid handling network 2700 (see FIGS. 24A-24B). Thus the fluid handling network 2700 includes a number of fluid handling elements (fluid passageways, centrifuge rotor, syringe pump) that are engaged by control elements (roller pump, valves, pump actuator) through openings in the front wall 2745 of the cassette 820, upon installation of the cassette 820 on the main instrument 810. The portions of the fluid handling elements of the network 2700 that are engaged by the control elements of the instrument 810 can be considered the control element interfaces of the network 2700. The number and arrangement of the fluid handling elements of the network 2700, and the number and arrangement of the control elements of the corresponding main instrument 810, as well as the operation thereof, vary somewhat from the components and operation of the network 2600, as discussed in greater detail above.

Although the invention(s) presented herein have been disclosed in the context of certain preferred embodiments and examples, it will be understood by those skilled in the art that the invention(s) extend beyond the specifically disclosed embodiments to other alternative embodiments and/or uses of the invention(s) and obvious modifications and equivalents thereof. Thus, it is intended that the scope of the invention(s) herein disclosed should not be limited by the particular embodiments described above.

What is claimed is:

1. A system for analyzing non-flowing blood plasma, the system comprising:
    an analysis system configured to determine the concentration of an analyte in plasma;
    a fluid controller configured to:
        withdraw blood from a patient;
        divide a sample portion from said withdrawn blood; and
        direct the sample portion toward a fluid handling element; the fluid handling element comprising a fluid interface and a sample element comprising a sample cell having a sample measurement location coinciding with an analysis region of the analysis system, the sample cell comprising a sample chamber for containing a first sample, an input fluid passageway for communicating the first sample into the sample chamber, and an output fluid passageway for communicating the first sample out of the sample chamber, the output fluid passageway adapted to permit a subsequent sample to be admitted into the sample chamber, the fluid handling element configured to prepare the sample portion for analysis by:
            removing non-plasma from plasma in the sample portion;
            positioning at least a portion of the remaining plasma at the sample measurement location;
            aligning the sample measurement location with the analysis region of the analysis system; and
            holding at least the plasma in a non-flowing state while the plasma at the sample measurement location is analyzed by the analysis system;
    wherein said fluid controller is further configured to transfer the sample portion through the fluid interface into the sample element and, after analysis, allow the flow of a flush fluid into the sample element through the fluid interface to prepare the fluid handling element to analyze a subsequent sample portion.

2. The system of claim 1, wherein the fluid controller comprises a pump.

3. The system of claim 1, wherein the sample element comprises a disposable container.

4. The system of claim 1, wherein the fluid interface comprises a fluid injection probe.

5. The system of claim 1, wherein the fluid interface comprises a fluid removal probe.

6. The system of claim 1, wherein the fluid handling element comprises a fluid component separator.

7. The system of claim 6, wherein the fluid component separator comprises a centrifuge.

8. The system of claim 1, wherein the analysis region optically engages the sample measurement location.

9. The system of claim 1, wherein the analysis region physically engages the sample measurement location.

10. The system of claim 1, wherein the sample measurement location comprises a window configured allow the passage of electromagnetic radiation.

11. The system of claim 1, wherein the analysis region of the analysis system comprises a source of electromagnetic radiation.

12. The system of claim 1, wherein the analysis region of the analysis system comprises a photo-detector configured to detect electromagnetic radiation.

13. An apparatus for automatically preparing and analyzing a fluid analyte, the apparatus comprising:
    a fluid handling element comprising:
        a fluid interface having an input fluid passageway and an output fluid passageway; and
        a sample cell with a sample chamber, the input fluid passageway leading to the sample chamber and the output fluid passageway leading from the sample chamber;
    a fluid controller configured to withdraw blood from a patient and direct a sample portion thereof toward the fluid handling element; and
    an analyzer integrated with the fluid handling element and configured to determine the concentration of a body fluid analyte, the analyzer having an analysis region configured to coincide with the sample cell;
    the fluid controller and fluid handling element configured to prepare the sample portion for analysis by:
        positioning at least one component of the sample portion in the sample chamber;
        aligning the sample chamber with the analysis region of the analyzer; and
        holding the at least one component of the sample portion in a non-flowing state within the sample chamber to facilitate analysis of the at least one component of the sample portion while it is at the sample measurement location;
    the fluid controller and fluid handling element further configured to prepare the sample chamber for analysis of a subsequent sample portion by allowing the flow of a flush fluid through the fluid interface and through the sample chamber.

14. The apparatus of claim 13, wherein the sample portion is directed away from the patient after analysis.

15. The apparatus of claim 13, wherein, after analysis, the flush fluid flowing through the fluid interface and the waste chamber conveys the sample portion toward a waste chamber.

16. The apparatus of claim 13, wherein the fluid handling element comprises a fluid component separator to separate the at least one component of the sample portion.

17. The apparatus of claim 16, wherein the fluid component separator comprises a rotating portion of a centrifuge.

18. The apparatus of claim 13, wherein the analysis region optically engages the sample measurement location.

19. The apparatus of claim 18, wherein the sample measurement location comprises a window configured allow the passage of electromagnetic radiation.

20. The apparatus of claim 19, wherein the analysis region of the analyzer comprises a source of electromagnetic radiation.

21. The apparatus of claim 20, wherein the analysis region of the analyzer further comprises a photo-detector configured to detect electromagnetic radiation.

22. The apparatus of claim 21, wherein the fluid handling element comprises a disposable fluid cartridge, and the fluid cartridge is removably engageable with the fluid controller and configured to be positioned such that the sample cell is located between the source of electromagnetic radiation and the photo-detector.

* * * * *